(12) United States Patent
Park et al.

(10) Patent No.: US 11,844,273 B2
(45) Date of Patent: *Dec. 12, 2023

(54) HETEROCYCLIC COMPOUND AND ORGANIC LIGHT-EMITTING DEVICE INCLUDING THE SAME

(71) Applicant: SAMSUNG DISPLAY CO., LTD., Yongin-si (KR)

(72) Inventors: Junha Park, Yongin-si (KR); Munki Sim, Yongin-si (KR); Hyoyoung Lee, Yongin-si (KR); Youngkook Kim, Yongin-si (KR); Seokhwan Hwang, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 20 days.

This patent is subject to a terminal disclaimer.

(21) Appl. No.: 17/395,913

(22) Filed: Aug. 6, 2021

(65) Prior Publication Data

US 2021/0367158 A1 Nov. 25, 2021

Related U.S. Application Data

(63) Continuation of application No. 15/867,357, filed on Jan. 10, 2018.

(30) Foreign Application Priority Data

Jun. 21, 2017 (KR) .......................... 10-2017-0078597

(51) Int. Cl.
*H10K 85/60* (2023.01)
*C07D 401/04* (2006.01)
(Continued)

(52) U.S. Cl.
CPC ......... *H10K 85/654* (2023.02); *C07D 251/24* (2013.01); *C07D 401/04* (2013.01);
(Continued)

(58) Field of Classification Search
None
See application file for complete search history.

(56) References Cited

U.S. PATENT DOCUMENTS 5,645,948 A 7/1997 Shi et al.
6,465,115 B2 10/2002 Shi et al.
(Continued)

FOREIGN PATENT DOCUMENTS

CN 105315219 A 2/2016
CN 105315265 A 2/2016
(Continued)

OTHER PUBLICATIONS

"Fused pyridine derivatives," Heterocycles, vol. 57, 2002, 1 page.
(Continued)

*Primary Examiner* — Gregory D Clark
(74) *Attorney, Agent, or Firm* — Lewis Roca Rothgerber Christie LLP

(57) ABSTRACT

Provided are a heterocyclic compound and an organic light-emitting device including the same. The heterocyclic compound includes a fluoro-containing cyclic group. The heterocyclic compound does not include a carbazole group, a dibenzofuran group, a dibenzothiophene group, and/or a triphenylene group. The organic light-emitting device includes: a first electrode; a second electrode facing the first electrode; and an organic layer between the first electrode and the second electrode and including an organic layer, the organic layer including an emission layer and at least one of the heterocyclic compound.

20 Claims, 4 Drawing Sheets

(51) Int. Cl.
*C07F 5/02* (2006.01)
*C07D 251/24* (2006.01)
*H10K 50/11* (2023.01)
*H10K 50/15* (2023.01)
*H10K 50/16* (2023.01)
*H10K 50/17* (2023.01)
*H10K 50/18* (2023.01)
*H10K 50/81* (2023.01)
*H10K 50/82* (2023.01)
*H10K 50/852* (2023.01)
*H10K 101/30* (2023.01)
*H10K 101/40* (2023.01)

(52) U.S. Cl.
CPC ........... *C07F 5/027* (2013.01); *H10K 85/615* (2023.02); *H10K 85/626* (2023.02); *H10K 85/6572* (2023.02); *H10K 50/11* (2023.02); *H10K 50/15* (2023.02); *H10K 50/16* (2023.02); *H10K 50/166* (2023.02); *H10K 50/17* (2023.02); *H10K 50/171* (2023.02); *H10K 50/18* (2023.02); *H10K 50/81* (2023.02); *H10K 50/82* (2023.02); *H10K 50/852* (2023.02); *H10K 2101/30* (2023.02); *H10K 2101/40* (2023.02)

(56) References Cited

U.S. PATENT DOCUMENTS

| | | |
|---|---|---|
| 6,596,415 B2 | 7/2003 | Shi et al. |
| 6,818,919 B2 | 11/2004 | Robeson et al. |
| 7,189,989 B2 | 3/2007 | Ise |
| 7,982,213 B2 | 7/2011 | Okajima et al. |
| 8,436,344 B2 | 5/2013 | Seo et al. |
| 8,455,272 B2 | 6/2013 | Sato |
| 8,999,525 B2 | 4/2015 | Lee et al. |
| 9,178,001 B2 | 11/2015 | Kwak et al. |
| 9,252,368 B2 | 2/2016 | Aihara et al. |
| 9,391,281 B2 | 7/2016 | Lee et al. |
| 9,425,407 B2 | 8/2016 | Hwang et al. |
| 9,705,088 B2 | 7/2017 | Park et al. |
| 9,718,764 B2 | 8/2017 | Stoessel et al. |
| 9,997,716 B2 | 6/2018 | Zeng et al. |
| 10,023,599 B2 | 7/2018 | Bierbach et al. |
| 10,236,452 B2 | 3/2019 | Jeong et al. |
| 10,249,824 B2 | 4/2019 | Park et al. |
| 10,297,762 B2 | 5/2019 | Zeng et al. |
| 10,361,375 B2 | 7/2019 | Zeng et al. |
| 10,367,147 B2 | 7/2019 | Kim et al. |
| 10,903,432 B2 | 1/2021 | Sim et al. |
| 11,152,576 B2 | 10/2021 | Heo et al. |
| 11,208,402 B2 | 12/2021 | Jung et al. |
| 11,228,001 B2 | 1/2022 | Heo et al. |
| 11,370,782 B2 | 6/2022 | Jung et al. |
| 2002/0132134 A1 | 9/2002 | Hu et al. |
| 2003/0165715 A1 | 9/2003 | Yoon et al. |
| 2004/0036077 A1 | 2/2004 | Ise |
| 2004/0053069 A1 | 3/2004 | Sotoyama et al. |
| 2004/0137270 A1 | 7/2004 | Seo et al. |
| 2005/0002857 A1 | 1/2005 | Pez et al. |
| 2005/0221124 A1 | 10/2005 | Hwang et al. |
| 2005/0274961 A1 | 12/2005 | Iou |
| 2006/0252857 A1 | 11/2006 | Schäfer et al. |
| 2007/0200490 A1 | 8/2007 | Kawamura et al. |
| 2009/0019768 A1 | 1/2009 | Toseland et al. |
| 2009/0134784 A1 | 5/2009 | Lin et al. |
| 2010/0039026 A1 | 2/2010 | Yang et al. |
| 2010/0155714 A1 | 6/2010 | Seo et al. |
| 2010/0200883 A1 | 8/2010 | Sato |
| 2010/0320451 A1 | 12/2010 | Kawamura |
| 2011/0121268 A1 | 5/2011 | Nagao et al. |
| 2011/0121274 A1 | 5/2011 | Parham et al. |
| 2011/0156013 A1 | 6/2011 | Kim et al. |
| 2011/0198629 A1 | 8/2011 | Lee et al. |
| 2011/0227053 A1 | 9/2011 | Bae et al. |
| 2012/0056165 A1 | 3/2012 | Kawamura et al. |
| 2012/0126692 A1 | 5/2012 | Ise et al. |
| 2012/0223276 A1 | 9/2012 | Parham et al. |
| 2012/0256172 A1 | 10/2012 | Ito et al. |
| 2012/0267620 A1 | 10/2012 | Min et al. |
| 2012/0286249 A1 | 11/2012 | Lee et al. |
| 2013/0001526 A1 | 1/2013 | Kwak et al. |
| 2013/0306959 A1 | 11/2013 | Ikeda et al. |
| 2013/0306962 A1* | 11/2013 | Yamamoto ........... H10K 50/121 257/40 |
| 2014/0027754 A1 | 1/2014 | Ueoka et al. |
| 2014/0138659 A1 | 5/2014 | Shin et al. |
| 2014/0299192 A1 | 10/2014 | Lee et al. |
| 2014/0323723 A1 | 10/2014 | Ahn et al. |
| 2014/0330013 A1 | 11/2014 | Aihara et al. |
| 2015/0014656 A1 | 1/2015 | Lim et al. |
| 2015/0041773 A1 | 2/2015 | Park et al. |
| 2015/0060787 A1 | 3/2015 | Park et al. |
| 2015/0069342 A1 | 3/2015 | Lee et al. |
| 2015/0069347 A1 | 3/2015 | Kim et al. |
| 2015/0069355 A1 | 3/2015 | Hwang et al. |
| 2015/0171336 A1 | 6/2015 | Park |
| 2015/0303380 A1 | 10/2015 | Kambe et al. |
| 2015/0318510 A1 | 11/2015 | Ito et al. |
| 2015/0349268 A1 | 12/2015 | Zeng et al. |
| 2016/0028021 A1 | 1/2016 | Zeng et al. |
| 2016/0043327 A1 | 2/2016 | Yoo et al. |
| 2016/0046563 A1 | 2/2016 | Stoessel et al. |
| 2016/0164004 A1 | 6/2016 | Seo et al. |
| 2016/0197289 A1 | 7/2016 | Sado et al. |
| 2016/0218298 A1 | 7/2016 | Lee et al. |
| 2016/0315268 A1 | 10/2016 | Stoessel |
| 2016/0351817 A1 | 12/2016 | Kim |
| 2017/0098779 A1 | 4/2017 | Lee et al. |
| 2017/0200902 A1 | 7/2017 | Lee et al. |
| 2017/0271596 A1 | 9/2017 | Lee |
| 2017/0317294 A1 | 11/2017 | Kim et al. |
| 2018/0051003 A1 | 2/2018 | Koo et al. |
| 2018/0066180 A1 | 3/2018 | Huh et al. |
| 2018/0102484 A1 | 4/2018 | Mizutani et al. |
| 2019/0198780 A1 | 6/2019 | Kim et al. |
| 2019/0233398 A1 | 8/2019 | Oh et al. |
| 2019/0245149 A1 | 8/2019 | Heo |
| 2019/0263834 A1 | 8/2019 | Jeong et al. |
| 2019/0341558 A1 | 11/2019 | Yang et al. |
| 2020/0048232 A1 | 2/2020 | Cha et al. |
| 2020/0131138 A1 | 4/2020 | Han |
| 2020/0287142 A1 | 9/2020 | Huh et al. |
| 2021/0020848 A1 | 1/2021 | Yang et al. |
| 2021/0119137 A1 | 4/2021 | Cha et al. |

FOREIGN PATENT DOCUMENTS

| | | |
|---|---|---|
| EP | 3072943 A1 | 9/2016 |
| EP | 3246963 A2 | 11/2017 |
| JP | 10-17860 A | 1/1998 |
| JP | 1998-017860 A | 1/1998 |
| JP | 10-338871 A | 12/1998 |
| JP | 11-87067 A | 3/1999 |
| JP | 2003045662 A | 2/2003 |
| JP | 2003-123983 A | 4/2003 |
| JP | 2004-022334 | 1/2004 |
| JP | 2004-103576 A | 4/2004 |
| JP | 2004-107263 A | 4/2004 |
| JP | 2004-281390 A | 10/2004 |
| JP | 2007-508275 A | 4/2007 |
| JP | 4060669 B2 | 12/2007 |
| JP | 4060669 B2 | 3/2008 |
| JP | 2008-120688 A | 5/2008 |
| JP | 2009-021336 A | 1/2009 |
| JP | 2010-141353 A | 6/2010 |
| JP | 2010-182637 A | 8/2010 |
| JP | 2010-195708 A | 9/2010 |
| JP | 2011-012190 A | 1/2011 |
| JP | 2011-49512 A | 3/2011 |
| JP | 2013-100239 A | 5/2013 |
| JP | 2015-504600 A | 2/2015 |
| JP | 2015-524797 A | 8/2015 |

(56) References Cited

FOREIGN PATENT DOCUMENTS

| | | |
|---|---|---|
| JP | 2016-6039 A | 1/2016 |
| JP | 2016-19002 A | 2/2016 |
| JP | 2016-516084 A | 6/2016 |
| JP | 2017-31131 A | 2/2017 |
| JP | 2017-509635 A | 4/2017 |
| JP | 2017-107992 A | 6/2017 |
| KR | 10-2003-0067773 A | 8/2003 |
| KR | 10-0525408 B1 | 11/2005 |
| KR | 10-0691543 B1 | 3/2007 |
| KR | 10-2010-0056398 A | 5/2010 |
| KR | 10-0958641 | 5/2010 |
| KR | 10-2010-0088612 A | 8/2010 |
| KR | 10-2010-0099327 A | 9/2010 |
| KR | 10-2010-0118690 A | 11/2010 |
| KR | 10-2011-0040874 A | 4/2011 |
| KR | 10-2011-0075690 A | 7/2011 |
| KR | 10-2011-0094271 A | 8/2011 |
| KR | 10-2012-0020901 A | 3/2012 |
| KR | 10-2012-0051598 A | 5/2012 |
| KR | 10-2012-0057198 A | 5/2012 |
| KR | 10-2012-0065214 A | 6/2012 |
| KR | 10-2012-0101558 A | 9/2012 |
| KR | 10-2012-0104087 A | 9/2012 |
| KR | 10-2012-0104246 A | 9/2012 |
| KR | 10-2012-0116838 A | 10/2012 |
| KR | 10-2012-0127683 A | 11/2012 |
| KR | 10-2012-0138671 A | 12/2012 |
| KR | 10-2013-0116041 A | 10/2013 |
| KR | 10-2013-0127567 A | 11/2013 |
| KR | 10-2013-0135181 A | 12/2013 |
| KR | 10-2013-0142969 A | 12/2013 |
| KR | 10-2014-0009918 A | 1/2014 |
| KR | 10-2014-0009919 A | 1/2014 |
| KR | 10-2014-0076520 A | 6/2014 |
| KR | 10-2014-0079306 A | 6/2014 |
| KR | 10-2014-0082351 A | 7/2014 |
| KR | 10-2014-0091049 A | 7/2014 |
| KR | 20140132244 A | 11/2014 |
| KR | 10-2015-0018229 A | 2/2015 |
| KR | 10-2015-0025259 A | 3/2015 |
| KR | 10-2015-0027897 A | 3/2015 |
| KR | 10-2015-0028860 A | 3/2015 |
| KR | 10-2015-0028935 A | 3/2015 |
| KR | 20150054797 A | 5/2015 |
| KR | 10-2015-0069346 A | 6/2015 |
| KR | 10-2015-0099750 A | 9/2015 |
| KR | 10-2015-0124000 A | 11/2015 |
| KR | 10-2015-0124637 A | 11/2015 |
| KR | 10-2015-0132873 A | 11/2015 |
| KR | 10-2015-0136579 A | 12/2015 |
| KR | 10-2016-0006633 A | 1/2016 |
| KR | 10-2016-0018332 A | 2/2016 |
| KR | 10-2016-0046046 A | 4/2016 |
| KR | 10-1627691 | 6/2016 |
| KR | 10-2016-0141359 A | 12/2016 |
| KR | 10-2017-0023025 A | 3/2017 |
| KR | 20170032833 A | 3/2017 |
| KR | 20170049440 A | 5/2017 |
| KR | 10-2017-0104718 | 9/2017 |
| KR | 10-2017-0134264 A | 12/2017 |
| KR | 10-2018-0005533 A | 1/2018 |
| KR | 20180010132 A | 1/2018 |
| KR | 10-2018-0051355 A | 5/2018 |
| KR | 10-2018-0059286 A | 6/2018 |
| KR | 10-2018-0061075 A | 6/2018 |
| KR | 10-2018-0086126 A | 7/2018 |
| KR | 10-2018-0115217 A | 10/2018 |
| KR | 10-2018-0120569 A | 11/2018 |
| KR | 10-2018-0130329 A | 12/2018 |
| KR | 10-2019-0013527 A | 2/2019 |
| KR | 10-2019-0016638 A | 2/2019 |
| KR | 10-2019-0079341 A | 7/2019 |
| KR | 10-2019-0101882 A | 9/2019 |
| KR | 10-2019-0106753 A | 9/2019 |
| TW | 201100522 A1 | 1/2011 |
| WO | WO 2004/106311 A2 | 12/2004 |
| WO | WO 2010/126270 A1 | 11/2010 |
| WO | WO 2010/015306 A1 | 2/2012 |
| WO | WO 2012/086170 A1 | 6/2012 |
| WO | WO 2012/173073 A1 | 12/2012 |
| WO | WO 2014/104720 A1 | 7/2014 |
| WO | WO 2016/002864 A1 | 1/2016 |
| WO | WO 2016/121597 A1 | 8/2016 |
| WO | WO 2018/190522 A1 | 10/2018 |
| WO | WO 2018/199466 A1 | 11/2018 |

OTHER PUBLICATIONS

Rahman, A.F.M. Motiur, et al., "Synthesis and Properties of Benzo[b]-1,10-phenanthrolines and Their Ruthenium(II) Complexes," Heteroatom Chemistry, vol. 18, No. 6, 2007, pp. 650-656.
Heterocycles, vol. 78, No. 6, 2009, 7 pages.
Jahng, Yurngdong, et al., "Synthesis and Properties of 2,2'-Di(heteroaryl)-9,9'-spirobifluorenes," Bulletin of the Chemical Society of Japan, vol. 83, No. 6, 2010, pp. 672-677.
Notice of Allowance for U.S. Appl. No. 15/866,885 dated Oct. 21, 2022, 27 pages.
Korean Notice of Allowance, for Patent Application No. 10-2017-0100434, dated Mar. 23, 2022, 6 pages.
Chinese Office Action dated Jan. 18, 2022, issued in Chinese Patent Application No. 201810652269.6 (9 pages).
U.S. Final Office Action dated Feb. 3, 2022, issued in U.S. Appl. No. 15/867,357 (9 pages).
U.S. Advisory Action from U.S. Appl. No. 15/866,885, dated Nov. 9, 2020, 2 pages.
U.S. Advisory Action from U.S. Appl. No. 15/867,357, dated Aug. 17, 2020, 3 pages.
U.S. Notice of Allowance from U.S. Appl. No. 14/198,372, dated Apr. 13, 2016, 9 pages.
U.S. Notice of Allowance from U.S. Appl. No. 14/290,950, dated Mar. 9, 2017, 8 pages.
U.S. Notice of Allowance from U.S. Appl. No. 15/866,885, dated Apr. 15, 2022, 27 pages.
U.S. Notice of Allowance from U.S. Appl. No. 15/866,885, dated Nov. 10, 2021, 27 pages.
U.S. Notice of Allowance from U.S. Appl. No. 15/867,357, dated Apr. 4, 2022, 8 pages.
U.S. Notice of Allowance from U.S. Appl. No. 15/913,162, dated Aug. 12, 2020, 5 pages.
U.S. Office Action from U.S. Appl. No. 15/866,885, dated Sep. 2, 2020, 12 pages.
U.S. Restriction Requirement from U.S. Appl. No. 15/866,885, dated Jan. 13, 2020, 7 pages.
Office Action for U.S. Appl. No. 16/250,946 dated Nov. 25, 2022, 28 pages.
U.S. Notice of Allowance dated Aug. 29, 2022, issued in U.S. Appl. No. 15/867,357 (10 pages).
Adachi, Chihaya et al.; "Confinement of charge carriers and molecular excitons within 5-nm-thick emitter layer in organic electroluminescent devices with a double heterostructure"; Applied Physics Letters; 57 (6); Aug. 6, 1990; pp. 531-533.
Berger, Ricarda, et al., "New symmetrically substituted 1,3,5-triazines as host compounds for channel-type inclusion formation," CrystEngComm, 2012, vol. 14, 3 pages.
Debnath, Pradip, et al., "A novel straightforward synthesis of 2,4,6-triaryl-1,3,5-triazines via copper-catalyzed cyclization of N-benzylbenzanidines," Tetrahedron Letters, 2014, vol. 55, 3 pages.
EPO Extended Search Report dated Sep. 21, 2018, for corresponding European Patent Application No. 18178734.2 (11 pages).
Ishi-I, Tsutomu, et al., "High Electron Drift Mobility in an Amorphous Film of 2,4,6,-Tris[4-(1-naphthyl)phenyl]-1,3,5-triazine," Chemistry Letters, 2004, vol. 33, No. 10, 2 pages.
Johansson, Nicklas et al.; "Solid-State Amplified Spontaneous Emission in Some Spiro-Type Molecules: A New Concept for the Design of Solid-State Lasing Molecules"; Advanced Materials; 10; No. 14; 1998; pp. 1136-1141.
Kotha, Sambasivarao, et al., "Synthesis of nano-sized $C_3$-symmetric 2,4,6-triphenyl-1,3,5-s-triazine and 1,3,5-triphenylbenzene deriva-

(56) References Cited

OTHER PUBLICATIONS tives via the trimerization followed by Suzuki-Miyaura cross-coupling or O-alkylation reactions and their biological evaluation," Indian Journal of Chemistry, Dec. 2009, vol. 48B, 5 pages.
Lee, Dong Ryun, et al., "Design Strategy for 25% External Quantum Efficiency in Green and Blue Thermally Activated Delayed Fluorescent Devices," Advanced Materials, 2015, vol. 27, 7 pages.
Sakamoto, Youichi et al.; "Synthesis, Characterization, and Electron-Transport Property of Perfluorinated Phenylene Dendrimers; J. Am. Chem. Soc."; 2000; 122 (8); pp. 1832-1833.
Swensen et al.; Blue phosphorescent organic light-emitting devices utilizing cesium-carbonate-doped 2,4,6-tris(2',4'-difluoro-[1, 1 '-biphenyl]-4-yl)-1,3,5-triazine; Journal of Photonics for Energy (2011 ), 1, 011008/1-011008/11 (Year: 2011).
Tang, C. W. et al.; "Organic electroluminescent diodes"; Applied Physics Letters; 51 (12); Sep. 21, 1987; pp. 913-915.
Tao, Y. T. et al.; "Sharp green electroluminescence from 1H-pyrazolo[3,4-b]quinoline-based light-emitting diodes"; Applied Physics Letters; vol. 77, No. 11; Sep. 11, 2000; pp. 1575-1577.
Yamaguchi, Shigehiro et al.; "Diphenylamino-Substituted 2,5-Diarylsiloles for Single-Layer Organic Electroluminescent Devices"; Chemistry Letters; 2001; pp. 98-99.
Zeika, Olaf, et al., "Synthesis of Polynitroxides Based on Nucleophilic Aromatic Substitution," Organic Letters, 2010, vol. 12, No. 16, 4 pages.
U.S. Notice of Allowance from U.S. Appl. No. 15/866,885, dated Jun. 29, 2021, 10 pages.
U.S. Notice of Allowance from U.S. Appl. No. 15/867,357, dated Mar. 31, 2021, 10 pages.
U.S. Office Action from U.S. Appl. No. 14/198,372, dated Dec. 10, 2015, 7 pages.
U.S. Office Action from U.S. Appl. No. 14/290,950, dated Oct. 6, 2016, 7 pages.
U.S. Office Action from U.S. Appl. No. 15/866,885, dated Apr. 15, 2020, 12 pages.
U.S. Office Action from U.S. Appl. No. 15/866,885, dated Jan. 28, 2021, 10 pages.
U.S. Office Action from U.S. Appl. No. 15/867,357, dated Dec. 9, 2020, 12 pages.
U.S. Office Action from U.S. Appl. No. 15/867,357, dated Feb. 20, 2020, 8 pages.
U.S. Office Action from U.S. Appl. No. 15/867,357, dated Jun. 25, 2020, 9 pages.
U.S. Office Action from U.S. Appl. No. 15/867,357, dated Sep. 16, 2021, 9 pages.
U.S. Office Action from U.S. Appl. No. 15/913,162, dated Jun. 15, 2020, 9 pages.
U.S. Office Action from U.S. Appl. No. 15/913,162, dated Mar. 6, 2020, 9 pages.
Fink, Ralf et al., "Aromatic polyethers with 1,3,5-triazine units as hole-blocking/elecgtron-transport materials in LEDs," Proceedings of SPIE, vol. 3148, 1997, 9 pages.
Japanese Office Action dated Jun. 7, 2022, issued in corresponding Japanese Patent Application No. 2018-117229, 5 pages.
U.S. Office Action dated Apr. 1, 2021, issued in U.S. Appl. No. 16/250,946 (25 pages).
U.S. Final Office Action dated Jul. 16, 2021, issued in U.S. Appl. No. 16/250,946 (31 pages).
Kwon, Jang Hyeok et al., "Preparation of phenanthroline derivatives for organic electric device," Sep. 18, 2017, XP002782646.
EPO Extended Search Report dated Jul. 11, 2018, for corresponding European Patent Application No. 18175088.6 (8 pages).
Machine translation of JP 2003045662, translation generated Feb. 2020, 70 pages. (Year: 2020).
Tong et al; Light-Driven Proton Reduction in Aqueous Medium Catalyzed by a Family of Cobalt Complexes with Tetradentate Polyoyridine-Type Ligands, 2015, Inorganic Chemistry, 54, 7873-7884. (Year: 2015).
Internet Material: 2009 Fall Assembly and Symposium. vol. 34, No. 2, 2009; Publication Date, Oct. 8, 2009-Oct. 9, 2009; Title: A novel conjugated polymer based on 4H-benzo[det]carbazole backbone for OLED, 1 page.
D'Andrade, et al. "Controlling exciton diffusion in multilayer white phosphorescent organic light emitting devices." Advanced Materials 14.2 (2002): 147-151.
Hatalis, et al. "Polysilicon TFT active matrix organic EL displays." Cockpit Displays IV: Flat Panel Displays for Defense Applications. vol. 3057. SPIE, 1997.
Korean Notice Of Allowance dated Feb. 21, 2023, issued in Korean Patent Application No. 10-2018-0034091 (2 pages).
U.S. Final Office Action dated Mar. 30, 2023, issued in U.S. Appl. No. 16/250,946 (14 pages).
U.S. Notice of Allowance dated Jul. 10, 2023, issued in U.S. Appl. No. 16/250,946 (9 pages).
U.S. Office Action dated Oct. 5, 2023, issued in U.S. Appl. No. 16/250,946 (17 pages).

* cited by examiner

| 190 |
|-----|
| 150 |
| 110 |

| 190 |
|---|
| 150 |
| 110 |
| 210 |

| 220 |
|---|
| 190 |
| 150 |
| 110 |

| 220 |
|-----|
| 190 |
| 150 |
| 110 |
| 210 |

HETEROCYCLIC COMPOUND AND ORGANIC LIGHT-EMITTING DEVICE INCLUDING THE SAME

CROSS-REFERENCE TO RELATED APPLICATIONS

This application is a continuation of U.S. patent application Ser. No. 15/867,357, filed Jan. 10, 2018, which claims priority to and the benefit of Korean Patent Application No. 10-2017-0078597, filed Jun. 21, 2017, the entire content of both of which is incorporated herein by reference.

BACKGROUND

1. Field

One or more embodiments relate to a heterocyclic compound and an organic light-emitting device including the same.

2. Description of the Related Art

Organic light-emitting devices include self-emission devices that have wide viewing angles, high contrast ratios, short response times, and excellent characteristics in terms of brightness, driving voltage, and response speed, as compared to other devices in the art.

An example of such an organic light-emitting device may include a first electrode disposed on a substrate, and a hole transport region, an emission layer, an electron transport region, and a second electrode, which are sequentially disposed on the first electrode. Holes provided from the first electrode may move toward the emission layer through the hole transport region, and electrons provided from the second electrode may move toward the emission layer through the electron transport region. Carriers, such as holes and electrons, recombine in the emission layer to produce excitons. These excitons transit (e.g., relax) from an excited state to a ground state, thereby generating light.

SUMMARY

Aspects of embodiments of the present disclosure provide a novel heterocyclic compound and an organic light-emitting device including the same.

Additional aspects of embodiments will be set forth in part in the description which follows and, in part, will be apparent from the description, or may be learned by practice of the presented embodiments.

An aspect of an embodiment of the present disclosure provides a heterocyclic compound represented by Formula 1 below:

Formula 1

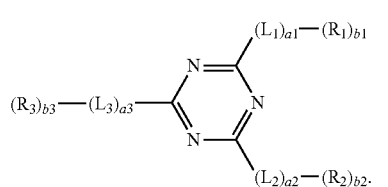

In Formula 1,
$L_1$ to $L_3$ may each independently be a single bond, a substituted or unsubstituted $C_3$-$C_{60}$ carbocyclic group, or a substituted or unsubstituted $C_1$-$C_{60}$ heterocyclic group, a1 to a3 may each independently be an integer from 1 to 5, $R_1$ to $R_3$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), and —B($Q_1$)($Q_2$), b1 to b3 may each independently be an integer from 1 to 20, at least one selected from $R_1$ to $R_3$ may be a fluoro-containing cyclic group, when at least one of $R_1$(s) in the number of b1 is the fluoro-containing cyclic group, $L_1$ may not be a substituted or unsubstituted triazine group, when at least one of $R_2$(s) in the number of b2 is the fluoro-containing cyclic group, $L_2$ may not be a substituted or unsubstituted triazine group, and when at least one of $R_3$(s) in the number of b3 is the fluoro-containing cyclic group, $L_3$ may not be a substituted or unsubstituted triazine group, the heterocyclic compound may not include a carbazole group, a dibenzofuran group, a dibenzothiophene group, and/or a triphenylene group, at least one substituent of the substituted $C_3$-$C_{60}$ carbocyclic group, the substituted $C_1$-$C_{60}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent non-aromatic condensed polycyclic group, and the substituted monovalent non-aromatic condensed heteropolycyclic group may be selected from:

deuterium, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), and —C(=O)($Q_{11}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group, each substituted with at least one selected from deuterium, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, a terphenyl group, —Si($Q_{21}$)($Q_{22}$)($Q_{23}$), —N($Q_{21}$)($Q_{22}$), —B($Q_{21}$)($Q_{22}$), and —C(=O)($Q_{21}$); and —Si($Q_{31}$)($Q_{32}$)($Q_{33}$), —N($Q_{31}$)($Q_{32}$), —B($Q_{31}$)($Q_{32}$), and —C(=O)($Q_{31}$), $Q_1$ to $Q_3$, $Q_{11}$ to $Q_{13}$, $Q_{21}$ to $Q_{23}$, and $Q_{31}$ to $Q_{33}$ may each independently be selected from hydrogen, deuterium, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with a $C_1$-$C_{60}$ alkyl group, a $C_1$-$C_{60}$ heteroaryl group, a monovalent non-aromatic condensed polycyclic group, a monovalent non-aromatic condensed heteropolycyclic group, a biphenyl group, and a terphenyl group, and indicates a binding site to a neighboring atom.

Another aspect of an embodiment of the present disclosure provides an organic light-emitting device including: a first electrode; a second electrode facing the first electrode; and an organic layer between the first electrode and the second electrode and including an organic layer, wherein the organic layer includes an emission layer and at least one of the heterocyclic compound.

BRIEF DESCRIPTION OF THE DRAWINGS

These and/or other aspects of embodiments will become apparent and more readily appreciated from the following description of the embodiments, taken in conjunction with the accompanying drawings in which:

FIG. 1 is a schematic view of an organic light-emitting device according to an embodiment;

FIG. 2 is a schematic view of an organic light-emitting device according to an embodiment;

FIG. 3 is a schematic view of an organic light-emitting device according to an embodiment; and FIG. 4 is a schematic view of an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the drawings, to explain aspects of embodiments of the present description. As used herein, the term "and/or" includes any and all combinations of one or more of the associated listed items. Expressions such as "at least one of," when preceding a list of elements, modify the entire list of elements and do not modify the individual elements of the list.

A heterocyclic compound according to an embodiment is represented by Formula 1 below:

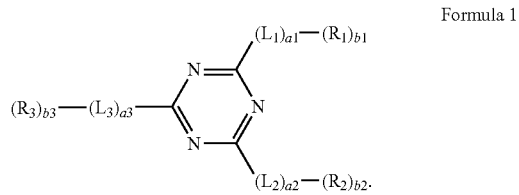

Formula 1

In Formula 1, $L_1$ to $L_3$ may each independently be a single bond, a substituted or unsubstituted $C_3$-$C_{60}$ carbocyclic group, or a substituted or unsubstituted $C_1$-$C_{60}$ heterocyclic group.

In one embodiment, $L_1$ to $L_3$ may each independently be selected from:

a single bond, a benzene group, a pentalene group, an indene group, a naphthalene group, an azulene group, a heptalene group, an indacene group, an acenaphthalene group, a fluorene group, a spiro-bifluorene group, a spiro-benzofluorene-fluorene group, a benzofluorene group, a dibenzofluorene group, a phenalene group, a phenanthrene group, an anthracene group, a fluoranthene group, a pyrene group, a chrysene group, a naphthacene group, a picene group, a perylene group, a pyrrole group, a thiophene group, a furan group, a silole group, an imidazole group, a pyrazole group, a thiazole group, an isothiazole group, an oxazole group, an isoxazole group, a pyridine group, a pyrazine group, a pyrimidine group, a pyridazine group, a triazine group, a benzofuran group, a benzothiophene group, a benzosilole group, a dibenzosilole group, a quinoline group, an isoquinoline group, a benzimidazole group, an imidazopyridine group, and an imidazopyrimidine group;

a benzene group, a pentalene group, an indene group, a naphthalene group, an azulene group, a heptalene group, an indacene group, an acenaphthalene group, a fluorene group, a spiro-bifluorene group, a spiro-benzofluorene-fluorene group, a benzofluorene group, a dibenzofluorene group, a phenalene group, a phenanthrene group, an anthracene group, a fluoranthene group, a pyrene group, a chrysene group, a naphthacene group, a picene group, a perylene group, a pyrrole group, a thiophene group, a furan group, a silole group, an imidazole group, a pyrazole group, a thiazole group, an isothiazole group, an oxazole group, an isoxazole group, a pyridine group, a pyrazine group, a pyrimidine group, a pyridazine group, a triazine group, a benzofuran group, a benzothiophene group, a benzosilole group, a dibenzosilole group, a quinoline group, an isoquinoline group, a benzimidazole group, an imidazopyridine group, and an imidazopyrimidine group, each substituted with at least one selected from deuterium, —Cl, —Br, —I, a hydroxyl group, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, a pyridinyl group, a pyrazinyl group, a pyrimidinyl group, a pyridazinyl group, a quinolinyl group, an isoquinolinyl group, a benzofuranyl group, a benzothiophenyl group, —Si($Q_{31}$)($Q_{32}$)($Q_{33}$), —N($Q_{31}$)($Q_{32}$), and —B($Q_{31}$)($Q_{32}$), and $Q_1$ and $Q_{31}$ to $Q_{33}$ may each independently be selected from a $C_1$-$C_{20}$ alkyl group, a $C_1$-$C_{20}$ alkoxy group, a phenyl group, a biphenyl group, a terphenyl group, a naphthyl group, and a pyridinyl group.

For example, $L_1$ to $L_3$ may each independently be selected from a single bond and groups represented by Formulae 3-1 to 3-29, but embodiments of the present disclosure are not limited thereto:

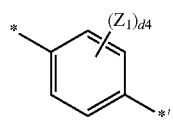

3-1

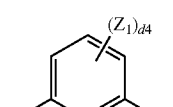

3-2

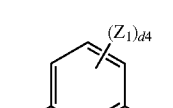

3-3

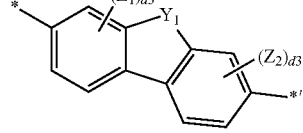

3-4

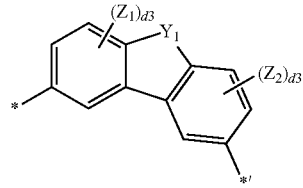

3-5

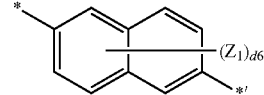

3-6

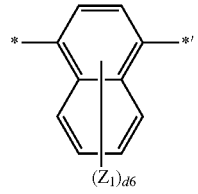

3-7

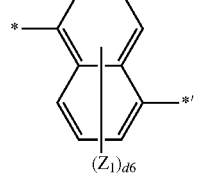

3-8

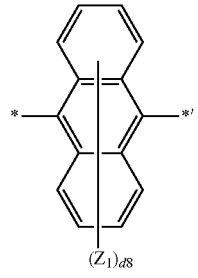

3-9

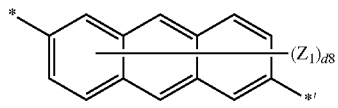

3-10

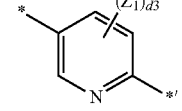

3-11

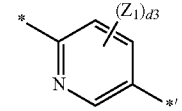

3-12

-continued 3-13
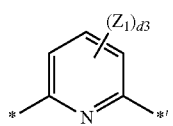

3-14
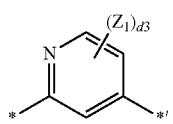

3-15
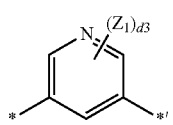

3-16
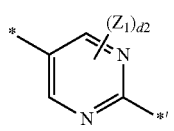

3-17
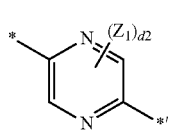

3-18
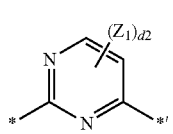

3-19
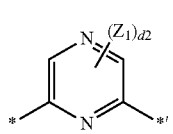

3-20
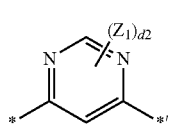

3-21
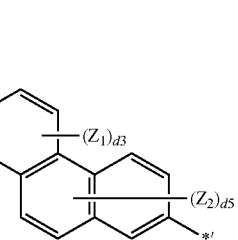

3-22
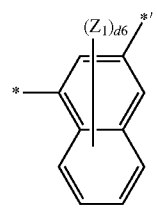

-continued 3-23
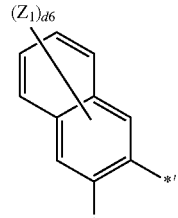

3-24
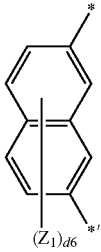

3-25
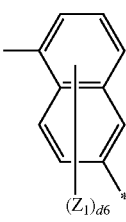

3-26
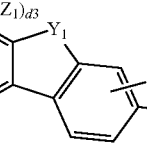

3-27
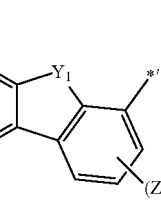

3-28
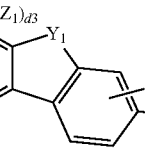

3-29
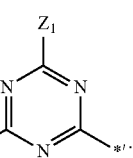

In Formulae 3-1 to 3-29, $Y_1$ may be $C(Z_3)(Z_4)$ or $Si(Z_6)(Z_7)$, $Z_1$ to $Z_7$ may each independently be selected from hydrogen, deuterium, —F, —Cl, —Br, —I, a hydroxyl group, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a pyrenyl group, a chrysenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a benzofuranyl group, a benzothiophenyl group, a benzosilolyl group, a dibenzosilolyl group, and —Si($Q_{31}$)($Q_{32}$)($Q_{33}$), $Q_{31}$ to $Q_{33}$ may each independently be selected from a $C_1$-$C_{20}$ alkyl group, a $C_1$-$C_{20}$ alkoxy group, a phenyl group, a biphenyl group, a terphenyl group, a naphthyl group, and a pyridinyl group, d2 may be an integer from 0 to 2, d3 may be an integer from 0 to 3, d4 may be an integer from 0 to 4, d6 may be an integer from 0 to 6, d8 may be an integer from 0 to 8, and and *' each indicate a binding site to a neighboring atom.

a1 to a3 in Formula 1 may each independently be an integer from 1 to 5, wherein, when a1 is two or more, two or more $L_1$(s) may be identical to or different from each other, when a2 is two or more, two or more $L_2$(s) may be identical to or different from each other, and when a3 is two or more, two or more $L_3$(s) may be identical to or different from each other.

In one embodiment, a1 to a3 may each independently be an integer from 1 to 3.

$R_1$ to $R_3$ in Formula 1 may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), and —B($Q_1$)($Q_2$).

In one embodiment, $R_1$ to $R_3$ may each independently be selected from:

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyridinyl group, a pyrazinyl group, a pyrimidinyl group, a pyridazinyl group, a triazinyl group, a thiophenyl group, a furanyl group, a quinolinyl group, an isoquinolinyl group, a benzofuranyl group, a benzothiophenyl group, a dibenzosilolyl group, a benzonaphthosilolyl group, a dinaphthosilolyl group, a benzimidazolyl group, a phenanthrolinyl group, and an imidazopyridinyl group;

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyridinyl group, a pyrazinyl group, a pyrimidinyl group, a pyridazinyl group, a triazinyl group, a thiophenyl group, a furanyl group, a quinolinyl group, an isoquinolinyl group, a benzofuranyl group, a benzothiophenyl group, a dibenzosilolyl group, a benzonaphthosilolyl group, a dinaphthosilolyl group, a benzimidazolyl group, a phenanthrolinyl group, and an imidazopyridinyl group, each substituted with at least one selected from deuterium, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyridinyl group, a pyrazinyl group, a pyrimidinyl group, a pyridazinyl group, a triazinyl group, a thiophenyl group, a furanyl group, a quinolinyl group, an isoquinolinyl group, a benzofuranyl group, a benzothiophenyl group, a dibenzosilolyl group, —N($Q_{31}$)($Q_{32}$), and —Si($Q_{31}$)($Q_{32}$)($Q_{33}$); and —N($Q_1$)($Q_2$) and —B($Q_1$)($Q_2$), and $Q_1$, $Q_2$, and $Q_{31}$ to $Q_{33}$ may each independently be selected from:

a $C_1$-$C_{20}$ alkyl group, a $C_1$-$C_{20}$ alkoxy group, a phenyl group, a biphenyl group, a terphenyl group, a naphthyl group, and a pyridinyl group; and a phenyl group, a biphenyl group, a terphenyl group, a naphthyl group, and a pyridinyl group, each substituted with a $C_1$-$C_{20}$ alkyl group or a $C_1$-$C_{20}$ alkoxy group.

b1 to b3 in Formula 1 may each independently be an integer from 1 to 20, wherein, when b1 is two or more, two or more $R_1$(s) may be identical to or different from each other, when b2 is two or more, two or more $R_2$(s) may be identical to or different from each other, and when b3 is two or more, two or more $R_3$(s) may be identical to or different from each other.

For example, b1 to b3 may each independently be an integer from 1 to 4.

at least one selected from $R_1$ to $R_3$ in Formula 1 may be a fluoro-containing cyclic group (e.g., a cyclic group containing at least one fluorine atom). The "fluoro-containing cyclic group" may include, for example, a $C_3$-$C_{60}$ carbocyclic group substituted with at least one —F or a $C_1$-$C_{60}$ heterocyclic group substituted with at least one —F. The "$C_3$-$C_{60}$ carbocyclic group substituted with at least one —F" may include, for example, a $C_3$-$C_{10}$ cycloalkyl group, a $C_3$-$C_{10}$ cycloalkenyl group, a $C_6$-$C_{60}$ aryl group, a $C_6$-$C_{60}$ aryloxy group, a $C_6$-$C_{60}$ arylthio group, and a monovalent non-aromatic condensed polycyclic group, each substituted with at least one —F, and the "$C_1$-$C_{60}$ heterocyclic group substituted with at least one —F" may include, for example, a $C_2$-$C_{10}$ heterocycloalkyl group, a $C_2$-$C_{10}$ heterocycloalkenyl group, a $C_2$-$C_{60}$ heteroaryl group, and a monovalent non-aromatic condensed heteropolycyclic group, each substituted with at least one —F.

In Formula 1, when at least one of $R_1$(s) in the number of b1 is the fluoro-containing cyclic group, $L_1$ may not be a substituted or unsubstituted triazine group, when at least one of $R_2$(s) in the number of b2 is the fluoro-containing cyclic group, $L_2$ may not be a substituted or unsubstituted triazine group, and when at least one of $R_3$(s) in the number of b3 is the fluoro-containing cyclic group, $L_3$ may not be a substituted or unsubstituted triazine group, and the heterocyclic compound may not include a carbazole group, a dibenzofuran group, a dibenzothiophene group, and/or a triphenylene group.

In one embodiment, the fluoro-containing cyclic group may include one to five fluoro groups. For example, the fluoro-containing cyclic group may include one, two, or five fluoro groups, but embodiments of the present disclosure are not limited thereto. For example, the fluoro-containing cyclic group may include two or more fluoro groups, but embodiments of the present disclosure are not limited thereto.

In one or more embodiments, the fluoro-containing cyclic group may be a $C_3$-$C_{60}$ carbocyclic group substituted with at least one —F. For example, the fluoro-containing cyclic group may be a $C_6$-$C_{60}$ aryl group or a monovalent non-aromatic condensed polycyclic group, each substituted with at least one —F, but embodiments of the present disclosure are not limited thereto. For example, the fluoro-containing cyclic group may be a phenyl group, a naphthyl group, or a fluorenyl group, each substituted with —F, but embodiments of the present disclosure are not limited thereto.

In one or more embodiments, the fluoro-containing cyclic group may be selected from groups represented by Formulae 4-1 to 4-19, but embodiments of the present disclosure are not limited thereto:

4-1

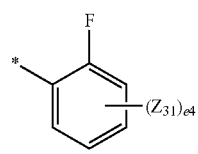

4-2

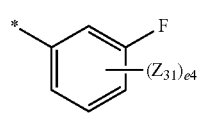

4-3

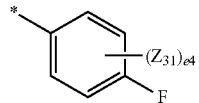

4-4

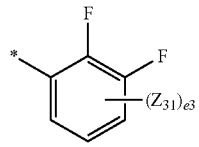

4-5

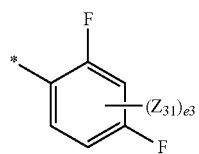

4-6

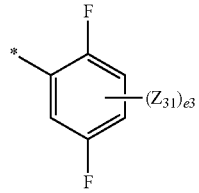

4-7

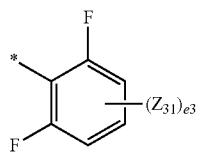

4-8

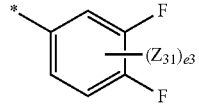

4-9

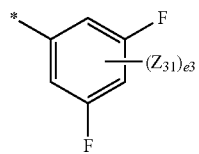

4-10

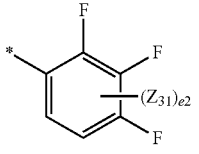

4-11

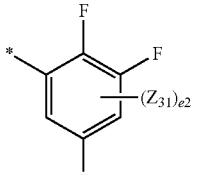

4-12

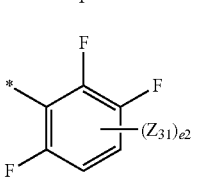

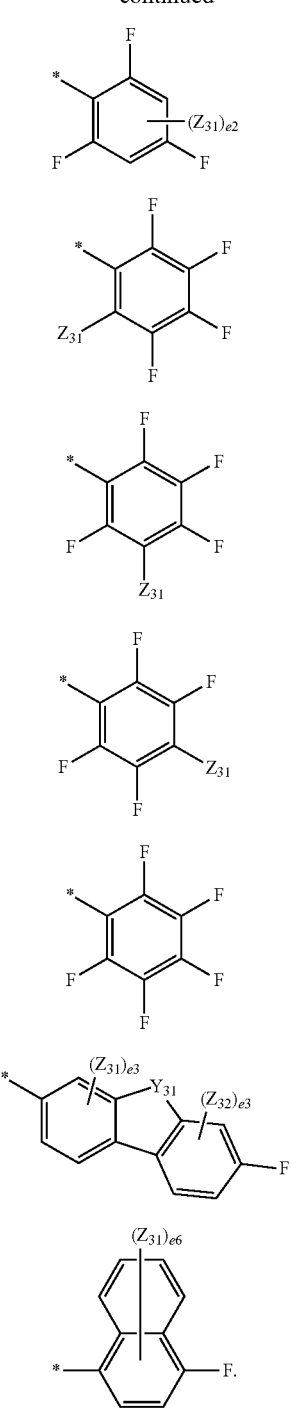

In Formulae 4-1 to 4-19, $Y_{31}$ may be O, S, $C(Z_{33})(Z_{34})$, $N(Z_{33})$, or $Si(Z_{33})(Z_{34})$, $Z_{31}$ to $Z_{34}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a triazinyl group, a biphenyl group, a terphenyl group, a phenyl group substituted with a $C_1$-$C_{20}$ alkyl group, and —$Si(Q_{31})(Q_{32})(Q_{33})$, $Q_{31}$ to $Q_{33}$ may each independently be selected from a $C_1$-$C_{10}$ alkyl group, a $C_1$-$C_{10}$ alkoxy group, a phenyl group, a naphthyl group, a pyridinyl group, a pyrimidinyl group, a triazinyl group, a biphenyl group, a terphenyl group, and a phenyl group substituted with a $C_1$-$C_{20}$ alkyl group, e2 may be an integer from 0 to 2, e3 may be an integer from 0 to 3, e4 may be an integer from 0 to 4, e6 may be an integer from 0 to 6, and indicates a binding site to a neighboring atom.

For example, the fluoro-containing cyclic group may be a group represented by Formula 4-3 or 4-9, and $Z_{31}$ may be hydrogen, but embodiments of the present disclosure are not limited thereto.

In one embodiment, in Formula 1, i) when at least one of $R_1$(s) in the number of b1 is the fluoro-containing cyclic group, at least one of $L_1$(s) in the number of a1 may be a single bond or a substituted or unsubstituted $C_3$-$C_{60}$ carbocyclic group, ii) when at least one of $R_2$(s) in the number of b2 is the fluoro-containing cyclic group, at least one of $L_2$(s) in the number of a2 may be a single bond or a substituted or unsubstituted $C_3$-$C_{60}$ carbocyclic group, iii) when at least one of $R_3$(s) in the number of b3 is the fluoro-containing cyclic group, at least one of $L_3$(s) in the number of a3 may be a single bond or a substituted or unsubstituted $C_3$-$C_{60}$ carbocyclic group, and the substituent of the substituted $C_3$-$C_{60}$ carbocyclic group may be selected from a $C_1$-$C_{60}$ alkyl group, a $C_2$-$C_{60}$ alkenyl group, a $C_2$-$C_{60}$ alkynyl group, and a $C_1$-$C_{60}$ alkoxy group.

For example, the substituted or unsubstituted $C_3$-$C_{60}$ carbocyclic group may be selected from:

a benzene group, a naphthalene group, and a fluorene group; and a benzene group and a fluorene group, each substituted with a $C_1$-$C_{20}$ alkyl group, but embodiments of the present disclosure are not limited thereto.

In one or more embodiments, in Formula 1, i) at least one of $R_1$(s) in the number of b1 may be the fluoro-containing cyclic group, and $R_2$(s) in the number of b2 and $R_3$(s) in the number of b3 may each independently be selected from: a phenyl group, a biphenyl group, a terphenyl group, a naphthyl group, and a pyridinyl group; and a triazinyl group substituted with one or more phenyl groups;

ii) at least one of $R_1$(s) in the number of b1 and at least one of $R_2$(s) in the number of b2 may each be a fluoro-containing cyclic group, and $R_3$(s) in the number of b3 may each independently be selected from: a phenyl group, a biphenyl group, a terphenyl group, a naphthyl group, a pyridinyl group, a fluorenyl group, an anthracenyl group, a phenanthrenyl group, a quinolinyl group, a phenanthrolinyl group, a triazinyl group, and a pyrimidinyl group; phenyl group, a biphenyl group, a terphenyl group, a naphthyl group, a pyridinyl group, a fluorenyl group, an anthracenyl group, a phenanthrenyl group, a quinolinyl group, a phenanthrolinyl group, a triazinyl group, and a pyrimidinyl group, each substituted with at least one selected from a cyano group, a $C_1$-$C_{20}$ alkyl group, a phenyl group, a biphenyl group, a terphenyl group, a naphthyl group, a pyridinyl group, a fluorenyl group, an anthracenyl group, a phenanthrenyl group, a triazinyl group, and a pyrimidinyl group; and —B($Q_1$)($Q_2$); or iii) at least one of $R_1$(s) in the number of b1, at least one of $R_2$(s) in the number of b2, and at least one of $R_3$(s) in the number of b3 may each be a fluoro-containing cyclic group, and $Q_1$ and $Q_2$ may each independently be a phenyl group substituted with one or more $C_1$-$C_{20}$ alkyl groups.

In one or more embodiments, i) when b1 is two or more and at least one of $R_1$(s) in the number of b1 is a fluoro-containing cyclic group, one or more $R_1$(s) that are not the fluoro-containing cyclic group are included between the fluoro-containing cyclic group and $L_1$, ii) when b2 is two or more and at least one of $R_2$(s) in the number of b2 is a fluoro-containing cyclic group, one or more $R_2$(s) that are not the fluoro-containing cyclic group may be included between the fluoro-containing cyclic group and $L_2$, and iii) when b3 is two or more and at least one of $R_3$(s) in the number of b3 is a fluoro-containing cyclic group, one or more $R_3$(s) that are not the fluoro-containing cyclic group may be included between the fluoro-containing cyclic group and $L_3$.

In one embodiment, $L_1$ to $L_3$ and $R_1$ to $R_3$ in Formula 1 may each not include a triazine group.

In one or more embodiments, the heterocyclic compound may include one to five fluoro groups.

In one embodiment, the heterocyclic compound may be selected from Compounds 1 to 90:

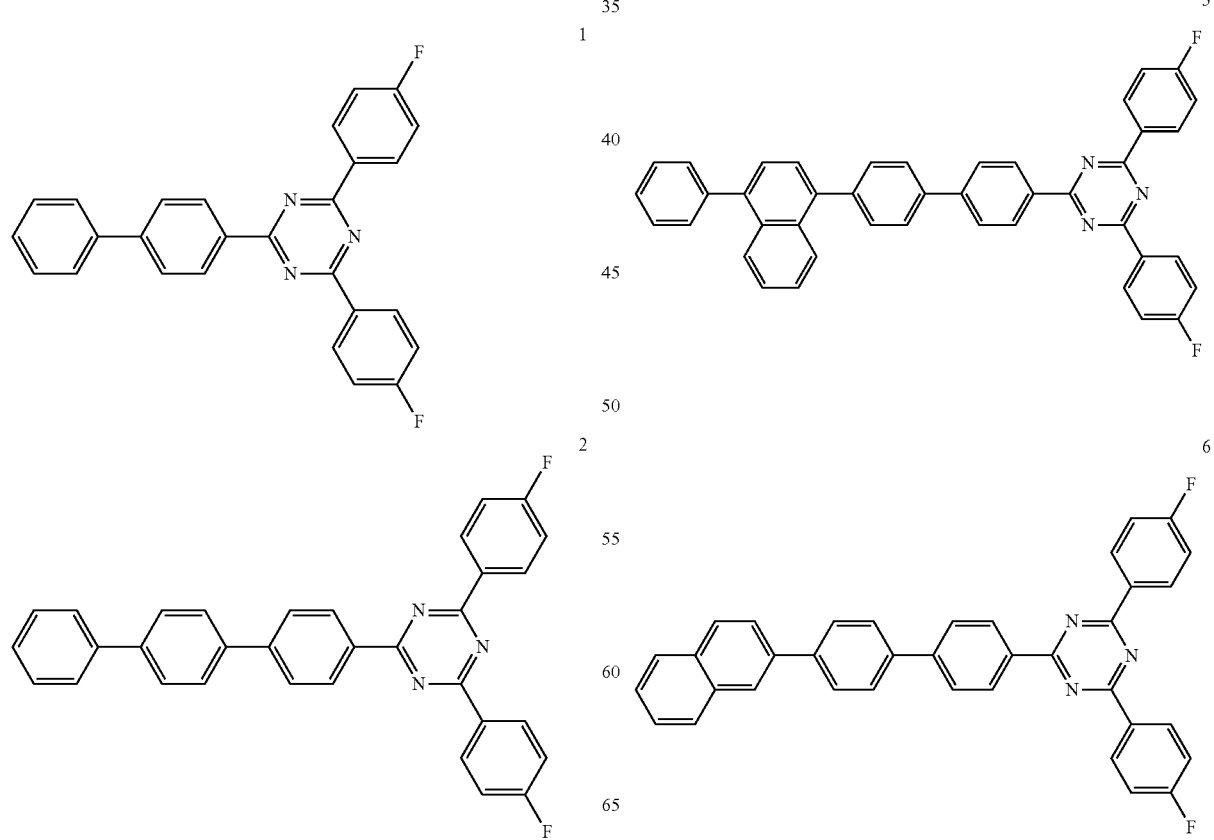

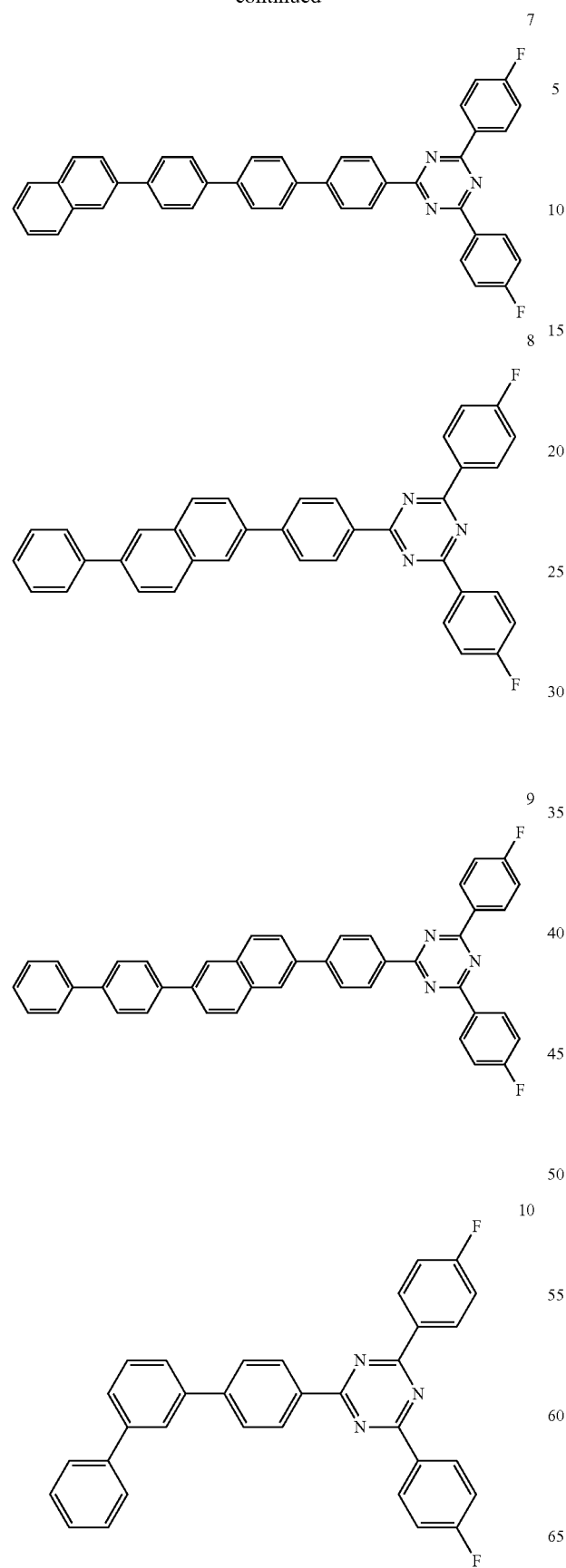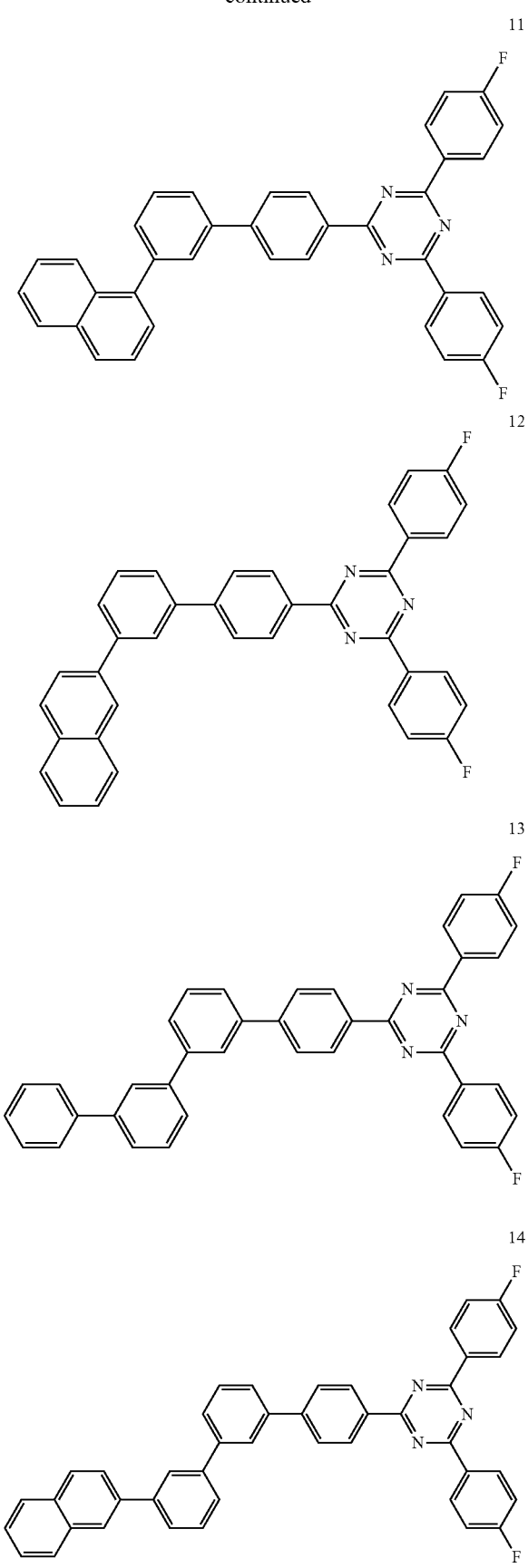

15
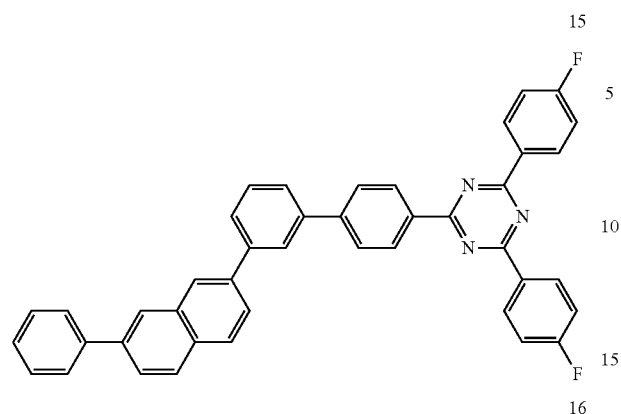
16
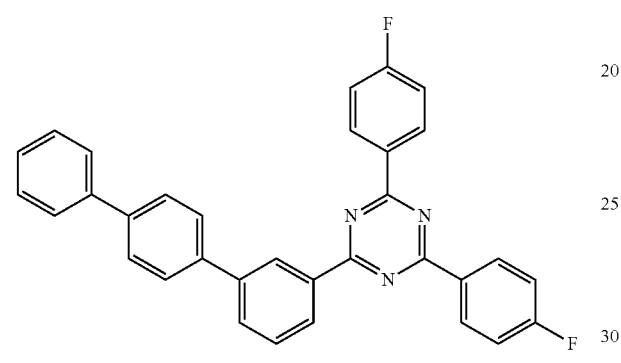
17
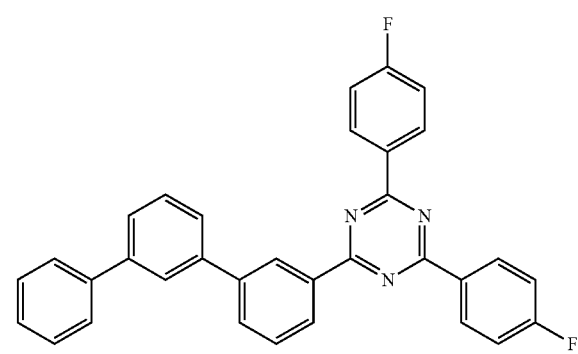
18
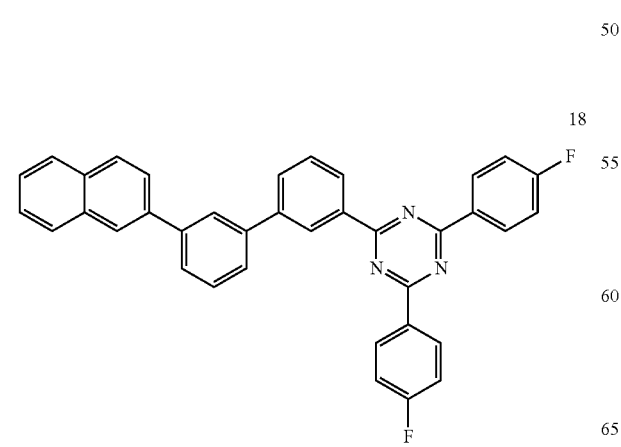
19
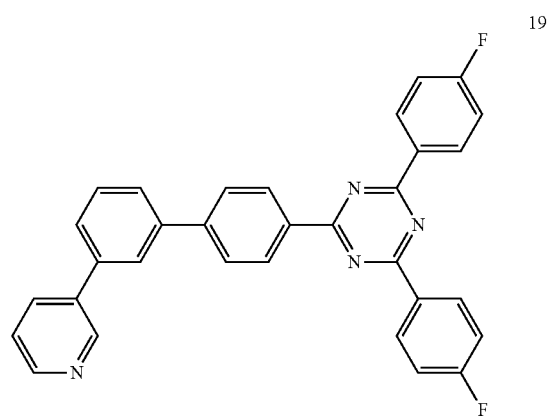
20
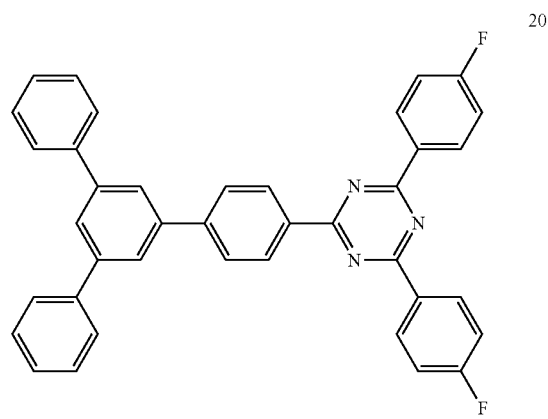
21
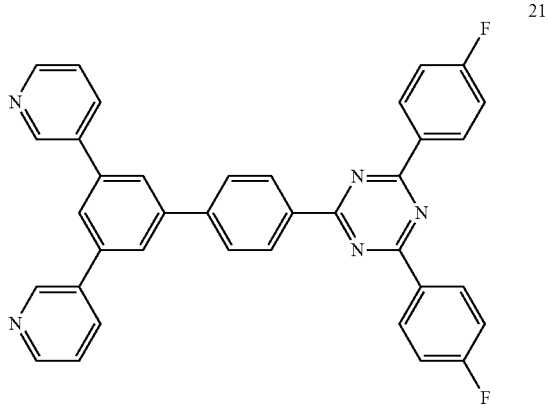
22
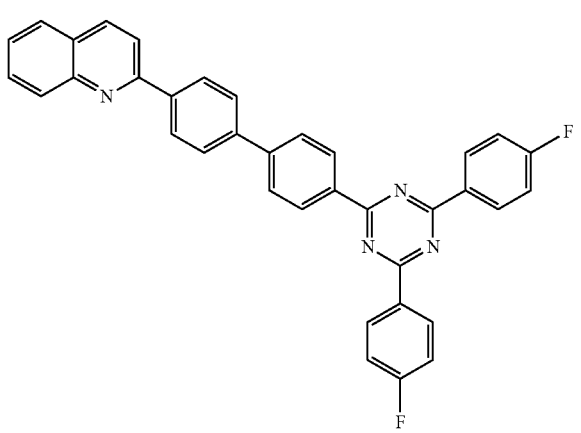

23
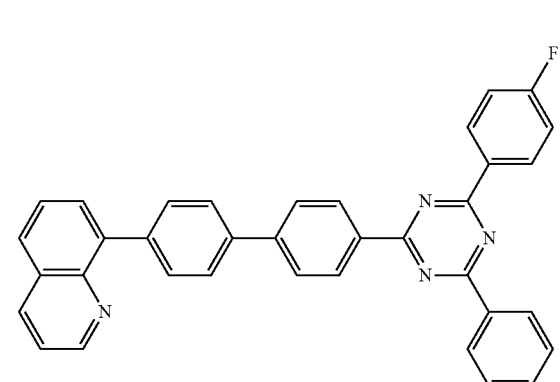
24
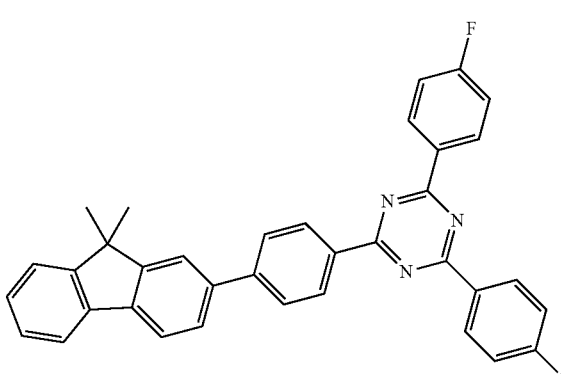
25
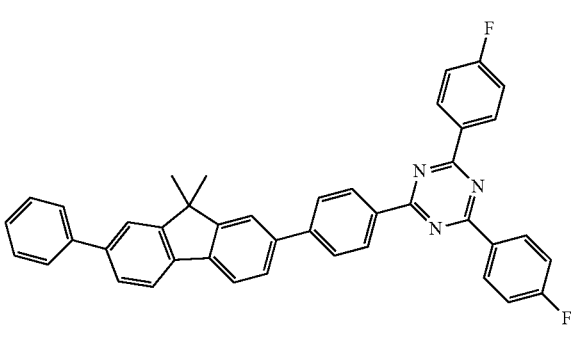
26
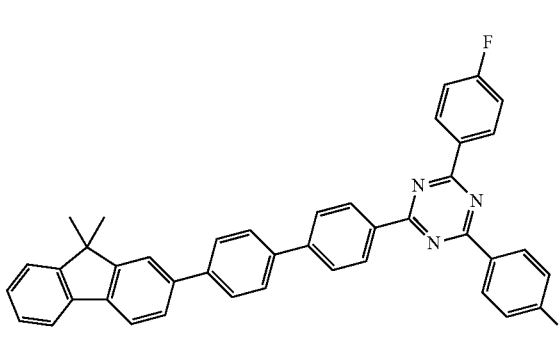
27
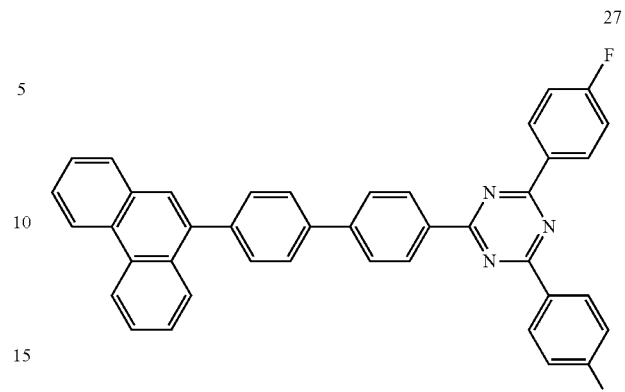
28
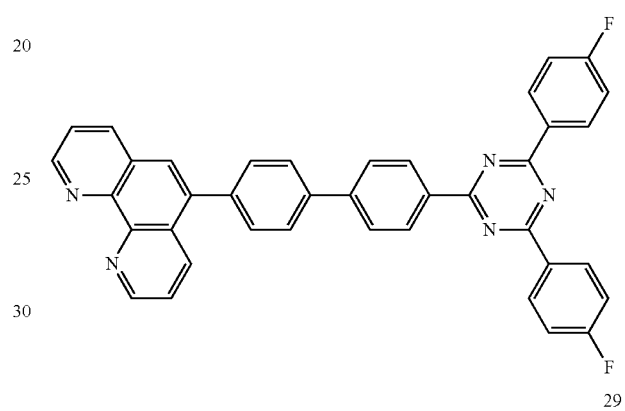
29
30
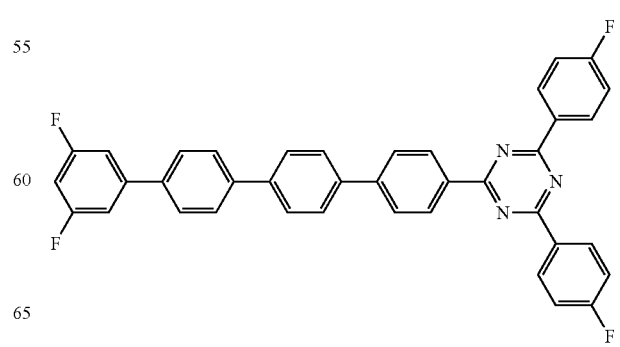

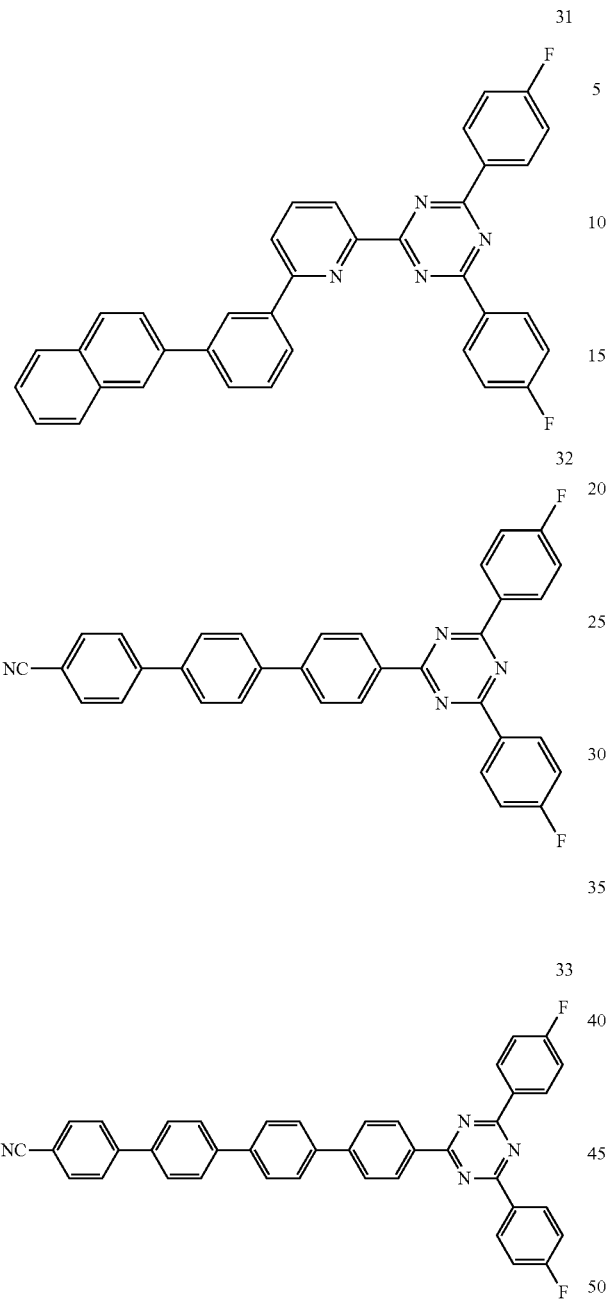
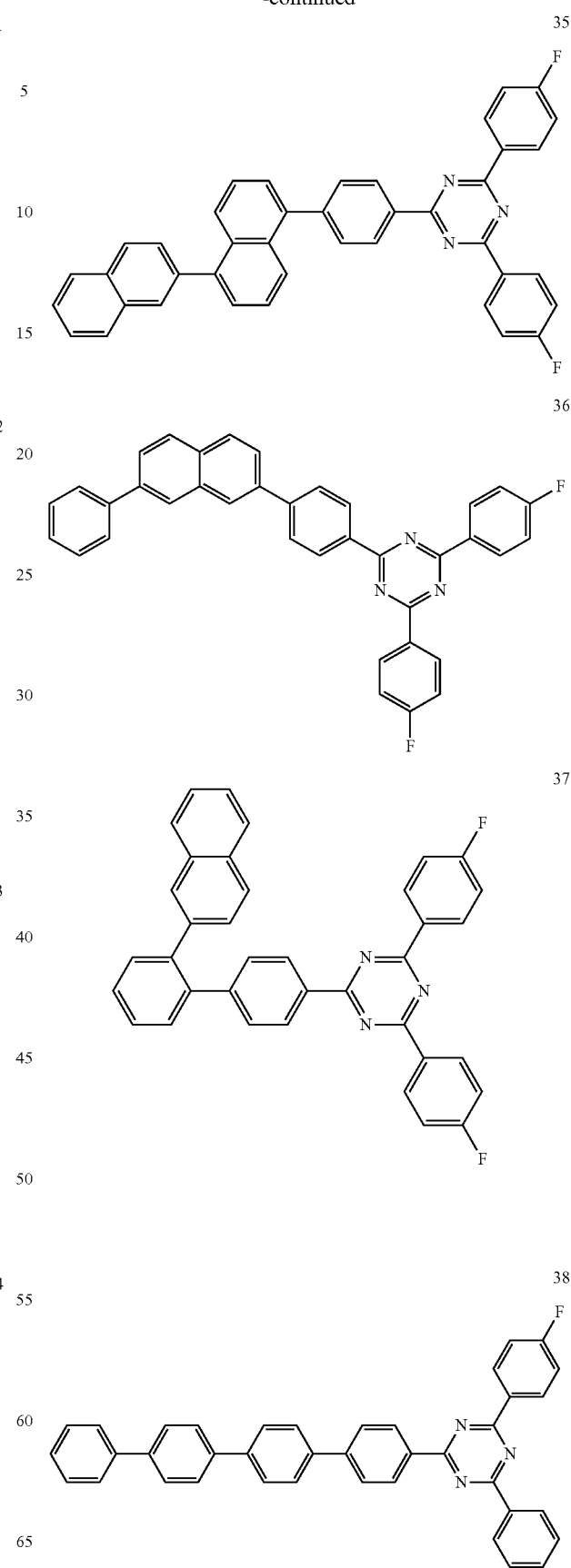

39
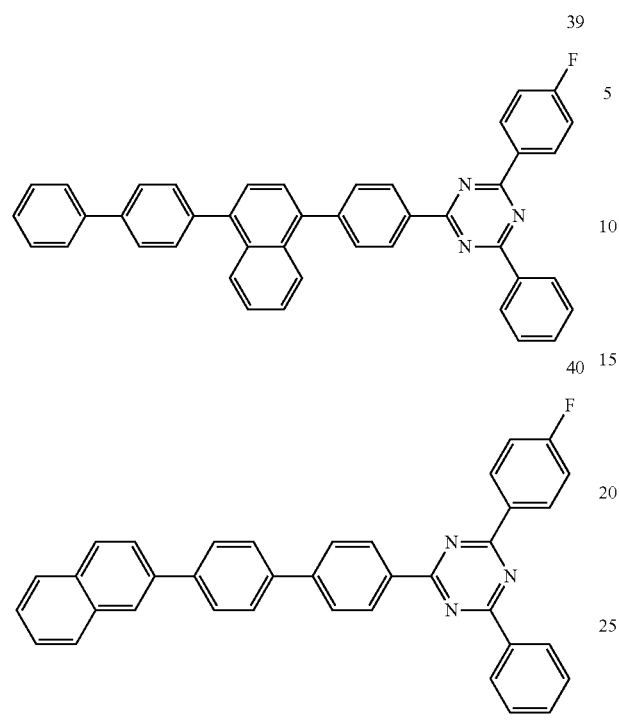
40
41
42
43
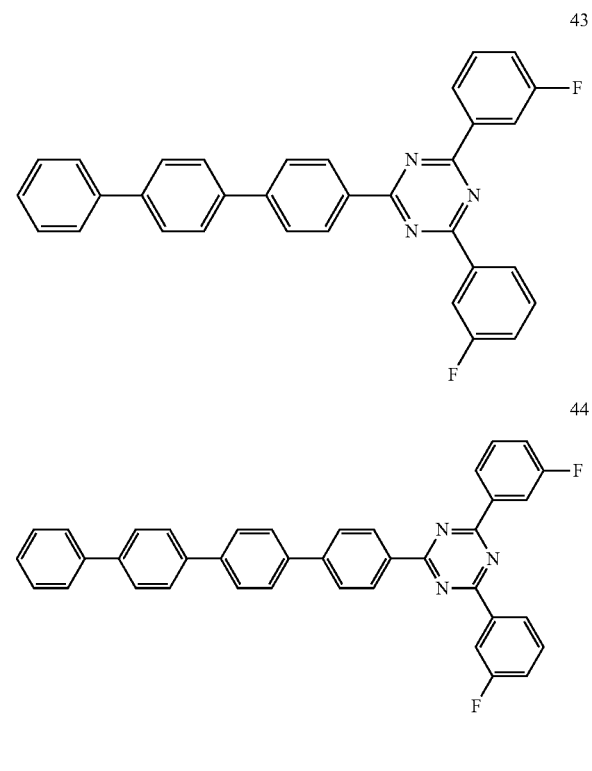
44
45
46
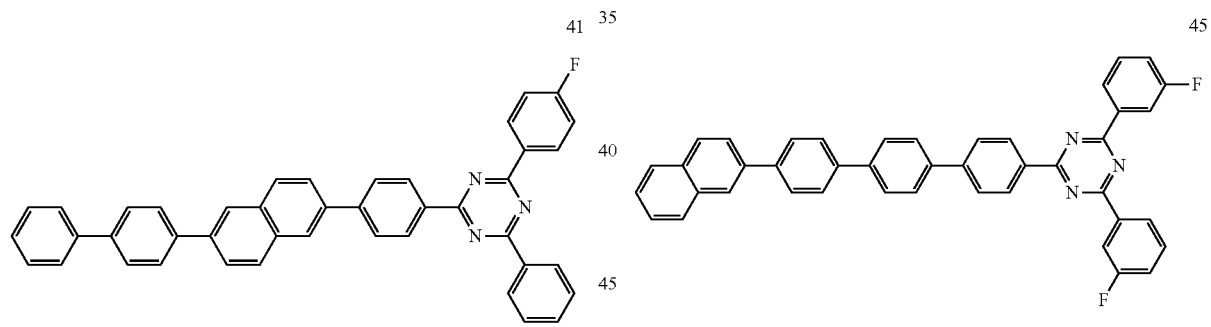
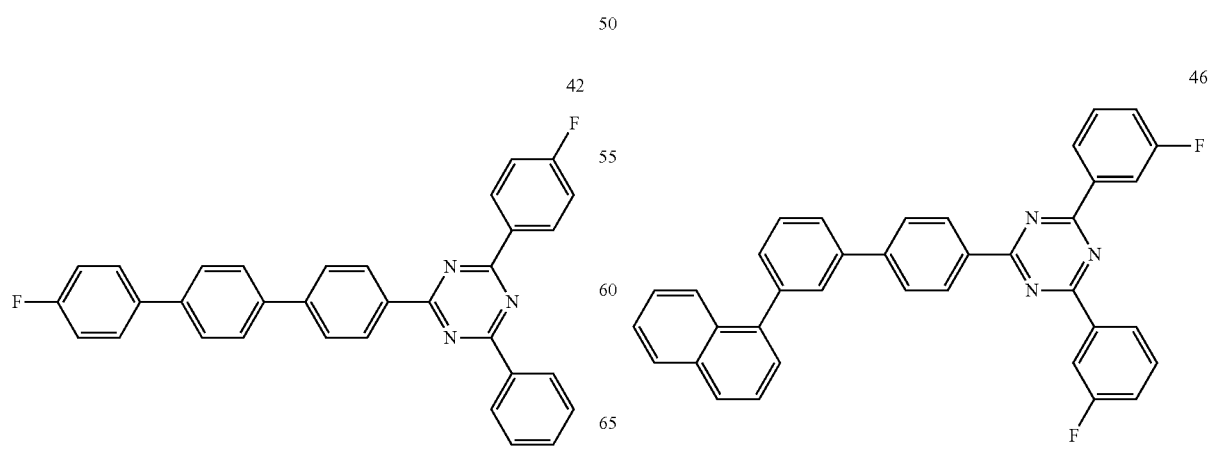

47
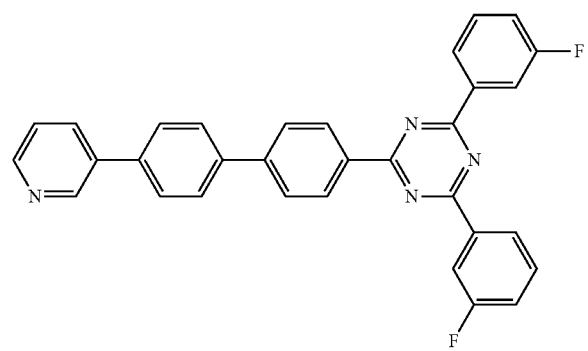
48
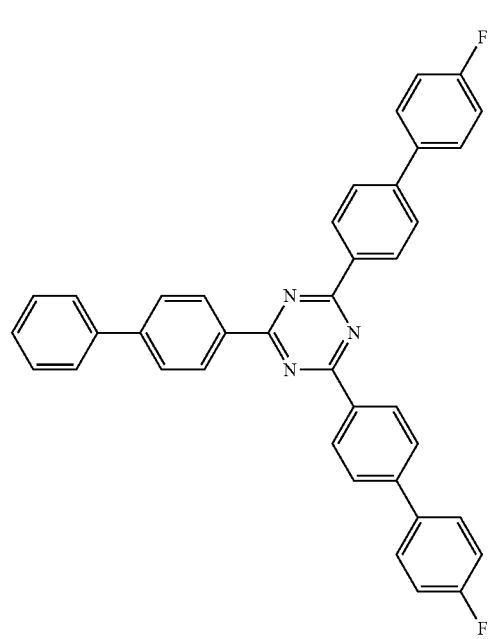
49
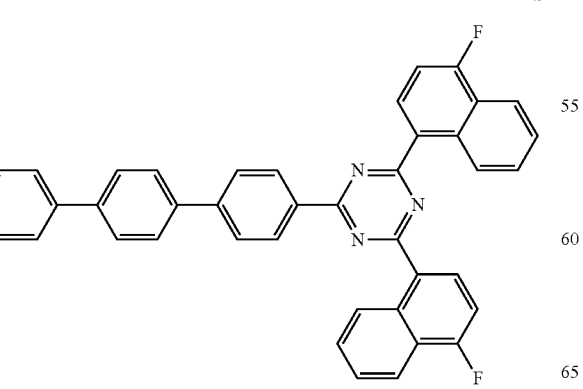
50
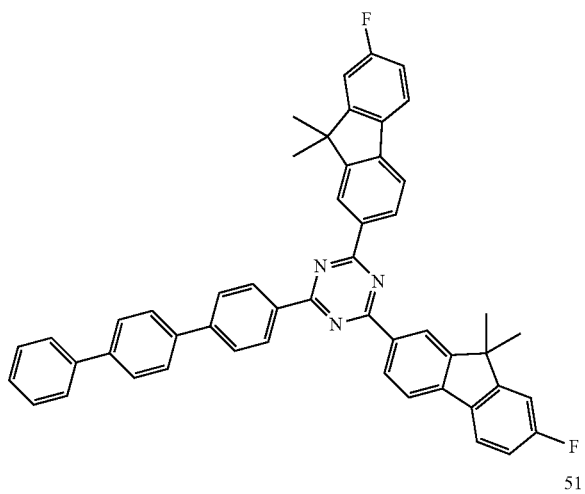
51
52
53

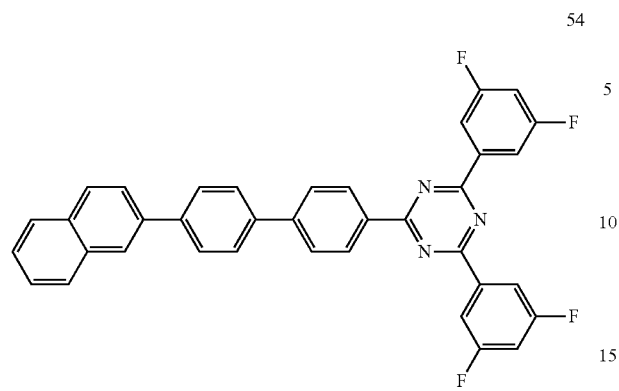
54
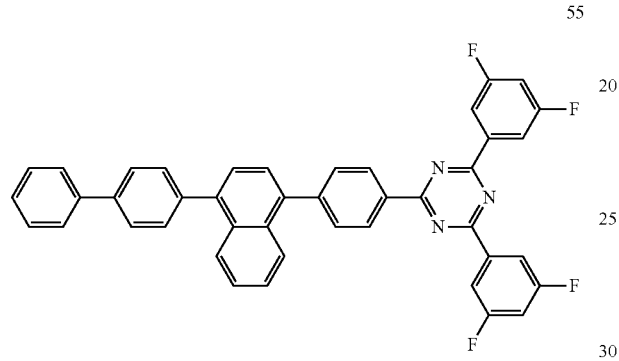
55
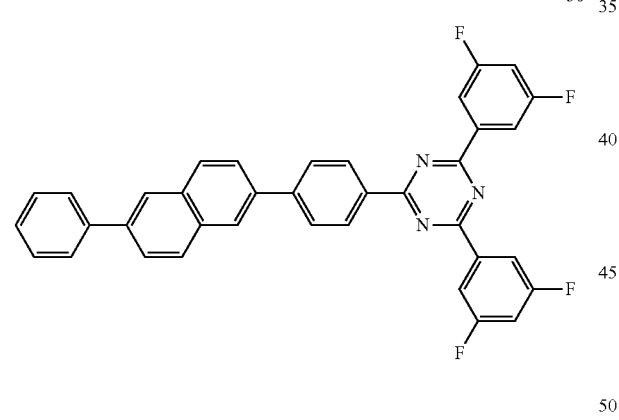
56
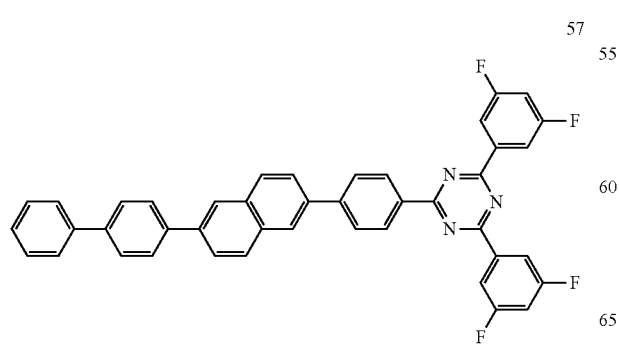
57
58
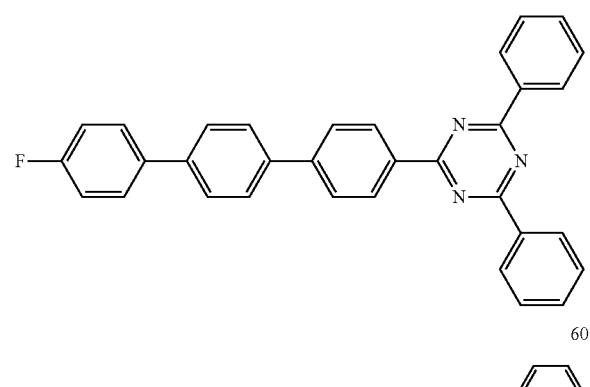
59
60
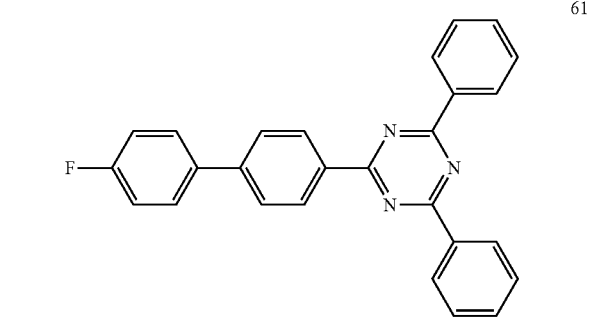
61
62

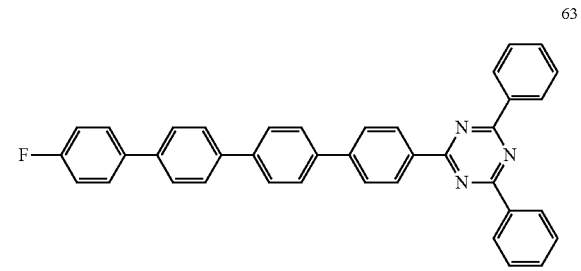
63
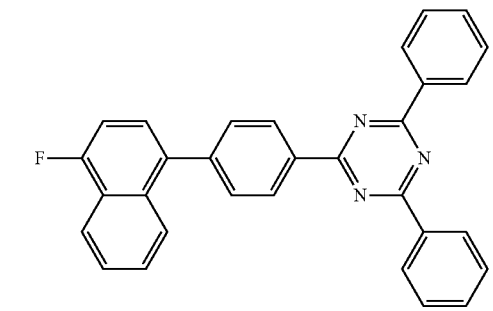
64
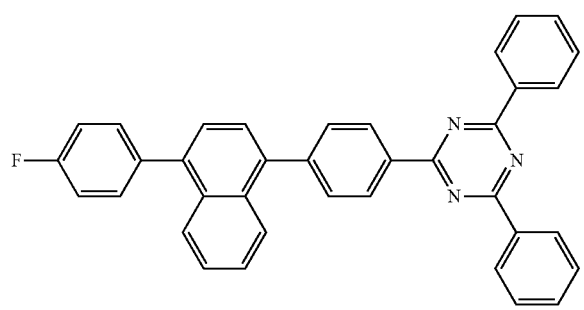
65
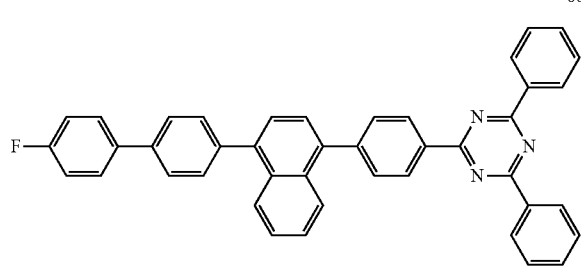
66
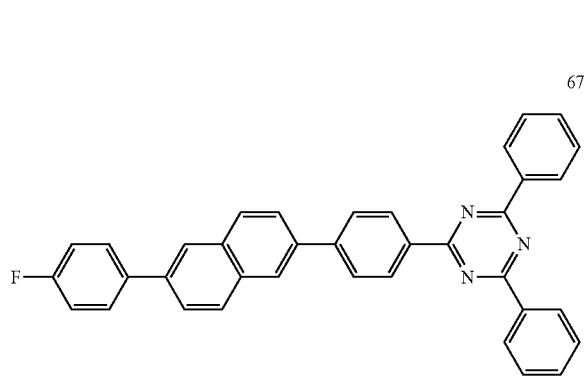
67
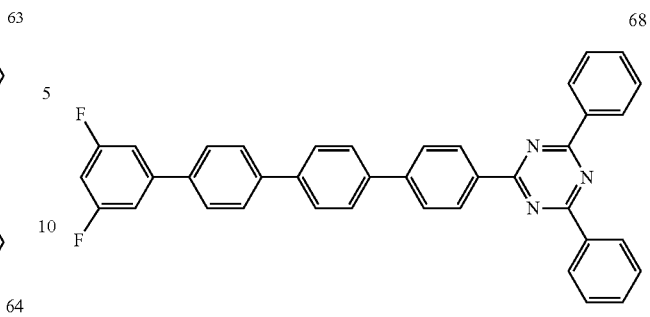
68
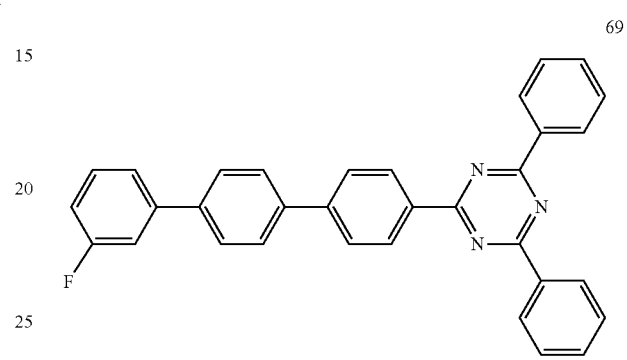
69
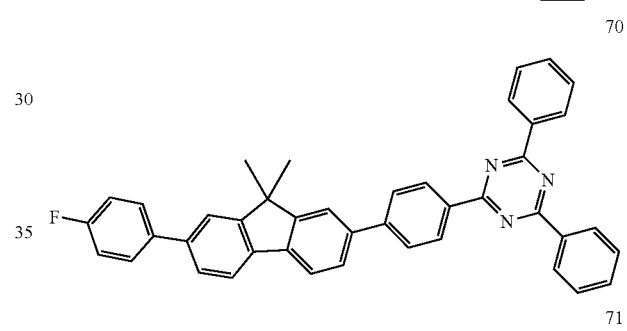
70
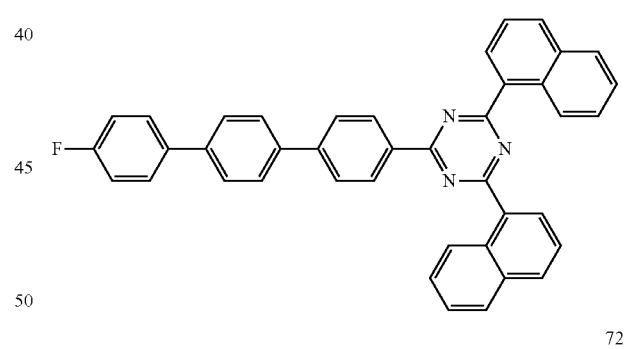
71
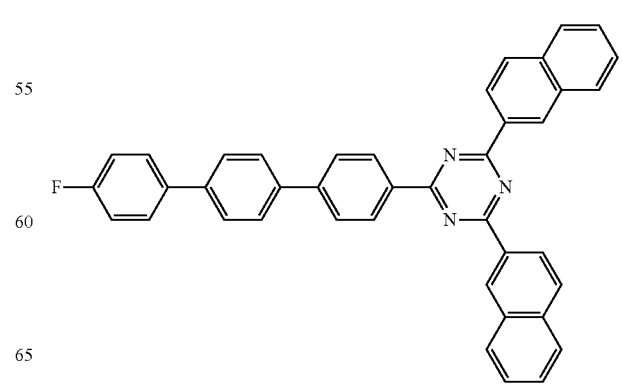
72

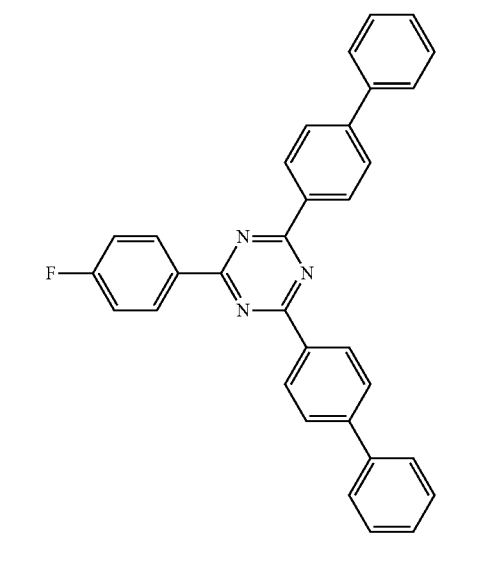
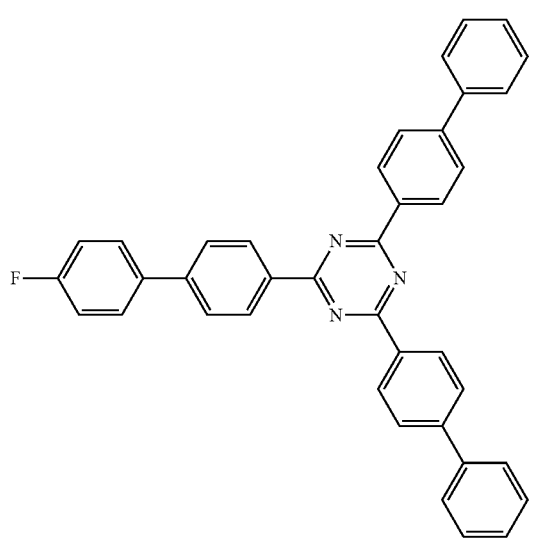
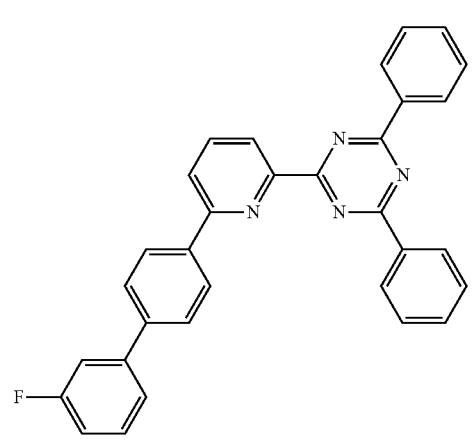
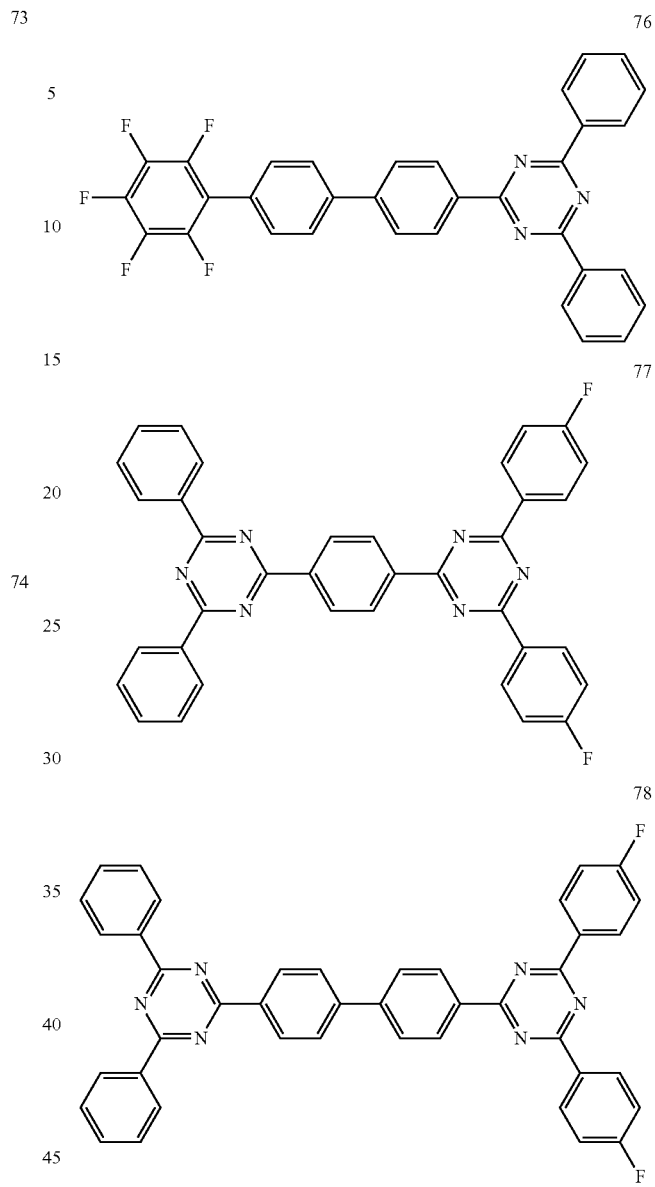

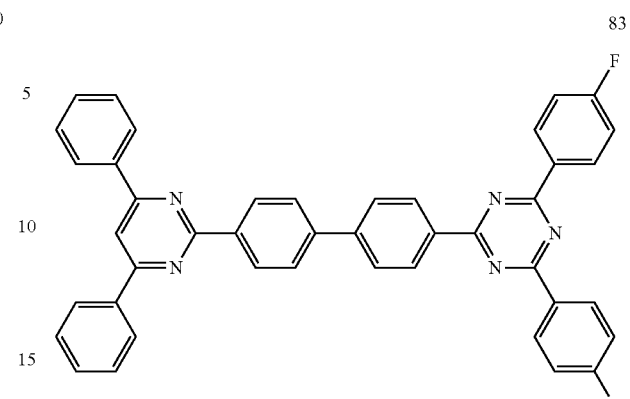
83
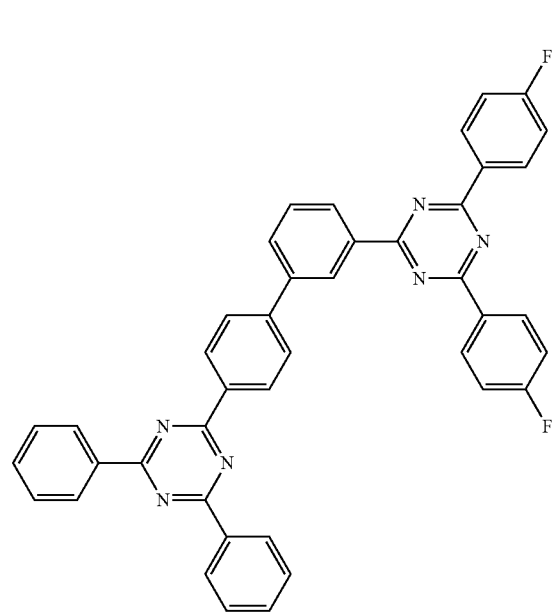
80
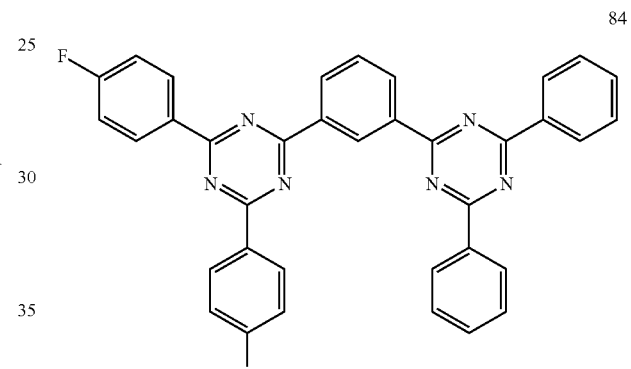
84
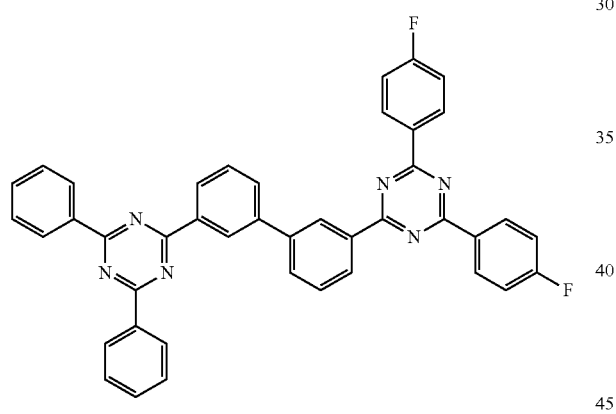
81
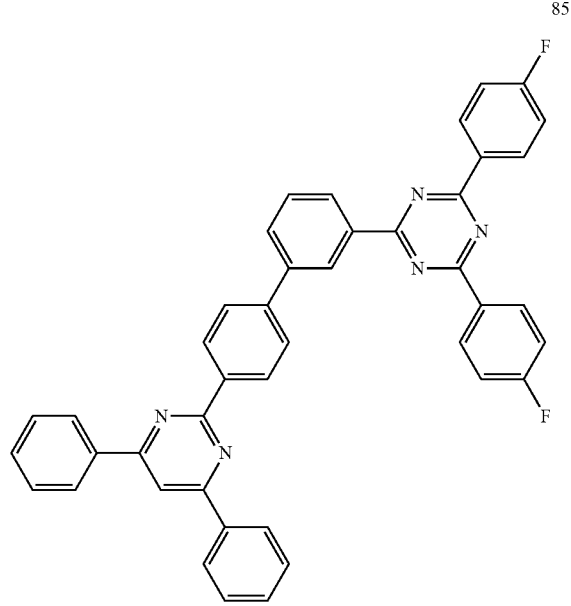
85
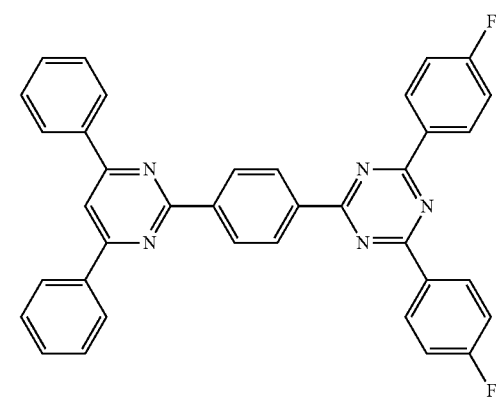
82

86

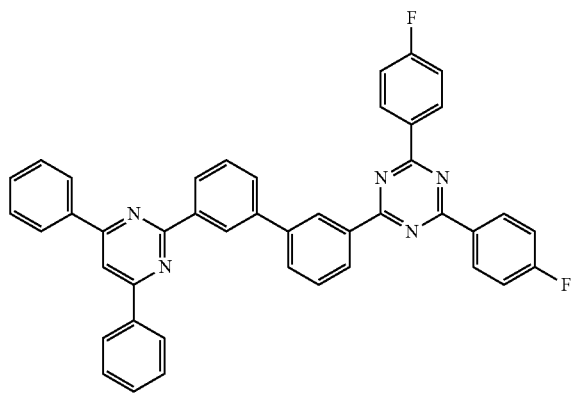

87

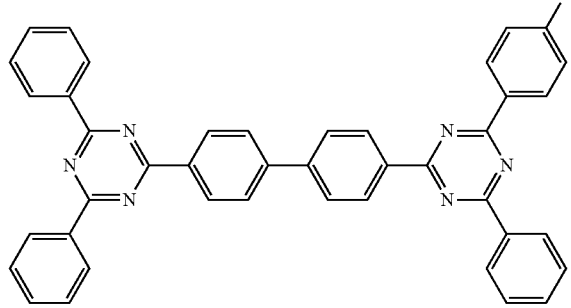

88

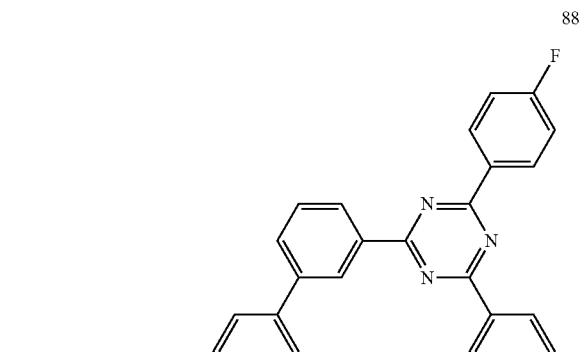

89

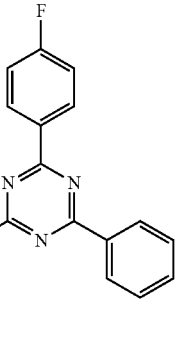

90

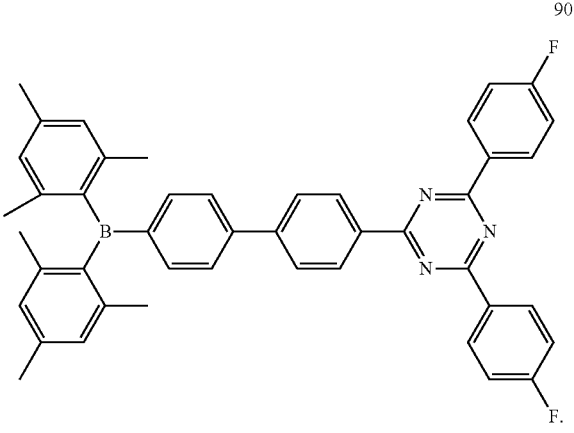

The heterocyclic compound includes the structure of Formula 1. While the present application is not limited by any particular mechanism or theory it is believed that since the heterocyclic compound includes at least one fluoro (fluorine) that is an element having high electronegativity, heterocyclic compound molecules form a strong dipole (e.g., each molecule of the heterocyclic compound may have a strong dipole moment). It is further believed, without limiting the present application, that as a result, an interfacial vacuum level is lowered by intermolecular interfacial dipole-dipole interaction (e.g., intermolecular interfacial dipole-dipole interaction between molecules of the heterocyclic compound), thereby facilitating electron injection. Also, it is believed that even in an electron transport layer (ETL), electron transport is facilitated by strong secondary bonding such as hydrogen bonding caused by unshared electrons of the fluoro element (fluorine), but the present application is not limited by any particular mechanism or theory.

Also, since the heterocyclic compound does not include another triazine group between a terminus including the fluoro-containing cyclic group and a triazine core, a molecular structure of the heterocyclic compound may be designed to be not symmetrical but asymmetrical. Accordingly, the molecules may have stronger polarity.

A synthesis method for the heterocyclic compound represented by Formula 1 would be apparent to those of ordinary skill in the art by referring to the following examples.

At least one of the heterocyclic compound of Formula 1 may be used between a pair of electrodes of an organic light-emitting device. For example, the heterocyclic compound may be included in at least one layer selected from a hole transport region, an electron transport region, and an emission layer. In one or more embodiments, the heterocyclic compound of Formula 1 may be used as a material for a capping layer located outside a pair of electrodes of an organic light-emitting device.

Accordingly, provided is an organic light-emitting device including: a first electrode; a second electrode facing the first electrode; and an organic layer between the first electrode and the second electrode and including an emission layer, wherein the organic layer includes at least one condensed cyclic compound.

The expression "(an organic layer) includes at least one heterocyclic compound," as used herein, may include a case in which "(an organic layer) includes identical compounds represented by Formula 1" and a case in which "(an organic layer) includes two or more different heterocyclic compounds."

In one embodiment, the first electrode is an anode, and the second electrode is a cathode, and the organic layer further a hole transport region between the first electrode and the emission layer and an electron transport region between the emission layer and the second electrode, and the hole transport region includes a hole injection layer, a hole transport layer, an emission auxiliary layer, an electron blocking layer, or any combination thereof, and the electron transport region includes a buffer layer, a hole blocking layer, an electron control layer, an electron transport layer, an electron injection layer, or any combination thereof.

In one embodiment, the electron transport region may include at least one of the heterocyclic compounds disclosed herein.

In one or more embodiments, the electron transport region may include an electron transport layer, and the electron transport layer may include the heterocyclic compound.

In one or more embodiments, the electron transport region may include an emission auxiliary layer, and the emission auxiliary layer may include the heterocyclic compound.

In one or more embodiments, the hole transport region may include a p-dopant, and the p-dopant may have a lowest unoccupied molecular orbital (LUMO) energy level of about −3.5 eV or less.

In one or more embodiments, the p-dopant may include a cyano group-containing compound.

The host in the emission layer may include at least one selected from an anthracene-based compound, a pyrene-based compound, and a spiro-bifluorene-based compound, but embodiments of the present disclosure are not limited thereto.

The dopant in the emission layer may include at least one selected from a styryl-based compound and an amine-based compound, but embodiments of the present disclosure are not limited thereto.

In the organic light-emitting device, the emission layer may be a first emission layer for emitting first color light, between the first electrode and second electrode, i) at least one second emission layer for emitting second color light may be further included, and ii) at least one second emission layer for emitting second color light and at least one third emission layer for emitting third color light may be further included, a maximum (e.g., an upper end) emission wavelength of the first color light, a maximum (e.g., an upper end) emission wavelength of the second color light, and a maximum (e.g., an upper end) emission wavelength of the third color light may be identical to or different from each other, and the first color light and the second color light may be emitted in the form of mixed light, or the first color light, the second color light, and the third color light may be emitted in the form of mixed light.

The organic light-emitting device may further include at least one selected from a first capping layer disposed in a pathway along which light generated in an emission layer proceeds toward the outside through the first electrode and a second capping layer disposed in a pathway along which light generated in an emission layer proceeds toward the outside through the second electrode, and the at least one selected from the first capping layer and the second capping layer may include at least one heterocyclic compound represented by Formula 1.

For example, the organic light-emitting device may have i) a stacked structure including a first electrode, an organic layer, a second electrode, and a second capping layer which are sequentially stacked in this stated order, ii) a stacked structure including a first capping layer, a first electrode, an organic layer, and a second electrode which are sequentially stacked in this stated order, or iii) a stacked structure including a first capping layer, a first electrode, an organic layer, a second electrode, and a second capping layer which are sequentially stacked in this stated order, and at least one selected from the first capping layer and the second capping layer may include the heterocyclic compound.

The term "organic layer," as used herein, refers to a single layer and/or a plurality of layers disposed between the first electrode and the second electrode of the organic light-emitting device. A material included in the "organic layer" is not limited to an organic material.

Description of FIG. 1

Figure 1:
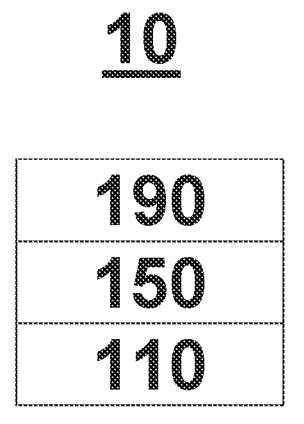

FIG. 1 is a schematic view of an organic light-emitting device 10 according to an embodiment. The organic light-emitting device 10 includes a first electrode 110, an organic layer 150, and a second electrode 190.

Hereinafter, the structure of the organic light-emitting device 10 according to an embodiment and a method of manufacturing the organic light-emitting device 10 will be described in connection with FIG. 1.

[First Electrode 110]

In FIG. 1, a substrate may be additionally disposed under the first electrode 110 or above the second electrode 190. The substrate may be a glass substrate or a plastic substrate, each having excellent mechanical strength, thermal stability, transparency, surface smoothness, ease of handling, and water resistance.

The first electrode 110 may be formed by depositing or sputtering a material for forming the first electrode 110 on the substrate. When the first electrode 110 is an anode, the material for a first electrode may be selected from materials having a high work function to facilitate hole injection.

The first electrode 110 may be a reflective electrode, a semi-transmissive electrode, or a transmissive electrode. When the first electrode 110 is a transmissive electrode, a material for forming a first electrode may be selected from indium tin oxide (ITO), indium zinc oxide (IZO), tin oxide (SnO$_2$), zinc oxide (ZnO), and any combinations thereof, but embodiments of the present disclosure are not limited thereto. In one or more embodiments, when the first electrode 110 is a semi-transmissive electrode or a reflectable (reflective) electrode, a material for forming a first electrode may be selected from magnesium (Mg), silver (Ag), aluminum (Al), aluminum-lithium (Al—Li), calcium (Ca), magnesium-indium (Mg—In), magnesium-silver (Mg—Ag), and any combinations thereof, but embodiments of the present disclosure are not limited thereto.

The first electrode 110 may have a single-layered structure, or a multi-layered structure including two or more layers. For example, the first electrode 110 may have a three-layered structure of ITO/Ag/ITO, but the structure of the first electrode 110 is not limited thereto.

[Organic Layer 150]

The organic layer 150 is disposed on the first electrode 110. The organic layer 150 may include an emission layer.

The organic layer 150 may further include a hole transport region between the first electrode 110 and the emission layer, and an electron transport region between the emission layer and the second electrode 190.

[Hole Transport Region in Organic Layer 150]

The hole transport region may have i) a single-layered structure including a single layer including a single material, ii) a single-layered structure including a single layer including a plurality of different materials, or iii) a multi-layered structure having a plurality of layers including a plurality of different materials.

The hole transport region may include at least one layer selected from a hole injection layer, a hole transport layer, an emission auxiliary layer, and an electron blocking layer.

For example, the hole transport region may have a single-layered structure including a single layer including a plurality of different materials, or a multi-layered structure having a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/electron blocking layer structure, wherein for each structure, constituting layers are sequentially stacked from the first electrode 110 in this stated order, but the structure of the hole transport region is not limited thereto.

The hole transport region may include at least one selected from m-MTDATA, TDATA, 2-TNATA, NPB (NPD), β-NPB, TPD, Spiro-TPD, Spiro-NPB, methylated-NPB, TAPC, HMTPD, 4,4',4"-tris(N-carbazolyl)triphenylamine (TCTA), polyaniline/dodecylbenzenesulfonic acid (PANI/DBSA), poly(3,4-ethylenedioxythiophene)/poly (4-styrenesulfonate) (PEDOT/PSS), polyaniline/camphor sulfonic acid (PANI/CSA), polyaniline/poly(4-styrene-sulfonate) (PANI/PSS), a compound represented by Formula 201, and a compound represented by Formula 202:

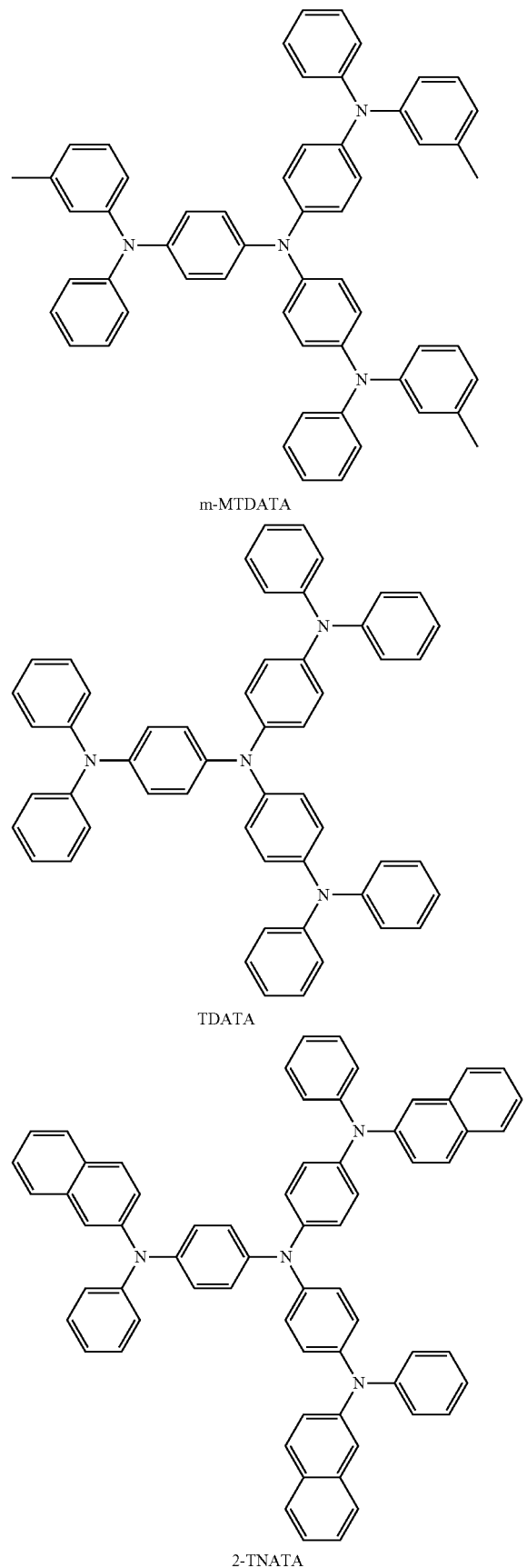

m-MTDATA

TDATA

2-TNATA

-continued

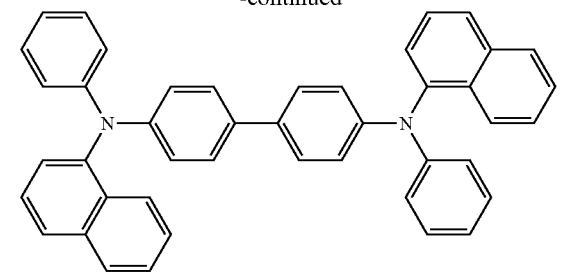

NPB

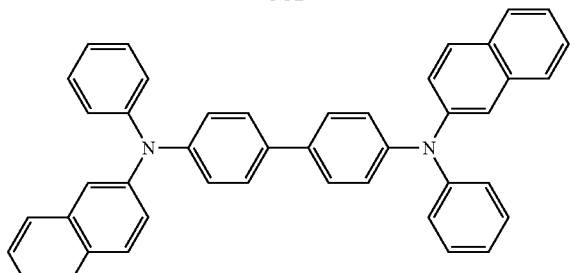

β-NPB

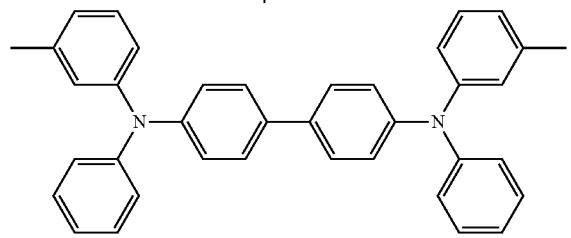

TPD

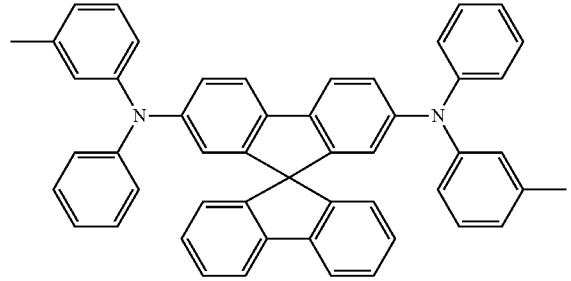

Spiro-TPD

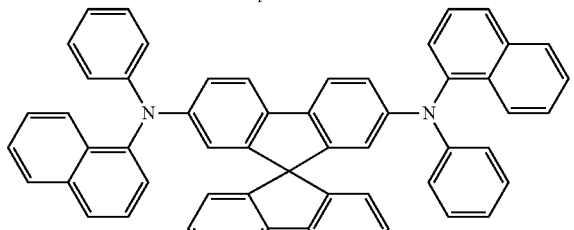

Spiro-NPB

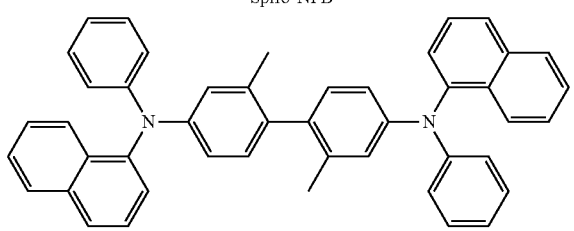

methylated NPB

-continued

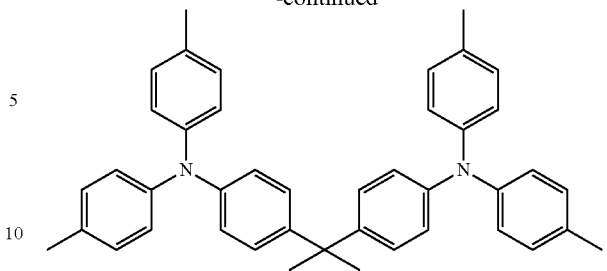

TAPC

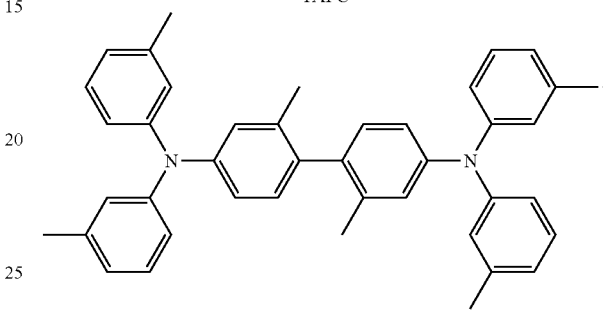

HMTPD

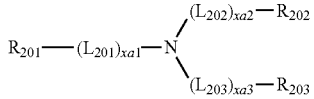

Formula 201

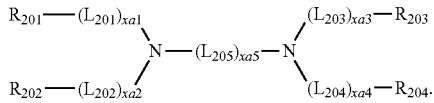

Formula 202

In Formulae 201 and 202, $L_{201}$ to $L_{204}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, $L_{205}$ may be selected from *—O—*', *—S—*', *—N($Q_{201}$)-*', a substituted or unsubstituted $C_1$-$C_{20}$ alkylene group, a substituted or unsubstituted $C_2$-$C_{20}$ alkenylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xa1 to xa4 may each independently be an integer from 0 to 3, xa5 may be an integer from 1 to 10, and $R_{201}$ to $R_{204}$ and $Q_{201}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

For example, in Formula 202, $R_{201}$ and $R_{202}$ may optionally be linked via a single bond, a dimethyl-methylene group, or a diphenyl-methylene group, and $R_{203}$ and $R_{204}$ may optionally be linked via a single bond, a dimethyl-methylene group, or a diphenyl-methylene group.

In one embodiment, in Formulae 201 and 202, $L_{201}$ to $L_{205}$ may each independently be selected from:

a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one or more embodiments, xa1 to xa4 may each independently be 0, 1, or 2.

In one or more embodiments, xa5 may be 1, 2, 3, or 4.

In one or more embodiments, $R_{201}$ to $R_{204}$ and $Q_{201}$ may each independently be selected from:

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), and $Q_{31}$ to $Q_{33}$ are the same as described elsewhere herein.

In one or more embodiments, at least one selected from $R_{201}$ to $R_{203}$ in Formula 201 may independently be selected from:

a fluorenyl group, a spiro-bifluorenyl group, a carbazolyl group, a dibenzofuranyl group, and a dibenzothiophenyl group; and a fluorenyl group, a spiro-bifluorenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group, but embodiments of the present disclosure are not limited thereto.

In one or more embodiments, in Formula 202, i) $R_{201}$ and $R_{202}$ may be linked via a single bond, and/or ii) $R_{203}$ and $R_{204}$ may be linked via a single bond.

In one or more embodiments, at least one selected from $R_{201}$ to $R_{204}$ in Formula 202 may each independently be selected from:

a carbazolyl group; and a carbazolyl group substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group, but embodiments of the present disclosure are not limited thereto.

The compound represented by Formula 201 may be represented by Formula 201A:

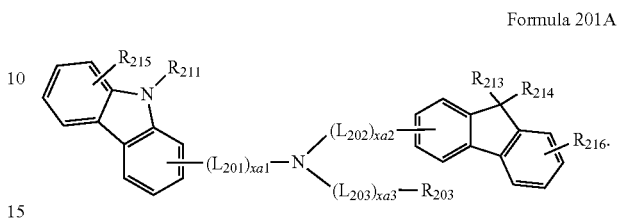

Formula 201A

In one embodiment, the compound represented by Formula 201 may be represented by Formula 201A(1) below, but embodiments of the present disclosure are not limited thereto:

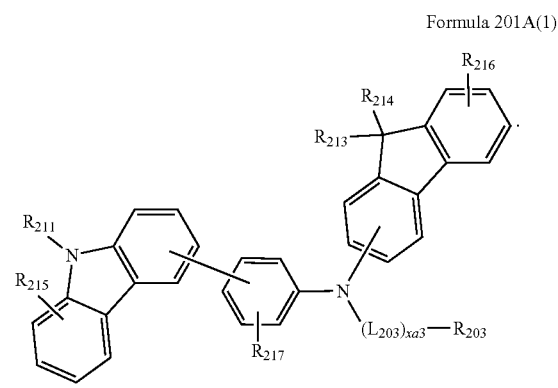

Formula 201A(1)

In one embodiment, the compound represented by Formula 201 may be represented by Formula 201A-1 below, but embodiments of the present disclosure are not limited thereto:

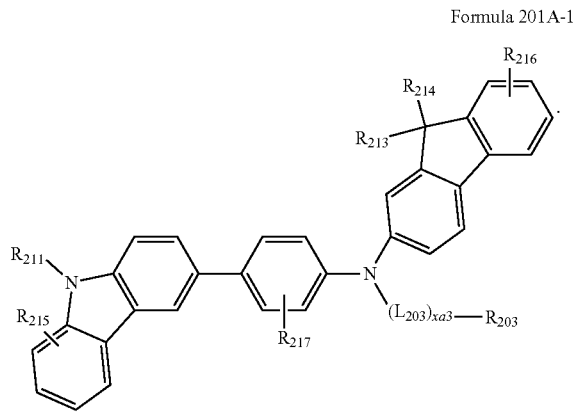

Formula 201A-1

In one embodiment, the compound represented by Formula 202 may be represented by Formula 202A:

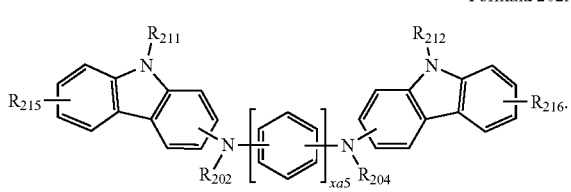

Formula 202A

In one embodiment, the compound represented by Formula 202 may be represented by Formula 202A-1:

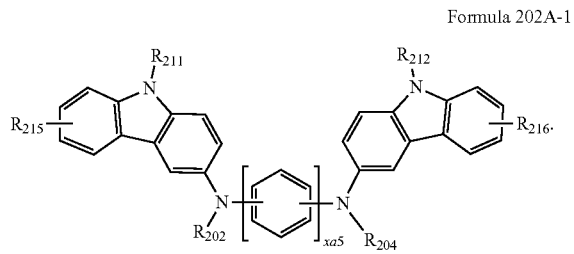

Formula 202A-1

In Formulae 201A, 201A(1), 201A-1, 202A, and 202A-1, $L_{201}$ to $L_{203}$, xa1 to xa3, xa5, and $R_{202}$ to $R_{204}$ are the same as described above, $R_{211}$ and $R_{212}$ may be understood by referring to the description provided herein in connection with $R_{203}$, and $R_{213}$ to $R_{217}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

The hole transport region may include at least one compound selected from Compounds HT1 to HT39, but embodiments of the present disclosure are not limited thereto:

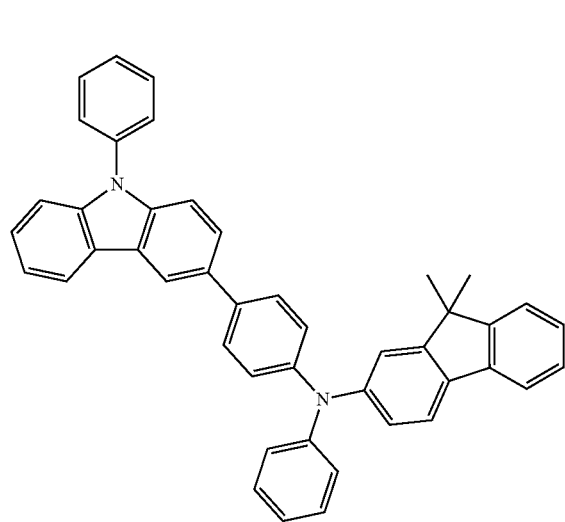

HT1

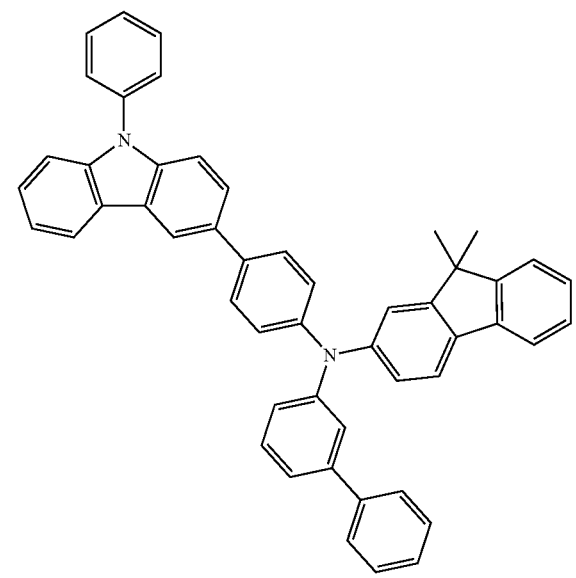

HT2

-continued
HT3
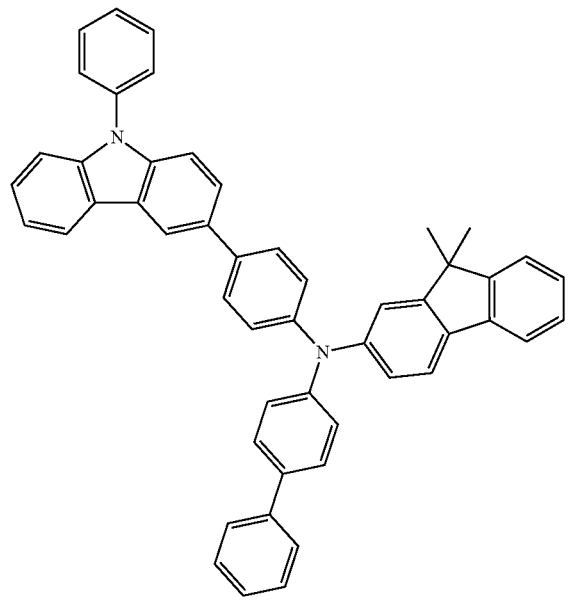
HT4
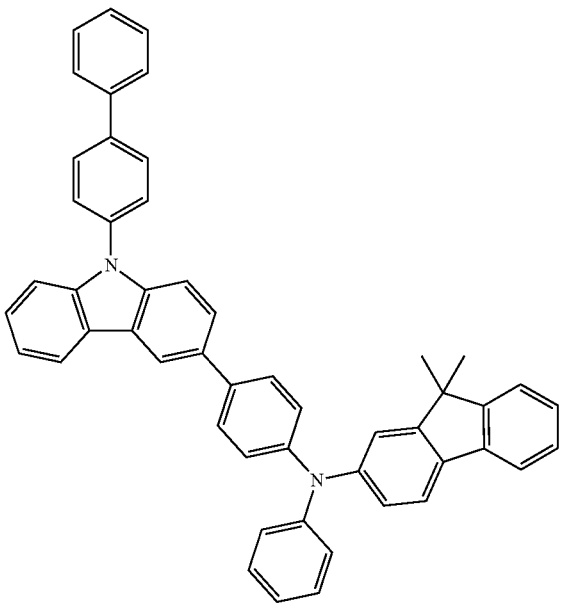
HT5
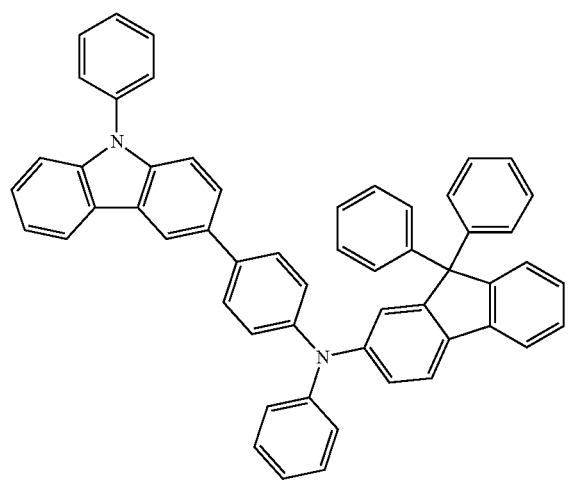
HT6
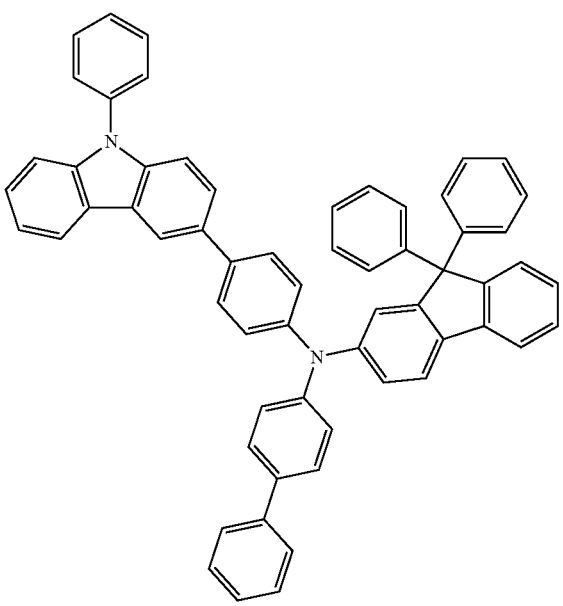

-continued
HT7
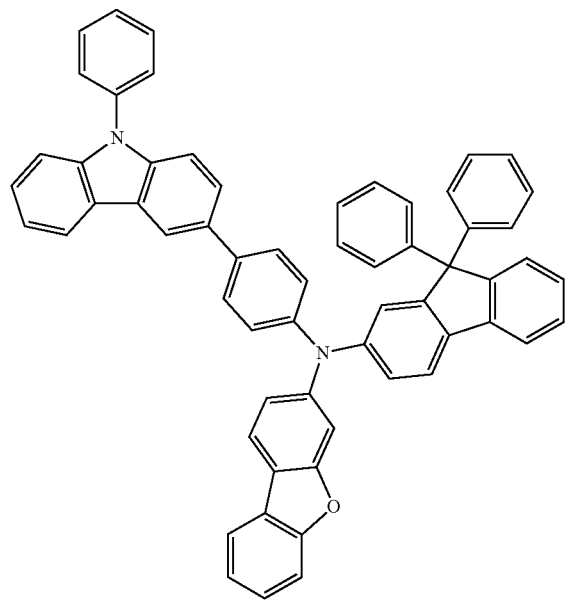
HT8
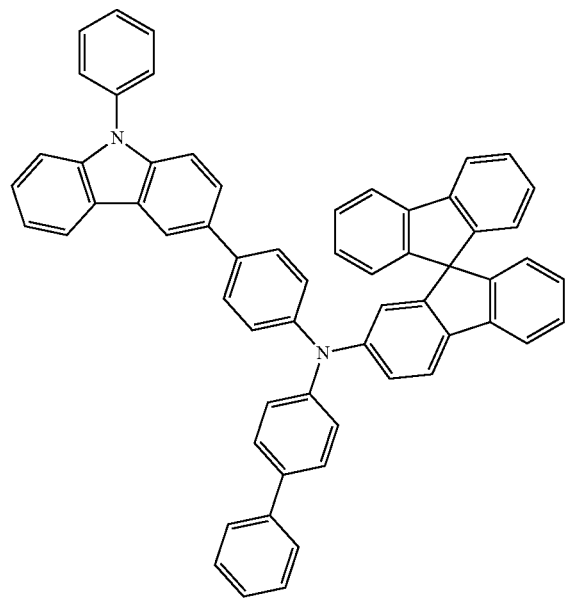
HT9
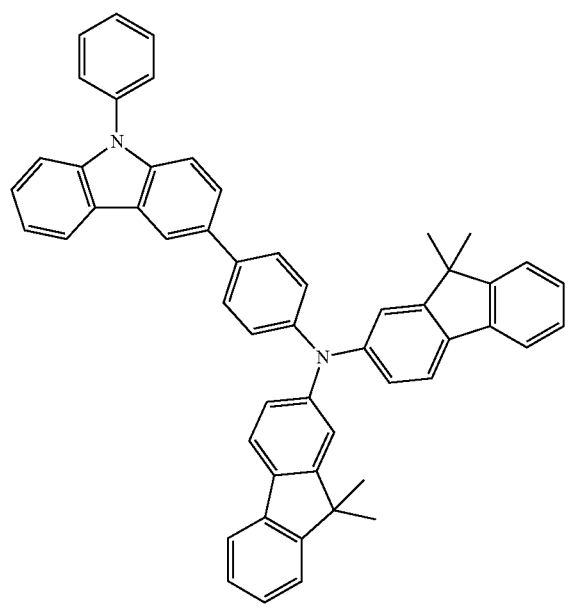
HT10
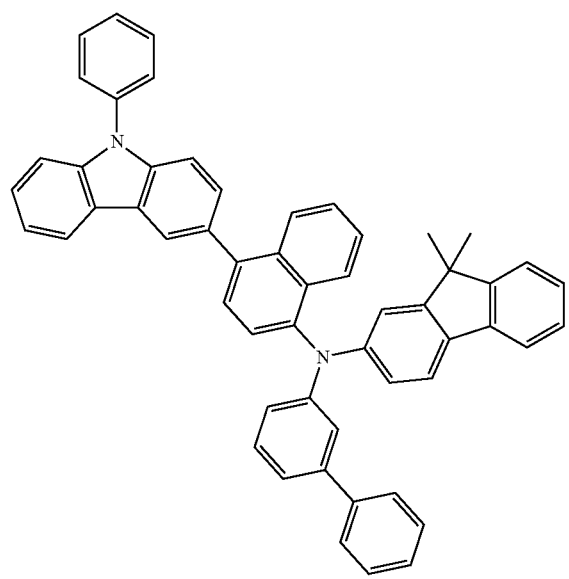

-continued
HT11
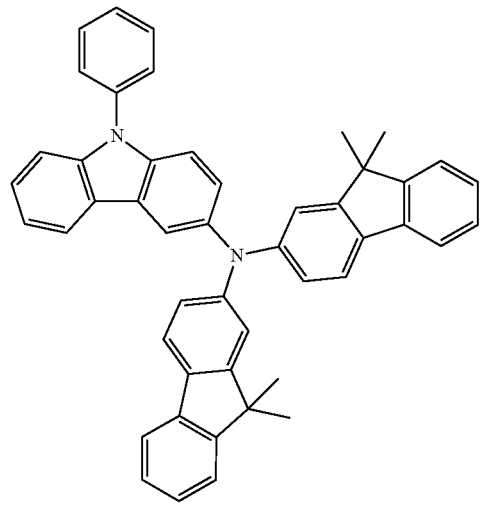
HT12
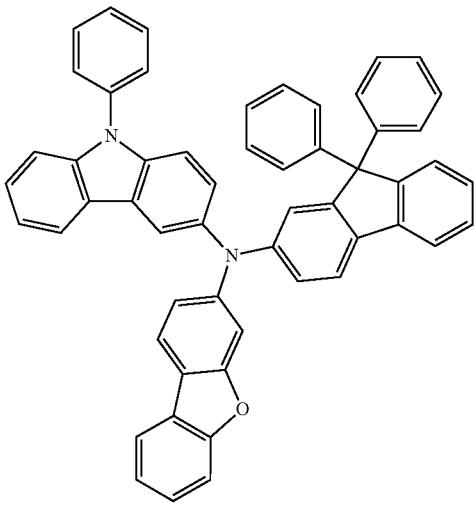
HT13
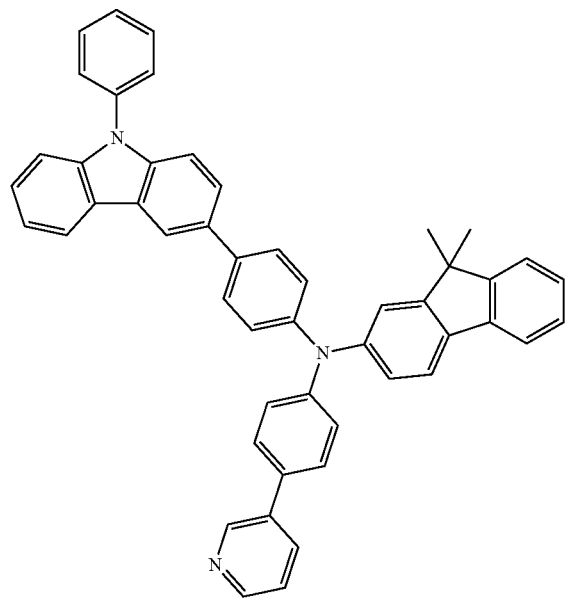
HT14
HT15
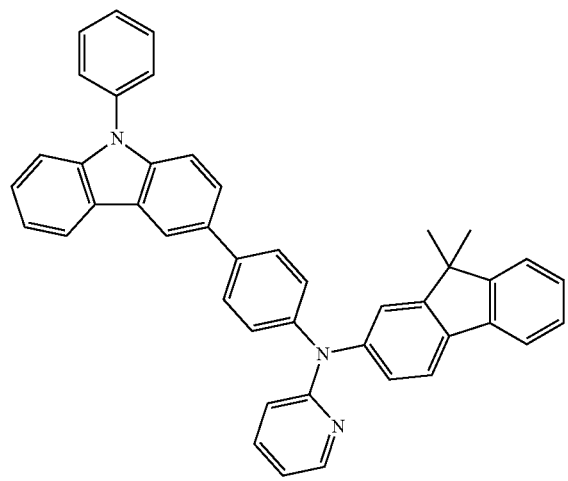
HT16
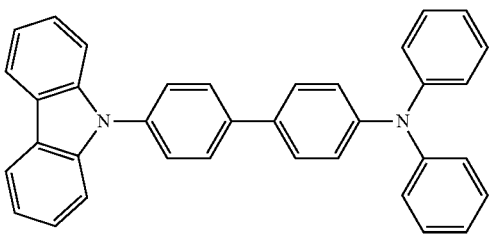

-continued
HT17
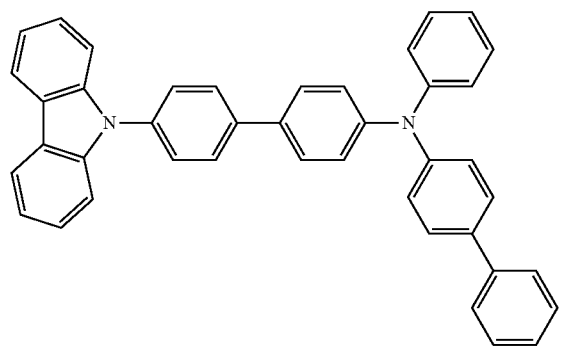
HT18
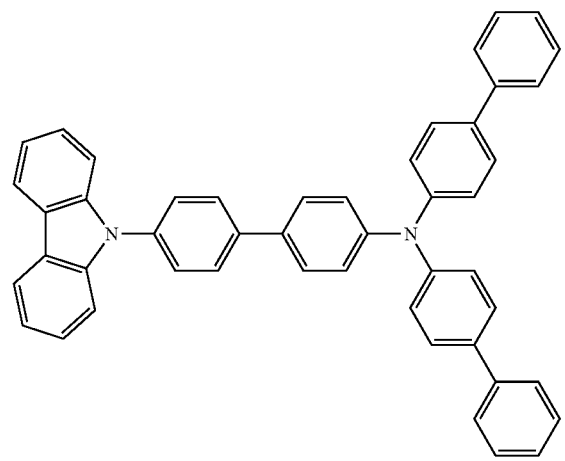
HT19
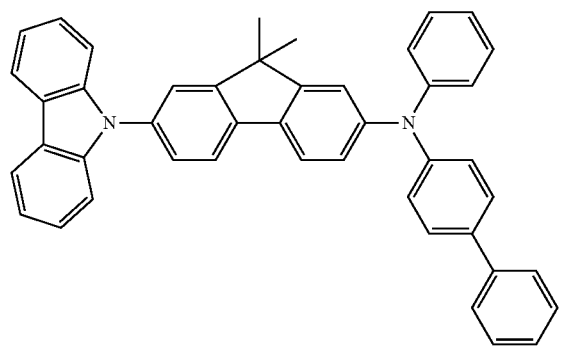
HT20
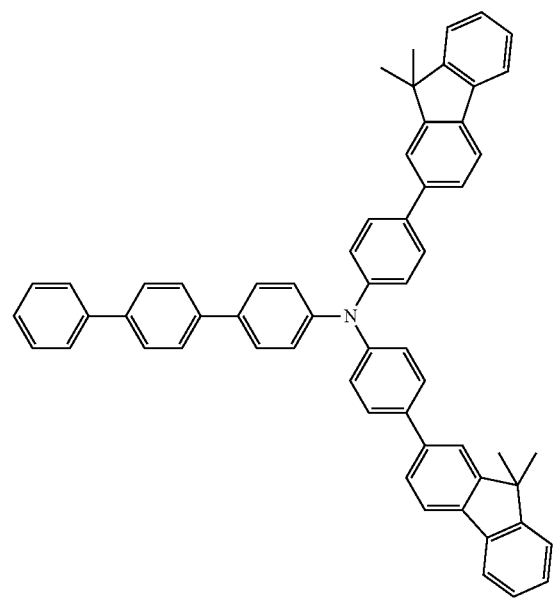

-continued
HT21
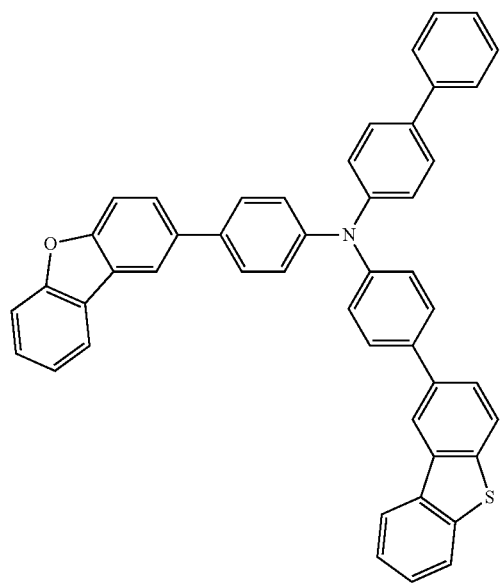
HT22
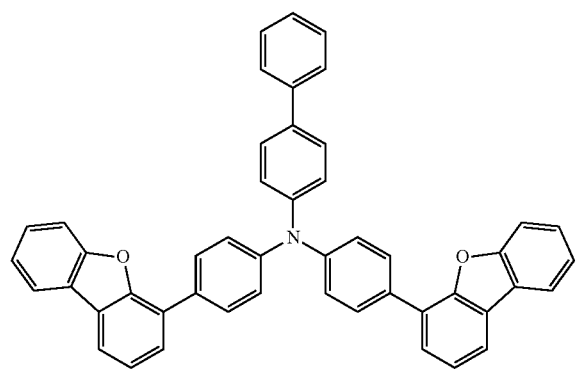
HT23
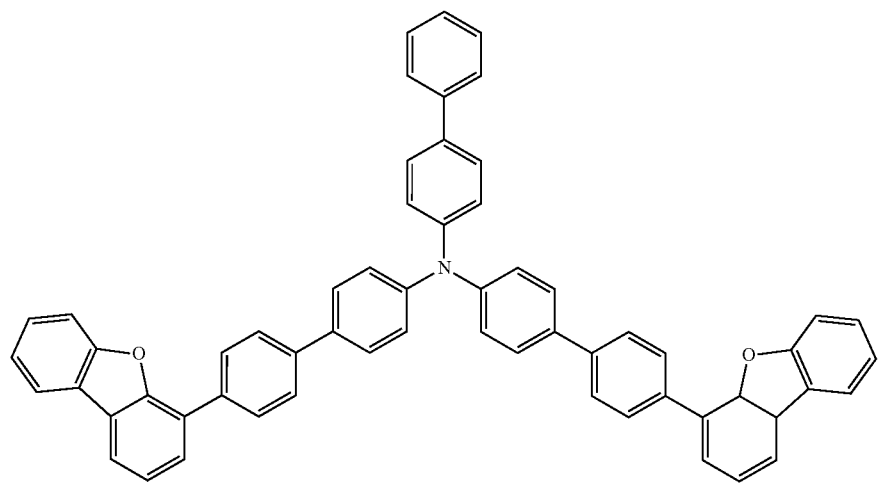
HT24
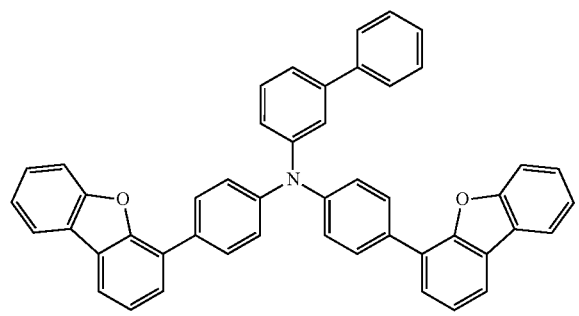
HT25
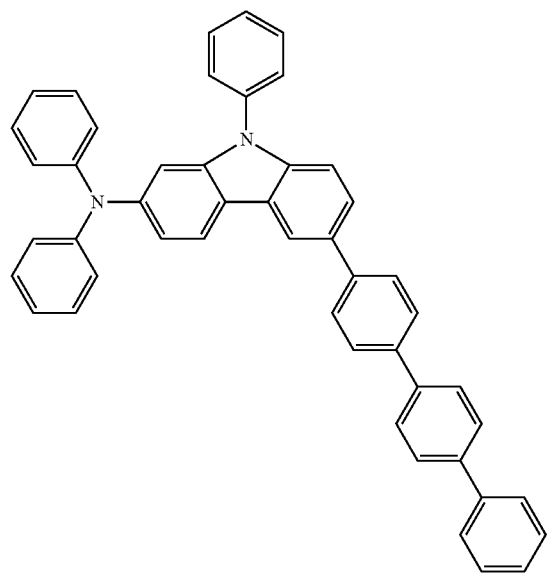

-continued
HT26
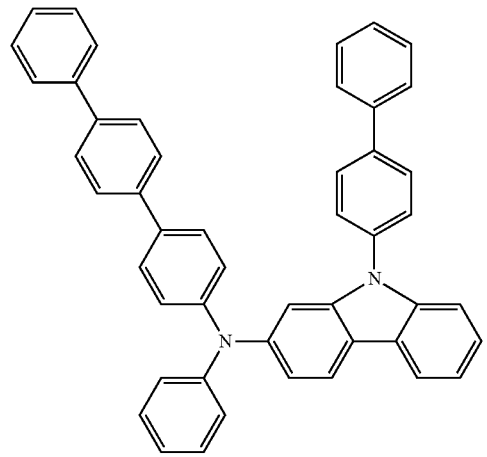
HT27
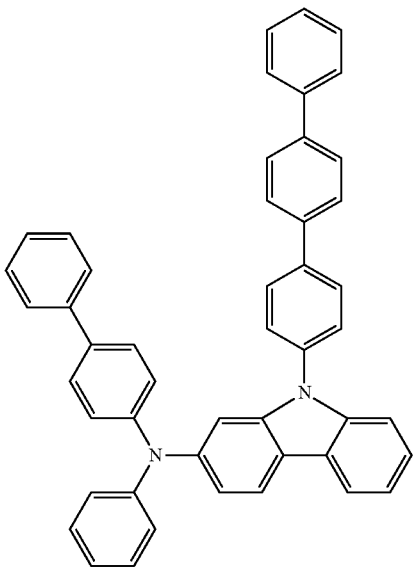
HT28
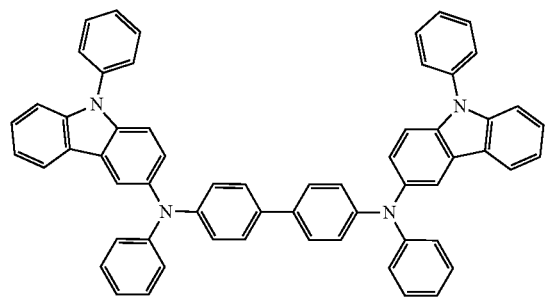
HT29
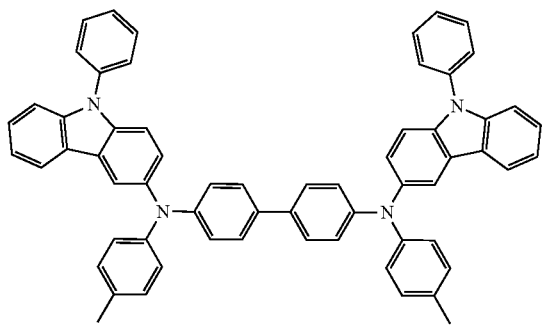
HT30
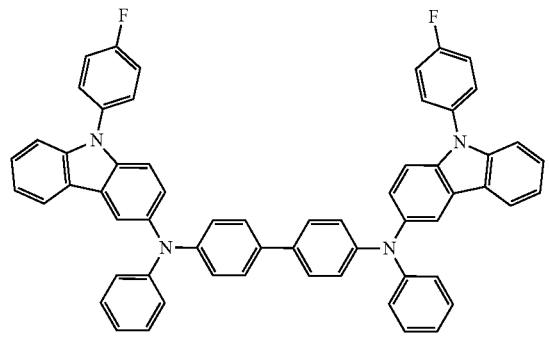
HT31
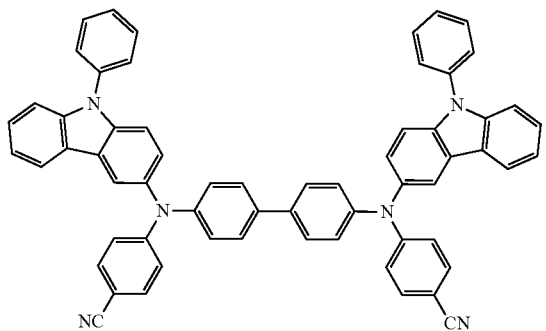

-continued
HT32
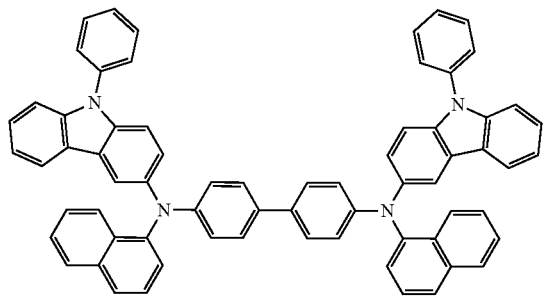
HT33
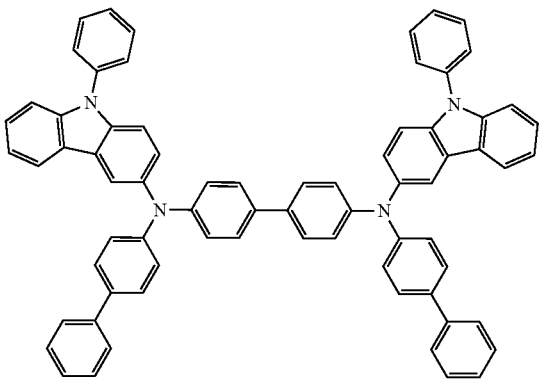
HT34
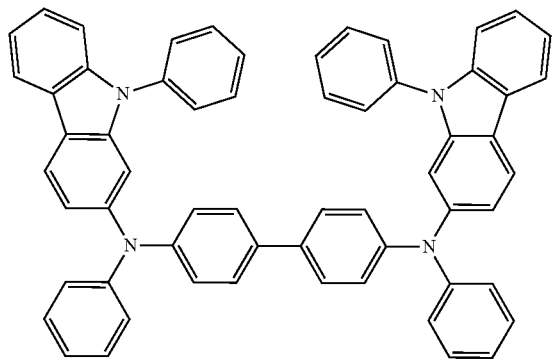
HT35
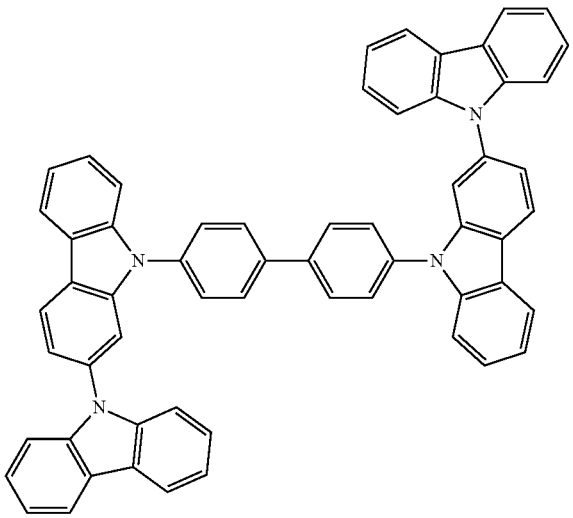
HT36
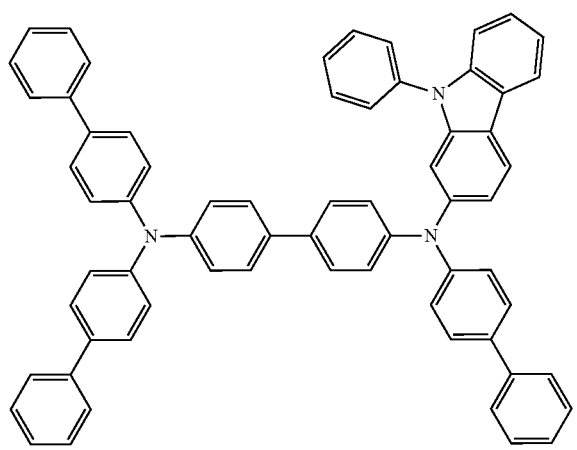
HT37
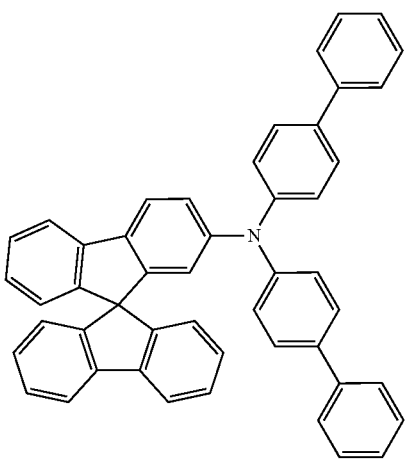

HT38

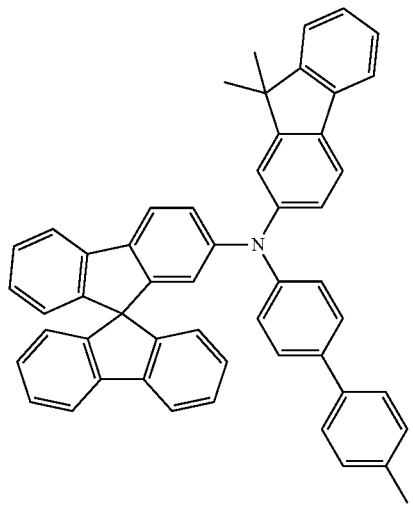

HT39

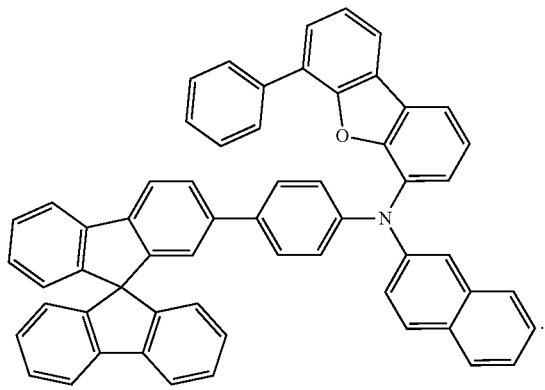

A thickness of the hole transport region may be in a range of about 100 Å to about 10,000 Å, for example, about 100 Å to about 1,000 Å. When the hole transport region includes at least one selected from a hole injection layer and a hole transport layer, the thickness of the hole injection layer may be in a range of about 100 Å to about 9,000 Å, and for example, about 100 Å to about 1,000 Å, and the thickness of the hole transport layer may be in a range of about 50 Å to about 2,000 Å, and for example, about 100 Å to about 1500 Å. When the thicknesses of the hole transport region, the hole injection layer, and the hole transport layer are within these ranges, suitable or satisfactory hole transporting characteristics may be obtained without a substantial increase in driving voltage.

The emission auxiliary layer may increase light-emission efficiency by compensating for an optical resonance distance according to the wavelength of light emitted by an emission layer, and the electron blocking layer may block the flow of electrons from an electron transport region. The emission auxiliary layer and the electron blocking layer may include the materials as described above.

[p-Dopant]

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant.

In one embodiment, the p-dopant may have a LUMO of about −3.5 eV or less.

The p-dopant may include at least one selected from a quinone derivative, a metal oxide, and a cyano group-containing compound, but embodiments of the present disclosure are not limited thereto.

For example, the p-dopant may include at least one selected from:
  a quinone derivative, such as tetracyanoquinodimethane (TCNQ) or 2,3,5,6-tetrafluoro-7,7,8,8-tetracyanoquinodimethane (F4-TCNQ);
  a metal oxide, such as tungsten oxide or molybdenum oxide;
  1,4,5,8,9,11-hexaazatriphenylene-hexacarbonitrile (HAT-CN); and
  a compound represented by Formula 221 below:
  but embodiments of the present disclosure are not limited thereto:

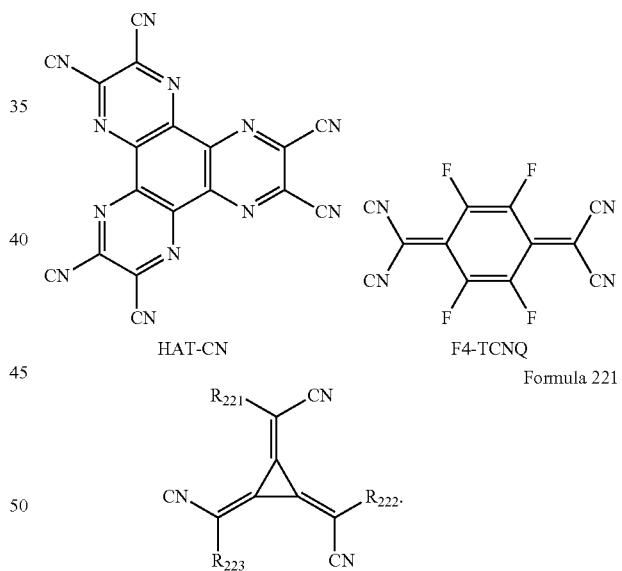

HAT-CN

F4-TCNQ

Formula 221

In Formula 221,
$R_{221}$ to $R_{223}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, provided that at least one selected from $R_{221}$ to $R_{223}$ has at least one substituent selected from a cyano group, —F, —Cl, —Br, —I, a $C_1$-$C_{20}$ alkyl group substituted with —F, a $C_1$-$C_{20}$ alkyl group substituted with —Cl, a $C_1$-$C_{20}$ alkyl group substituted with —Br, and a $C_1$-$C_{20}$ alkyl group substituted with —I.

[Emission Layer in Organic Layer 150]

When the organic light-emitting device 10 is a full-color organic light-emitting device, the emission layer may be patterned into a red emission layer, a green emission layer, or a blue emission layer, according to a sub-pixel. In one or more embodiments, the emission layer may have a stacked structure of two or more layers selected from a red emission layer, a green emission layer, and a blue emission layer, in which the two or more layers contact each other or are separated from each other. In one or more embodiments, the emission layer may include two or more materials selected from a red light-emitting material, a green light-emitting material, and a blue light-emitting material, in which the two or more materials are mixed with each other in a single layer to emit white light.

The emission layer may include a host and a dopant. The dopant may include at least one selected from a phosphorescent dopant and a fluorescent dopant.

An amount of the dopant in the emission layer may be in a range of about 0.01 parts by weight to about 15 parts by weight based on 100 parts by weight of the host, but embodiments of the present disclosure are not limited thereto.

A thickness of the emission layer may be in a range of about 100 Å to about 1,000 Å, for example, about 200 Å to about 600 Å. When the thickness of the emission layer is within this range, excellent light-emission characteristics may be obtained without a substantial increase in driving voltage.

[Host in Emission Layer]

In one or more embodiments, the host may further include a compound represented by Formula 301 below:

Formula 301

In Formula 301, $Ar_{301}$ may be a substituted or unsubstituted $C_5$-$C_{60}$ carbocyclic group or a substituted or unsubstituted $C_1$-$C_{60}$ heterocyclic group, xb11 may be 1, 2, or 3, $L_{301}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

xb1 may be an integer from 0 to 5, $R_{301}$ may be selected from deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$Si(Q_{301})(Q_{302})(Q_{303})$, —$N(Q_{301})(Q_{302})$, —$B(Q_{301})(Q_{302})$, —$C(=O)(Q_{301})$, —$S(=O)_2(Q_{301})$, and —$P(=O)(Q_{301})(Q_{302})$, xb21 may be an integer from 1 to 5, and $Q_{301}$ to $Q_{303}$ may each independently be selected from a $C_1$-$C_{10}$ alkyl group, a $C_1$-$C_{10}$ alkoxy group, a phenyl group, a biphenyl group, a terphenyl group, and a naphthyl group, but embodiments of the present disclosure are not limited thereto.

In one embodiment, in Formula 301, $Ar_{301}$ may be selected from:

a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group; and a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, and —$P(=O)(Q_{31})(Q_{32})$, and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group, but embodiments of the present disclosure are not limited thereto.

In Formula 301, xb11 may be two or more, and two or more of $Ar_{301}$(s) may be linked via a single bond.

In one or more embodiments, the compound represented by Formula 301 may be represented by Formula 301-1 or 301-2:

Formula 301-1

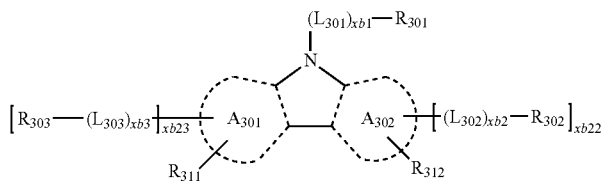

Formula 301-2

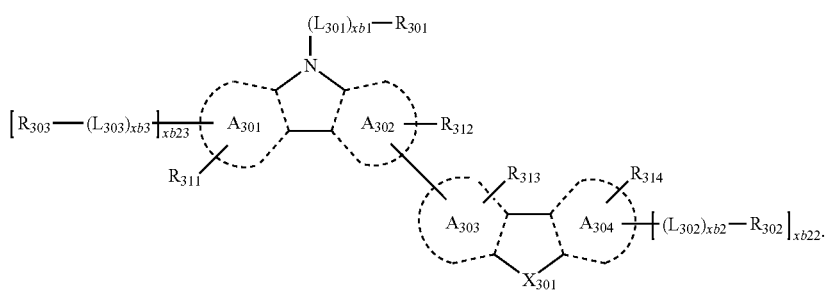

In Formulae 301-1 and 301-2, $A_{301}$ to $A_{304}$ may each independently be selected from a benzene group, a naphthalene group, a phenanthrene group, a fluoranthene group, a triphenylene group, a pyrene group, a chrysene group, a pyridine group, a pyrimidine group, an indene group, a fluorene group, a spiro-bifluorene group, a benzofluorene group, a dibenzofluorene group, an indole group, a carbazole group, a benzocarbazole group, a dibenzocarbazole group, a furan group, a benzofuran group, a dibenzofuran group, a naphthofuran group, a benzonaphthofuran group, a dinaphthofuran group, a thiophene group, a benzothiophene group, a dibenzothiophene group, a naphthothiophene group, a benzonaphthothiophene group, and a dinaphthothiophene group, $X_{301}$ may be O, S, or N-$[(L_{304})_{xb4}$-$R_{304}]$, $R_{311}$ to $R_{314}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$) and —P(=O)($Q_{31}$)($Q_{32}$), xb22 and xb23 may each independently be 0, 1, or 2, $L_{301}$, xb1, $R_{301}$, and $Q_{31}$ to $Q_{33}$ may each independently be the same as described above, $L_{302}$ to $L_{304}$ may each independently be the same as described in connection with $L_{301}$, xb2 to xb4 may each independently be the same as described in connection with xb1, and $R_{302}$ to $R_{304}$ may each independently be the same as described in connection with $R_{301}$.

For example, in Formulae 301, 301-1, and 301-2, $L_{301}$ to $L_{304}$ may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{31}$ to $Q_{33}$ may be the same as described above.

In one embodiment, in Formulae 301, 301-1, and 301-2, $R_{301}$ to $R_{304}$ may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N(Q$_{31}$)(Q$_{32}$), —B(Q$_{31}$)(Q$_{32}$), —C(=O)(Q$_{31}$), —S(=O)$_2$(Q$_{31}$), and —P(=O)(Q$_{31}$)(Q$_{32}$), and Q$_{31}$ to Q$_{33}$ may be the same as described above.

In one or more embodiments, the host may include an alkaline earth metal complex. For example, the host may be selected from a Be complex (for example, Compound H55), a Mg complex, and a Zn complex.

The host may include at least one selected from 9,10-di (2-naphthyl)anthracene (ADN), 2-methyl-9,10-bis(naphthalen-2-yl)anthracene (MADN), 9,10-di-(2-naphthyl)-2-t-butyl-anthracene (TBADN), 4,4'-bis(N-carbazolyl)-1,1'-biphenyl (CBP), 1,3-di-9-carbazolylbenzene (mCP), 1,3,5-tri(carbazol-9-yl)benzene (TCP), and Compounds H1 to H55, but embodiments of the present disclosure are not limited thereto:

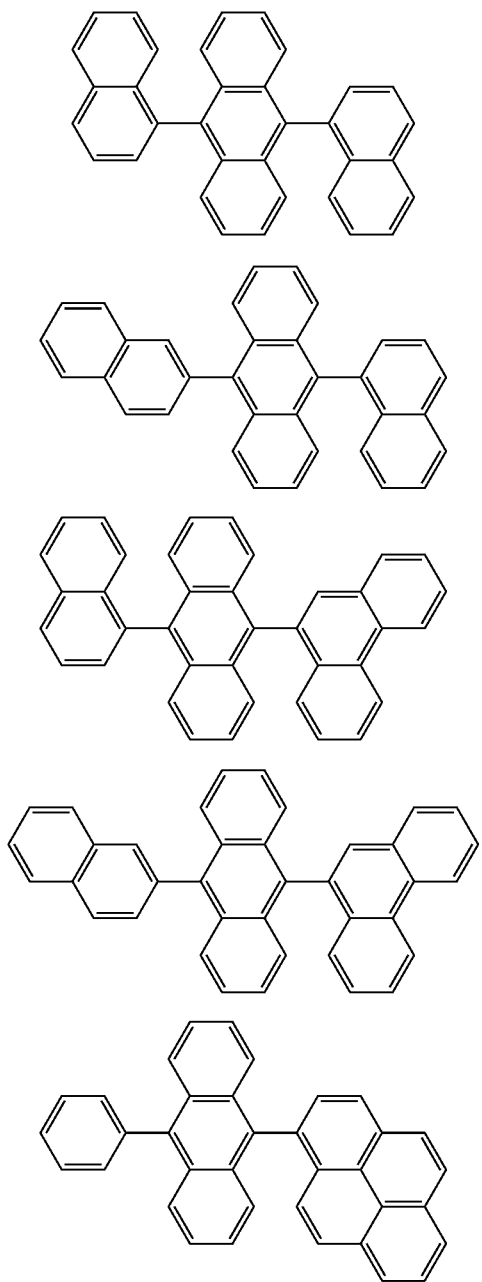

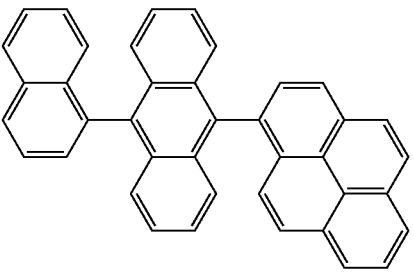

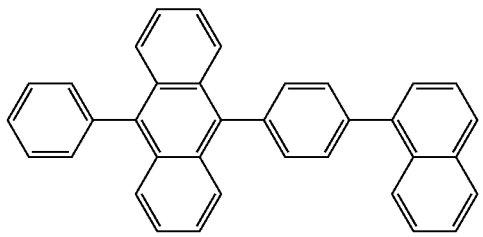

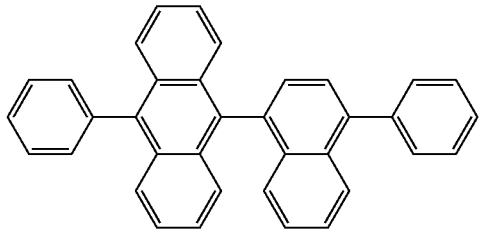

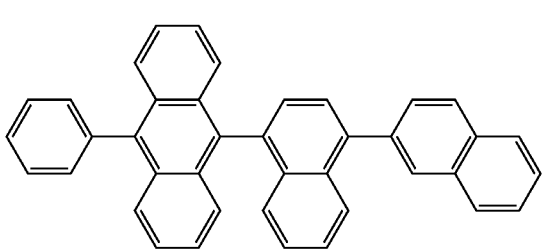

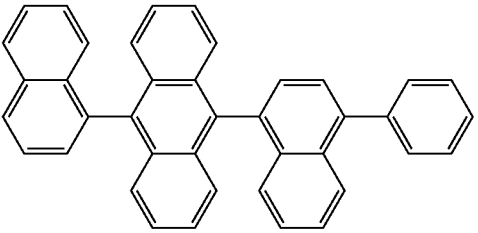

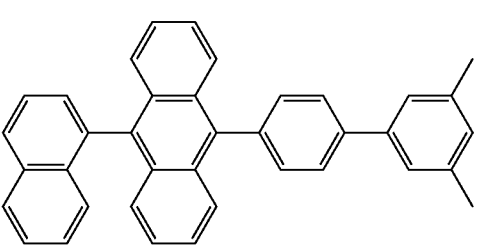

H12
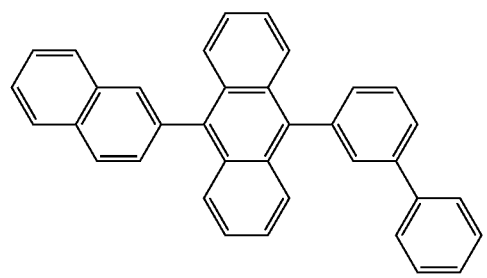
H13
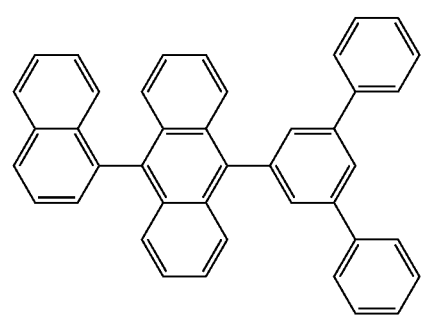
H14
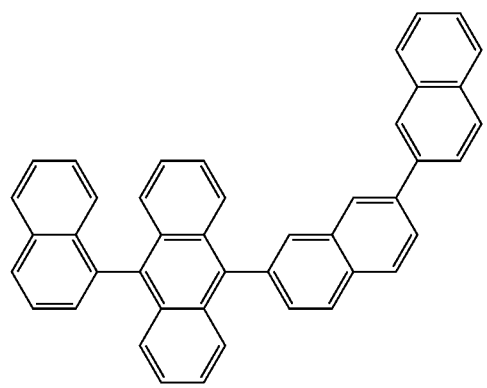
H15
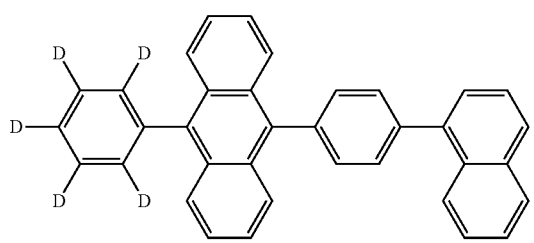
H16
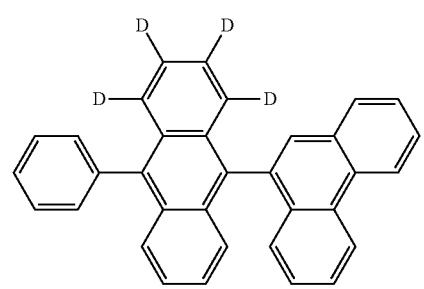
H17
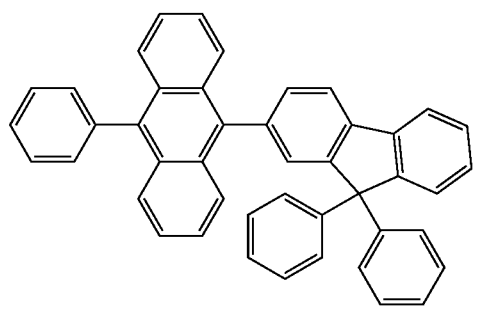
H18
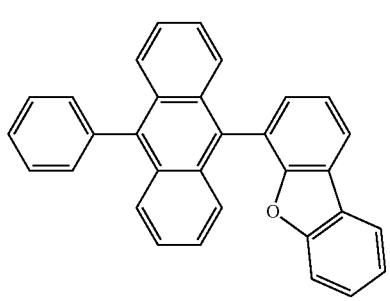
H19
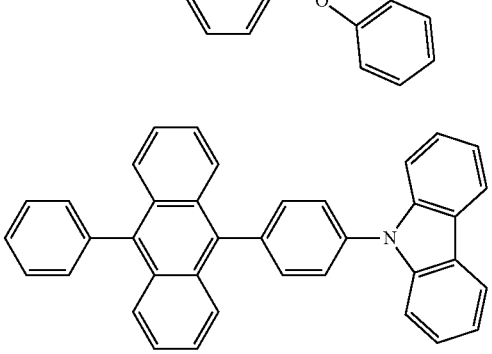
H20
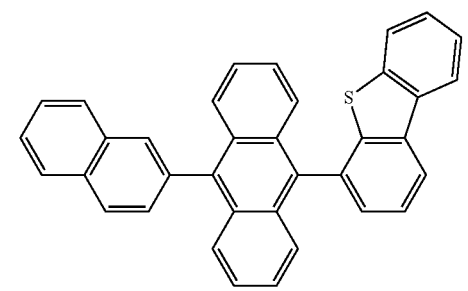
H21
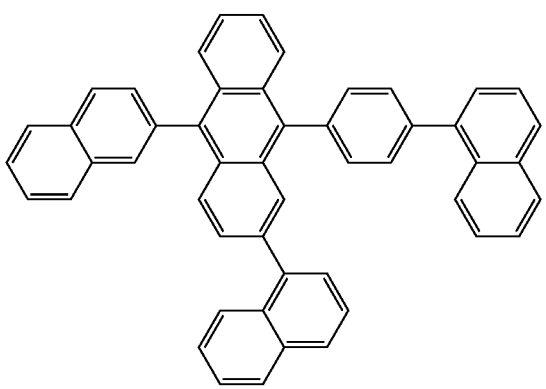

H22
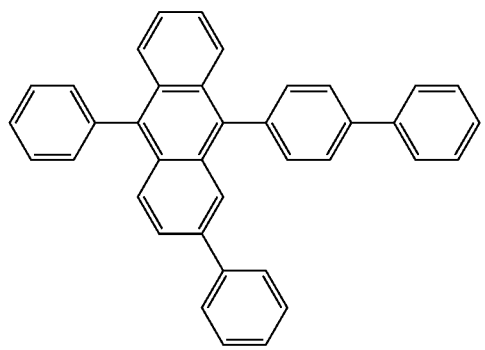
H23
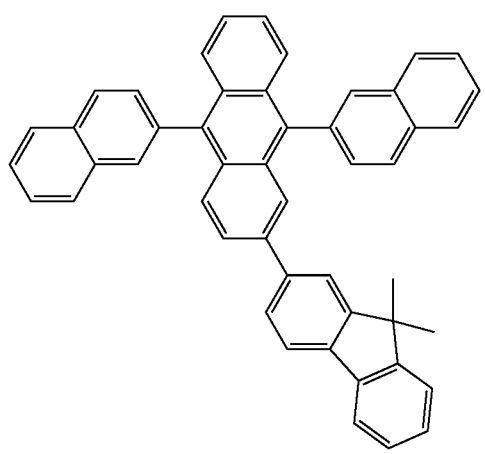
H24
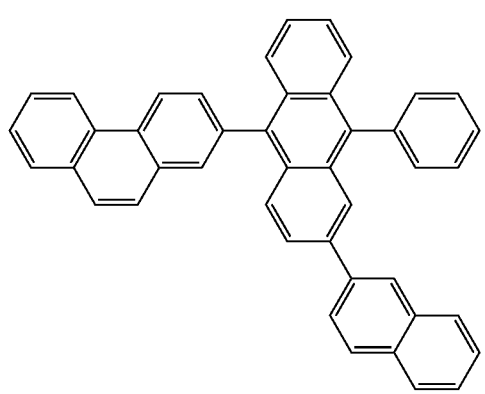
H25
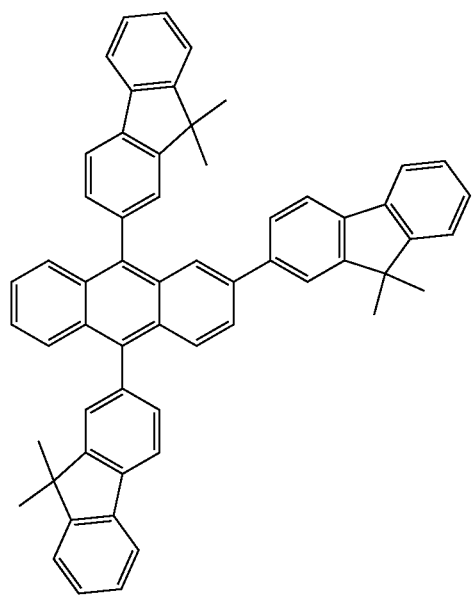
H26
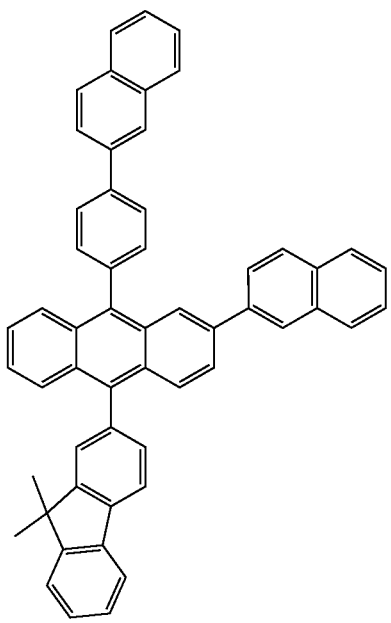

H27
H28
H29
H30
H31
H32
H33
H34
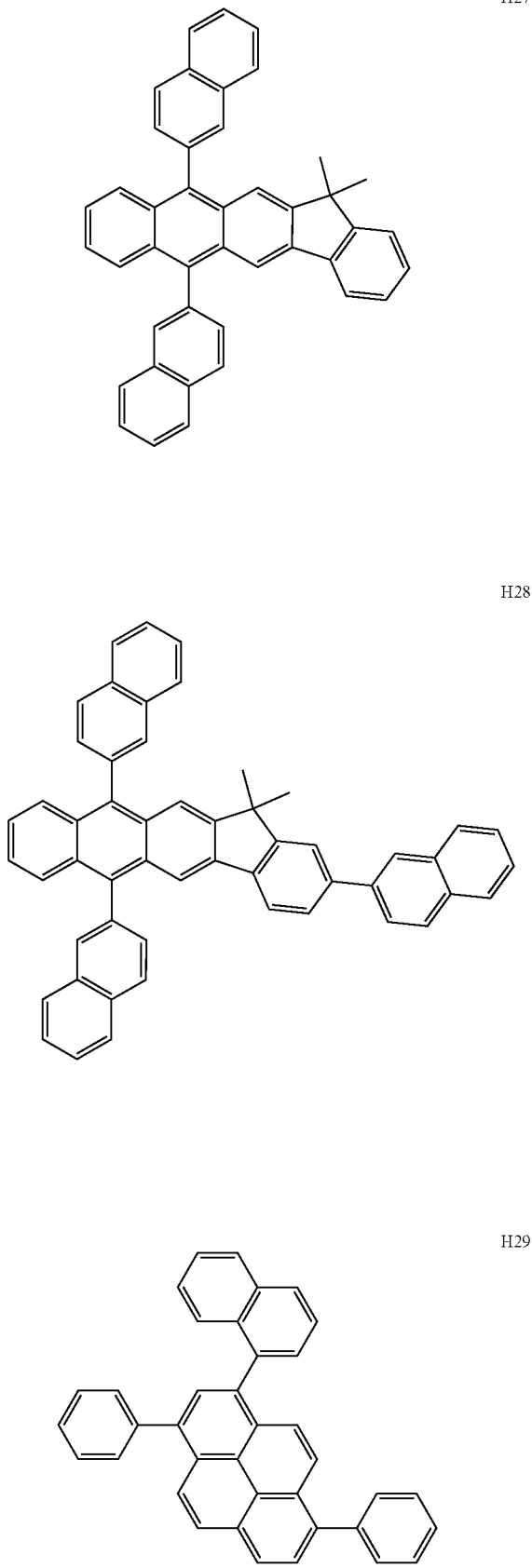
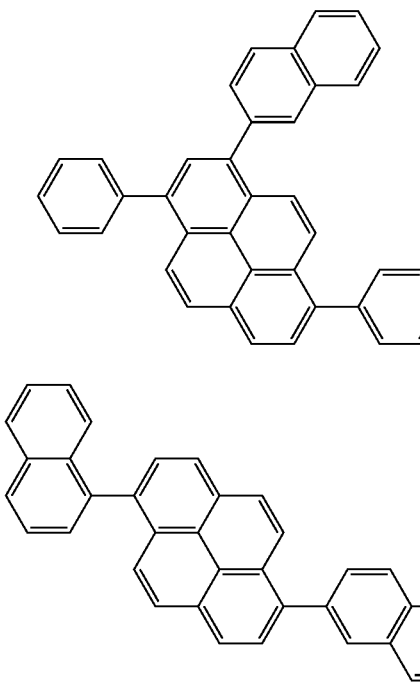
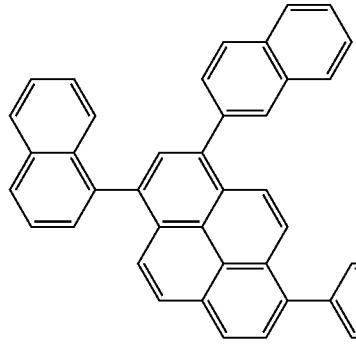
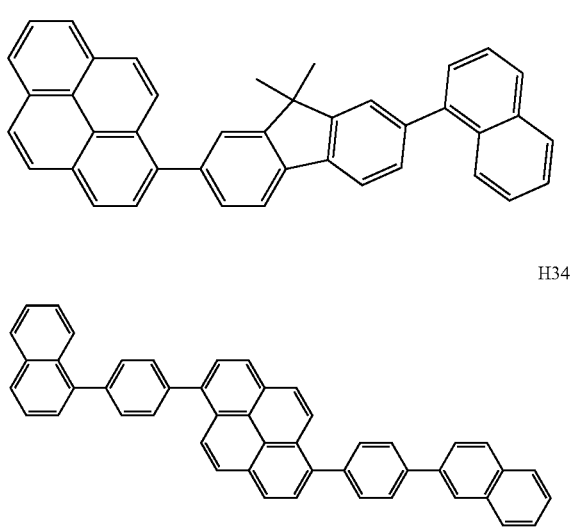

H35
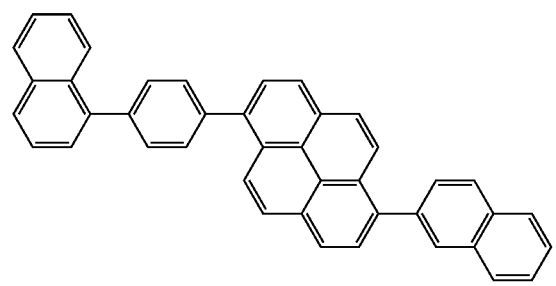
H36
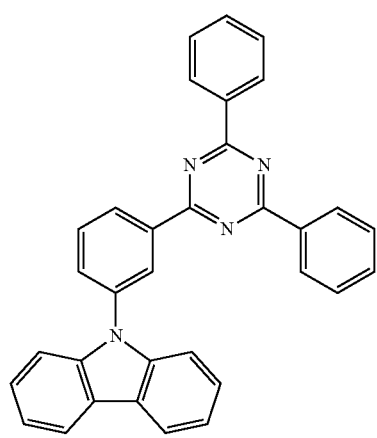
H37
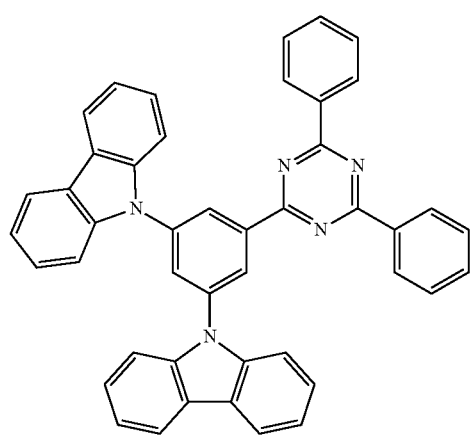
H38
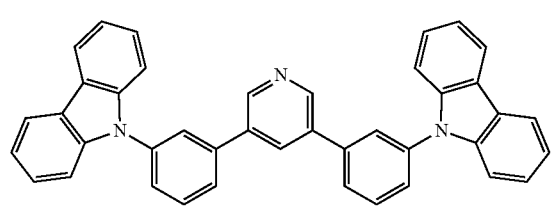
H39
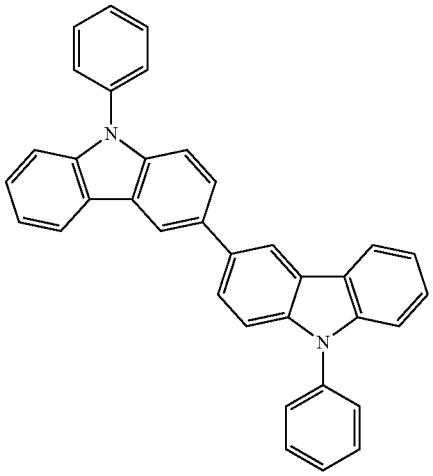
H40
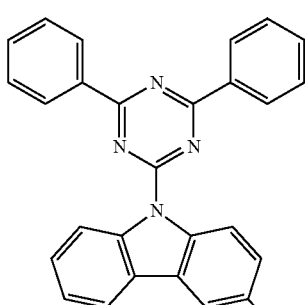
H41
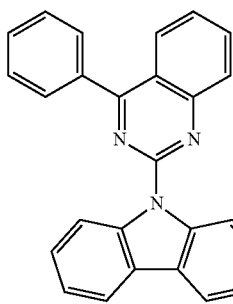
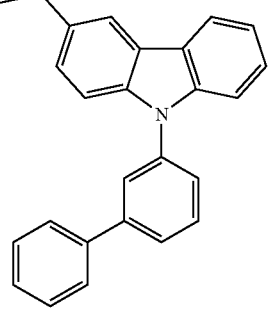

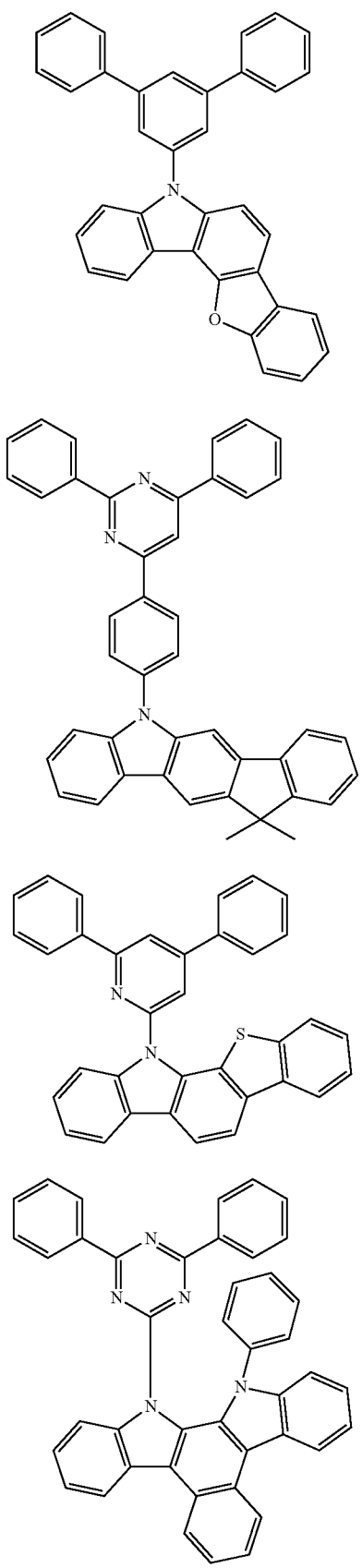
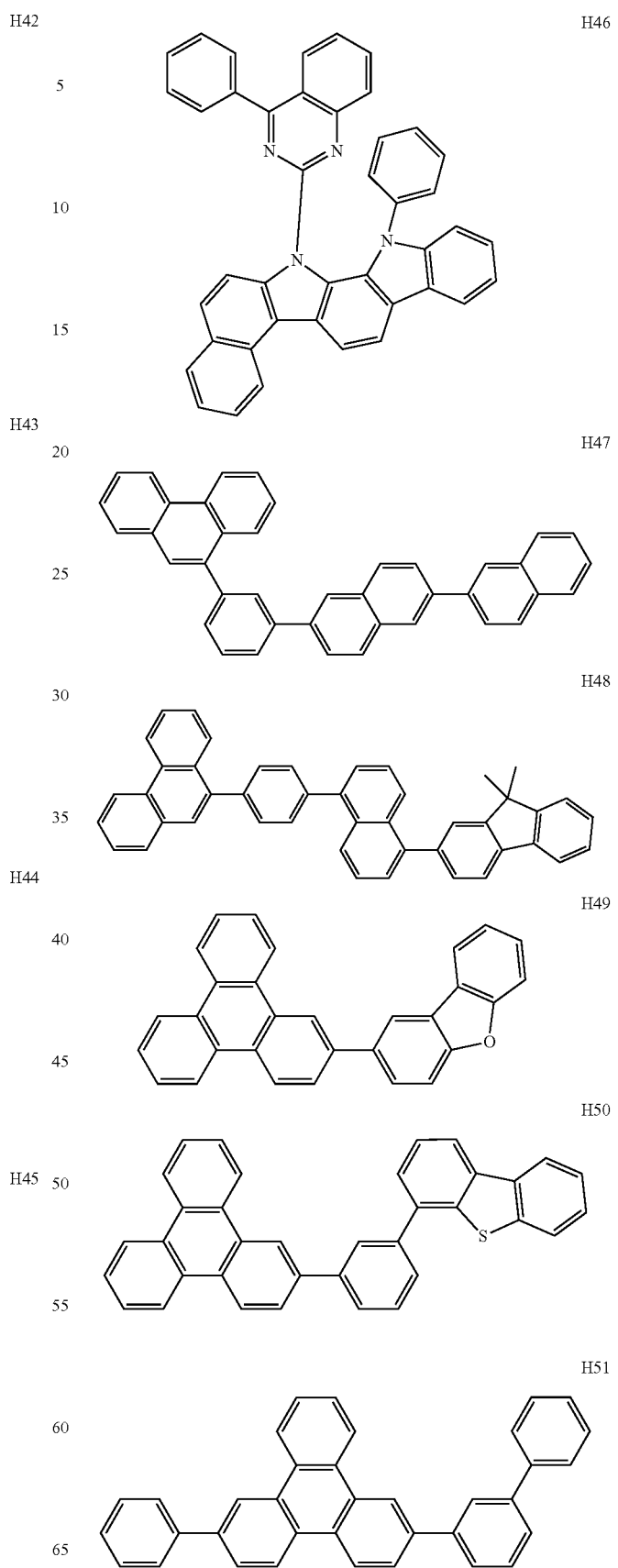

-continued

H52
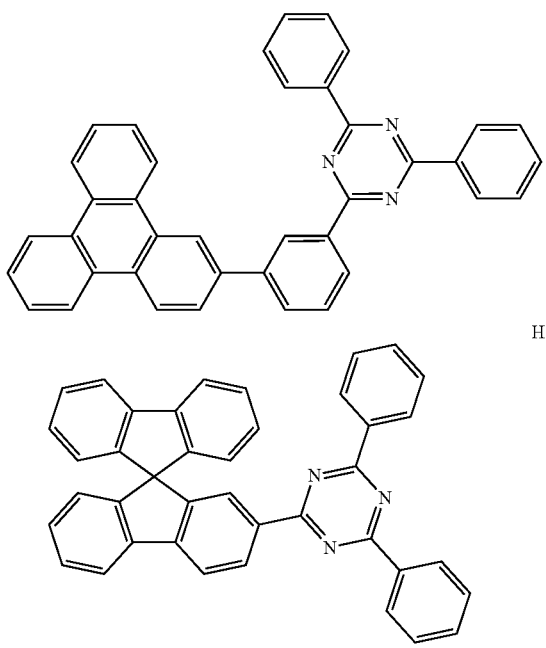

H53

H54
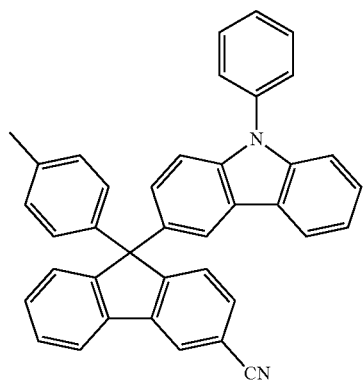

H55
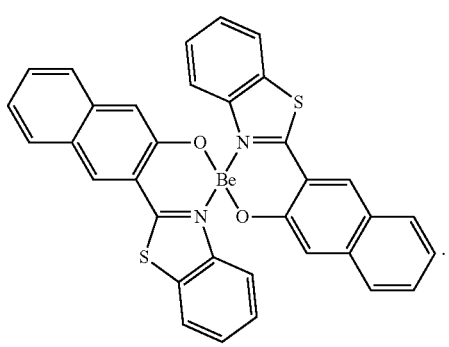

[Phosphorescent Dopant Included in Emission Layer in Organic Layer 150]

The phosphorescent dopant may include an organometallic complex represented by Formula 401 below:

$$M(L_{401})_{xc1}(L_{402})_{xc2}$$ Formula 401

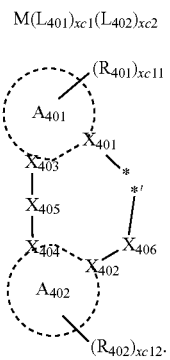

Formula 402

In Formulae 401 and 402,

M may be selected from iridium (Ir), platinum (Pt), palladium (Pd), osmium (Os), titanium (Ti), zirconium (Zr), hafnium (Hf), europium (Eu), terbium (Tb), rhodium (Rh), and thulium (Tm), $L_{401}$ may be selected from ligands represented by Formula 402, and xc1 may be 1, 2, or 3, wherein, when xc1 is two or more, two or more $L_{401}$(s) may be identical to or different from each other, $L_{402}$ may be an organic ligand, and xc2 may be an integer from 0 to 4, wherein, when xc2 is two or more, two or more $L_{402}$(s) may be identical to or different from each other, $X_{401}$ to $X_{404}$ may each independently be nitrogen or carbon, $X_{401}$ and $X_{403}$ may be linked via a single bond or a double bond, and $X_{402}$ and $X_{404}$ may be linked via a single bond or a double bond, $A_{401}$ and $A_{402}$ may each independently be selected from a $C_5$-$C_{60}$ carbocyclic group or a $C_1$-$C_{60}$ heterocyclic group, $X_{406}$ may be a single bond, *—O—*', *—S—*', *—C(=O)—*', *—N($Q_{411}$)—*', *—C($Q_{411}$)($Q_{412}$)-*', *—C($Q_{411}$)=C($Q_{412}$)-*', *—C($Q_{411}$)=*', or *=C=*', and $Q_{411}$ and $Q_{412}$ may each independently be hydrogen, deuterium, a $C_1$-$C_{20}$ alkyl group, a $C_1$-$C_{20}$ alkoxy group, a phenyl group, a biphenyl group, a terphenyl group, or a naphthyl group, $X_{406}$ may be a single bond, O, or S, $R_{401}$ and $R_{402}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{20}$ alkyl group, a substituted or unsubstituted $C_1$-$C_{20}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$), $Q_{401}$ to $Q_{403}$ may each independently be selected from a $C_1$-$C_{10}$ alkyl group, a $C_1$-$C_{10}$ alkoxy group, a $C_6$-$C_{20}$ aryl group, and a $C_1$-$C_{20}$ heteroaryl group, xc11 and xc12 may each independently be an integer from 0 to 10, and and *' in Formula 402 each indicate a binding site to M in Formula 401.

In one embodiment, $A_{401}$ and $A_{402}$ in Formula 402 may each independently be selected from a benzene group, a naphthalene group, a fluorene group, a spiro-bifluorene group, an indene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzimidazole group, a benzofuran group, a benzothiophene group, an isobenzothiophene group, a benzoxazole group, an isobenzoxazole group, a triazole group, a tetrazole group, an oxadiazole group, a triazine group, a dibenzofuran group, and a dibenzothiophene group.

In one or more embodiments, in Formula 402, i) $X_{401}$ may be nitrogen, and $X_{402}$ may be carbon, or ii) $X_{401}$ and $X_{402}$ may each be nitrogen at the same time.

In one or more embodiments, $R_{402}$ and $R_{402}$ in Formula 401 may each independently be selected from:
hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;
a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a phenyl group, a naphthyl group, a cyclopentyl group, a cyclohexyl group, an adamantanyl group, a norbornanyl group, and a norbornenyl group;
a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group;
a cyclopentyl group, a cyclohexyl group, an adamantanyl group, a norbornanyl group, a norbornenyl group a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group; and —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$), and $Q_{401}$ to $Q_{403}$ may each independently be selected from a $C_1$-$C_{10}$ alkyl group, a $C_1$-$C_{10}$ alkoxy group, a phenyl group, a biphenyl group, and a naphthyl group, but are not limited thereto.

In one or more embodiments, when xc1 in Formula 401 is two or more, two $A_{401}$(s) in two or more $L_{401}$(s) may optionally be linked via $X_{407}$, which is a linking group, or two $A_{402}$(s) in two or more $L_{401}$(s) may optionally be linked via $X_{408}$, which is a linking group (see Compounds PD1 to PD4 and PD7). $X_{407}$ and $X_{408}$ may each independently be a single bond, *—O—*', *—S—*', *—C(=O)—*', *—N($Q_{413}$)-*', *—C($Q_{413}$)($Q_{414}$)-*', or *—C($Q_{413}$)=C($Q_{414}$)-*' (wherein $Q_{413}$ and $Q_{414}$ may each independently be hydrogen, deuterium, a $C_1$-$C_{20}$ alkyl group, a $C_1$-$C_{20}$ alkoxy group, a phenyl group, a biphenyl group, a terphenyl group, or a naphthyl group), but embodiments of the present disclosure are not limited thereto.

$L_{402}$ in Formula 401 may be a monovalent, divalent, or trivalent organic ligand. For example, $L_{402}$ may be selected from a halogen, a diketone (for example, acetylacetonate), a carboxylic acid (for example, picolinate), —C(=O), an isonitrile, —CN, and a phosphorus-containing material (for example, phosphine or phosphite), but embodiments of the present disclosure are not limited thereto.

In one or more embodiments, the phosphorescent dopant may be selected from, for example, Compounds PD1 to PD25, but embodiments of the present disclosure are not limited thereto:

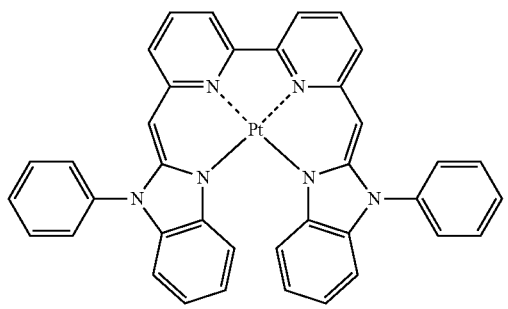

PD1

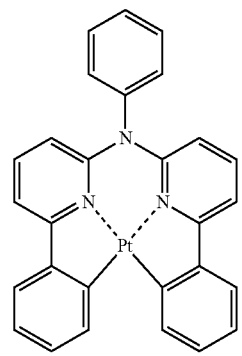

PD2

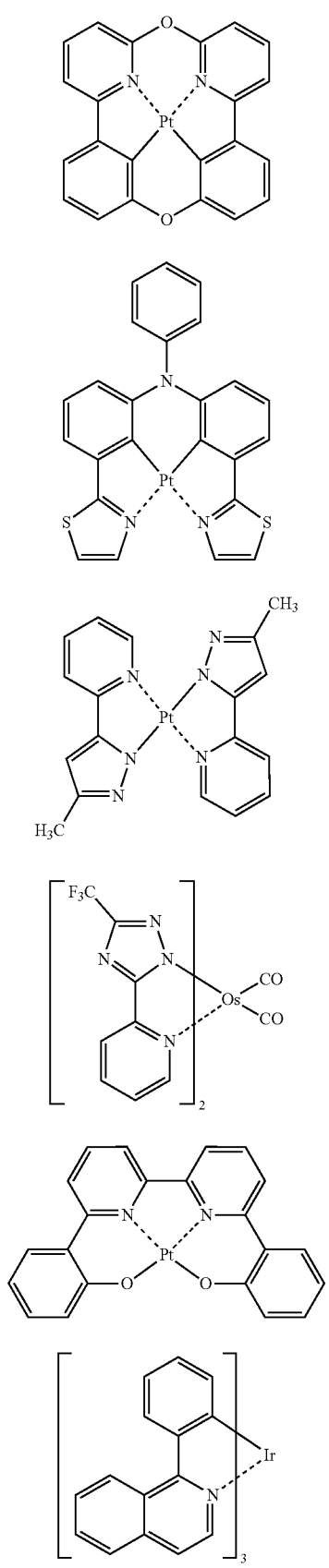
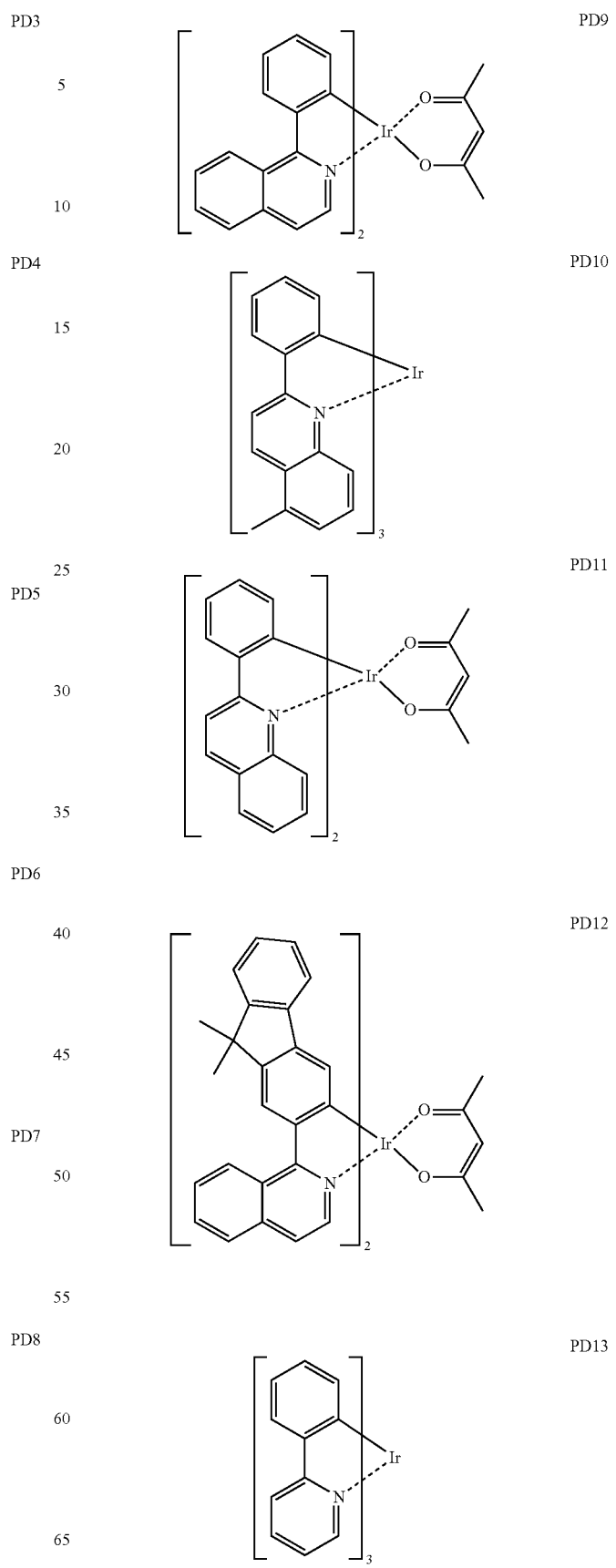

PD14
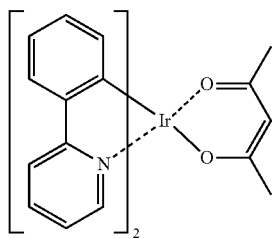
PD15
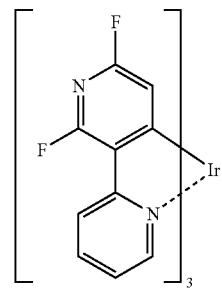
PD16
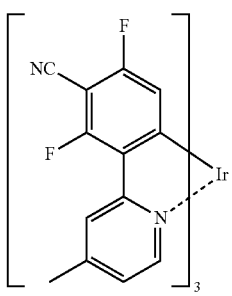
PD17
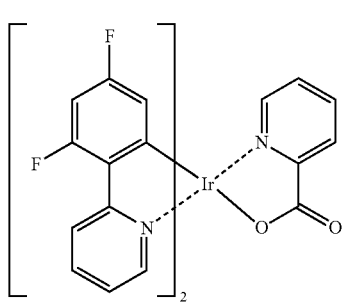
PD18
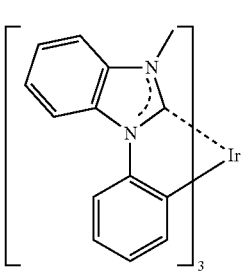
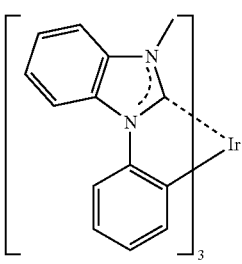
PD19
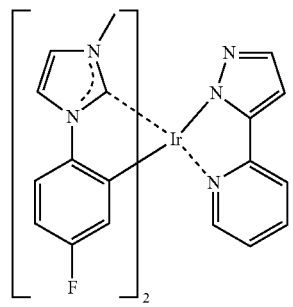
PD20
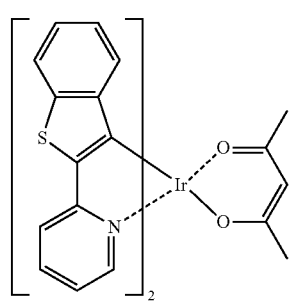
PD21
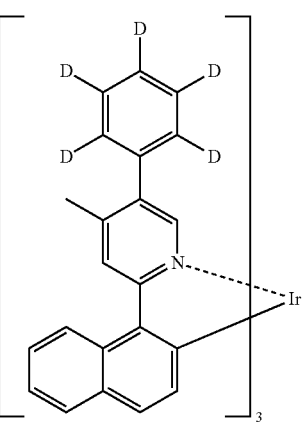
PD22
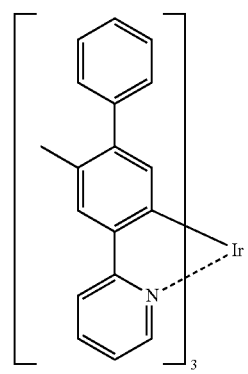

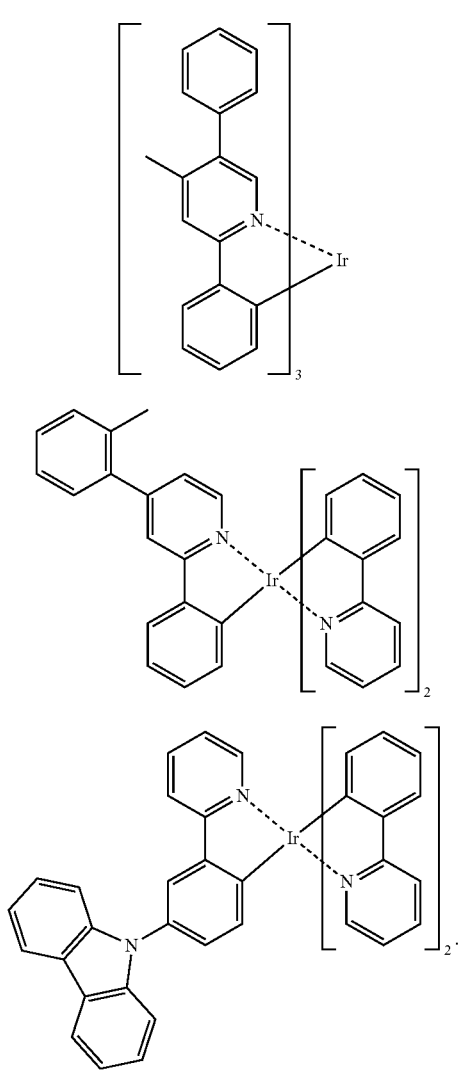

[Fluorescent Dopant in Emission Layer]

The fluorescent dopant may include an arylamine compound or a styrylamine compound.

The fluorescent dopant may include a compound represented by Formula 501 below:

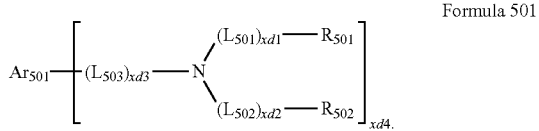

In Formula 501,

Ar$_{501}$ may be a substituted or unsubstituted C$_5$-C$_{60}$ carbocyclic group or a substituted or unsubstituted C$_1$-C$_{60}$ heterocyclic group, L$_{501}$ to L$_{503}$ may each independently be selected from a substituted or unsubstituted C$_3$-C$_{10}$ cycloalkylene group, a substituted or unsubstituted C$_1$-C$_{10}$ heterocycloalkylene group, a substituted or unsubstituted C$_3$-C$_{10}$ cycloalkenylene group, a substituted or unsubstituted C$_1$-C$_{10}$ heterocycloalkenylene group, a substituted or unsubstituted C$_6$-C$_{60}$ arylene group, a substituted or unsubstituted C$_1$-C$_{60}$ heteroarylene group, a substituted or unsubstituted divalent non-aromatic condensed polycyclic group, and a substituted or unsubstituted divalent non-aromatic condensed heteropolycyclic group, xd1 to xd3 may each independently be an integer of 0 to 3, R$_{501}$ and R$_{502}$ may each independently be selected from a substituted or unsubstituted C$_3$-C$_{10}$ cycloalkyl group, a substituted or unsubstituted C$_1$-C$_{10}$ heterocycloalkyl group, a substituted or unsubstituted C$_3$-C$_{10}$ cycloalkenyl group, a substituted or unsubstituted C$_1$-C$_{10}$ heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, a substituted or unsubstituted C$_1$-C$_{60}$ heteroaryl group, a substituted or unsubstituted monovalent non-aromatic condensed polycyclic group, and a substituted or unsubstituted monovalent non-aromatic condensed heteropolycyclic group, and xd4 may be an integer of 1 to 6.

In one embodiment, Ar$_{501}$ in Formula 501 may be selected from:

a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group; and a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group, each substituted with at least one selected from deuterium, —F, —Cl, —Br, —I, a hydroxyl group, a cyano group, a nitro group, an amidino group, a hydrazino group, a hydrazono group, a C$_1$-C$_{20}$ alkyl group, a C$_1$-C$_{20}$ alkoxy group, a phenyl group, a biphenyl group, a terphenyl group, and a naphthyl group.

In one or more embodiments, L$_{501}$ to L$_{503}$ in Formula 501 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

In one or more embodiments, $R_{501}$ and $R_{502}$ in Formula 501 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, and —Si($Q_{31}$)($Q_{32}$)($Q_{33}$), and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one or more embodiments, xd4 in Formula 501 may be 2, but embodiments of the present disclosure are not limited thereto.

For example, the fluorescent dopant may be selected from Compounds FD1 to FD22:

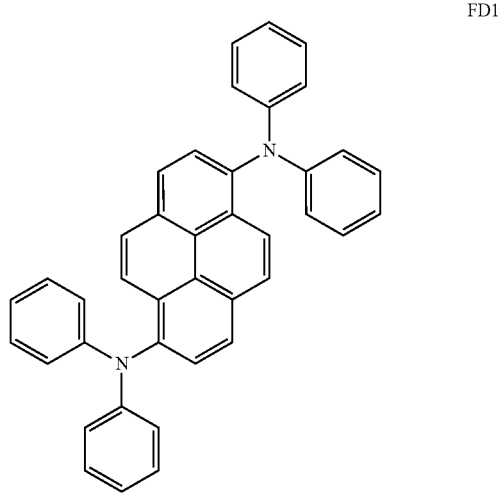

FD1

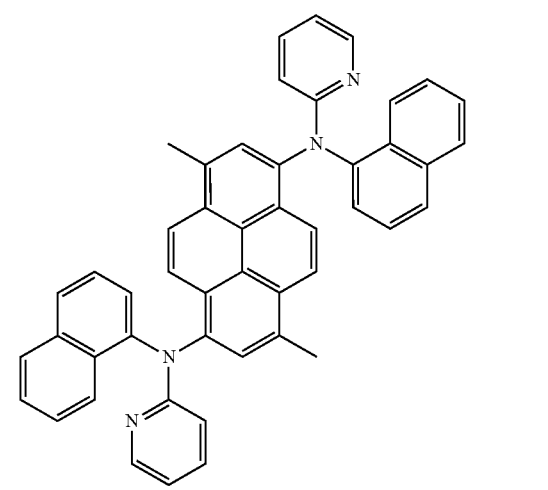

FD2

FD3
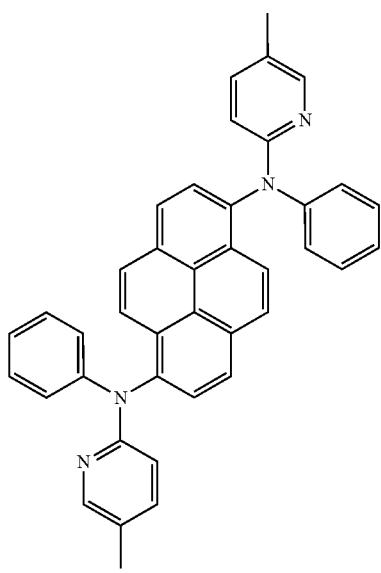
FD6
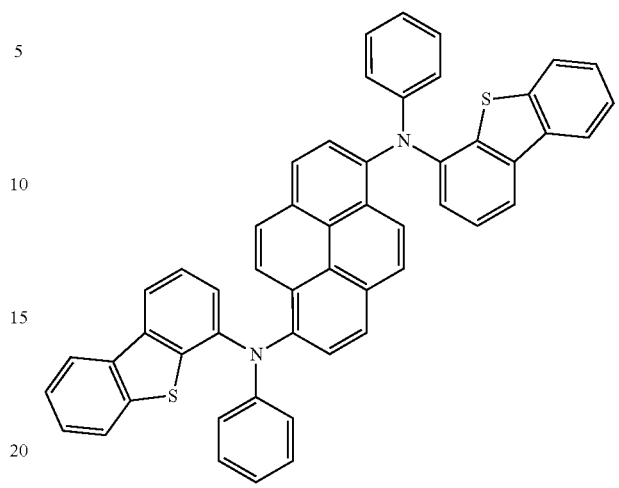
FD4
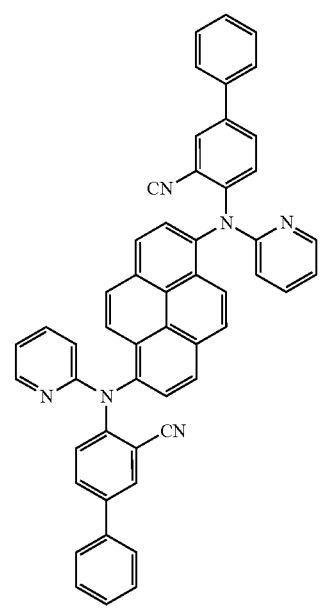
FD7
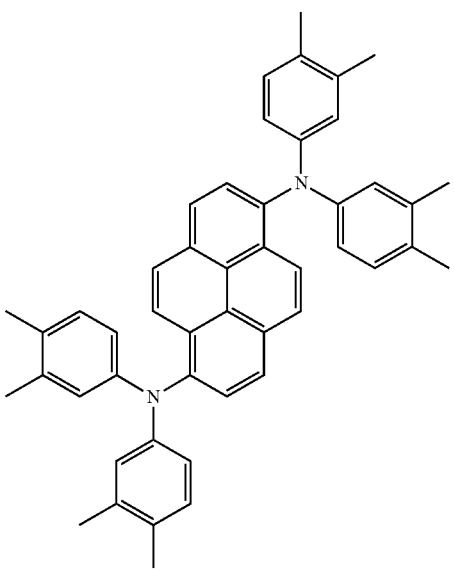
FD5
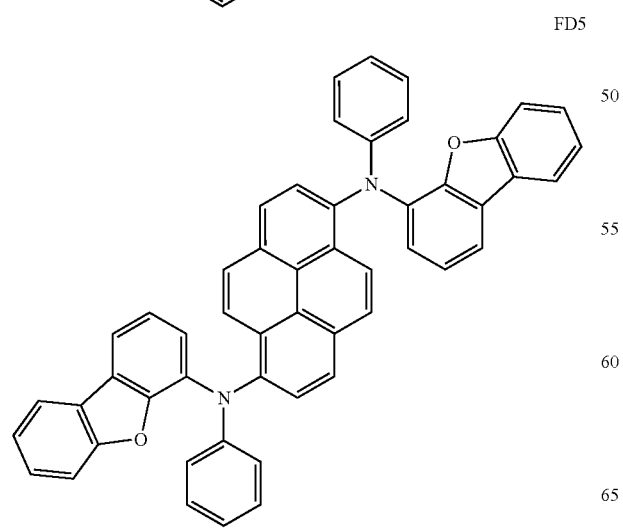
FD8
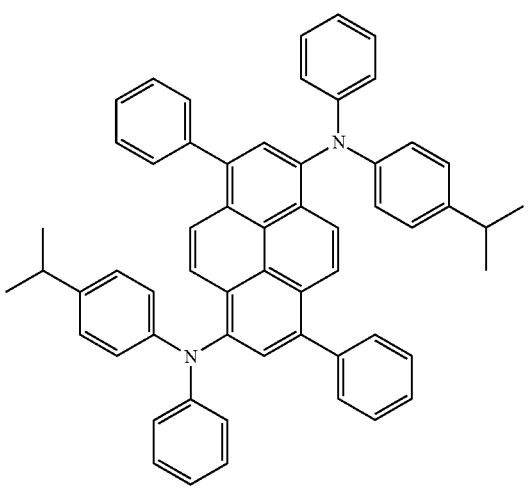

FD9
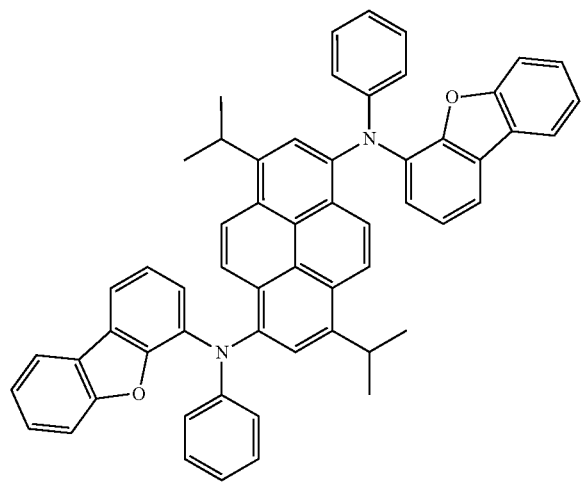
FD13
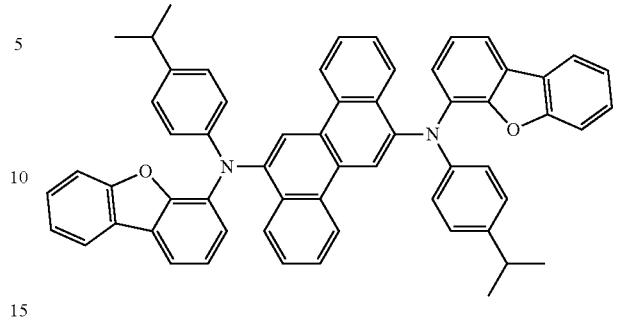
FD10
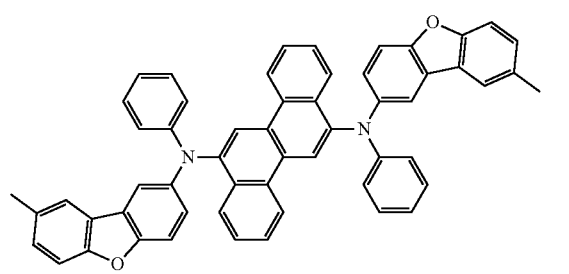
FD14
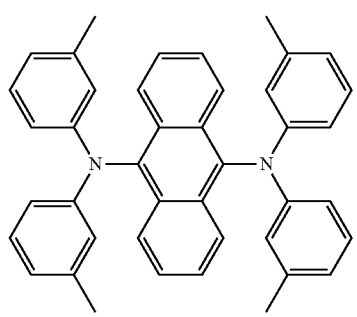
FD11
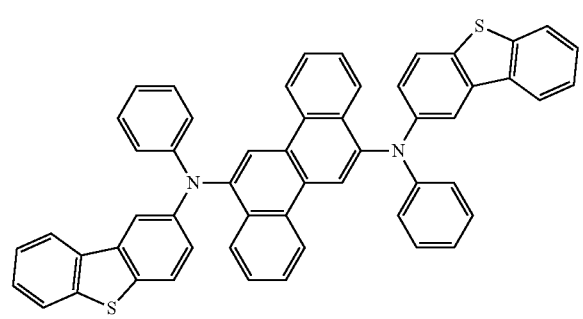
FD15
FD12
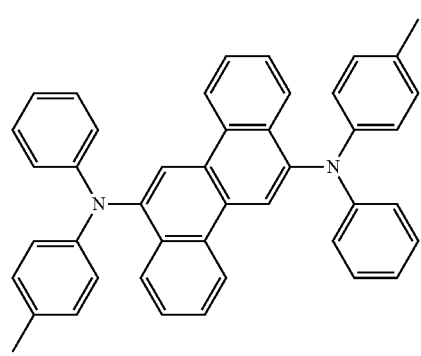
FD16
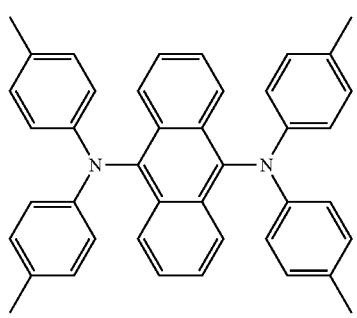

-continued
FD17
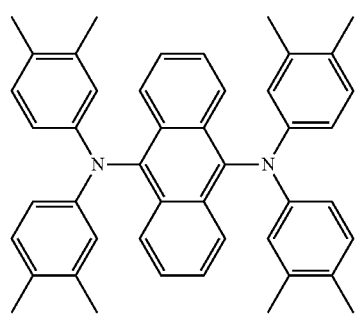
FD18
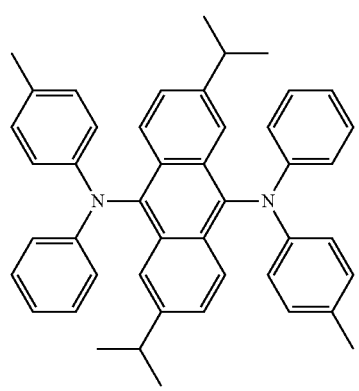
FD19
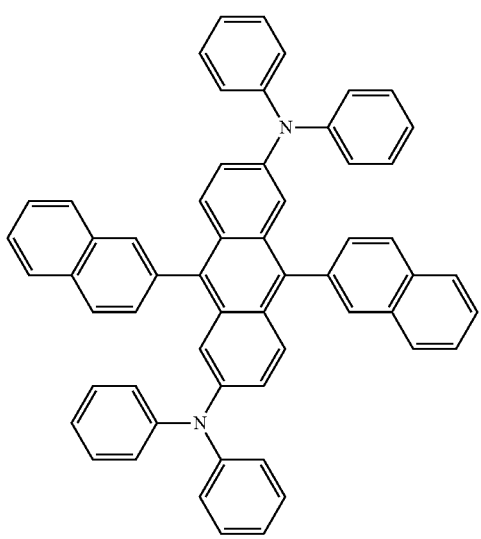
-continued
FD20
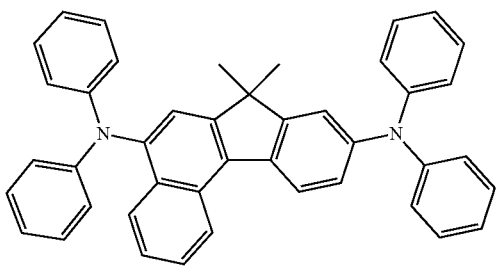
FD21
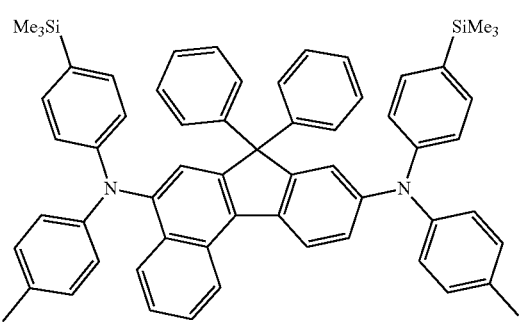
FD22
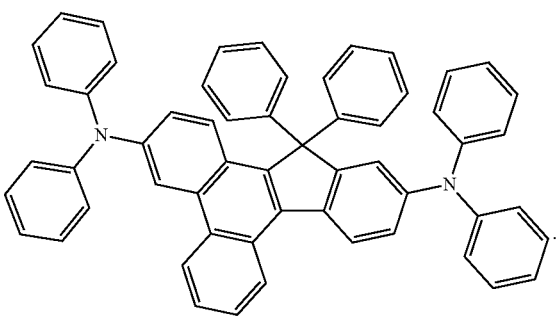
In one or more embodiments, the fluorescent dopant may be selected from the following compounds, but embodiments of the present disclosure are not limited thereto:
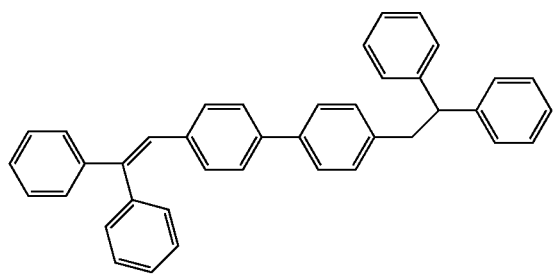
DPVBi

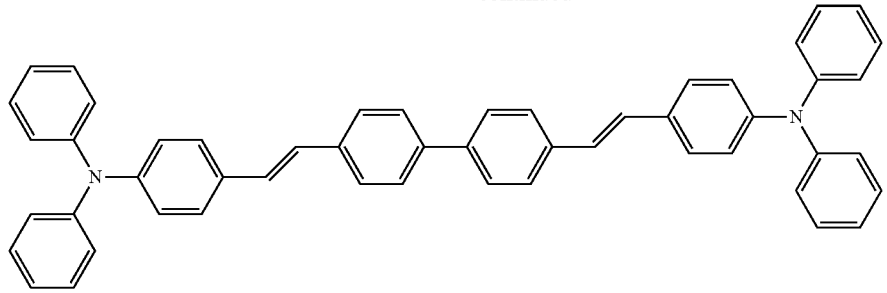
DPAVBi

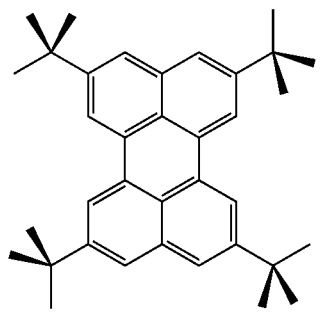
TBPe

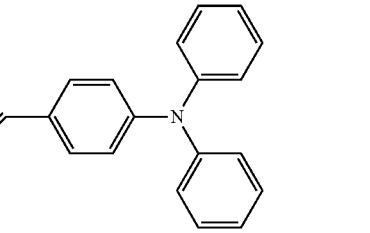
DCM

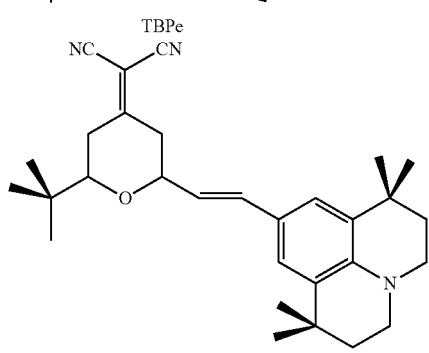
DCJTB

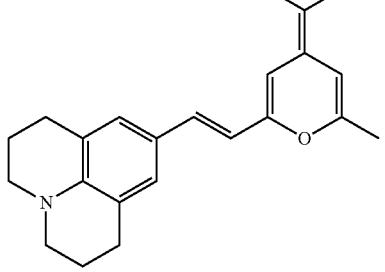
Coumarin 6

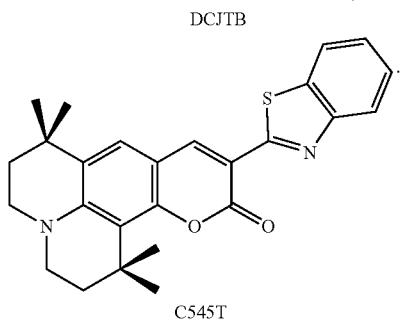
C545T

[Electron Transport Region in Organic Layer 150]

The electron transport region may have i) a single-layered structure including a single layer including a single material, ii) a single-layered structure including a single layer including a plurality of different materials, or iii) a multi-layered structure having a plurality of layers including a plurality of different materials.

The electron transport region may include at least one selected from a buffer layer, a hole blocking layer, an electron control layer, an electron transport layer, and an electron injection layer, but embodiments of the present disclosure are not limited thereto.

For example, the electron transport region may have an electron transport layer/electron injection layer structure, a hole blocking layer/electron transport layer/electron injection layer structure, an electron control layer/electron transport layer/electron injection layer structure, or a buffer layer/electron transport layer/electron injection layer structure, wherein for each structure, constituting layers are sequentially stacked from an emission layer. However, embodiments of the structure of the electron transport region are not limited thereto.

The electron transport region may include a compound represented by Formula 1.

In one embodiment, the electron transport region (for example, a buffer layer, a hole blocking layer, an electron control layer, or an electron transport layer in the electron transport region) may include a metal-free compound containing at least one π electron-depleted nitrogen-containing ring.

The term "π electron-depleted nitrogen-containing ring," as used herein, indicates a $C_1$-$C_{60}$ heterocyclic group having at least one *—N=*' moiety as a ring-forming moiety.

For example, the "π electron-depleted nitrogen-containing ring" may be i) at least one selected from a 6-membered to 7-membered heteromonocyclic group having at least one *—N=*' moiety, ii) a heteropolycyclic group in which two or more selected from 5-membered to 7-membered heteromonocyclic groups each having at least one *—N=*' moiety are condensed with each other (e.g., combined together), or iii) a heteropolycyclic group in which at least one selected from 5-membered to 7-membered heteromonocyclic groups, each having at least one *—N=*' moiety, is condensed with (e.g., combined with) at least one $C_5$-$C_{60}$ carbocyclic group.

Examples of the π electron-depleted nitrogen-containing ring include an imidazole, a pyrazole, a thiazole, an isothiazole, an oxazole, an isoxazole, a pyridine, a pyrazine, a pyrimidine, a pyridazine, an indazole, a purine, a quinoline, an isoquinoline, a benzoquinoline, a phthalazine, a naphthyridine, a quinoxaline, a quinazoline, a cinnoline, a phenanthridine, an acridine, a phenanthroline, a phenazine, a benzimidazole, an isobenzothiazole, a benzoxazole, an isobenzoxazole, a triazole, a tetrazole, an oxadiazole, a triazine, thiadiazol, an imidazopyridine, an imidazopyrimidine, and an azacarbazole, but are not limited thereto.

For example, the electron transport region may include a compound represented by Formula 601:

$$[Ar_{601}]_{xe11}-[(L_{601})_{xe1}-R_{601}]_{xe21}. \quad \text{Formula 601}$$

In Formula 601,
Ar$_{601}$ may be a substituted or unsubstituted $C_5$-$C_{60}$ carbocyclic group or a substituted or unsubstituted $C_1$-$C_{60}$ heterocyclic group,
xe11 may be 1, 2, or 3,
L$_{601}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group,
xe1 may be an integer from 0 to 5,
R$_{601}$ may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si(Q$_{601}$)(Q$_{602}$)(Q$_{603}$), —C(=O)(Q$_{601}$), —S(=O)$_2$(Q$_{601}$), and —P(=O)(Q$_{601}$)(Q$_{602}$),
Q$_{601}$ to Q$_{603}$ may each independently be a $C_1$-$C_{10}$ alkyl group, a $C_1$-$C_{10}$ alkoxy group, a phenyl group, a biphenyl group, a terphenyl group, or a naphthyl group, and
xe21 may be an integer from 1 to 5.

In one embodiment, at least one of Ar$_{601}$(s) in the number of xe11 and R$_{601}$(s) in the number of xe21 may include the π electron-depleted nitrogen-containing ring.

In one embodiment, ring Ar$_{601}$ in Formula 601 may be selected from:
a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an iso-benzothiazole group, a benzoxazole group, an isobenzoxazole group, a triazole group, a tetrazole group, an oxadiazole group, a triazine group, a thiadiazole group, an imidazopyridine group, an imidazopyrimidine group, and an azacarbazole group; and
a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an iso-benzothiazole group, a benzoxazole group, an isobenzoxazole group, a triazole group, a tetrazole group, an oxadiazole group, a triazine group, a thiadiazole group, an imidazopyridine group, an imidazopyrimidine group, and an azacarbazole group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si(Q$_{31}$)(Q$_{32}$)(Q$_{33}$), —S(=O)$_2$(Q$_{31}$), and —P(=O)(Q$_{31}$)(Q$_{32}$), and
Q$_{31}$ to Q$_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

When xe11 in Formula 601 is two or more, two or more Ar$_{601}$(s) may be linked via a single bond.

In one or more embodiments, Ar$_{601}$ in Formula 601 may be an anthracene group.

In one or more embodiments, a compound represented by Formula 601 may be represented by Formula 601-1:

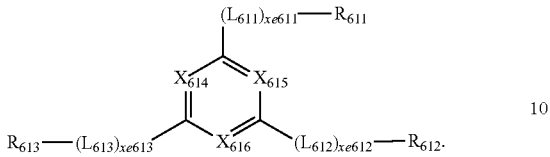

Formula 601-1

In Formula 601-1, $X_{614}$ may be N or $C(R_{614})$, $X_{615}$ may be N or $C(R_{615})$, $X_{616}$ may be N or $C(R_{616})$, and at least one selected from $X_{614}$ to $X_{616}$ may be N, $L_{611}$ to $L_{613}$ may each independently be the same as described in connection with $L_{601}$, xe611 to xe613 may each independently be the same as described in connection with xe1, $R_{611}$ to $R_{613}$ may each independently be the same as described in connection with $R_{601}$, and $R_{614}$ to $R_{616}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In one embodiment, $L_{601}$ and $L_{611}$ to $L_{613}$ in Formulae 601 and 601-1 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, but embodiments of the present disclosure are not limited thereto.

In one or more embodiments, xe1 and xe611 to xe613 in Formulae 601 and 601-1 may each independently be 0, 1, or 2.

In one or more embodiments, in Formulae 601 and 601-1, $R_{601}$ and $R_{611}$ to $R_{613}$ may each independently be selected from:
- a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group;
- a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and
- —S(=O)$_2$(Q$_{601}$) and —P(=O)(Q$_{601}$)(Q$_{602}$), and Q$_{601}$ and Q$_{602}$ may be the same as described above.

The electron transport region may include at least one compound selected from Compounds ET1 to ET36, but embodiments of the present disclosure are not limited thereto:

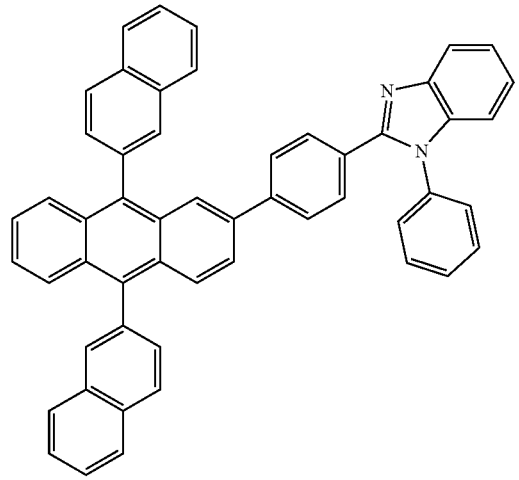

ET1

ET2
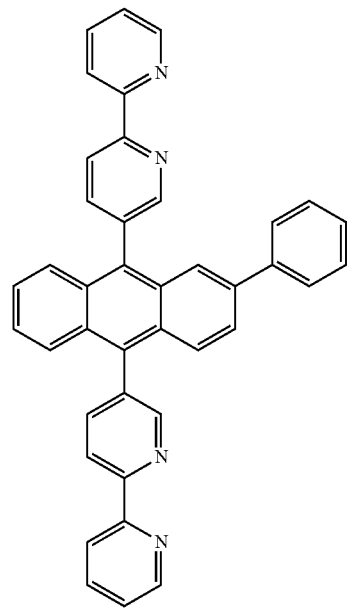
ET5
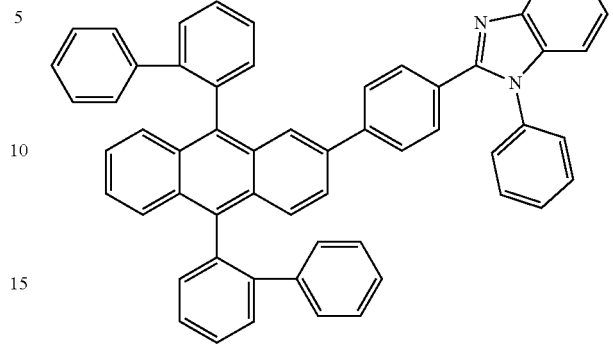
ET3
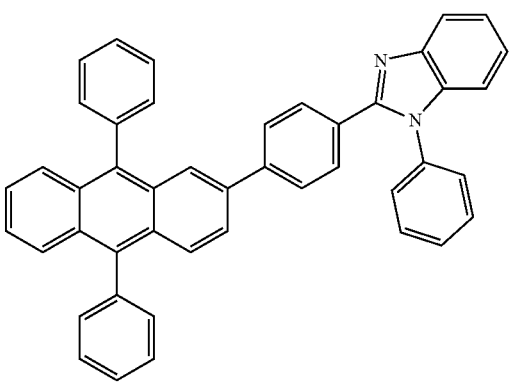
ET6
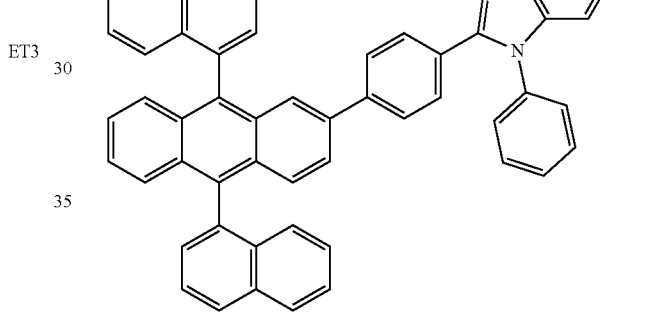
ET4
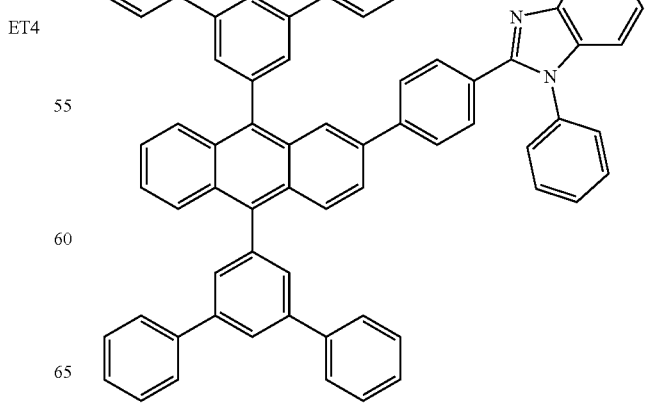
ET7

ET8
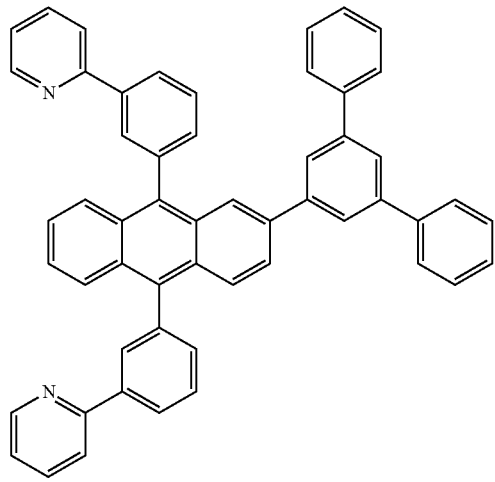
ET9
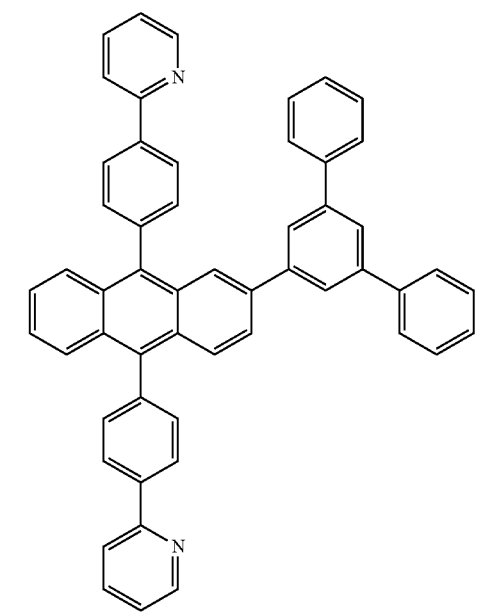
ET10
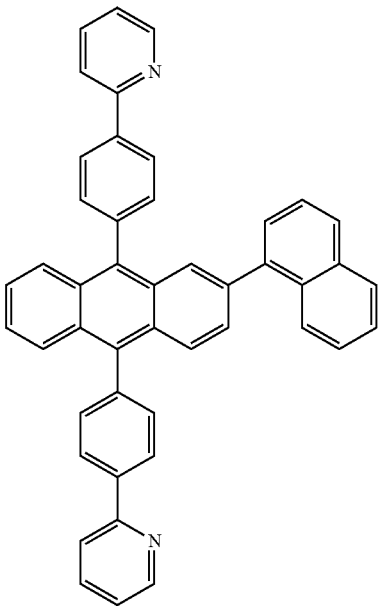
ET11
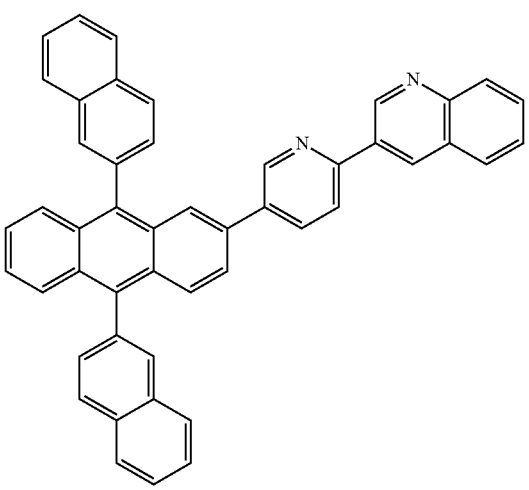
ET12
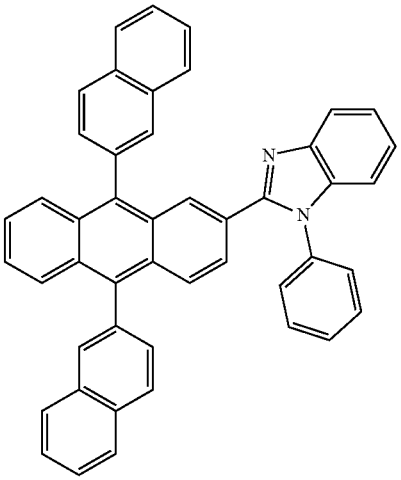

ET13
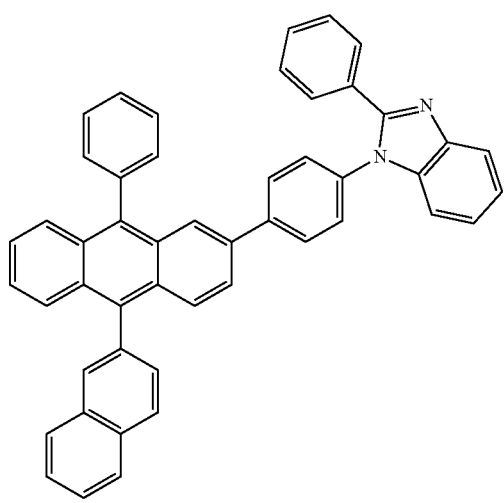
ET14
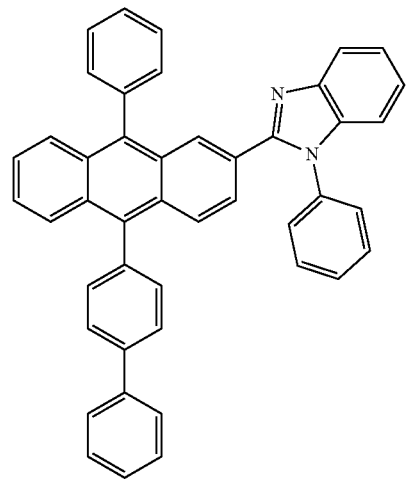
ET15
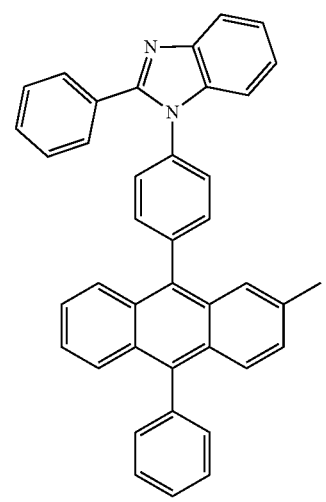
ET16
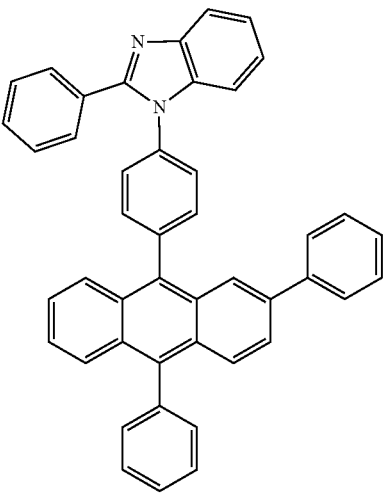
ET17
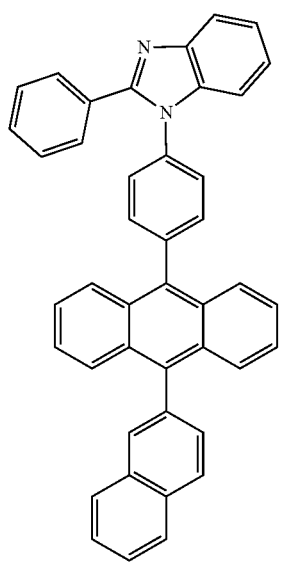
ET18
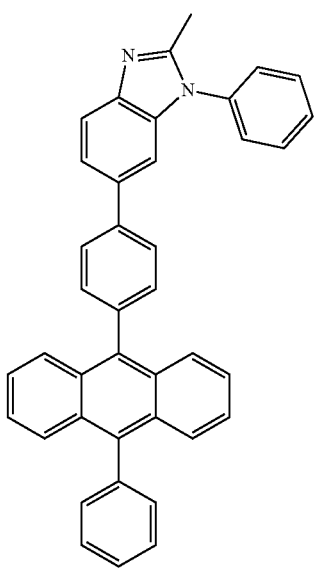

117
-continued
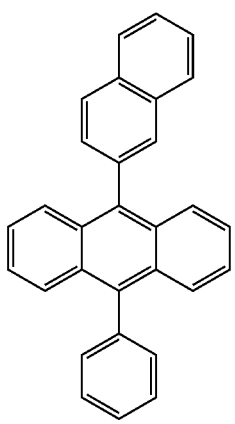
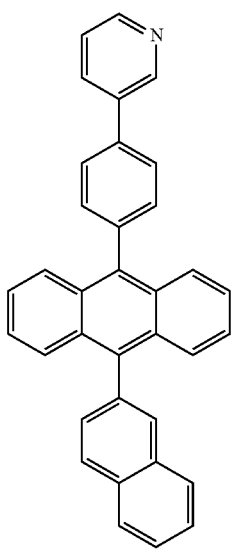
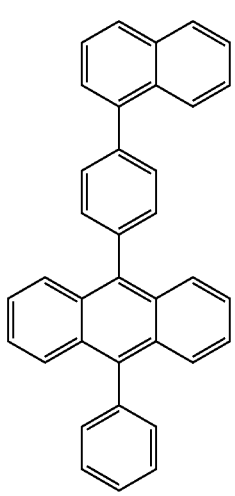
118
-continued
ET19
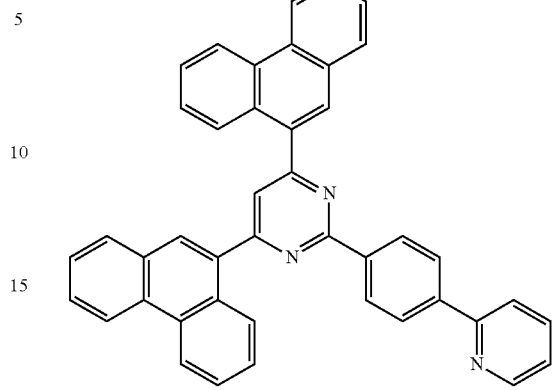
ET22
ET20
ET23
ET21
ET24
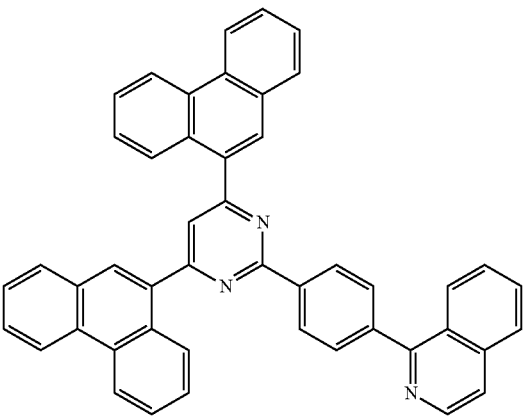

ET25
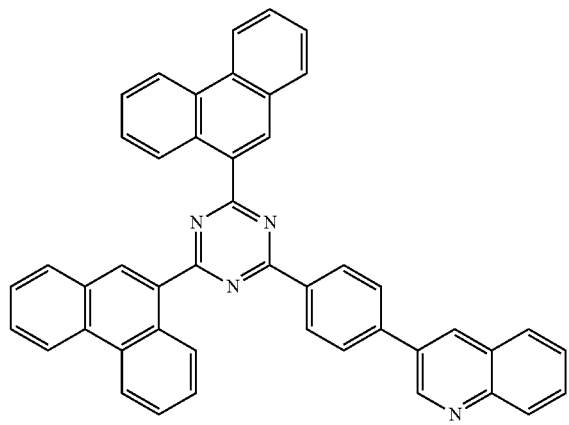
ET26
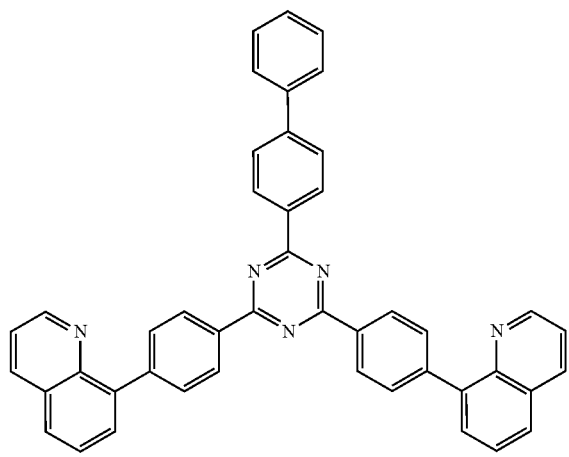
ET27
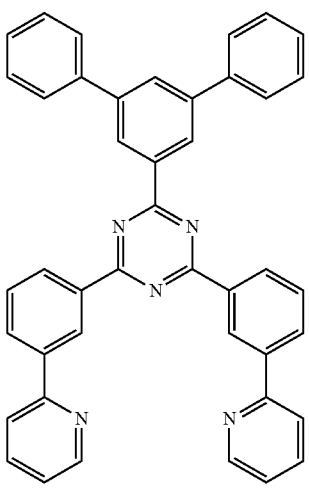
ET28
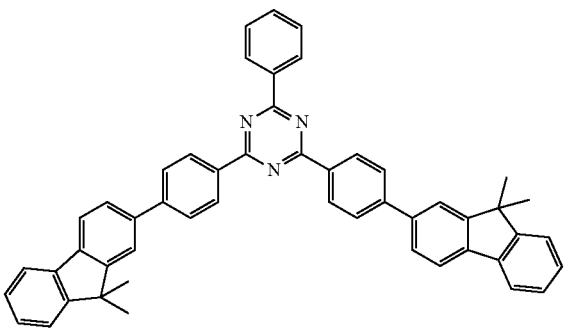
ET29
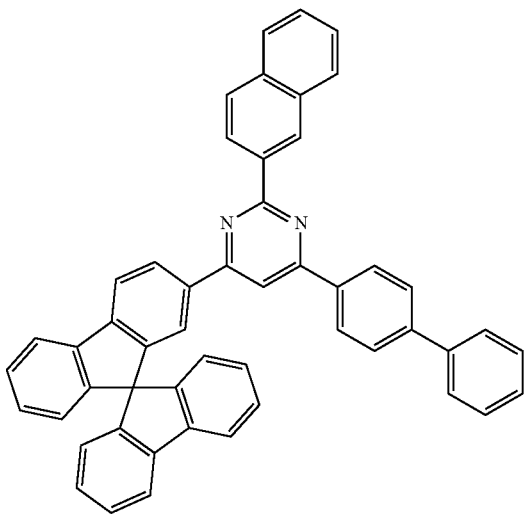
ET30

-continued
ET31
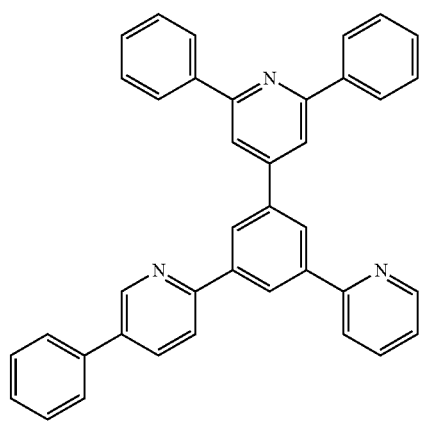
ET32
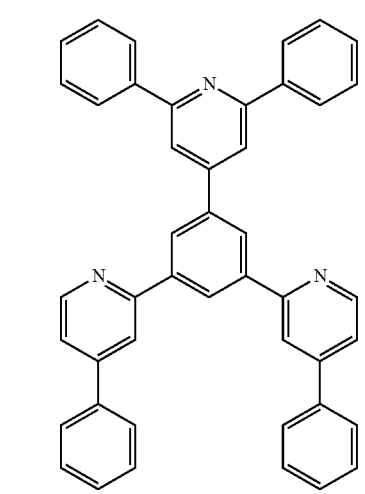
ET33
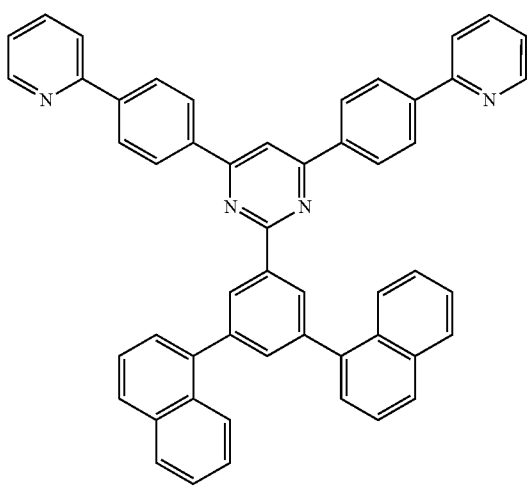
-continued
ET34
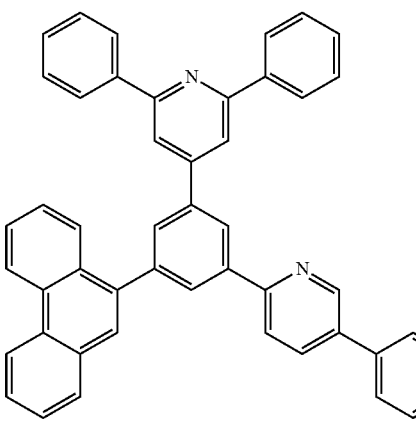
ET35
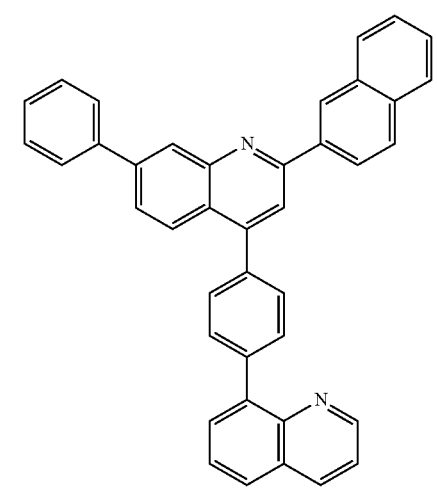
ET36
In one or more embodiments, the electron transport region may include at least one selected from 2,9-dimethyl-4,7-diphenyl-1,10-phenanthroline (BCP), 4,7-diphenyl-1,10-phenanthroline (Bphen), Alq$_3$, BAlq, 3-(biphenyl-4-yl)-5-(4-tert-butylphenyl)-4-phenyl-4H-1,2,4-triazole (TAZ), and NTAZ:

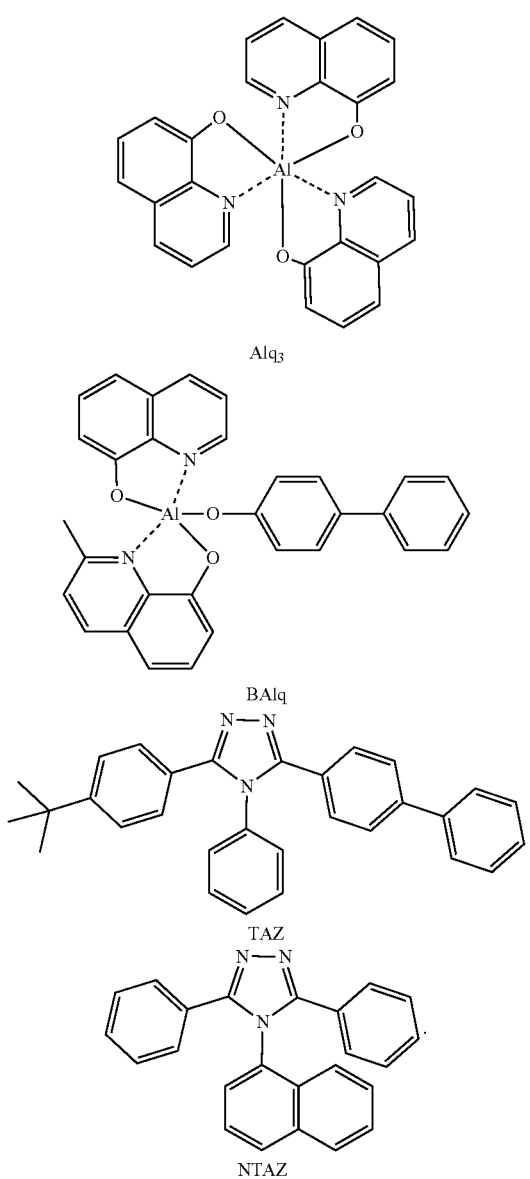

Alq₃

BAlq

TAZ

NTAZ

Thicknesses of the buffer layer, the hole blocking layer, and the electron control layer may each be in a range of about 20 Å to about 1,000 Å, for example, about 30 Å to about 300 Å. When the thicknesses of the buffer layer, the hole blocking layer, and the electron control layer are within these ranges, the electron blocking layer may have excellent electron blocking characteristics or electron control characteristics without a substantial increase in driving voltage.

A thickness of the electron transport layer may be in a range of about 100 Å to about 1,000 Å, for example, about 150 Å to about 500 Å. When the thickness of the electron transport layer is within the range described above, the electron transport layer may have suitable or satisfactory electron transport characteristics without a substantial increase in driving voltage.

The electron transport region (for example, the electron transport layer in the electron transport region) may further include, in addition to the materials described above, a metal-containing material.

The metal-containing material may include at least one selected from alkali metal complex and alkaline earth-metal complex. The alkali metal complex may include a metal ion selected from a $L_1$ ion, a Na ion, a K ion, a Rb ion, and a Cs ion, and the alkaline earth-metal complex may include a metal ion selected from a Be ion, a Mg ion, a Ca ion, a Sr ion, and a Ba ion. A ligand coordinated with the metal ion of the alkali metal complex or the alkaline earth-metal complex may be selected from a hydroxy quinoline, a hydroxy isoquinoline, a hydroxy benzoquinoline, a hydroxy acridine, a hydroxy phenanthridine, a hydroxy phenyloxazole, a hydroxy phenylthiazole, a hydroxy diphenyloxadiazole, a hydroxy diphenylthiadiazol, a hydroxy phenylpyridine, a hydroxy phenylbenzimidazole, a hydroxy phenylbenzothiazole, a bipyridine, a phenanthroline, and a cyclopentadiene, but embodiments of the present disclosure are not limited thereto.

For example, the metal-containing material may include a $L_1$ complex. The $L_1$ complex may include, for example, Compound ET-D1 (lithium quinolate, LiQ) or ET-D2:

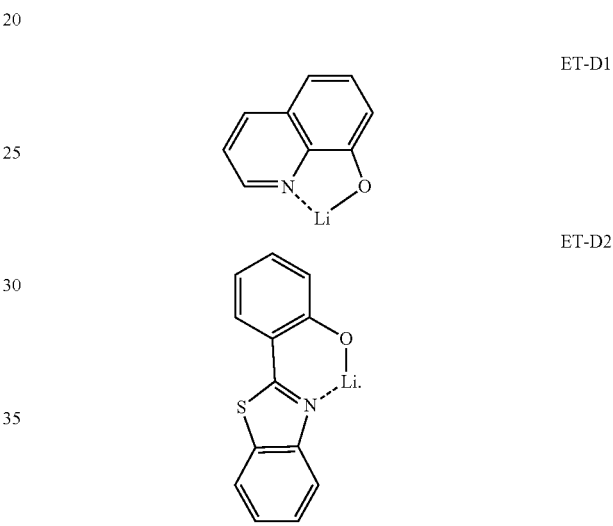

ET-D1

ET-D2

The electron transport region may include an electron injection layer that facilitates injection of electrons from the second electrode 190. The electron injection layer may directly contact the second electrode 190.

The electron injection layer may have i) a single-layered structure including a single layer including a single material, ii) a single-layered structure including a single layer including a plurality of different materials, or iii) a multi-layered structure having a plurality of layers including a plurality of different materials.

The electron injection layer may include an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof.

The alkali metal may be selected from $L_1$, Na, K, Rb, and Cs. In one embodiment, the alkali metal may be $L_1$, Na, or Cs. In one or more embodiments, the alkali metal may be $L_1$ or Cs, but embodiments of the present disclosure are not limited thereto.

The alkaline earth metal may be selected from Mg, Ca, Sr, and Ba.

The rare earth metal may be selected from Sc, Y, Ce, Tb, Yb, and Gd.

The alkali metal compound, the alkaline earth-metal compound, and the rare earth metal compound may be selected from oxides and halides (for example, fluorides, chlorides, bromides, or iodides) of the alkali metal, the alkaline earth-metal, and the rare earth metal.

The alkali metal compound may be selected from alkali metal oxides, such as $Li_2O$, $Cs_2O$, or $K_2O$, and alkali metal halides, such as LiF, NaF, CsF, KF, LiI, NaI, CsI, or KI. In one embodiment, the alkali metal compound may be selected from LiF, $Li_2O$, NaF, LiI, NaI, CsI, and KI, but embodiments of the present disclosure are not limited thereto.

The alkaline earth metal compound may be selected from BaO, SrO, CaO, $Ba_xSr_{1-x}O$ (0<x<1), and $Ba_xCa_{1-x}O$ (0<x<1). In one embodiment, the alkaline earth metal compound may be selected from BaO, SrO, and CaO, but embodiments of the present disclosure are not limited thereto.

The rare earth metal compound may be selected from $YbF_3$, $ScF_3$, $ScO_3$, $Y_2O_3$, $Ce_2O_3$, $GdF_3$, and $TbF_3$. In one embodiment, the rare earth metal compound may be selected from $YbF_3$, $ScF_3$, $TbF_3$, $YbI_3$, $ScI_3$, and $TbI_3$, but embodiments of the present disclosure are not limited thereto.

The alkali metal complex, the alkaline earth-metal complex, and the rare earth metal complex may include an ion of alkali metal, alkaline earth-metal, and rare earth metal as described above, and a ligand coordinated with a metal ion of the alkali metal complex, the alkaline earth-metal complex, or the rare earth metal complex may be selected from hydroxy quinoline, hydroxy isoquinoline, hydroxy benzoquinoline, hydroxy acridine, hydroxy phenanthridine, hydroxy phenyl oxazole, hydroxy phenylthiazole, hydroxy diphenyl oxadiazole, hydroxy diphenylthiadiazol, hydroxy phenylpyridine, hydroxy phenylbenzimidazole, hydroxy phenylbenzothiazole, bipyridine, phenanthroline, and cyclopentadiene, but embodiments of the present disclosure are not limited thereto.

The electron injection layer may consist of an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof, as described above. In one or more embodiments, the electron injection layer may further include an organic material. When the electron injection layer further includes an organic material, an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof may be homogeneously or non-homogeneously dispersed in a matrix including the organic material.

A thickness of the electron injection layer may be in a range of about 1 Å to about 100 Å, for example, about 3 Å to about 90 Å. When the thickness of the electron injection layer is within the range described above, the electron injection layer may have suitable or satisfactory electron injection characteristics without a substantial increase in driving voltage.

[Second Electrode 190]

The second electrode 190 may be disposed on the organic layer 150 having such a structure. The second electrode 190 may be a cathode which is an electron injection electrode, and in this regard, a material for forming the second electrode 190 may be selected from metal, an alloy, an electrically conductive compound, and a combination thereof, which have a relatively low work function.

The second electrode 190 may include at least one selected from lithium ($L_i$), silver (Ag), magnesium (Mg), aluminum (Al), aluminum-lithium (Al—Li), calcium (Ca), magnesium-indium (Mg—In), magnesium-silver (Mg—Ag), ITO, and IZO, but embodiments of the present disclosure are not limited thereto. The second electrode 190 may be a transmissive electrode, a semi-transmissive electrode, or a reflective electrode.

The second electrode 190 may have a single-layered structure, or a multi-layered structure including two or more layers.

Figure 3:
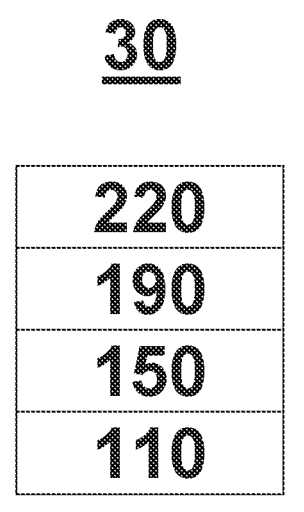
Figure 4:
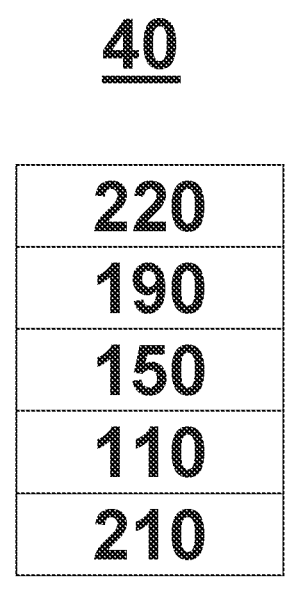

Description of FIGS. 2 to 4

Figure 2:
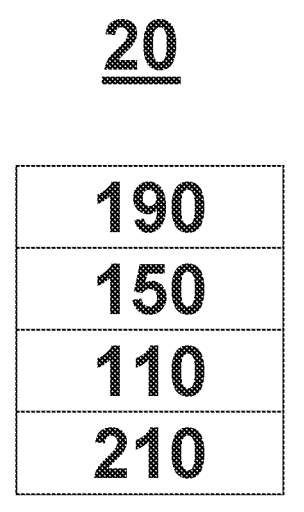

An organic light-emitting device 20 of FIG. 2 includes a first capping layer 210, a first electrode 110, an organic layer 150, and a second electrode 190 which are sequentially stacked in this stated order, an organic light-emitting device 30 of FIG. 3 includes a first electrode 110, an organic layer 150, a second electrode 190, and a second capping layer 220 which are sequentially stacked in this stated order, and an organic light-emitting device 40 of FIG. 4 includes a first capping layer 210, a first electrode 110, an organic layer 150, a second electrode 190, and a second capping layer 220.

Regarding FIGS. 2 to 4, the first electrode 110, the organic layer 150, and the second electrode 190 may be understood by referring to the description presented in connection with FIG. 1.

In the organic layer 150 of each of the organic light-emitting devices 20 and 40, light generated in an emission layer may pass through the first electrode 110, which is a semi-transmissive electrode or a transmissive electrode, and the first capping layer 210 toward the outside, and in the organic layer 150 of each of the organic light-emitting devices 30 and 40, light generated in an emission layer may pass through the second electrode 190, which is a semi-transmissive electrode or a transmissive electrode, and the second capping layer 220 toward the outside.

The first capping layer 210 and the second capping layer 220 may increase external luminescent efficiency according to the principle of constructive interference.

The first capping layer 210 and the second capping layer 220 may each independently be an organic capping layer including an organic material, an inorganic capping layer including an inorganic material, or a composite capping layer including an organic material and an inorganic material.

At least one selected from the first capping layer 210 and the second capping layer 220 may each independently include at least one material selected from carbocyclic compounds, heterocyclic compounds, amine-based compounds, porphyrine derivatives, phthalocyanine derivatives, naphthalocyanine derivatives, alkali metal complexes, and alkaline earth-based complexes. The carbocyclic compound, the heterocyclic compound, and the amine-based compound may be optionally substituted with a substituent containing at least one element selected from O, N, S, Se, Si, F, Cl, Br, and I.

In one embodiment, at least one selected from the first capping layer 210 and the second capping layer 220 may each independently include an amine-based compound.

In one embodiment, at least one selected from the first capping layer 210 and the second capping layer 220 may each independently include the compound represented by Formula 201 or the compound represented by Formula 202.

In one or more embodiments, at least one selected from the first capping layer 210 and the second capping layer 220 may each independently include a compound selected from Compounds HT28 to HT33 (shown elsewhere herein) and Compounds CP1 to CP5, but embodiments of the present disclosure are not limited thereto:

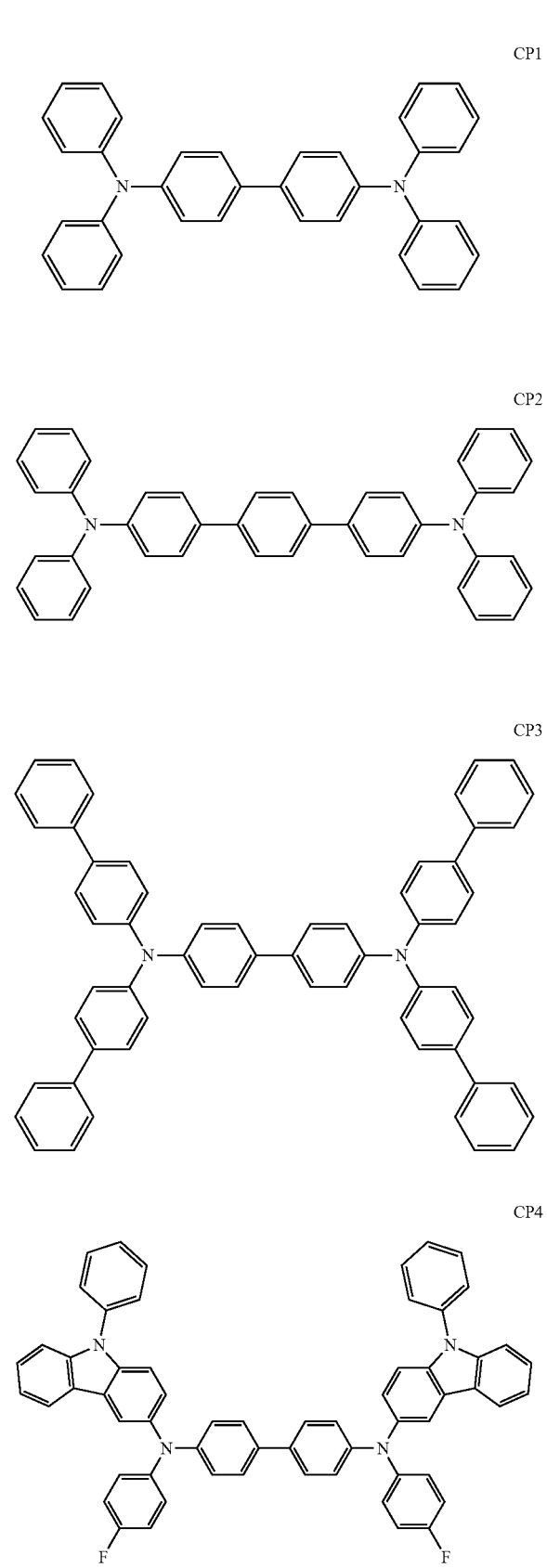

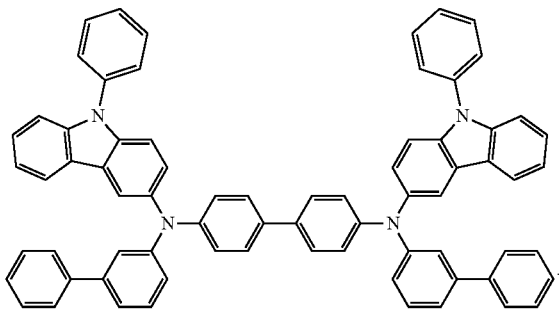

Hereinbefore, the organic light-emitting device according to an embodiment has been described in connection with FIGS. 1 to 4. However, embodiments of the present disclosure are not limited thereto.

Layers constituting the hole transport region, an emission layer, and layers constituting the electron transport region may be formed in a certain region by using one or more suitable methods selected from vacuum deposition, spin coating, casting, Langmuir-Blodgett (LB) deposition, ink-jet printing, laser-printing, and laser-induced thermal imaging.

When layers constituting the hole transport region, an emission layer, and layers constituting the electron transport region are formed by vacuum deposition, the vacuum deposition may be performed at a deposition temperature of about 100° C. to about 500° C., at a vacuum degree of about $10^{-8}$ to torr to about $10^{-3}$ torr, and at a deposition speed of about 0.01 Å/sec to about 100 Å/sec by taking into account a material to be included in a layer to be formed, and the structure of a layer to be formed.

When layers constituting the hole transport region, an emission layer, and layers constituting the electron transport region are formed by spin coating, the spin coating may be performed at a coating speed of about 2,000 rpm to about 5,000 rpm and at a heat treatment temperature of about 80° C. to 200° C. by taking into account a material to be included in a layer to be formed, and the structure of a layer to be formed.

[General Definition of Substituents]

The term "$C_1$-$C_{60}$ alkyl group," as used herein, refers to a linear or branched aliphatic saturated hydrocarbon monovalent group having 1 to 60 carbon atoms, and examples thereof include a methyl group, an ethyl group, a propyl group, an isobutyl group, a sec-butyl group, a tert-butyl group, a pentyl group, an iso-amyl group, and a hexyl group. The term "$C_1$-$C_{60}$ alkylene group," as used herein, refers to a divalent group having substantially the same structure as the $C_1$-$C_{60}$ alkyl group, except that the $C_1$-$C_{60}$ alkylene group is divalent instead of monovalent.

The term "$C_2$-$C_{60}$ alkenyl group," as used herein, refers to a hydrocarbon group having at least one carbon-carbon double bond at a main chain (e.g., in the middle) or at a terminus of the $C_2$-$C_{60}$ alkyl group, and examples thereof include an ethenyl group, a propenyl group, and a butenyl group. The term "$C_2$-$C_{60}$ alkenylene group," as used herein, refers to a divalent group having substantially the same structure as the $C_2$-$C_{60}$ alkenyl group, except that the $C_2$-$C_{60}$ alkenylene group is divalent instead of monovalent.

The term "$C_2$-$C_{60}$ alkynyl group," as used herein, refers to a hydrocarbon group having at least one carbon-carbon triple bond at a main chain (e.g., in the middle) or at a terminus of the $C_2$-$C_{60}$ alkyl group, and examples thereof include an ethynyl group, and a propynyl group. The term "$C_2$-$C_{60}$ alkynylene group," as used herein, refers to a divalent group having substantially the same structure as the $C_2$-$C_{60}$ alkynyl group, except that the $C_2$-$C_{60}$ alkynylene group is divalent instead of monovalent.

The term "$C_1$-$C_{60}$ alkoxy group," as used herein, refers to a monovalent group represented by —$OA_{101}$ (wherein $A_{101}$ is the $C_1$-$C_{60}$ alkyl group), and examples thereof include a methoxy group, an ethoxy group, and an isopropyloxy group.

The term "$C_3$-$C_{10}$ cycloalkyl group," as used herein, refers to a monovalent saturated hydrocarbon monocyclic group having 3 to 10 carbon atoms, and examples thereof include a cyclopropyl group, a cyclobutyl group, a cyclopentyl group, a cyclohexyl group, and a cycloheptyl group. The term "$C_3$-$C_{10}$ cycloalkylene group," as used herein, refers to a divalent group having substantially the same structure as the $C_3$-$C_{10}$ cycloalkyl group, except that the $C_3$-$C_{10}$ cycloalkylene group is divalent instead of monovalent.

The term "$C_1$-$C_{10}$ heterocycloalkyl group," as used herein, refers to a monovalent monocyclic group having at least one heteroatom selected from N, O, Si, P, and S as a ring-forming atom and 1 to 10 carbon atoms, and examples thereof include a 1,2,3,4-oxatriazolidinyl group, a tetrahydrofuranyl group, and a tetrahydrothiophenyl group. The term "$C_1$-$C_{10}$ heterocycloalkylene group," as used herein, refers to a divalent group having substantially the same structure as the $C_1$-$C_{10}$ heterocycloalkyl group, except that the $C_1$-$C_{10}$ heterocycloalkylene group is divalent instead of monovalent.

The term "$C_3$-$C_{10}$ cycloalkenyl group," as used herein, refers to a monovalent monocyclic group that has 3 to 10 carbon atoms and at least one carbon-carbon double bond in the ring thereof and no aromaticity (e.g., the monocyclic group is not aromatic), and examples thereof include a cyclopentenyl group, a cyclohexenyl group, and a cycloheptenyl group. The term "$C_3$-$C_{10}$ cycloalkenylene group," as used herein, refers to a divalent group having substantially the same structure as the $C_3$-$C_{10}$ cycloalkenyl group, except that the $C_3$-$C_{10}$ cycloalkenylene group is divalent instead of monovalent.

The term "$C_1$-$C_{10}$ heterocycloalkenyl group," as used herein, refers to a monovalent monocyclic group that has at least one heteroatom selected from N, O, Si, P, and S as a ring-forming atom, 1 to 10 carbon atoms, and at least one carbon-carbon double bond in its ring. Non-limiting examples of the $C_1$-$C_{10}$ heterocycloalkenyl group include a 4,5-dihydro-1,2,3,4-oxatriazolyl group, a 2,3-dihydrofuranyl group, and a 2,3-dihydrothiophenyl group. The term "$C_1$-$C_{10}$ heterocycloalkenylene group," as used herein, refers to a divalent group having substantially the same structure as the $C_1$-$C_{10}$ heterocycloalkenyl group, except that the $C_1$-$C_{10}$ heterocycloalkenylene group is divalent instead of monovalent.

The term "$C_6$-$C_{60}$ aryl group," as used herein, refers to a monovalent group having a carbocyclic aromatic system having 6 to 60 carbon atoms, and a $C_6$-$C_{60}$ arylene group used herein refers to a divalent group having a carbocyclic aromatic system having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other (e.g., combined together).

The term "$C_1$-$C_{60}$ heteroaryl group," as used herein, refers to a monovalent group having a carbocyclic aromatic system that has at least one heteroatom selected from N, O, Si, P, and S as a ring-forming atom, in addition to 1 to 60 carbon atoms. The term "$C_1$-$C_{60}$ heteroarylene group," as used herein, refers to a divalent group having a carbocyclic aromatic system that has at least one heteroatom selected from N, O, Si, P, and S as a ring-forming atom, in addition to 1 to 60 carbon atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be condensed with each other (e.g., combined together).

The term "$C_6$-$C_{60}$ aryloxy group," as used herein, refers to —$OA_{102}$ (wherein $A_{102}$ is the $C_6$-$C_{60}$ aryl group), and a $C_6$-$C_{60}$ arylthio group used herein indicates —$SA_{103}$ (wherein $A_{103}$ is the $C_6$-$C_{60}$ aryl group).

The term "monovalent non-aromatic condensed polycyclic group," as used herein, refers to a monovalent group (for example, having 8 to 60 carbon atoms) having two or more rings condensed with each other (e.g., combined together), only carbon atoms as ring-forming atoms, and no aromaticity in its entire molecular structure (e.g., the entire molecule is not aromatic). A detailed example of the monovalent non-aromatic condensed polycyclic group is a fluorenyl group. The term "divalent non-aromatic condensed polycyclic group," used herein, refers to a divalent group having substantially the same structure as the monovalent non-aromatic condensed polycyclic group, except that the divalent non-aromatic condensed polycyclic group is divalent instead of monovalent.

The term "monovalent non-aromatic condensed heteropolycyclic group," as used herein, refers to a monovalent group (for example, having 1 to 60 carbon atoms) having two or more rings condensed to each other (e.g., combined together), at least one heteroatom selected from N, O, Si, P, and S, other than carbon atoms, as a ring-forming atom, and no aromaticity in its entire molecular structure (e.g., the entire molecule is not aromatic). An example of the monovalent non-aromatic condensed heteropolycyclic group is a carbazolyl group. The term "divalent non-aromatic condensed heteropolycyclic group," as used herein, refers to a divalent group having substantially the same structure as the monovalent non-aromatic condensed heteropolycyclic group, except that the divalent non-aromatic condensed heteropolycyclic group is divalent instead of monovalent.

The term "$C_5$-$C_{60}$ carbocyclic group," as used herein, refers to a monocyclic or polycyclic group having 5 to 60 carbon atoms in which a ring-forming atom is a carbon atom only (e.g., the ring itself only includes carbon atoms). The $C_5$-$C_{60}$ carbocyclic group may be an aromatic carbocyclic group or a non-aromatic carbocyclic group. The $C_5$-$C_{60}$ carbocyclic group may be a ring, such as benzene, a monovalent group, such as a phenyl group, or a divalent group, such as a phenylene group. In one or more embodiments, depending on the number of substituents connected to the $C_5$-$C_{60}$ carbocyclic group, the $C_5$-$C_{60}$ carbocyclic group may be a trivalent group or a quadrivalent group.

The term "$C_1$-$C_{60}$ heterocyclic group," as used herein, refers to a group having the same structure as the $C_1$-$C_{60}$ carbocyclic group, except that as a ring-forming atom, at least one heteroatom selected from N, O, Si, P, and S is used in addition to carbon (the number of carbon atoms may be in a range of 1 to 60).

At least one substituent of the substituted $C_5$-$C_{60}$ carbocyclic group, the substituted $C_1$-$C_{60}$ heterocyclic group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium (-D), —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$) and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

The term "Ph," as used herein, refers to a phenyl group, the term "Me," as used herein, refers to a methyl group, the term "Et," as used herein, refers to an ethyl group, the term "ter-Bu" or "Bu$^t$," as used herein, refers to a tert-butyl group, and the term "OMe," as used herein, refers to a methoxy group.

The term "biphenyl group," as used herein, refers to "a phenyl group substituted with a phenyl group." In other words, the "biphenyl group" is a substituted phenyl group having a $C_6$-$C_{60}$ aryl group as a substituent.

The term "terphenyl group," as used herein, refers to "a phenyl group substituted with a biphenyl group." In other words, the "terphenyl group" is a phenyl group having, as a substituent, a $C_6$-$C_{60}$ aryl group substituted with a $C_6$-$C_{60}$ aryl group.

and *' used herein, unless defined otherwise, each refer to a binding site to a neighboring atom in a corresponding formula.

Hereinafter, a compound according to embodiments and an organic light-emitting device according to embodiments will be described in more detail with reference to Synthesis Examples and Examples. The wording "B was used instead of A" used in describing Synthesis Examples refers to that an identical (e.g., substantially identical) molar equivalent of B was used in place of A.

EXAMPLES

Synthesis Example 1: Synthesis of Compound 2

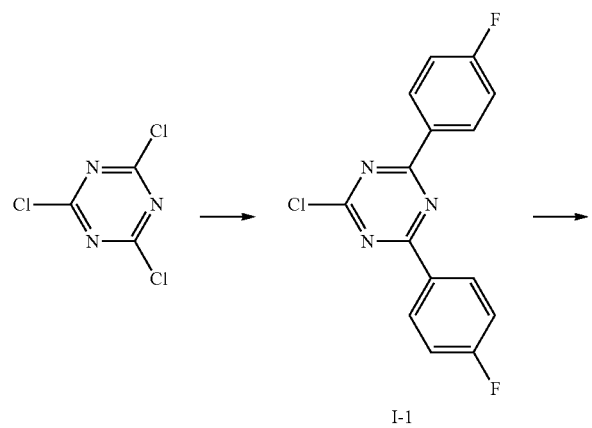

I-1

-continued

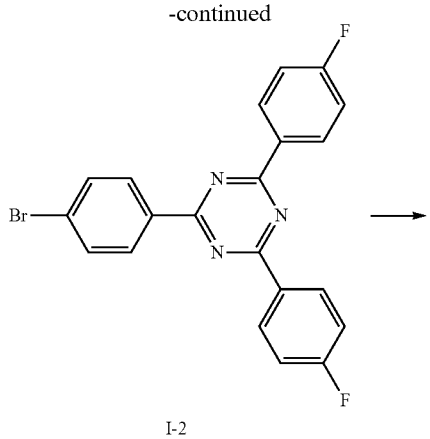

I-2

2

Synthesis of Intermediate 1-1

1.84 g (10 mmol) of cyanuric chloride was dissolved in 30 mL of tetrahydrofuran (THF), 26 mL of 4-fluorophenyl magnesium bromide (1.0 M in THF) was added thereto at a temperature of 0° C., and the reaction solution was stirred at a temperature of 35° C. for 12 hours. Then, the reaction solution was cooled to room temperature, and an organic layer was extracted therefrom three times by using 60 mL of water and 60 mL of diethylether. The extracted organic layer was dried by using magnesium sulfate, and a solvent was evaporated therefrom. Then, the residue obtained therefrom was separated and purified by silica gel column chromatography to obtain 1.36 g (yield: 45%) of Intermediate 1-1. The obtained compound was identified by LC-MS.

$C_{15}H_8ClF_2N_3$: M+1 303.4.

Synthesis of Intermediate 1-2

3.34 g (11.0 mmol) of Intermediate I-1, 2.00 g (10.0 mmol) of 4-bromophenyl boronic acid, 0.58 g (0.50 mmol) of Pd(PPh$_3$)$_4$, and 4.15 g (30.0 mmol) of K$_2$CO$_3$ were dissolved in 60 mL of a mixed solution including THF and H$_2$O (2/1) and stirred at a temperature of 80° C. for 16 hours. Then, the reaction solution was cooled to room temperature, and an organic layer was extracted therefrom three times by using 60 mL of water and 60 mL of diethylether. The extracted organic layer was dried by using magnesium sulfate, and a solvent was evaporated therefrom. Then, the residue obtained therefrom was separated and purified by silica gel column chromatography to obtain 2.12 g (yield: 50%) of Intermediate 1-2. The obtained compound was identified by LC-MS.

$C_{21}H_{12}BrF_2N_3$: M+1 423.0.

Synthesis of Compound 2

4.23 g (10 mmol) of Intermediate 1-2, 1.98 g (10 mmol) of [1,1'-biphenyl]-4-ylboronic acid, 0.58 g (0.5 mmol) of Pd(PPh$_3$)$_4$, and 4.14 g (30 mmol) of K$_2$CO$_3$ were dissolved in 60 mL of a mixed solution including THF and H$_2$O (2/1) and stirred at a temperature of 80° C. for 16 hours. Then, the reaction solution was cooled to room temperature, and an organic layer was extracted therefrom three times by using 40 mL of water and 50 mL of ethylether. The extracted organic layer was dried by using magnesium sulfate, and a solvent was evaporated therefrom. Then, the residue obtained therefrom was separated and purified by silica gel column chromatography to obtain 4.08 g (yield: 82%) of Compound 2. The obtained compound was identified by MS/FAB and $^1$H NMR.

$C_{33}H_{21}F_2N_3$ cal. 497.17. found 497.16.

Synthesis Example 2: Synthesis of Compound 5

5.17 g (yield: 83%) of Compound 5 was synthesized in substantially the same manner as in Synthesis of Compound 2, except that (4-(4-phenylnaphthalen-1-yl)phenyl)boronic acid was used instead of [1,1'-biphenyl]-4-ylboronic acid. The obtained compound was identified by MS/FAB and $^1$H NMR.

$C_{43}H_{27}F_2N_3$ cal. 623.22. found 623.23.

Synthesis Example 3: Synthesis of Compound 9

4.73 g (yield: 76%) of Compound 9 was synthesized in substantially the same manner as in Synthesis of Compound 2, except that (6-([1,1'-biphenyl]-4-yl)naphthalen-2-yl)boronic acid was used instead of [1,1'-biphenyl]-4-ylboronic acid. The obtained compound was identified by MS/FAB and $^1$H NMR.

$C_{43}H_{27}F_2N_3$ cal. 623.22. found 623.21.

Synthesis Example 4: Synthesis of Compound 25

4.42 g (yield: 72%) of Compound 25 was synthesized in substantially the same manner as in Synthesis of Compound 2, except that (9,9-dimethyl-7-phenyl-9H-fluoren-2-yl)boronic acid was used instead of [1,1'-biphenyl]-4-ylboronic acid. The obtained compound was identified by MS/FAB and $^1$H NMR.

$C_{42}H_{29}F_2N_3$ cal. 613.23. found 613.22.

Synthesis Example 5: Synthesis of Compound 31

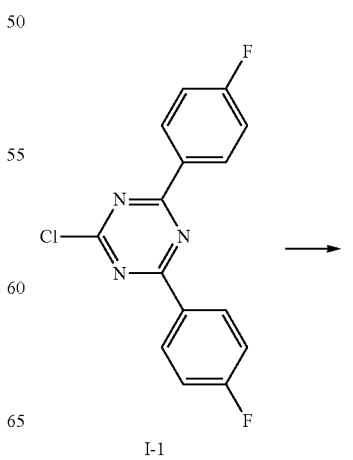

I-1

-continued

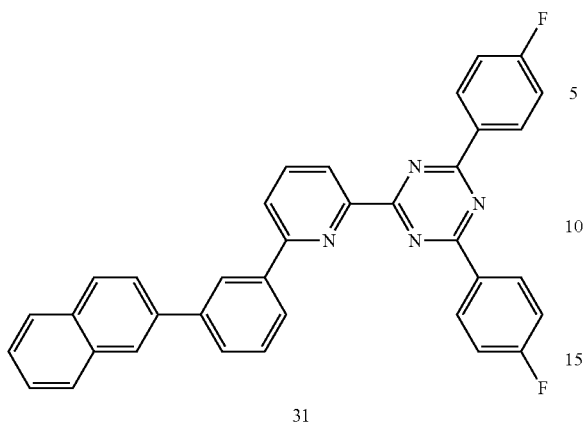

31

3.03 g (10 mmol) of Intermediate I-1, 3.25 g (10 mmol) of (6-(3-(naphthalen-2-yl)phenyl)pyridin-2-yl)boronic acid, 0.58 g (0.5 mmol) of Pd(PPh$_3$)$_4$, and 4.14 g (30 mmol) of K$_2$CO$_3$ were dissolved in 60 mL of a mixed solution including THF and H$_2$O (2/1) and stirred at a temperature of 80° C. for 16 hours. Then, the reaction solution was cooled to room temperature, and an organic layer was extracted therefrom three times by using 40 mL of water and 50 mL of ethylether. The extracted organic layer was dried by using magnesium sulfate, and a solvent was evaporated therefrom. Then, the residue obtained therefrom was separated and purified by silica gel column chromatography to obtain 3.12 g (yield: 57%) of Compound 31. The obtained compound was identified by MS/FAB and $^1$H NMR.

C$_{36}$H$_{22}$F$_2$N$_4$ cal. 548.18. found 548.19.

Synthesis Example 6: Synthesis of Compound 40

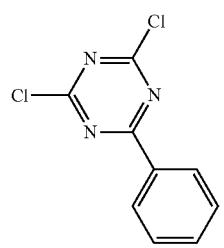

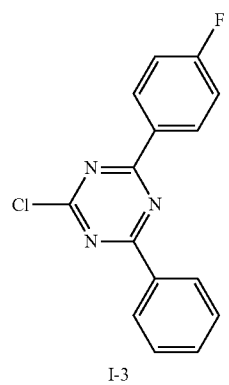

I-3

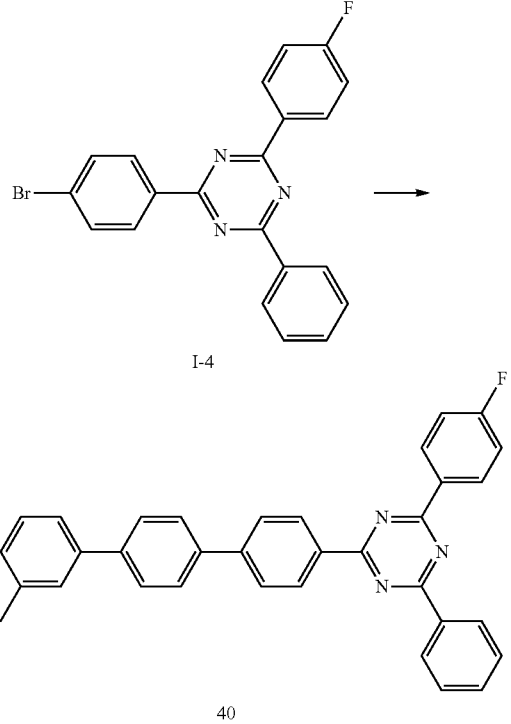

I-4

Synthesis of Intermediate 1-3

2.25 g (10 mmol) of 2,4-dichloro-6-phenyl-1,3,5-triazine was dissolved in 30 mL of THF, 10 mL of 4-fluorophenyl magnesium bromide (1.0 M in THF) was added thereto at a temperature of 0° C., and the reaction solution was stirred at a temperature of 35° C. for 12 hours. Then, the reaction solution was cooled to room temperature, and an organic layer was extracted therefrom three times by using 60 mL of water and 60 mL of diethylether. The extracted organic layer was dried by using magnesium sulfate, and a solvent was evaporated therefrom. Then, the residue obtained therefrom was separated and purified by silica gel column chromatography to obtain 1.31 g (yield: 46%) of Intermediate 1-3. The obtained compound was identified by LC-MS.

C$_{15}$H$_9$ClFN$_3$: M+1 285.1.

Synthesis of Intermediate 1-4

2.03 g (yield: 50%) of Intermediate 1-4 was synthesized in substantially the same manner as in Synthesis of Intermediate 1-2, except that Intermediate 1-3 was used instead of Intermediate 1-1. The obtained compound was identified by LC-MS.

C$_{21}$H$_{13}$BrFN$_3$: M+1 405.0.

Synthesis of Compound 40

4.05 g (10 mmol) of Intermediate 1-4, 2.48 g (10 mmol) of (4-(naphthalen-2-yl)phenyl)boronic acid, 0.58 g (0.5 mmol) of Pd(PPh$_3$)$_4$, and 4.14 g (30 mmol) of K$_2$CO$_3$ were dissolved in 60 mL of a mixed solution including THF and H$_2$O (2/1) and stirred at a temperature of 80° C. for 16 hours. The reaction solution was cooled to room temperature, and an organic layer was extracted therefrom three times by using 40 mL of water and 50 mL of ethylether. The extracted organic layer was dried by using magnesium sulfate, and a solvent was evaporated therefrom. Then, the residue obtained therefrom was separated and purified by silica gel column chromatography to obtain 4.07 g (yield: 77%) of Compound 40. The obtained compound was identified by MS/FAB and $^1$H NMR.

C$_{37}$H$_{24}$FN$_3$ cal. 529.20. found 529.21.

Synthesis Example 7: Synthesis of Compound 45

4.36 g (yield: 70%) of Compound 45 was synthesized in substantially the same manner as in Synthesis of Compound 2, except that 3-fluorophenyl magnesium bromide was used instead of 4-fluorophenyl magnesium bromide, and (4'-(naphthalen-2-yl)-[1,1'-biphenyl]-4-yl)boronic acid was used instead of [1,1'-biphenyl]-4-ylboronic acid. The obtained compound was identified by MS/FAB and $^1$H NMR.

$C_{43}H_{27}F_2N_3$ cal. 623.22. found 623.22.

Synthesis Example 8: Synthesis of Compound 60

Synthesis Example 9: Synthesis of Compound 74

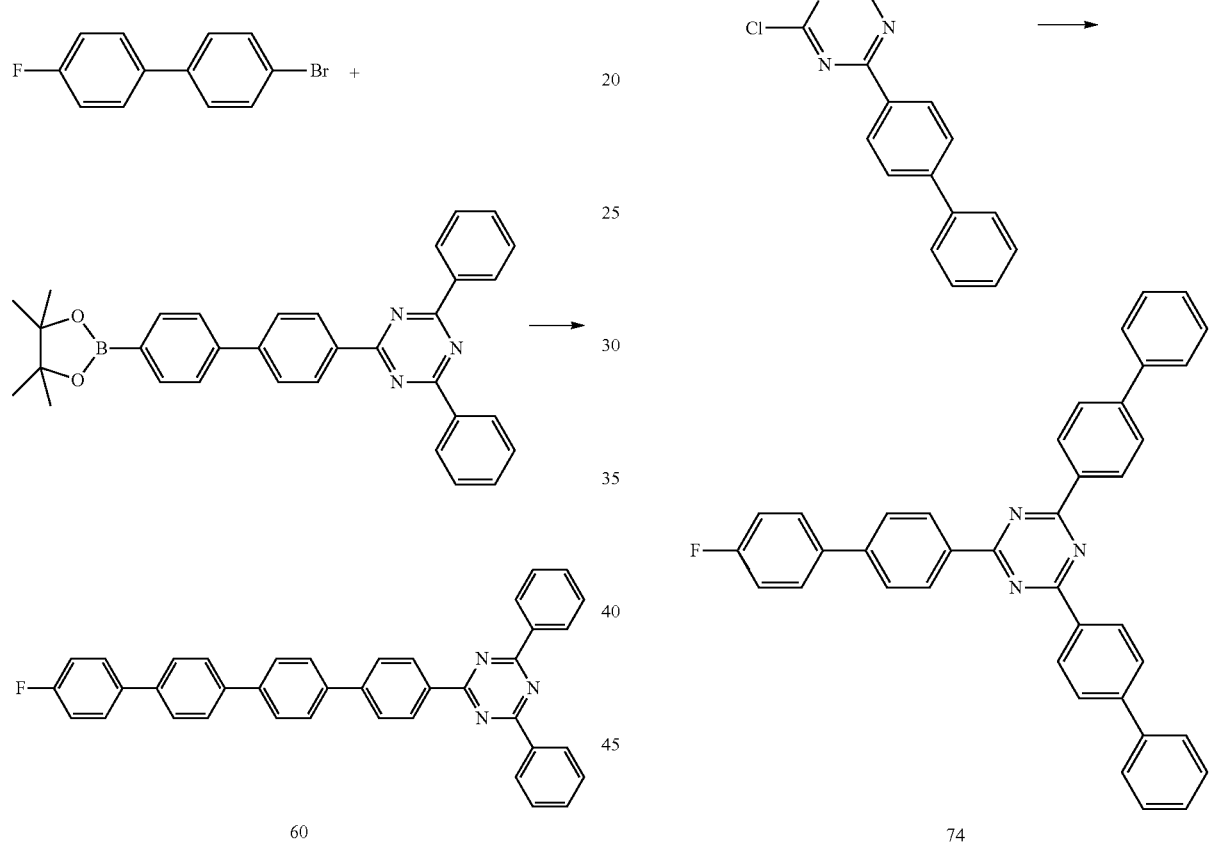

60

74

2.50 g (10 mmol) of 4-bromo-4'-fluoro-1,1'-biphenyl, 5.11 g (10 mmol) of 2,4-diphenyl-6-(4'-(4,4,5,5-tetramethyl-1,3,2-dioxaborolan-2-yl)-[1,1'-biphenyl]-4-yl)-1,3,5-triazine, 0.58 g (0.5 mmol) of Pd(PPh$_3$)$_4$, and 4.14 g (30 mmol) of K$_2$CO$_3$ were dissolved in 60 mL of a mixed solution including THF and H$_2$O (2/1) and stirred at a temperature of 80° C. for 16 hours. Then, the reaction solution was cooled to room temperature, and an organic layer was extracted therefrom three times by using 40 mL of water and 50 mL of ethylether. The extracted organic layer was dried by using magnesium sulfate, and a solvent was evaporated therefrom. Then, the residue obtained therefrom was separated and purified by silica gel column chromatography to obtain 4.39 g (yield: 79%) of Compound 60. The obtained compound was identified by MS/FAB and $^1$H NMR.

$C_{39}H_{26}FN_3$ cal. 555.21. found 555.20.

2.98 g (10 mmol) of 2-(4'-fluoro-[1,1'-biphenyl]-4-yl)-4,4,5,5-tetramethyl-1,3,2-dioxaborolane, 4.19 g (10 mmol) of 2,4-di([1,1'-biphenyl]-4-yl)-6-chloro-1,3,5-triazine, 0.58 g (0.5 mmol) of Pd(PPh$_3$)$_4$, and 4.14 g (30 mmol) of K$_2$CO$_3$ were dissolved in 60 mL of a mixed solution including THF and H$_2$O (2/1) and stirred at a temperature of 80° C. for 16 hours. Then, the reaction solution was cooled to room temperature, and an organic layer was extracted therefrom three times by using 40 mL of water and 50 mL of ethylether. The extracted organic layer was dried by using magnesium sulfate, and a solvent was evaporated therefrom. Then, the residue obtained therefrom was separated and purified by silica gel column chromatography to obtain 4.22 g (yield: 76%) of Compound 74. The obtained compound was identified by MS/FAB and 1H NMR.

$C_{39}H_{26}FN_3$ cal. 555.21. found 555.20.

Synthesis Example 10: Synthesis of Compound 81

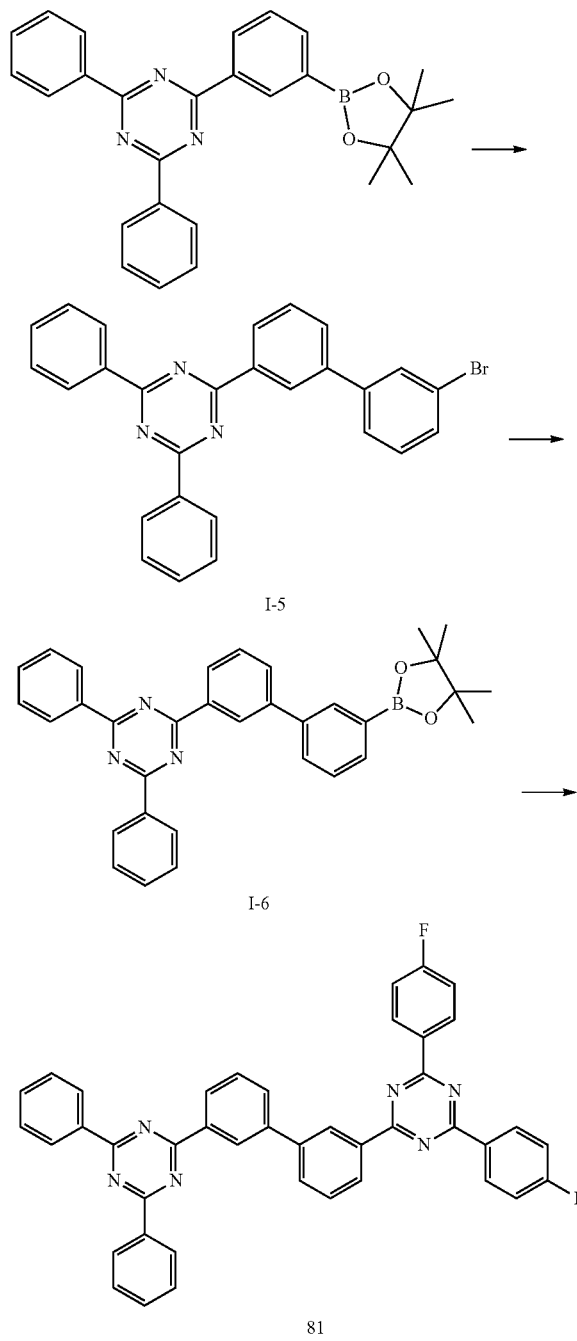

I-5

I-6

81

Synthesis of Intermediate 1-5

4.35 g (10 mmol) of 2,4-diphenyl-6-(3-(4,4,5,5-tetramethyl-1,3,2-dioxaborolan-2-yl)phenyl)-1,3,5-triazine, 3.38 g (12 mmol) of 1-bromo-4-iodobenzene, 0.58 g (0.5 mmol) of Pd(PPh$_3$)$_4$, and 4.14 g (30 mmol) of K$_2$CO$_3$ were dissolved in 60 mL of a mixed solution including THF and H$_2$O (2/1) and stirred at a temperature of 80° C. for 16 hours. Then, the reaction solution was cooled to room temperature, and an organic layer was extracted therefrom three times by using 40 mL of water and 50 mL of ethylether. Then extracted organic layer was dried by using magnesium sulfate, and a solvent was evaporated therefrom. Then, the residue obtained therefrom was separated and purified by silica gel column chromatography to obtain 3.38 g (yield: 73%) of Intermediate 1-5. The obtained compound was identified by LC-MS.

$C_{27}H_{18}BrN_3$: M+1 463.1.

Synthesis of Intermediate 1-6

4.36 g (10 mmol) of Intermediate 1-5, 2.54 g (10 mmol) of bis(pinacolato)diboron, 0.35 g (0.5 mmol) of Pd(PPh$_3$)$_2$Cl$_2$, and 2.94 g (30 mmol) of KOAc were dissolved in 60 mL of toluene and stirred at a temperature of 100° C. for 16 hours. The reaction solution was cooled to room temperature, and an organic layer was extracted therefrom three times by using 40 mL of water and 50 mL of ethylether. The extracted organic layer was dried by using magnesium sulfate, and a solvent was evaporated therefrom. Then, the residue obtained therefrom was separated and purified by silica gel column chromatography to obtain 3.63 g (yield: 71%) of Intermediate 1-6. The obtained compound was identified by LC-MS.

$C_{33}H_{30}BN_3O_2$: M+1 511.2.

Synthesis of Compound 81

3.03 g (10 mmol) of Intermediate 1-1, 5.11 g (10 mmol) of Intermediate 1-6, 0.58 g (0.5 mmol) of Pd(PPh$_3$)$_4$, and 4.14 g (30 mmol) of K$_2$CO$_3$ were dissolved in 60 mL of a mixed solution including THF and H$_2$O (2/1) and stirred at a temperature of 80° C. for 16 hours. Then, the reaction solution was cooled to room temperature, and an organic layer was extracted therefrom three times by using 40 mL of water and 50 mL of ethylether. The extracted organic layer was dried by using magnesium sulfate, and a solvent was evaporated therefrom. Then, the residue obtained therefrom was separated and purified by silica gel column chromatography to obtain 5.15 g (yield: 79%) of Compound 81. The obtained compound was identified by MS/FAB and $^1$H NMR.

$C_{42}H_{26}F_2N_6$ cal. 625.22. found 625.23.

Synthesis Example 11: Synthesis of Compound 90

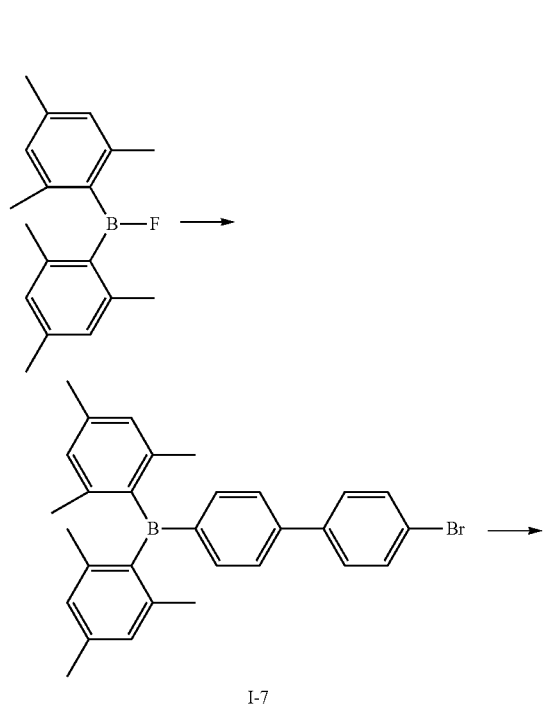

I-7

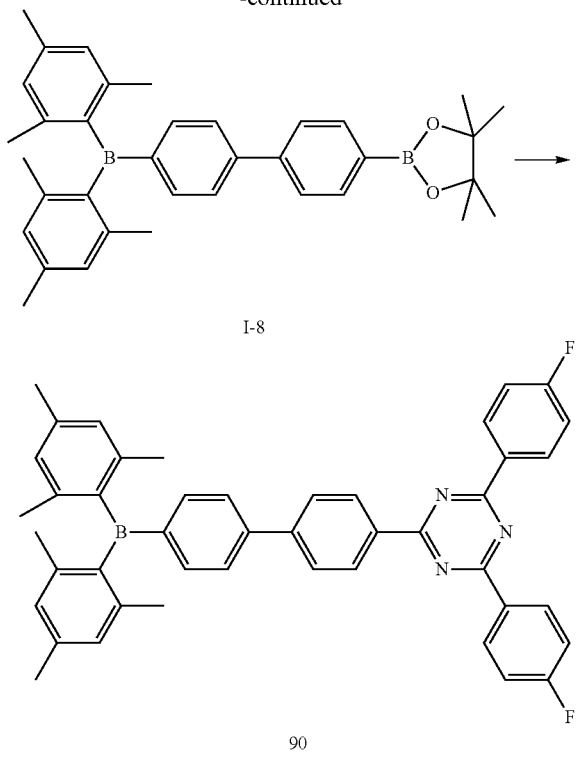

Synthesis of Intermediate 1-7

4.35 g (10 mmol) of 2,4-diphenyl-6-(3-(4,4,5,5-tetramethyl-1,3,2-dioxaborolan-2-yl)phenyl)-1,3,5-triazine, 3.38 g (12 mmol) of 1-bromo-4-iodobenzene, 0.58 g (0.5 mmol) of Pd(PPh$_3$)$_4$, and 4.14 g (30 mmol) of K$_2$CO$_3$ were dissolved in 60 mL of a mixed solution including THF and H$_2$O (2/1) and stirred at a temperature of 80° C. for 16 hours. Then, the reaction solution was cooled to room temperature, and an organic layer was extracted therefrom three times by using 40 mL of water and 50 mL of ethylether. The extracted organic layer was dried by using magnesium sulfate, and a solvent was evaporated therefrom. Then, the residue obtained therefrom was separated and purified by silica gel column chromatography to obtain 3.38 g (yield: 73%) of Intermediate 1-5. The obtained compound was identified by LC-MS.

C$_{33}$H$_{30}$BN$_3$O$_2$: M+1 511.2.

Synthesis of Intermediate 1-8

4.80 g (10 mmol) of Intermediate 1-7, 2.54 g (10 mmol) of bis(pinacolato)diboron, 0.35 g (0.5 mmol) of Pd(PPh$_3$)$_2$Cl$_2$, and 2.94 g (30 mmol) of KOAc were dissolved in 60 mL of toluene and stirred at a temperature of 100° C. for 16 hours. Then, the reaction solution was cooled to room temperature, and an organic layer was extracted therefrom three times by using 40 mL of water and 50 mL of ethylether. The extracted organic layer was dried by using magnesium sulfate, and a solvent was evaporated therefrom. Then, the residue obtained therefrom was separated and purified by silica gel column chromatography to obtain 3.70 g (yield: 70%) of Intermediate 1-8. The obtained compound was identified by LC-MS.

C$_{36}$H$_{42}$B2O2: M+1 528.3.

Synthesis of Compound 90

5.28 g (10 mmol) of Intermediate 1-8, 3.03 g (10 mmol) of 2-chloro-4,6-bis(4-fluorophenyl)-1,3,5-triazine, 0.58 g (0.5 mmol) of Pd(PPh$_3$)$_4$, and 4.14 g (30 mmol) of K$_2$CO$_3$ were dissolved in 60 mL of a mixed solution including THF and H$_2$O (2/1) and stirred at a temperature of 80° C. for 16 hours. Then, the reaction solution was cooled to room temperature, and an organic layer was extracted therefrom three times by using 40 mL of water and 50 mL of ethylether. The extracted organic layer was dried by using magnesium sulfate, and a solvent was evaporated therefrom. Then, the residue obtained therefrom was separated and purified by silica gel column chromatography to obtain 4.89 g (yield: 73%) of Compound 90. The obtained compound was identified by MS/FAB and $^1$H NMR.

C$_{45}$H$_{38}$BF$_2$N$_3$ cal. 669.31. found 669.30.

$^1$H NMR and MS/FAB of the synthesized Compounds are shown in Table 1. Methods of synthesizing compounds other than Compounds shown in Table 1 should be readily apparent to those of ordinary skill in the art by referring to the synthesis mechanisms and source materials described above.

TABLE 1

| Compound | $^1$H NMR (CDCl$_3$, 400 MHz) | MS/FAB found | MS/FAB calc. |
|---|---|---|---|
| 2 | δ = 8.49-8.46 (m, 2H), 8.35-8.30 (m, 4H), 7.96-7.93 (M, 2H), 7.72-7.65 (m, 4H), 7.61-7.58 (m, 2H), 7.53-7.49 (m, 2H), 7.42-7.39 (m, 1H), 7.30-7.24 (m, 4H) | 497.16 | 497.17 |
| 5 | δ = 8.48-8.45 (m, 2H), 8.35-8.31 (m, 4H), 8.05-8.01 (m, 2H), 7.96-7.93 (m, 2H), 7.52-7.78 (m, 2H), 7.74-7.58 (m, 6H), 7.49-7.44 (m, 2H), 7.41-7.36 (m, 1H), 7.30-7.24 (m, 4H), 7.01-6.96 (m, 2H) | 623.23 | 623.22 |
| 9 | δ = 8.53-8.50 (m, 2H), 8.35-8.31 (m, 4H), 8.11 (dd, 2H), 7.97-7.91 (m, 4H), 7.72-7.66 (m, 6H), 7.62-7.58 (m, 2H), 7.53-7.49 (m, 2H), 7.42-7.38 (m, 1H), 7.30-7.24 (m, 4H) | 623.21 | 623.22 |
| 25 | δ = 8.52-8.48 (m, 2H), 8.35-8.30 (m, 4H), 7.91-7.87 (m, 2H), 7.76-7.71 (m, 2H), 7.63-7.60 (m, 2H), 7.55-7.47 (m, 4H), 7.42-7.38 (m, 1H), 7.31-7.24 (m, 6H), 1.56 (s, 6H) | 613.22 | 613.23 |
| 31 | δ = 8.56-8.52 (m, 2H), 8.43-8.38 (m, 4H), 8.19-8.17 (m, 1H), 8.07-8.05 (m, 1H), 8.00 (t, 1H), 7.93-7.91 (m, 1H), 7.89-7.77 (m, 4H), 7.72-7.69 (m, 1H), 7.62-7.49 (m, 2H), 7.34-7.24 (m, 5H) | 548.19 | 548.18 |
| 40 | δ = 8.81-8.78 (m, 2H), 8.49-8.46 (m, 2H), 8.35-8.30 (m, 2H), 8.09 (dd, 1H), 7.96-7.85 (m, 5H), 7.77-7.49 (m, 9H), 7.42-7.39 (m, 1H), 7.30-7.25 (m, 2H) | 529.21 | 529.20 |
| 45 | δ = 8.81-8.78 (m, 2H), 8.49-8.46 (m, 2H), 8.35-8.30 (m, 2H), 8.10-8.08 (m, 1H), 7.96-7.85 (m, 5H), 7.77-7.49 (m, 9H), 7.42-7.39 (m, 1H), 7.30-7.25 (m, 2H) | 623.22 | 623.22 |
| 60 | δ = 8.81-8.78 (m, 4H), 8.49-8.46 (m, 2H), 7.96-7.93 (m, 2H), 7.76-7.59 (m, 12H), 7.42-7.38 (m, 2H), 7.18-7.13 (m, 2H), 6.71-6.65 (m, 2H) | 555.20 | 555.21 |
| 74 | δ = 8.49-8.43 (m, 6H), 8.00-7.92 (m, 6H), 7.60-7.58 (m, 4H), 7.52-7.49 (m, 4H), 7.42-7.39 (m, 2H), 7.18-7.13 (m, 2H), 6.71-6.65 (m, 2H) | 555.20 | 555.21 |
| 81 | δ = 8.80-8.78 (m, 4H), 8.65-8.64 (m, 2H), 8.59-8.56 (m, 2H), 8.35-8.30 (m, 4H), 7.86-7.83 (m, 2H), 7.63-7.52 (m, 6H), 7.42-7.38 (m, 2H), 7.30-7.24 (m, 4H) | 625.23 | 625.22 |

TABLE 1-continued

| Compound | $^1$H NMR (CDCl$_3$, 400 MHz) | MS/FAB found | calc. |
|---|---|---|---|
| 90 | δ = 8.49-8.46 (m, 2H), 8.35-8.30 (m, 4H), 7.97-7.93 (m, 2H), 7.67-7.64 (m, 2H), 7.56-7.53 (m, 2H), 7.30-7.24 (m, 4H), 6.80-6.77 (m, 4H), 2.19 (s, 18H) | 669.30 | 669.31 |

Methods of synthesizing compounds other than the Compounds synthesized according to Synthesis Examples 1 to 11 may also be readily apparent to those of ordinary skill in the art by referring to the synthesis mechanisms and source materials described above.

Example 1

As an anode, a Corning 15 Ω/cm$^2$ (1,200 Å) ITO glass substrate was cut to a size of 50 mm×50 mm×0.7 mm, sonicated with isopropyl alcohol and pure water each for 5 minutes, and then cleaned by exposure to ultraviolet rays and ozone for 30 minutes. Then, the resultant ITO glass substrate was provided to a vacuum deposition apparatus.

2-TNATA, which is a generally available material, was vacuum-deposited on the anode to form a hole injection layer having a thickness of 600 Å, and 4,4'-bis[N-(1-naphthyl)-N-phenylamino]biphenyl (NPB), which is a generally available material, was vacuum-deposited as a hole transport compound on the hole injection layer to form a hole transport layer having a thickness of 300 Å.

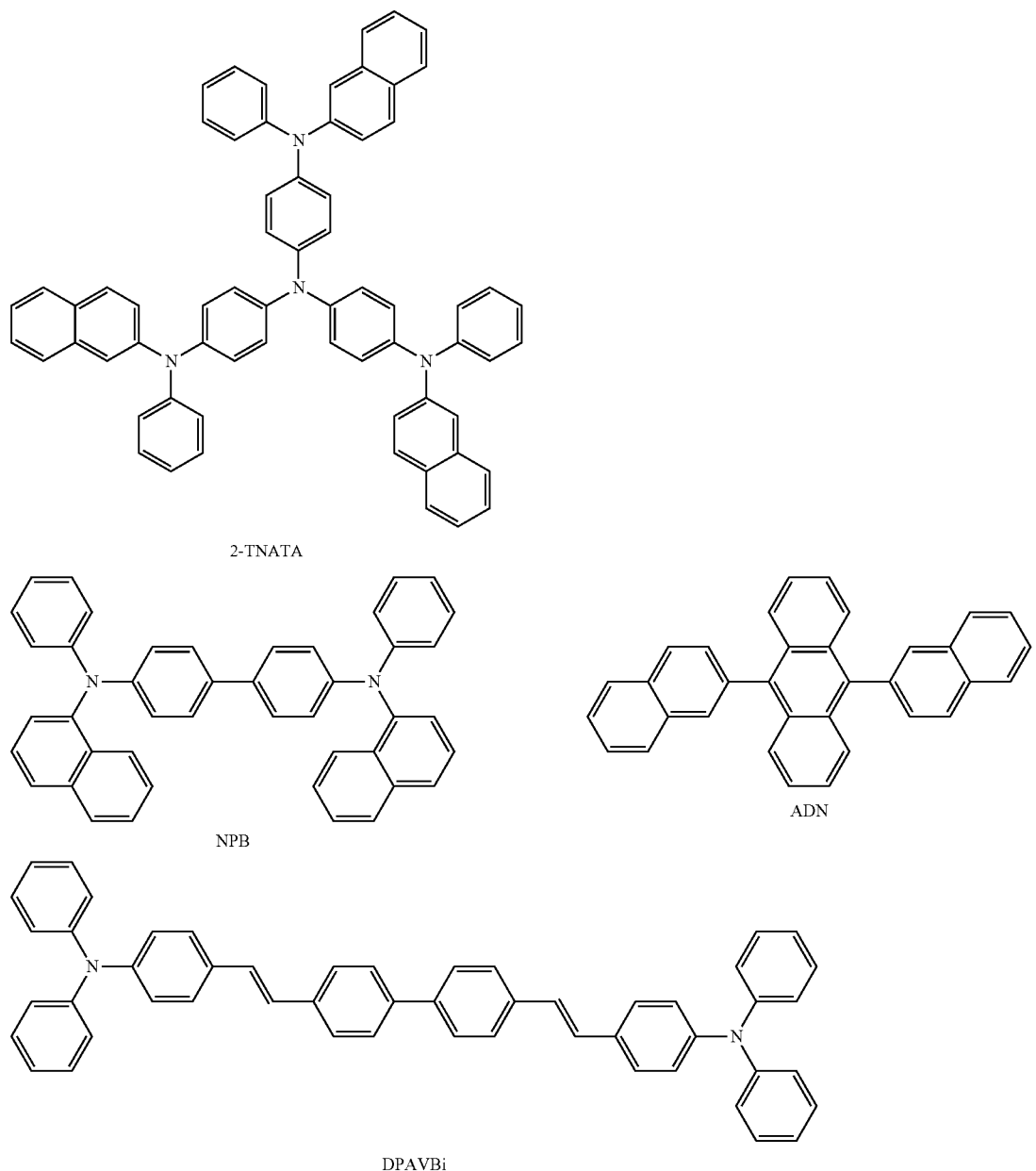

9,10-di-naphthalene-2-yl-anthracene (ADN) and 4,4'-bis[2-(4-(N,N-diphenylamino)phenyl)vinyl]biphenyl (DPAVBi), which are generally available compounds, were respectively co-deposited as a blue fluorescent host and a blue fluorescent dopant on the hole transport layer at a weight ratio of 98:2 to form an emission layer having a thickness of 300 Å.

Then, Compound 2 was deposited on the emission layer to form an electron transport layer having a thickness of 300 Å, LiF, which is an alkali metal halide, was deposited on the electron transport layer to form an electron injection layer having a thickness of 10 Å, and Al was vacuum-deposited on the electron injection layer to form a cathode electrode having a thickness of 3,000 Å, thereby forming a LiF/Al electrode. In this manner, an organic light-emitting device was manufactured.

Example 2

An organic light-emitting device was manufactured in substantially the same manner as in Example 1, except that Compound 5 was used instead of Compound 2 in forming an electron transport layer.

Example 3

An organic light-emitting device was manufactured in substantially the same manner as in Example 1, except that Compound 9 was used instead of Compound 2 in forming an electron transport layer.

Example 4

An organic light-emitting device was manufactured in substantially the same manner as in Example 1, except that Compound 25 was used instead of Compound 2 in forming an electron transport layer.

Example 5

An organic light-emitting device was manufactured in substantially the same manner as in Example 1, except that Compound 31 was used instead of Compound 2 in forming an electron transport layer.

Example 6

An organic light-emitting device was manufactured in substantially the same manner as in Example 1, except that Compound 40 was used instead of Compound 2 in forming an electron transport layer.

Example 7

An organic light-emitting device was manufactured in substantially the same manner as in Example 1, except that Compound 45 was used instead of Compound 2 in forming an electron transport layer.

Example 8

An organic light-emitting device was manufactured in substantially the same manner as in Example 1, except that Compound 60 was used instead of Compound 2 in forming an electron transport layer.

Example 9

An organic light-emitting device was manufactured in substantially the same manner as in Example 1, except that Compound 74 was used instead of Compound 2 in forming an electron transport layer.

Example 10

An organic light-emitting device was manufactured in substantially the same manner as in Example 1, except that Compound 81 was used instead of Compound 2 in forming an electron transport layer.

Example 11

An organic light-emitting device was manufactured in substantially the same manner as in Example 1, except that Compound 90 was used instead of Compound 2 in forming an electron transport layer.

Comparative Example 1

An organic light-emitting device was manufactured in substantially the same manner as in Example 1, except that Compound 200 was used instead of Compound 2 in forming an electron transport layer.

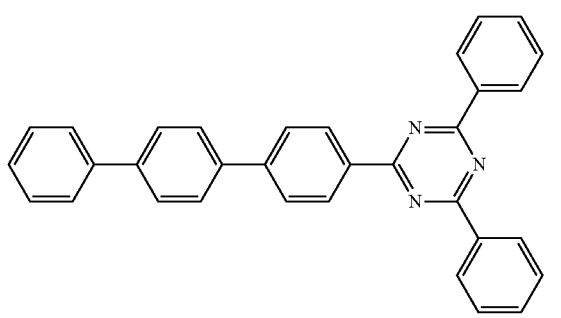

200

Comparative Example 2

An organic light-emitting device was manufactured in substantially the same manner as in Example 1, except that Compound 201 was used instead of Compound 2 in forming an electron transport layer.

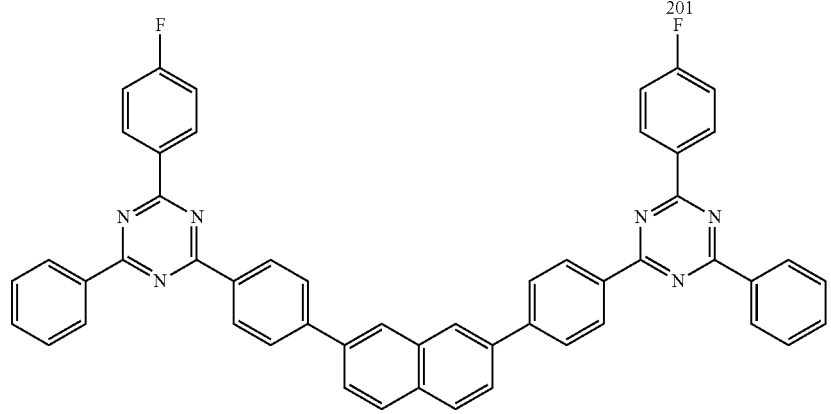 [SMILES: Fc1ccc(-c2nc(-c3ccccc3)nc(-c3ccc(-c4ccc5ccc(-c6ccc(-c7nc(-c8ccccc8)nc(-c8ccc(F)cc8)n7)cc6)cc5c4)cc3)n2)cc1]

Comparative Example 3

An organic light-emitting device was manufactured in substantially the same manner as in Example 1, except that Compound 202 was used instead of Compound 2 in forming an electron transport layer

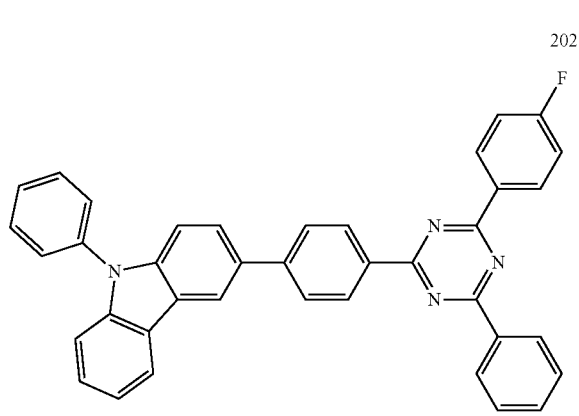 [SMILES: Fc1ccc(-c2nc(-c3ccccc3)nc(-c3ccc(-c4ccc5c(c4)c4ccccc4n5-c4ccccc4)cc3)n2)cc1]

The driving voltage, luminance, efficiency (cd/A), and half lifespan of the organic light-emitting devices manufactured according to Examples 1 to 11 and Comparative Examples 1 to 3 were measured at a current density of 50 mA/cm$^2$, and results thereof are shown in Table 2 below.

TABLE 2

| | Material | Driving voltage (V) | Current density (mA/ cm$^2$) | Luminance (cd/m$^2$) | Efficiency (cd/A) | Emission color | Half lifespan (hr @ 100 mA/ cm$^2$) |
|---|---|---|---|---|---|---|---|
| Example 1 | Compound 2 | 3.65 | 50 | 3,705 | 7.41 | Blue | 710 hr |
| Example 2 | Compound 5 | 3.63 | 50 | 3,890 | 7.78 | Blue | 706 hr |
| Example 3 | Compound 9 | 3.60 | 50 | 3,775 | 7.55 | Blue | 721 hr |
| Example 4 | Compound 25 | 3.69 | 50 | 3,750 | 7.50 | Blue | 759 hr |
| Example 5 | Compound 31 | 3.62 | 50 | 3,790 | 7.58 | Blue | 732 hr |
| Example 6 | Compound 40 | 3.64 | 50 | 3,820 | 7.64 | Blue | 745 hr |
| Example 7 | Compound 45 | 3.60 | 50 | 3,815 | 7.63 | Blue | 720 hr |
| Example 8 | Compound 60 | 3.55 | 50 | 3,785 | 7.57 | Blue | 726 hr |
| Example 9 | Compound 74 | 3.58 | 50 | 3,795 | 7.59 | Blue | 733 hr |
| Example 10 | Compound 81 | 3.61 | 50 | 3,800 | 7.60 | Blue | 750 hr |
| Example 11 | Compound 90 | 3.59 | 50 | 3,810 | 7.62 | Blue | 738 hr |
| Comparative Example 1 | Compound 200 | 3.85 | 50 | 3,555 | 7.11 | Blue | 633 hr |
| Comparative Example 2 | Compound 201 | 3.90 | 50 | 3,570 | 7.14 | Blue | 656 hr |
| Comparative Example 3 | Compound 202 | 4.32 | 50 | 3,500 | 7.00 | Blue | 602 hr |

From Table 2, when the compound according to one or more embodiments was used as an electron transport material, excellent I-V-L characteristics including a low driving voltage and remarkably improved efficiency and luminance were exhibited, as compared with Compounds 201 to 202 as well as Compound 200, which are generally available materials. For example, an excellent lifespan improvement effect was exhibited.

For example, when the compound according to one or more embodiments is used as an electron transport material of a device, excellent effects may be exhibited in terms of driving voltage, luminance, efficiency, and lifespan. Compounds 2, 5, 9, 25, 31, 40, 45, 60, 74, 81, and 90 are shown below.

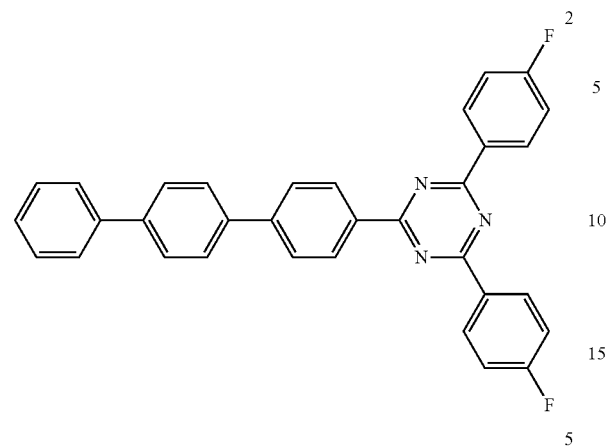
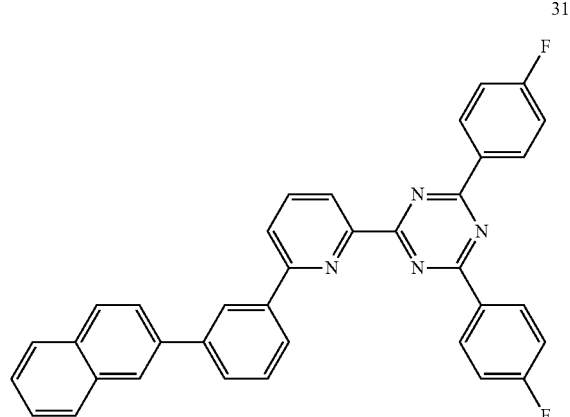
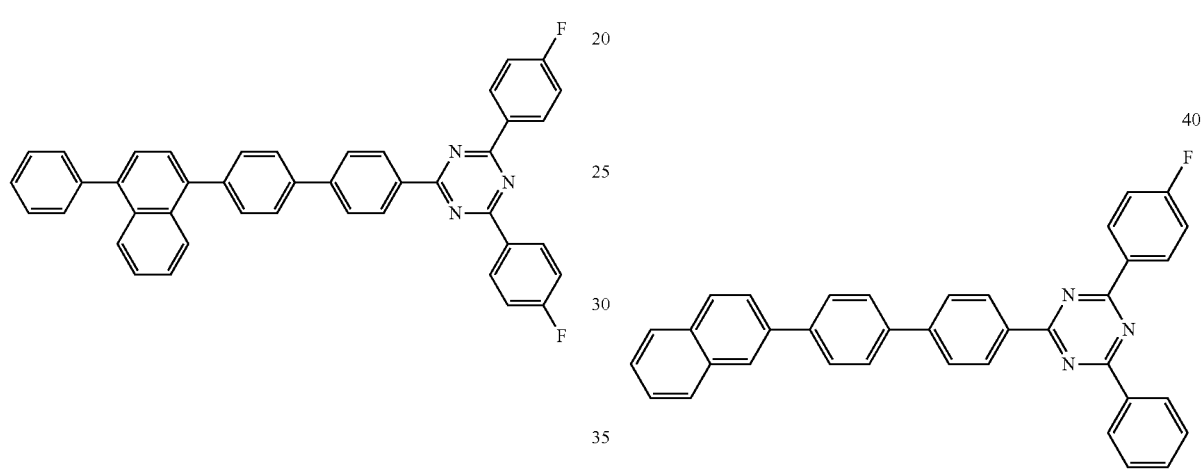
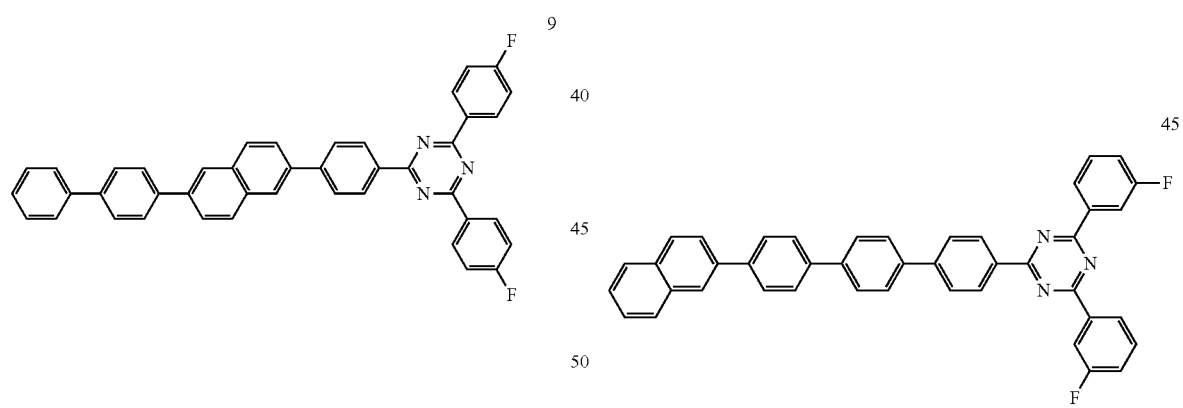
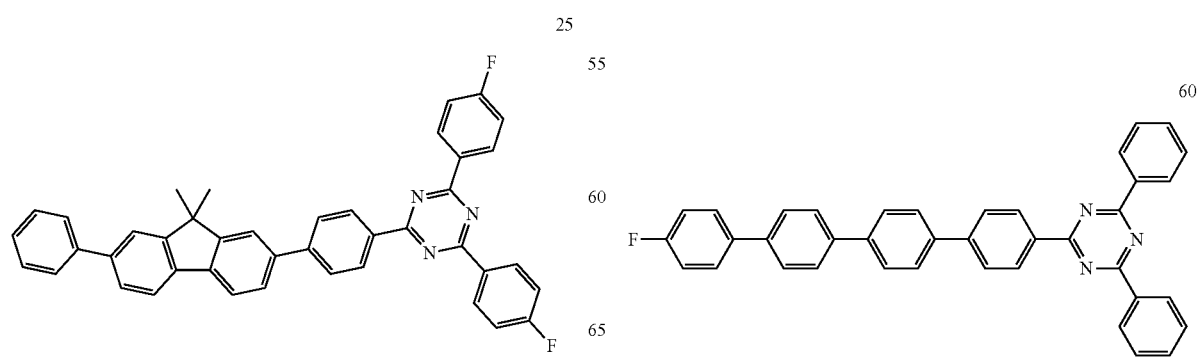

-continued

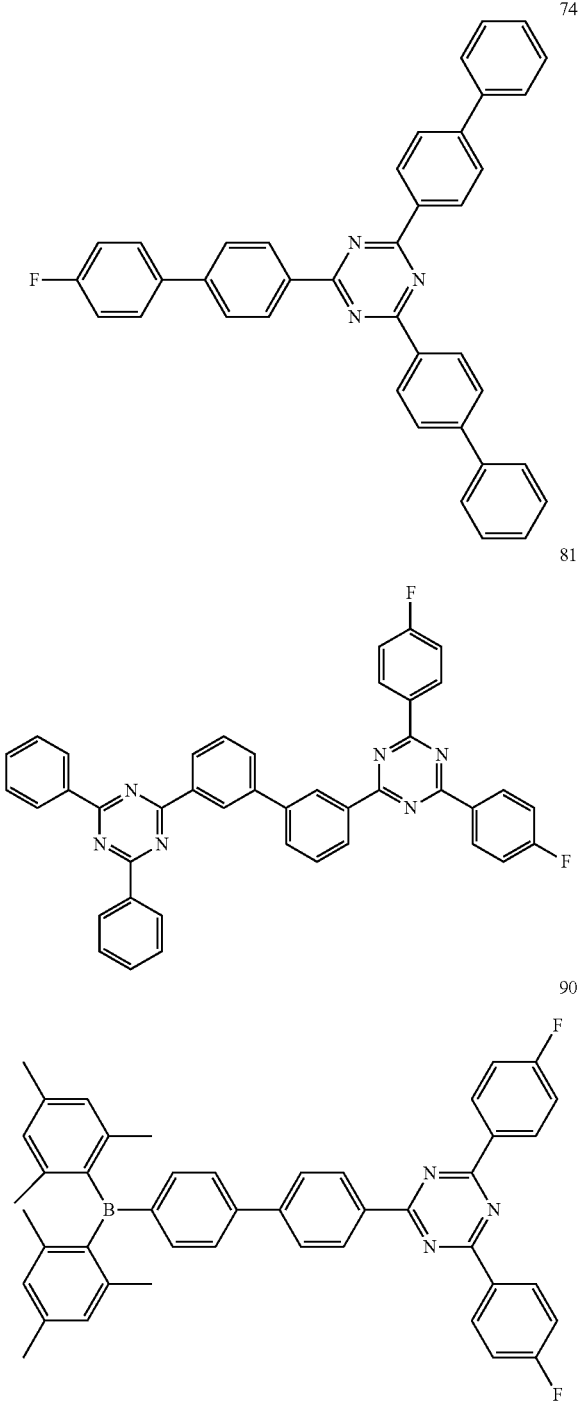

An organic light-emitting device according to an embodiment may have a low driving voltage, high efficiency, and a long lifespan.

It will be understood that, although the terms "first," "second," "third," etc., may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

Spatially relative terms, such as "beneath," "below," "lower," "under," "above," "upper," and the like, may be used herein for ease of explanation to describe one element or feature's relationship to another element(s) or feature(s) as illustrated in the figures. It will be understood that the spatially relative terms are intended to encompass different orientations of the device in use or in operation, in addition to the orientation depicted in the figures. For example, if the device in the figures is turned over, elements described as "below" or "beneath" or "under" other elements or features would then be oriented "above" the other elements or features. Thus, the example terms "below" and "under" can encompass both an orientation of above and below. The device may be otherwise oriented (e.g., rotated 90 degrees or at other orientations) and the spatially relative descriptors used herein should be interpreted accordingly.

It will be understood that when an element or layer is referred to as being "on," "connected to," or "coupled to" another element or layer, it can be directly on, connected to, or coupled to the other element or layer, or one or more intervening elements or layers may be present. In addition, it will also be understood that when an element or layer is referred to as being "between" two elements or layers, it can be the only element or layer between the two elements or layers, or one or more intervening elements or layers may also be present.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises," "comprising," "includes," and "including," when used in this specification, specify the presence of the stated features, integers, acts, operations, elements, and/or components, but do not preclude the presence or addition of one or more other features, integers, acts, operations, elements, components, and/or groups thereof.

As used herein, the terms "substantially," "about," and similar terms are used as terms of approximation and not as terms of degree, and are intended to account for the inherent deviations in measured or calculated values that would be recognized by those of ordinary skill in the art. Further, the use of "may" when describing embodiments of the present disclosure refers to "one or more embodiments of the present disclosure." As used herein, the terms "use," "using," and "used" may be considered synonymous with the terms "utilize," "utilizing," and "utilized," respectively.

Also, any numerical range recited herein is intended to include all subranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein, and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

What is claimed is:

1. A heterocyclic compound represented by Formula 1:

Formula 1

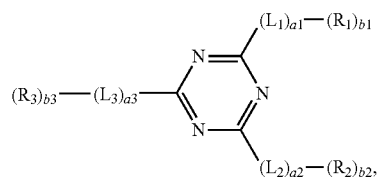

wherein, in Formula 1, $L_1$ to $L_3$ are each independently selected from a single bond and groups represented by Formulae 3-1 and 3-4 to 3-29:

3-1

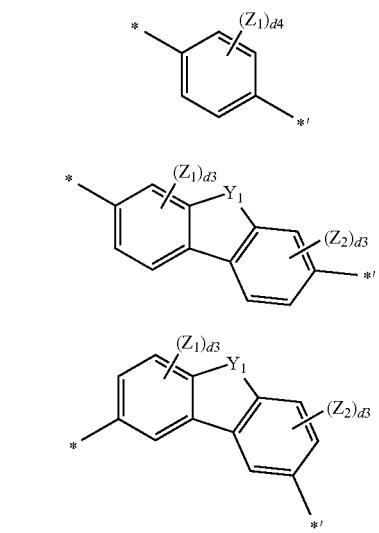

3-4

3-5

3-6

3-7

3-8

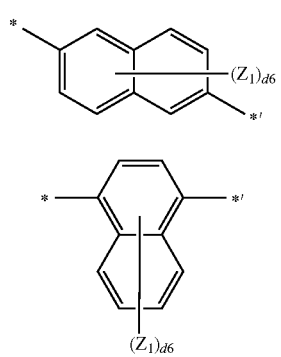

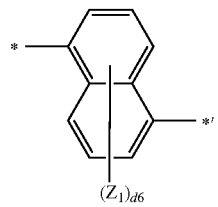

3-9

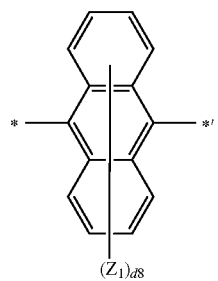

3-10

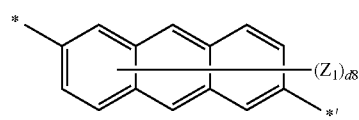

3-11

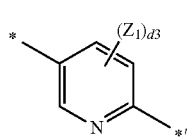

3-12

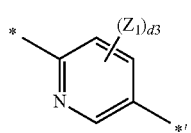

3-13

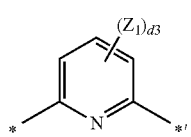

3-14

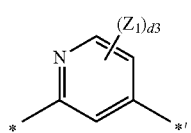

3-15

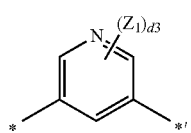

3-16

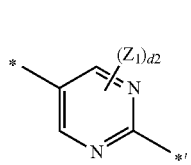

-continued 3-17
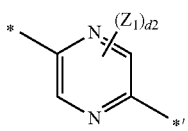

3-18
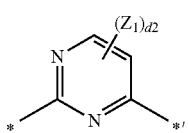

3-19
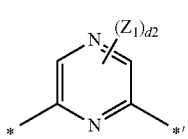

3-20
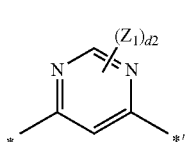

3-21
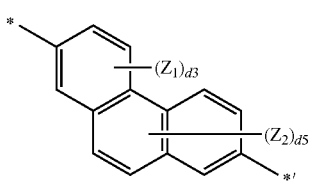

3-22
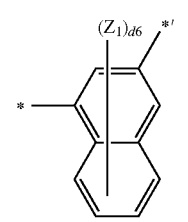

3-23
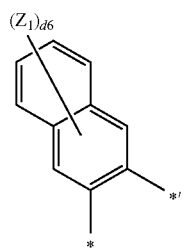

3-24
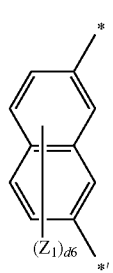

-continued 3-25
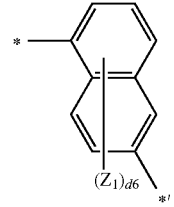

3-26
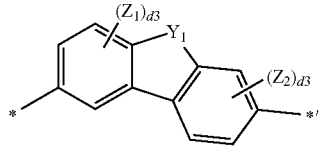

3-27
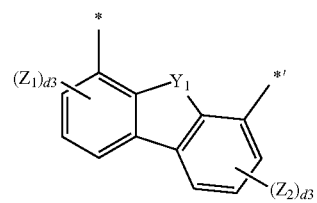

3-28
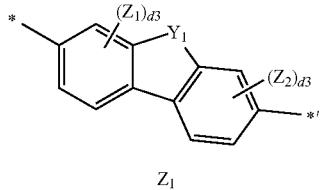

3-29
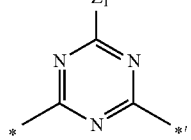

wherein, in Formulae 3-1 and 3-4 to 3-29, $Y_1$ may be $C(Z_3)(Z_4)$ or $Si(Z_6)(Z_7)$, $Z_1$ to $Z_7$ may each independently be selected from hydrogen, deuterium, —F, —Cl, —Br, —I, a hydroxyl group, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a pyrenyl group, a chrysenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a benzofuranyl group, a benzothiophenyl group, a benzosilolyl group, a dibenzosilolyl group, and —Si($Q_{31}$)($Q_{32}$)($Q_{33}$), a1 to a3 are each independently an integer from 1 to 5, $R_1$ to $R_3$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), and —B($Q_1$)($Q_2$), b1 to b3 are each independently an integer from 1 to 20, at least one selected from $R_1$ to $R_3$ is a fluoro-containing cyclic group and at least one selected from $R_1$ to $R_3$ does not include a fluoro-containing cyclic group, the case where all substituents of the fluoro-containing cyclic group are —F is excluded, when at least one of $R_1$(s) in the number of b1 is the fluoro-containing cyclic group, $L_1$ is not a substituted or unsubstituted triazine group, when at least one of $R_2$(s) in the number of b2 is the fluoro-containing cyclic group, $L_2$ is not a substituted or unsubstituted triazine group, and when at least one of $R_3$(s) in the number of b3 is the fluoro-containing cyclic group, $L_3$ is not a substituted or unsubstituted triazine group, the heterocyclic compound does not include a carbazole group, a benzocarbazole group, a dibenzofuran group, a dibenzothiophene group, and a triphenylene group, at least one substituent of the substituted $C_3$-$C_{60}$ carbocyclic group, the substituted $C_1$-$C_{60}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent non-aromatic condensed polycyclic group, and the substituted monovalent non-aromatic condensed heteropolycyclic group is selected from:

deuterium, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), and —C(=O)($Q_{11}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group, each substituted with at least one selected from deuterium, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, a terphenyl group, —Si($Q_{21}$)($Q_{22}$)($Q_{23}$), —N($Q_{21}$)($Q_{22}$), —B($Q_{21}$)($Q_{22}$), and —C(=O)($Q_{21}$); and —Si($Q_{31}$)($Q_{32}$)($Q_{33}$), —N($Q_{31}$)($Q_{32}$), —B($Q_{31}$)($Q_{32}$), and —C(=O)($Q_{31}$), $Q_1$ to $Q_3$, $Q_{11}$ to $Q_{13}$, $Q_{21}$ to $Q_{23}$, and $Q_{31}$ to $Q_{33}$ are each independently selected from hydrogen, deuterium, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with a $C_1$-$C_{60}$ alkyl group, a $C_1$-$C_{60}$ heteroaryl group, a monovalent non-aromatic condensed polycyclic group, a monovalent non-aromatic condensed heteropolycyclic group, a biphenyl group, and a terphenyl group, indicates a binding site to a neighboring atom, and wherein the heterocyclic compound represented by Formula 1 is asymmetric.

2. The heterocyclic compound of claim 1, wherein:

$L_1$ to $L_3$ are each independently selected from:

a single bond, a pentalene group, an indene group, a naphthalene group, an azulene group, a heptalene group, an indacene group, an acenaphthalene group, a fluorene group, a spiro-bifluorene group, a spiro-benzofluorene-fluorene group, a benzofluorene group, a dibenzofluorene group, a phenalene group, a phenanthrene group, an anthracene group, a fluoranthene group, a pyrene group, a chrysene group, a naphthacene group, a picene group, a perylene group, a pyrrole group, a thiophene group, a furan group, a silole group, an imidazole group, a pyrazole group, a thiazole group, an isothiazole group, an oxazole group, an isoxazole group, a pyridine group, a pyrazine group, a pyrimidine group, a pyridazine group, a triazine group, a benzofuran group, a benzothiophene group, a benzosilole group, a dibenzosilole group, a quinoline group, an isoquinoline group, a benzimidazole group, an imidazopyridine group, and an imidazopyrimidine group; and a benzene group, a pentalene group, an indene group, a naphthalene group, an azulene group, a heptalene group, an indacene group, an acenaphthalene group, a fluorene group, a spiro-bifluorene group, a spiro-benzofluorene-fluorene group, a benzofluorene group, a dibenzofluorene group, a phenalene group, a phenanthrene group, an anthracene group, a fluoranthene group, a pyrene group, a chrysene group, a naphthacene group, a picene group, a perylene group, a pyrrole group, a thiophene group, a furan group, a silole group, an imidazole group, a pyrazole group, a thiazole group, an isothiazole group, an oxazole group, an isoxazole group, a pyridine group, a pyrazine group, a pyrimidine group, a pyridazine group, a triazine group, a benzofuran group, a benzothiophene group, a benzosilole group, a dibenzosilole group, a quinoline group, an isoquinoline group, a benzimidazole group, an imidazopyridine group, and an imidazopyrimidine group, each substituted with at least one selected from deuterium, —Cl, —Br, —I, a hydroxyl group, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, a pyridinyl group, a pyrazinyl group, a pyrimidinyl group, a pyridazinyl group, a quinolinyl group, an isoquinolinyl group, a benzofuranyl group, a benzothiophenyl group, —Si($Q_{31}$)($Q_{32}$)($Q_{33}$), —N($Q_{31}$)($Q_{32}$), and —B($Q_{31}$)($Q_{32}$), and $Q_1$ and $Q_{31}$ to $Q_{33}$ are each independently selected from a $C_1$-$C_{20}$ alkyl group, a $C_1$-$C_{20}$ alkoxy group, a phenyl group, a biphenyl group, a terphenyl group, a naphthyl group, and a pyridinyl group.

3. The heterocyclic compound of claim 1, wherein:
a1 to a3 are each independently an integer from 1 to 3.

4. The heterocyclic compound of claim 1, wherein:
$R_1$ to $R_3$ are each independently selected from:

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyridinyl group, a pyrazinyl group, a pyrimidinyl group, a pyridazinyl group, a triazinyl group, a thiophenyl group, a furanyl group, a quinolinyl group, an isoquinolinyl group, a benzofuranyl group, a benzothiophenyl group, a dibenzosilolyl group, a benzonaphthosilolyl group, a dinaphthosilolyl group, a benzimidazolyl group, a phenanthrolinyl group, and an imidazopyridinyl group;

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyridinyl group, a pyrazinyl group, a pyrimidinyl group, a pyridazinyl group, a triazinyl group, a thiophenyl group, a furanyl group, a quinolinyl group, an isoquinolinyl group, a benzofuranyl group, a benzothiophenyl group, a dibenzosilolyl group, a benzonaphthosilolyl group, a dinaphthosilolyl group, a benzimidazolyl group, a phenanthrolinyl group, and an imidazopyridinyl group, each substituted with at least one selected from deuterium, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyridinyl group, a pyrazinyl group, a pyrimidinyl group, a pyridazinyl group, a triazinyl group, a thiophenyl group, a furanyl group, a quinolinyl group, an isoquinolinyl group, a benzofuranyl group, a benzothiophenyl group, a dibenzosilolyl group, —N($Q_{31}$)($Q_{32}$), and —Si($Q_{31}$)($Q_{32}$)($Q_{33}$); and —N($Q_1$)($Q_2$) and —B($Q_1$)($Q_2$), and $Q_1$, $Q_2$, and $Q_{31}$ to $Q_{33}$ are each independently selected from:

a $C_1$-$C_{20}$ alkyl group, a $C_1$-$C_{20}$ alkoxy group, a phenyl group, a biphenyl group, a terphenyl group, a naphthyl group, and a pyridinyl group; and a phenyl group, a biphenyl group, a terphenyl group, a naphthyl group, and a pyridinyl group, each substituted with a $C_1$-$C_{20}$ alkyl group or a $C_1$-$C_{20}$ alkoxy group.

5. The heterocyclic compound of claim 1, wherein:
the fluoro-containing cyclic group comprises one or two fluoro groups.

6. The heterocyclic compound of claim 1, wherein:
the fluoro-containing cyclic group is a $C_3$-$C_{60}$ carbocyclic group substituted with at least one —F.

7. The heterocyclic compound of claim 1, wherein:
the fluoro-containing cyclic group is a $C_6$-$C_{60}$ aryl group or a monovalent non-aromatic condensed polycyclic group, each substituted with at least one —F.

8. The heterocyclic compound of claim 1, wherein:
the fluoro-containing cyclic group is selected from groups represented by Formulae 4-1 to 4-16, 4-18, and 4-19:
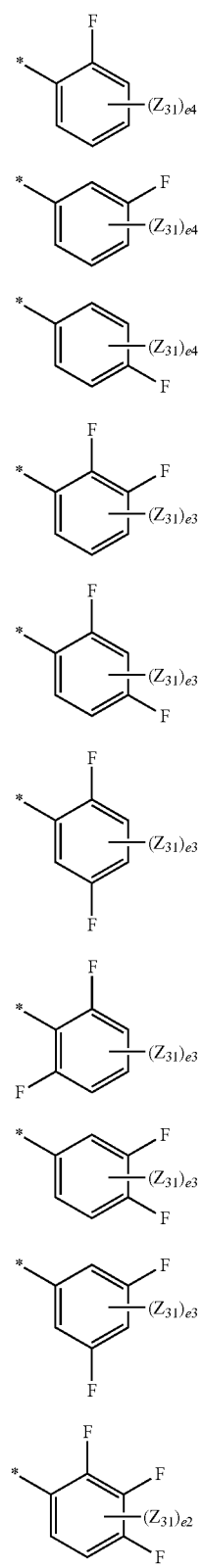
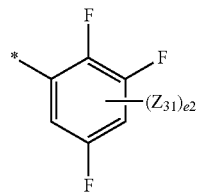
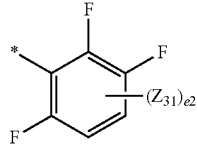
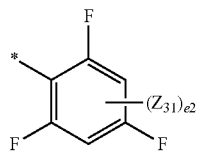
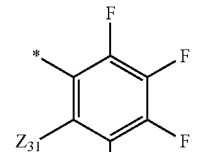
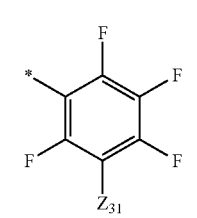
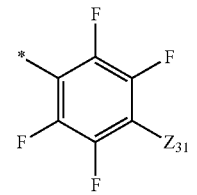
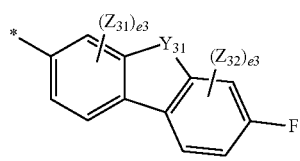
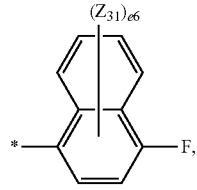
wherein, in Formulae 4-1 to 4-16, 4-18, and 4-19,
$Y_{31}$ is O, S, $C(Z_{33})(Z_{34})$, $N(Z_{33})$, or $Si(Z_{33})(Z_{34})$,
$Z_{31}$ and $Z_{32}$ are each independently selected from hydrogen, deuterium, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a triazinyl group, a biphenyl group, a terphenyl group, a phenyl group substituted with a $C_1$-$C_{20}$ alkyl group, and —Si($Q_{31}$)($Q_{32}$)($Q_{33}$), $Q_{31}$ to $Q_{33}$ are each independently selected from a $C_1$-$C_{10}$ alkyl group, a $C_1$-$C_{10}$ alkoxy group, a phenyl group, a naphthyl group, a pyridinyl group, a pyrimidinyl group, a triazinyl group, a biphenyl group, a terphenyl group, and a phenyl group substituted with a $C_1$-$C_{20}$ alkyl group, e2 is an integer from 0 to 2,
e3 is an integer from 0 to 3,
e4 is an integer from 0 to 4,
e6 is an integer from 0 to 6, and
* indicates a binding site to a neighboring atom.

9. The heterocyclic compound of claim 1, wherein:
i) when at least one of $R_1$(s) in the number of b1 is the fluoro-containing cyclic group, at least one of $L_1$(s) in the number of a1 is a single bond or a substituted or unsubstituted $C_3$-$C_{60}$ carbocyclic group,
ii) at least one of $R_2$(s) in the number of b2 is the fluoro-containing cyclic group, at least one of $L_2$(s) in the number of a2 is a single bond or a substituted or unsubstituted $C_3$-$C_{60}$ carbocyclic group,
iii) at least one of $R_3$(s) in the number of b3 is the fluoro-containing cyclic group, at least one of $L_3$(s) in the number of a3 is a single bond or a substituted or unsubstituted $C_3$-$C_{60}$ carbocyclic group, and
the substituent of the substituted $C_3$-$C_{60}$ carbocyclic group is selected from a $C_1$-$C_{60}$ alkyl group, a $C_2$-$C_{60}$ alkenyl group, a $C_2$-$C_{60}$ alkynyl group, and a $C_1$-$C_{60}$ alkoxy group.

10. The heterocyclic compound of claim 9, wherein:
the substituted or unsubstituted $C_3$-$C_{60}$ carbocyclic group is selected from:
a benzene group, a naphthalene group, and a fluorene group; and
a benzene group and a fluorene group, each substituted with a $C_1$-$C_{20}$ alkyl group.

11. The heterocyclic compound of claim 1, wherein:
i) at least one of $R_1$(s) in the number of b1 is a fluoro-containing cyclic group, and $R_2$(s) in the number of b2 and $R_3$(s) in the number of b3 are each independently selected from: a phenyl group, a biphenyl group, a terphenyl group, a naphthyl group, and a pyridinyl group; and a triazinyl group substituted with one or more phenyl groups;
ii) at least one of $R_1$(s) in the number of b1 and at least one of $R_2$(s) in the number of b2 are each a fluoro-containing cyclic group, and $R_3$(s) in the number of b3 are each independently selected from: a phenyl group, a biphenyl group, a terphenyl group, a naphthyl group, a pyridinyl group, a fluorenyl group, an anthracenyl group, a phenanthrenyl group, a quinolinyl group, a phenanthrolinyl group, a triazinyl group, and a pyrimidinyl group; a phenyl group, a biphenyl group, a terphenyl group, a naphthyl group, a pyridinyl group, a fluorenyl group, an anthracenyl group, a phenanthrenyl group, a quinolinyl group, a phenanthrolinyl group, a triazinyl group, and a pyrimidinyl group, each substituted with at least one selected from a cyano group, a $C_1$-$C_{20}$ alkyl group, a phenyl group, a biphenyl group, a terphenyl group, a naphthyl group, a pyridinyl group, a fluorenyl group, an anthracenyl group, a phenanthrenyl group, a triazinyl group, and a pyrimidinyl group; and —B($Q_1$)($Q_2$); or
iii) at least one of $R_1$(s) in the number of b1, at least one of $R_2$(s) in the number of b2, and at least one of $R_3$(s) in the number of b3 are each a fluoro-containing cyclic group, and
$Q_1$ and $Q_2$ are each a substituted phenyl group substituted with one or more $C_1$-$C_{20}$ alkyl groups.

12. A heterocyclic compound, wherein:
the heterocyclic compound is selected from Compounds 1 to 90:

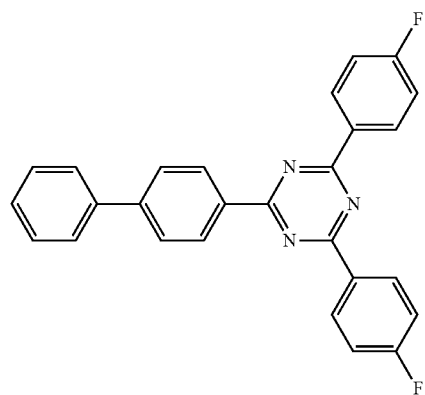

1

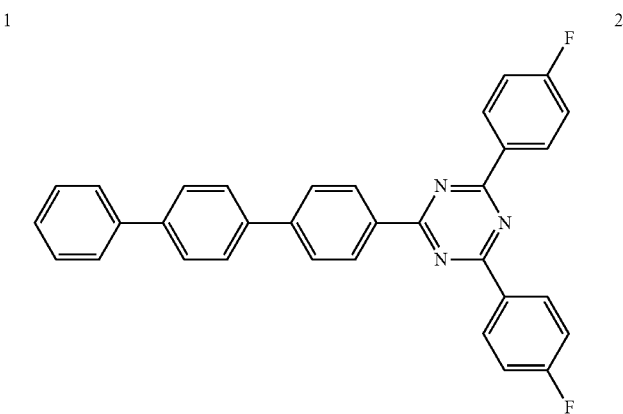

2

-continued
3
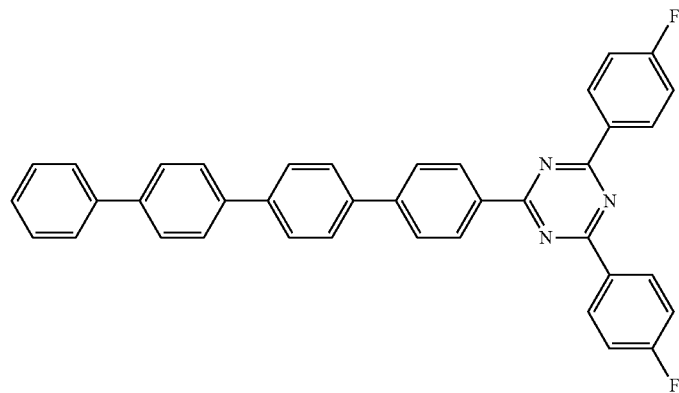
4
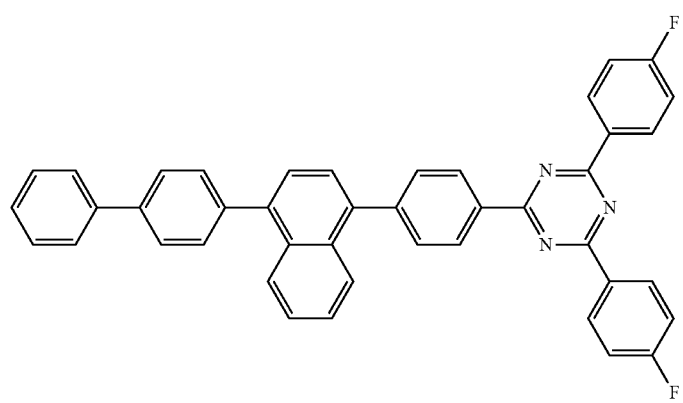
5
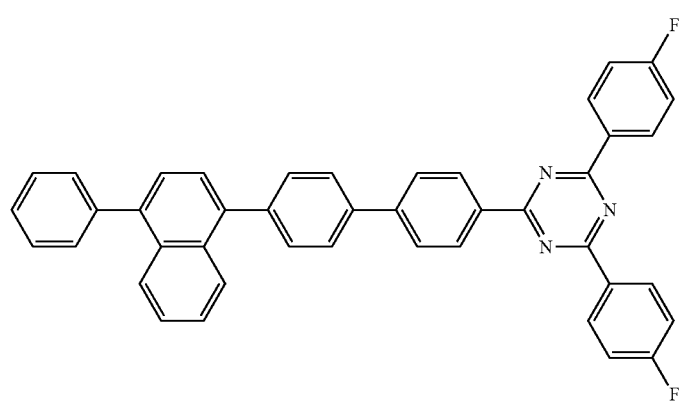
6
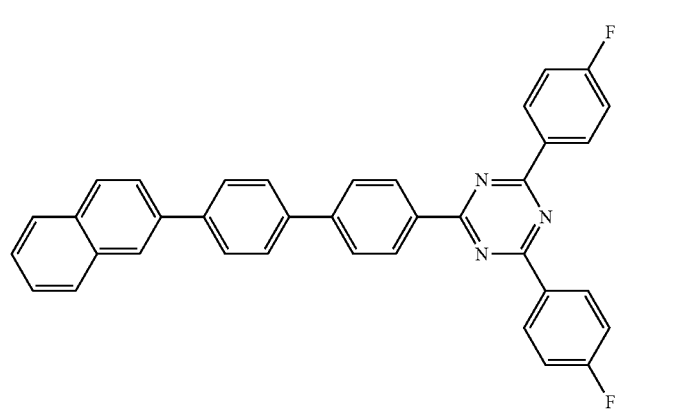

-continued
7
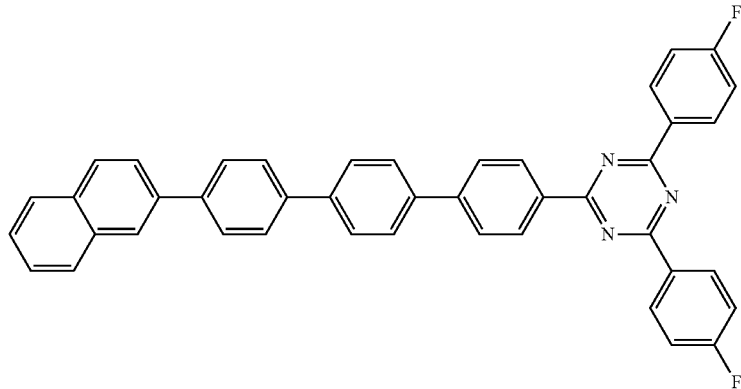
8
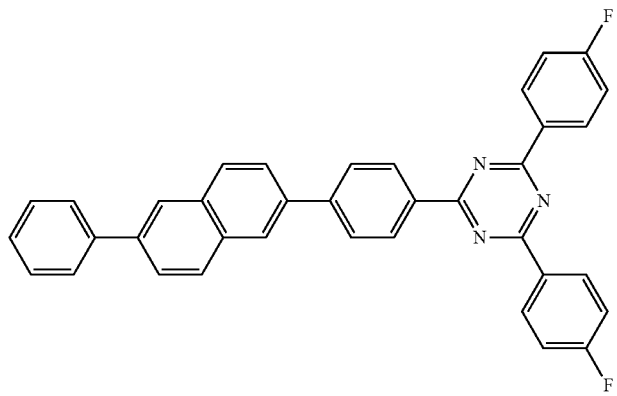
9
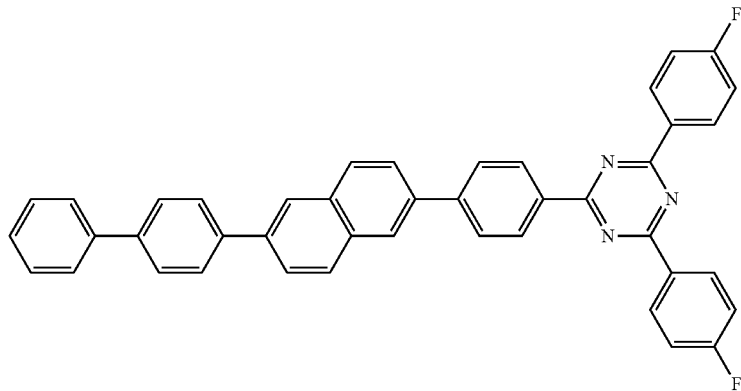
10
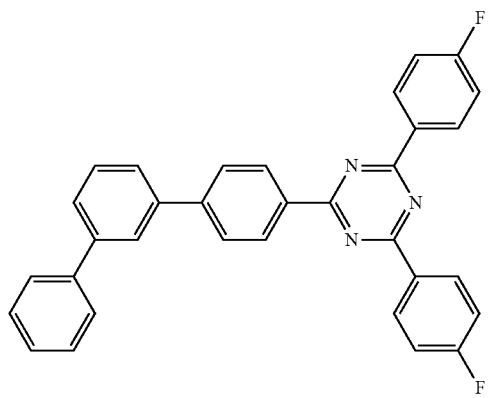
11
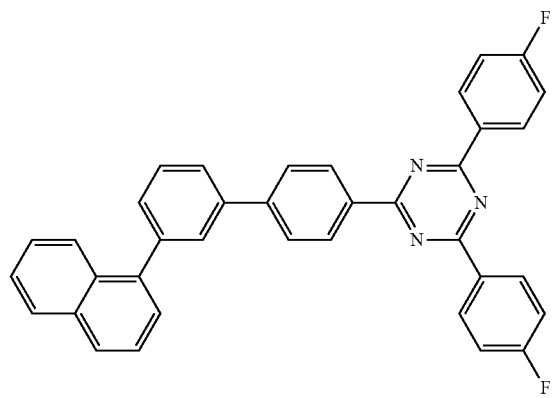

12
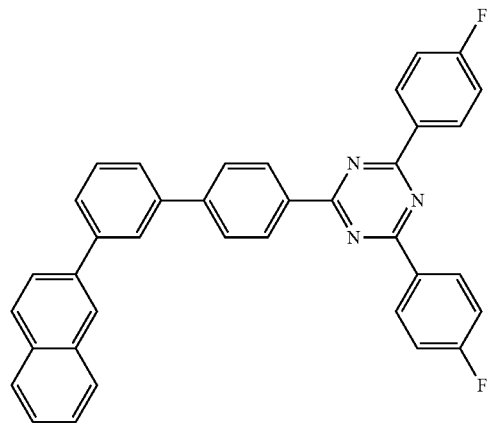
13
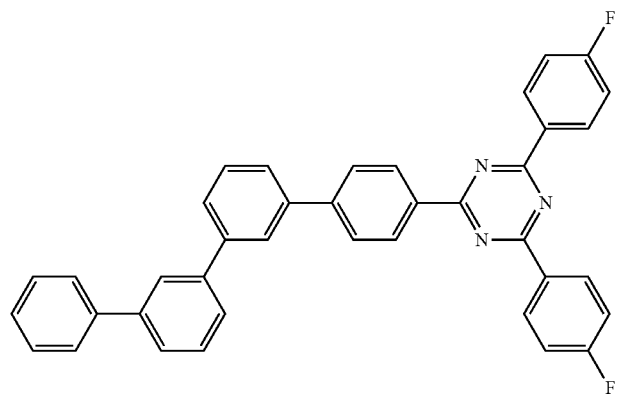
14
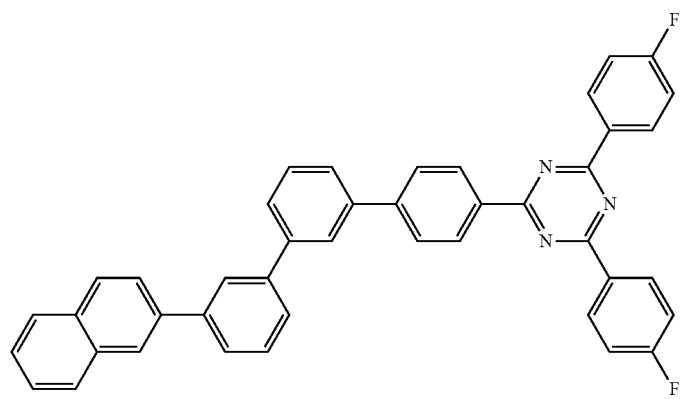
15
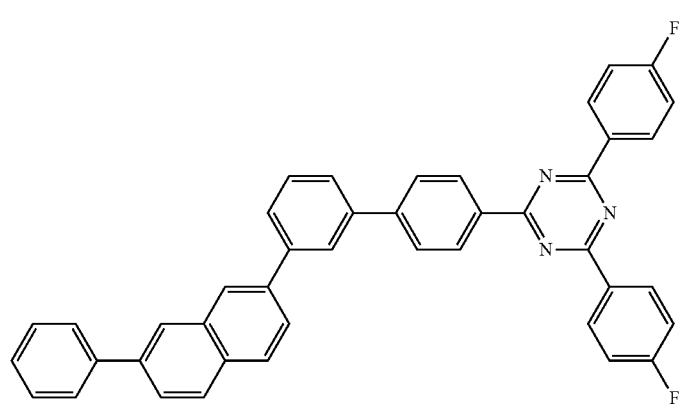

-continued
16
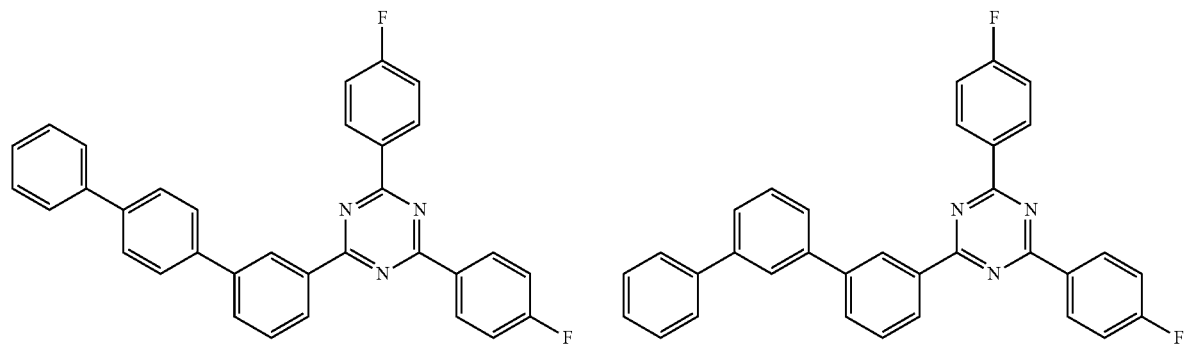
17
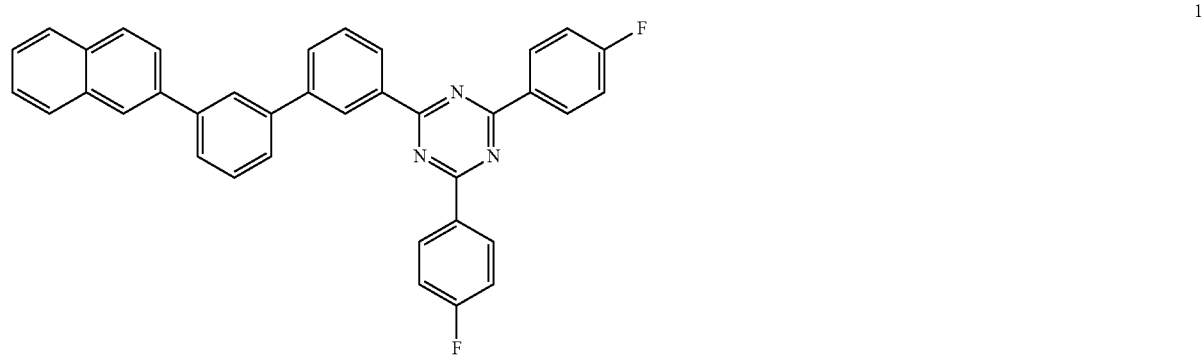
18
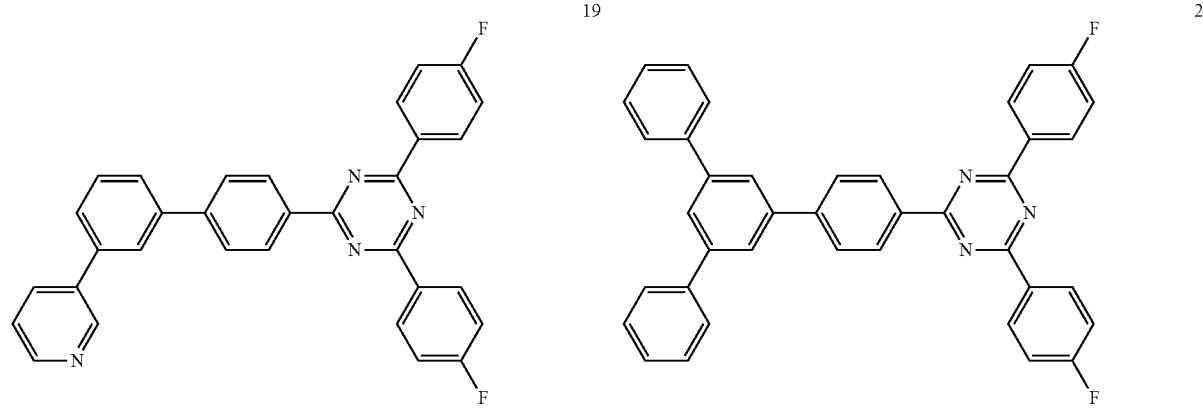
19
20
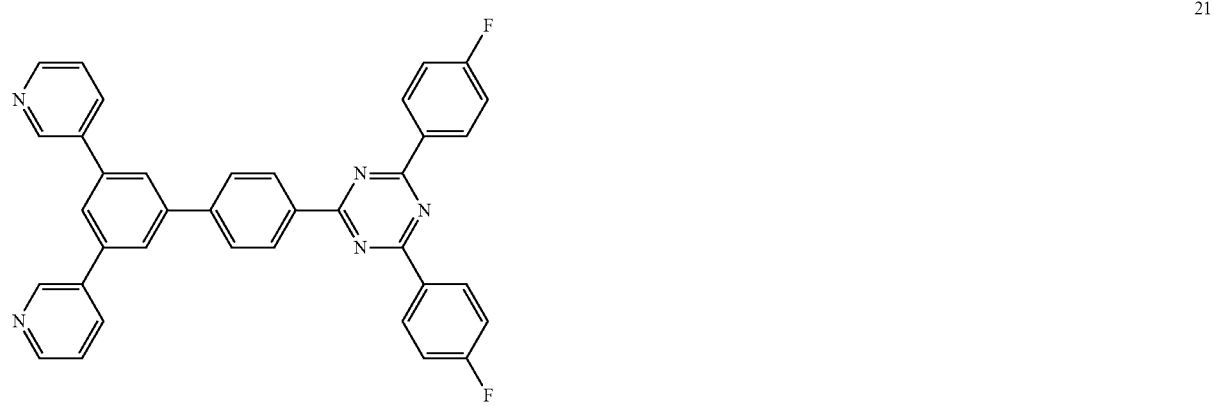
21

22
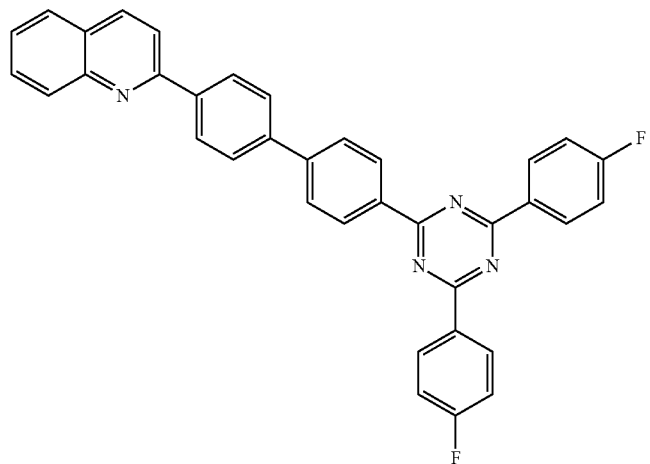
23
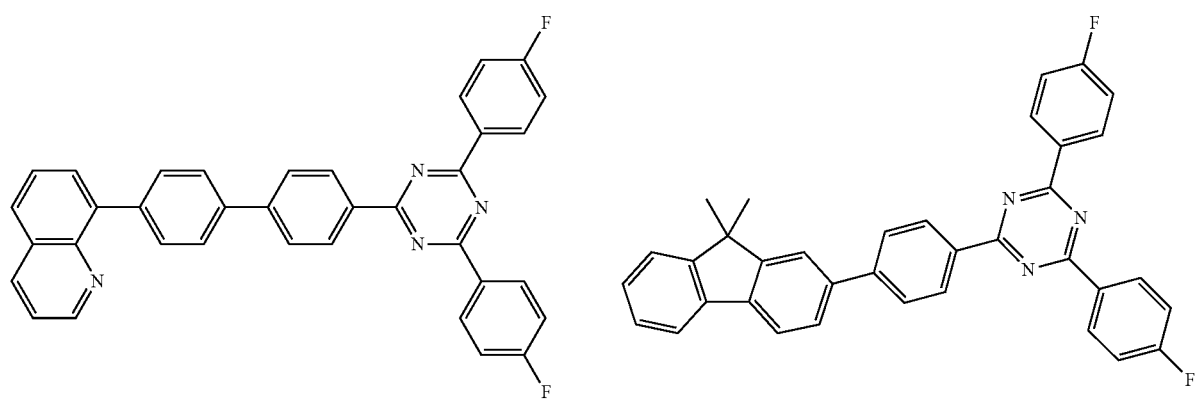
24
25
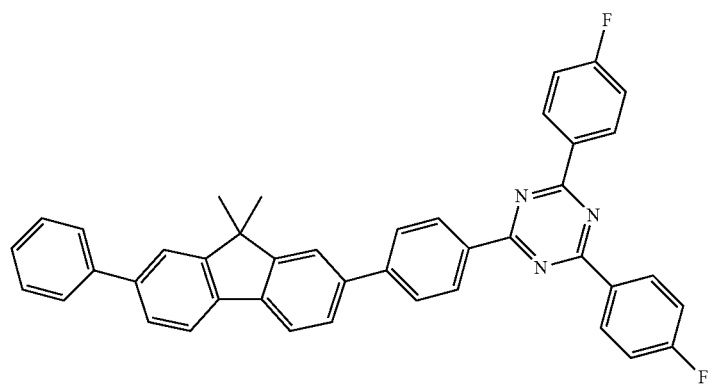
26
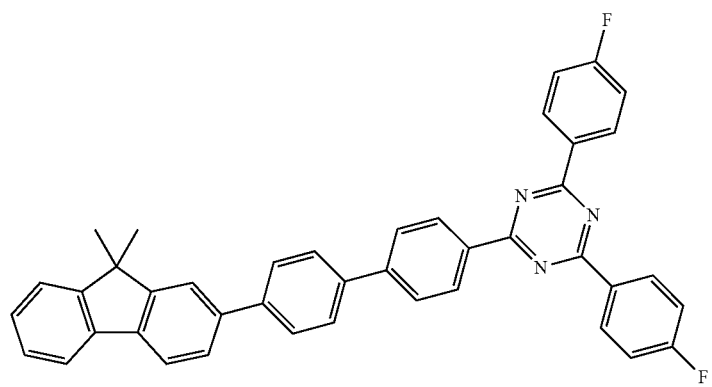

-continued
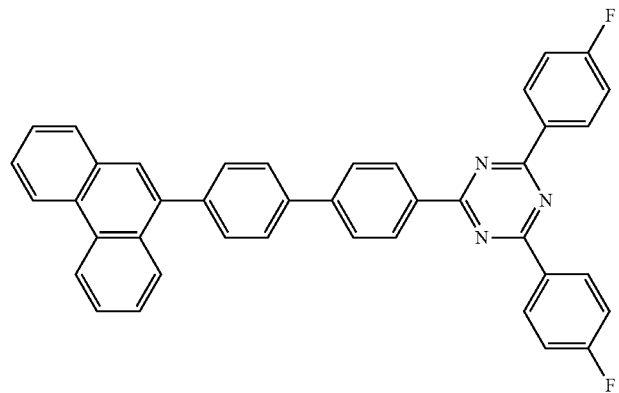
27
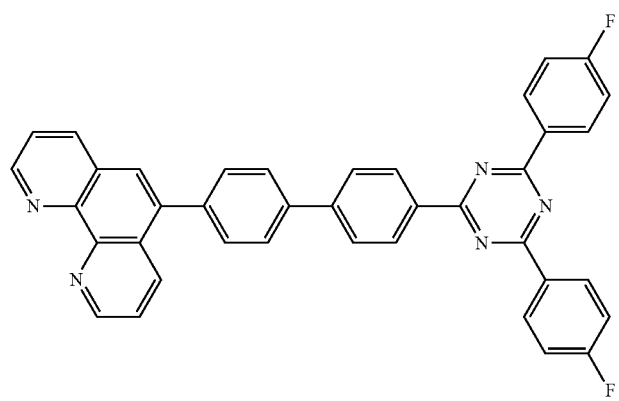
28
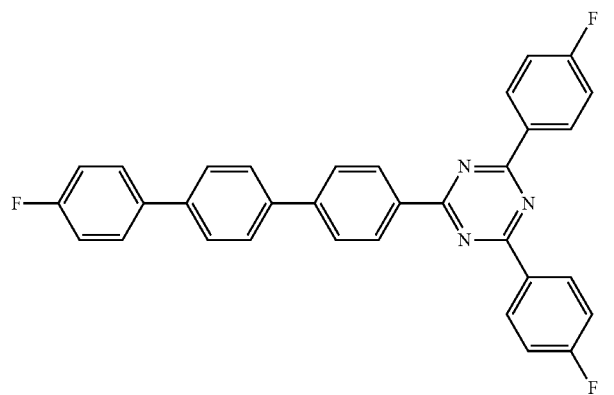
29
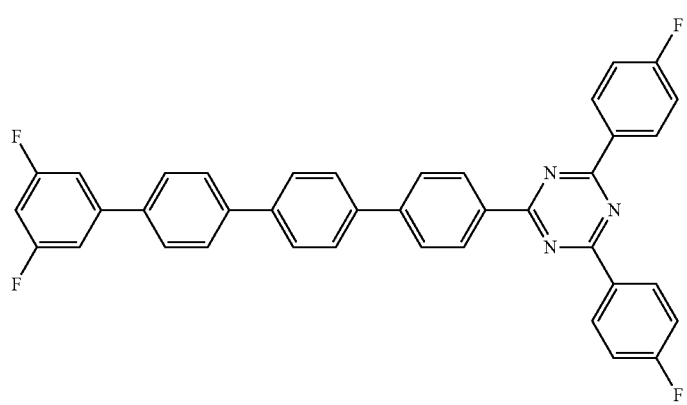
30

-continued
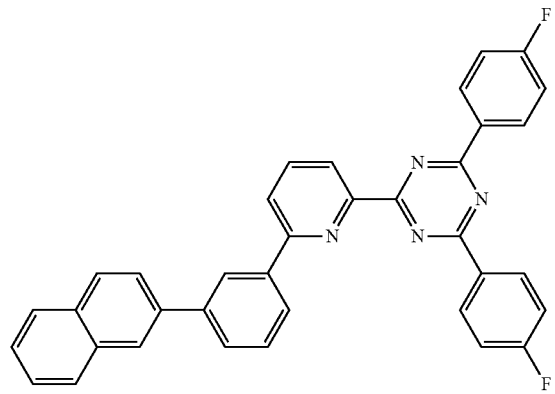
31
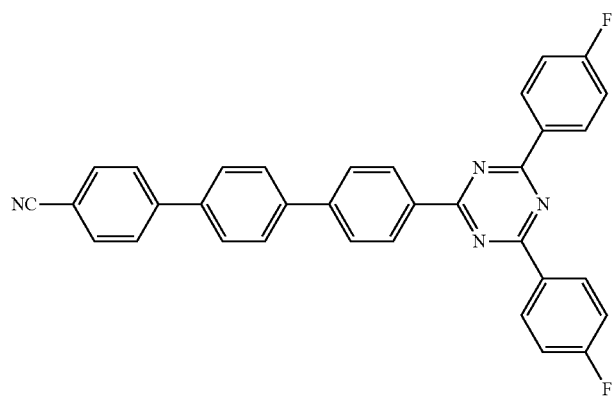
32
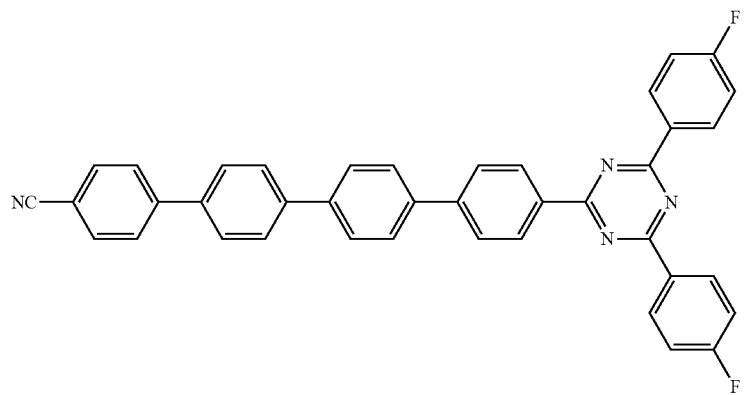
33
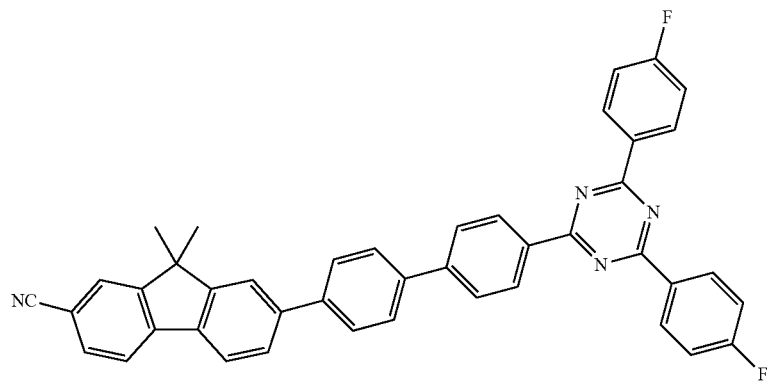
34

-continued
35
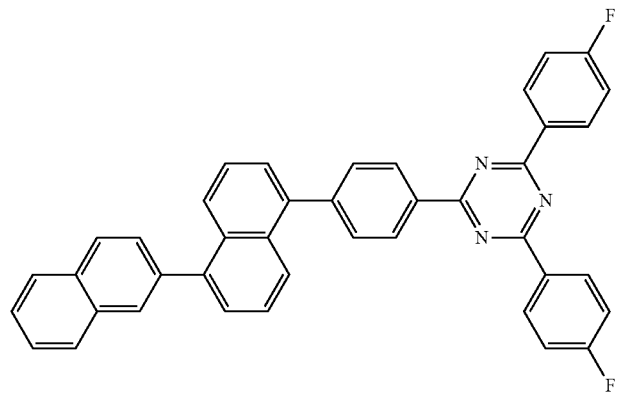
36
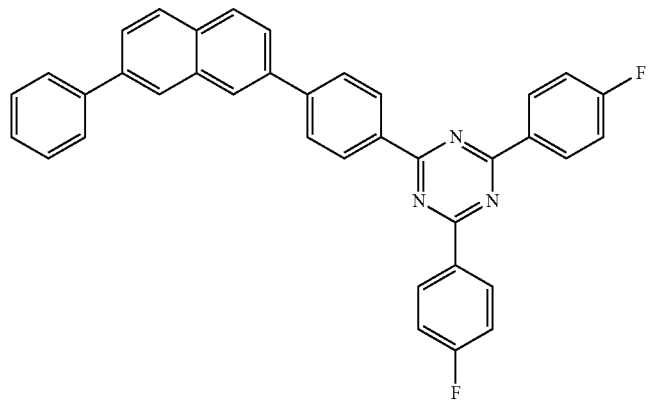
37
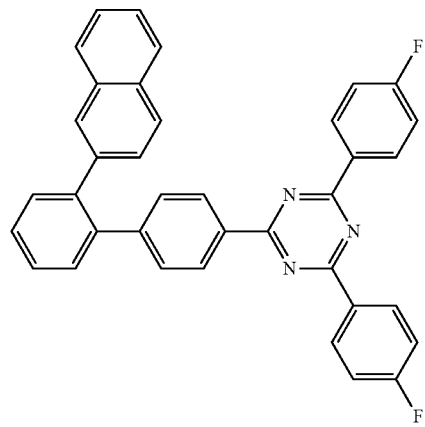
38
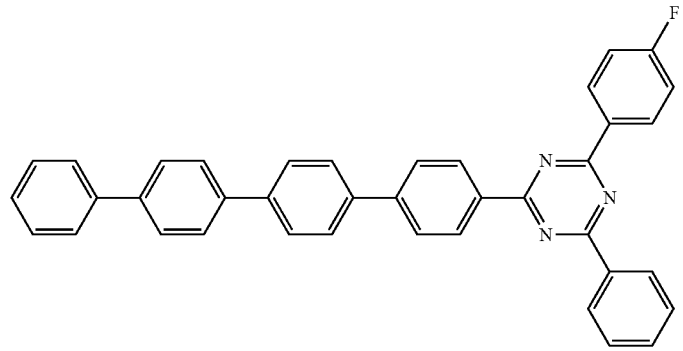

-continued
39
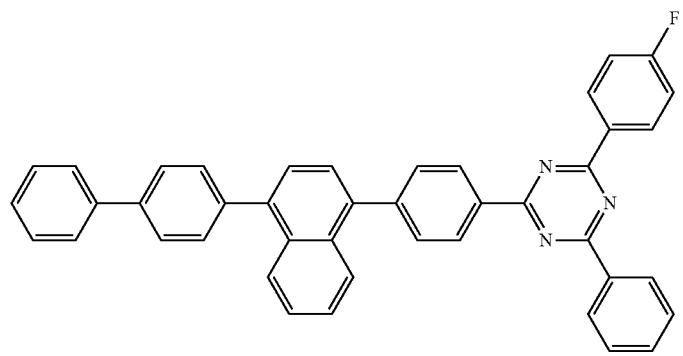
40
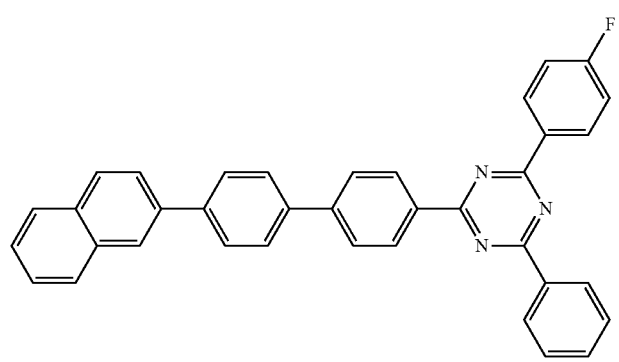
41
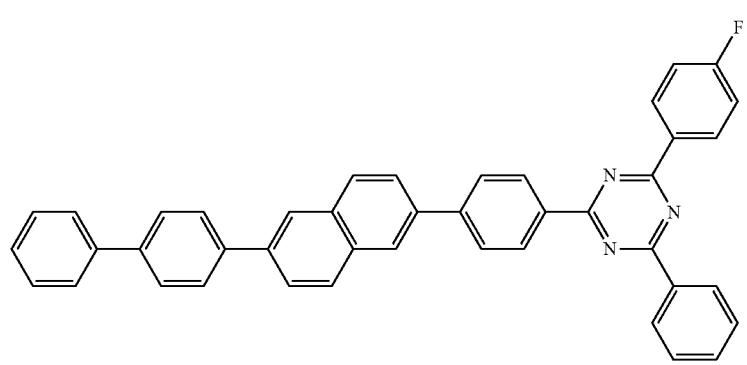
42
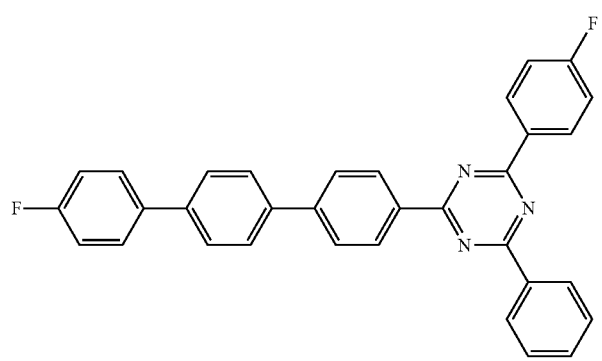

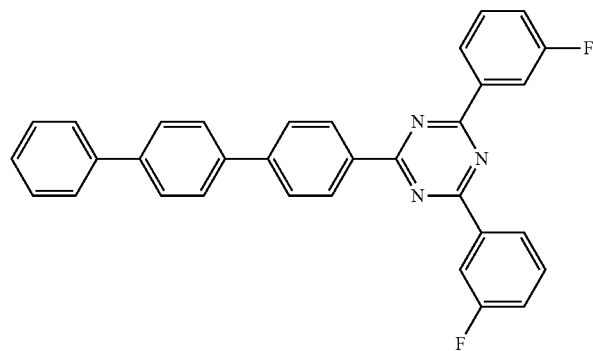
43
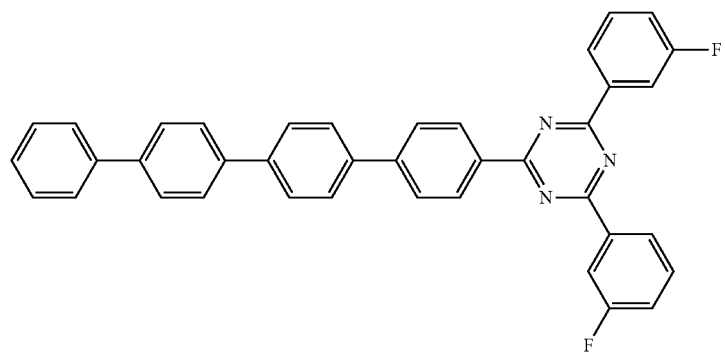
44
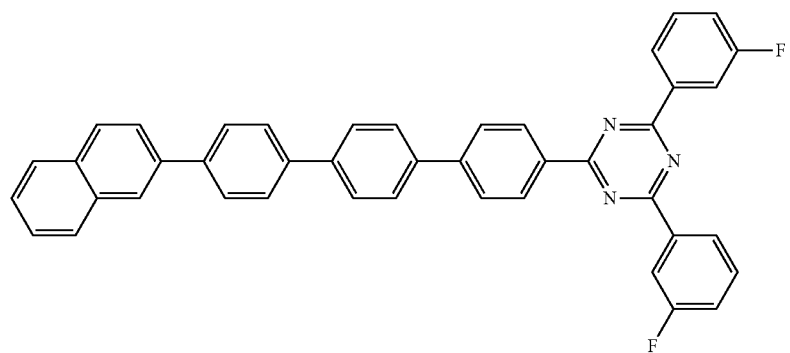
45
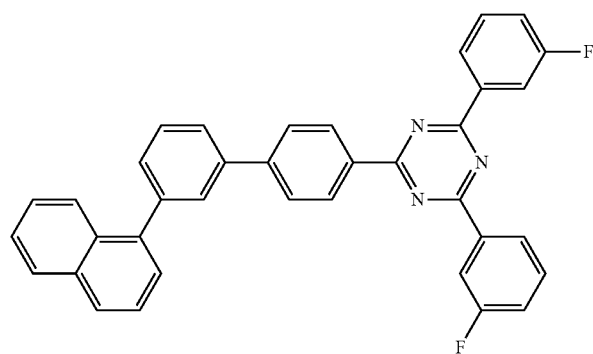
46

47
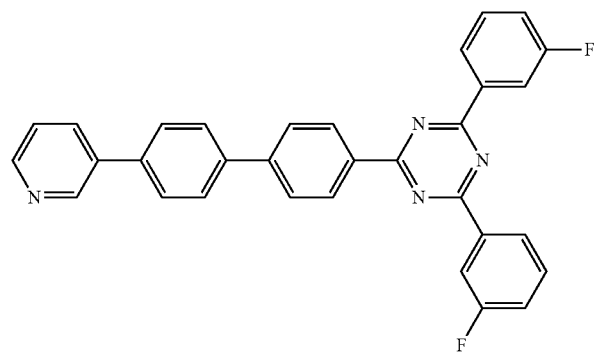
48
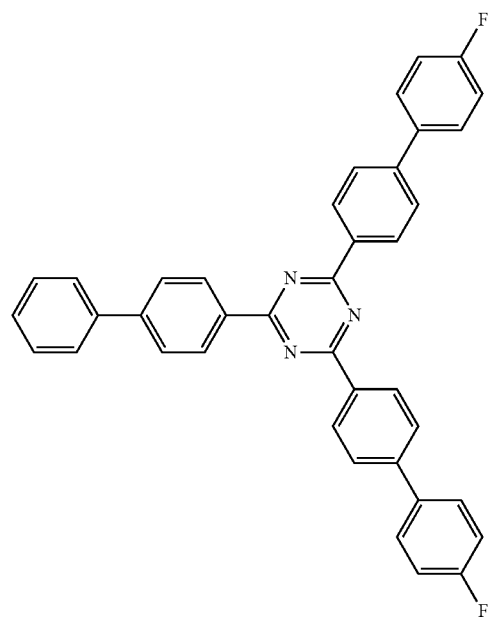
49
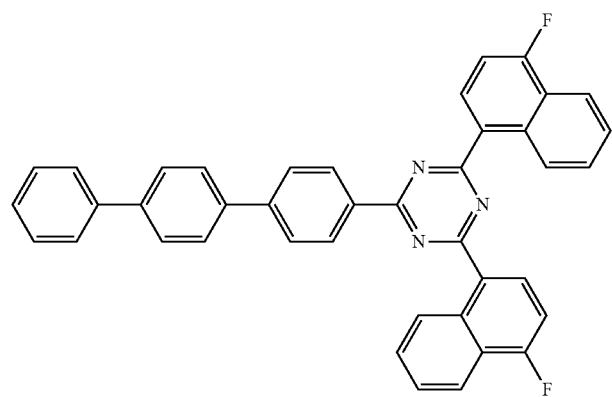

50
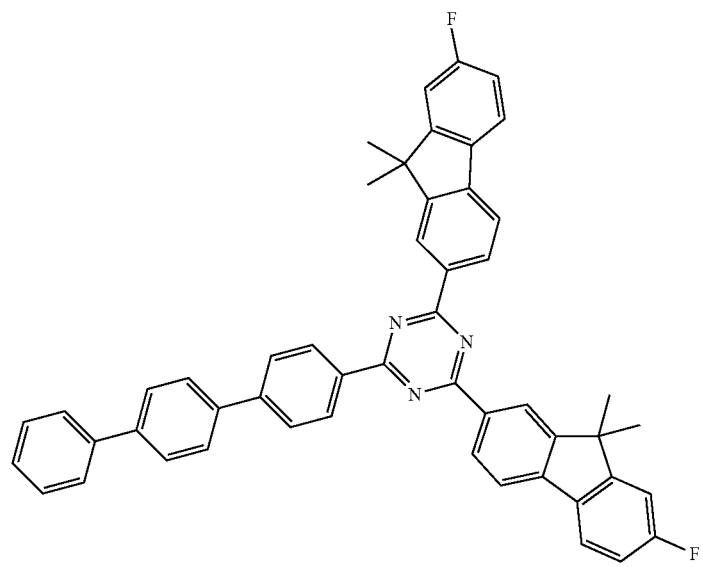
51
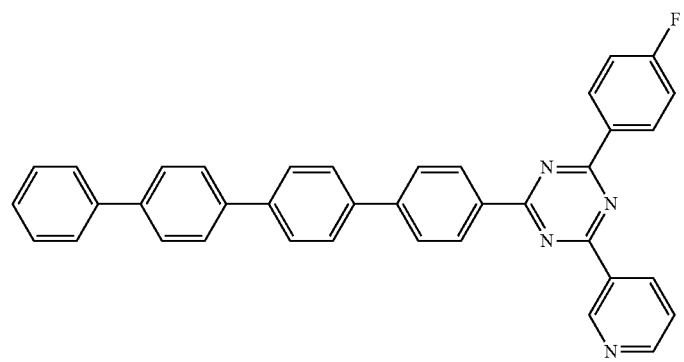
52
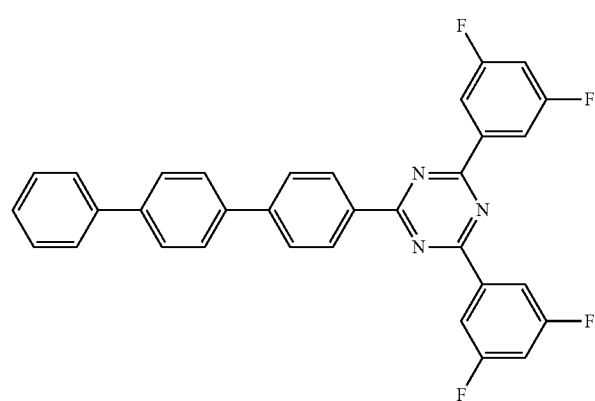

-continued
53
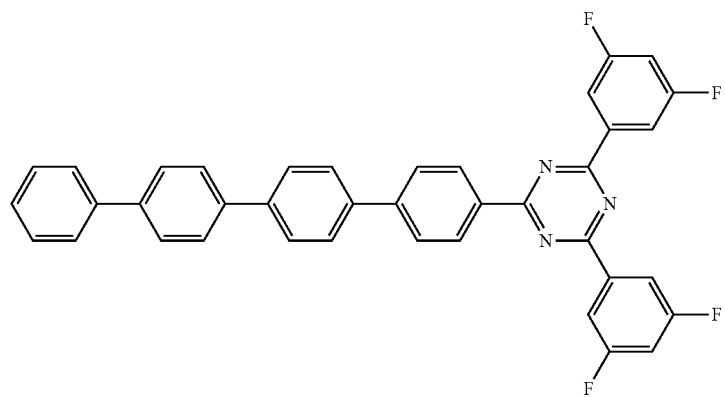
54
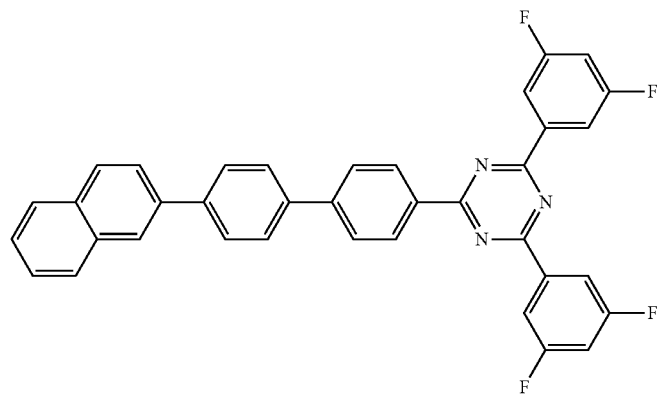
55
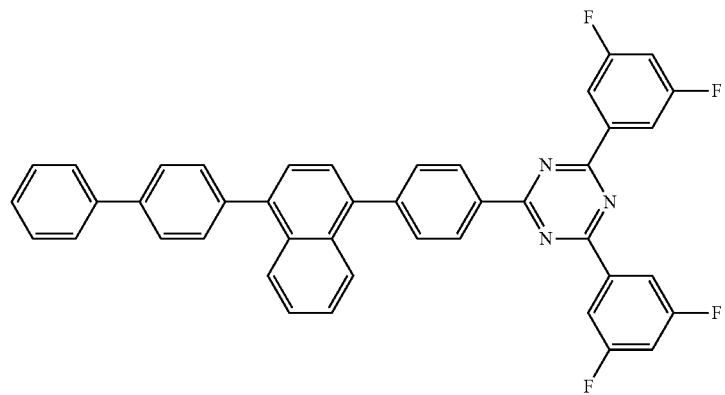
56
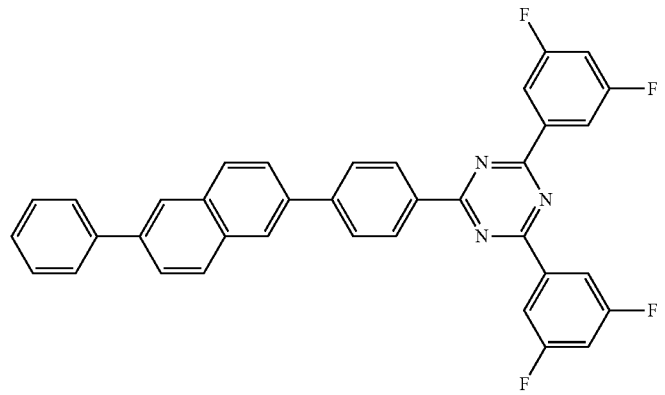

-continued
57
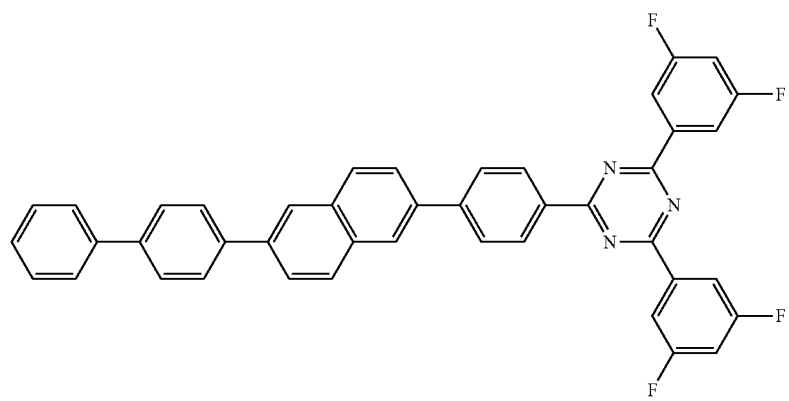
58
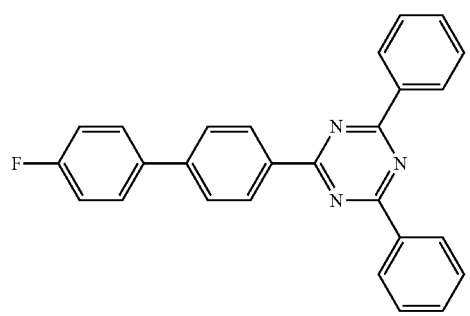
59
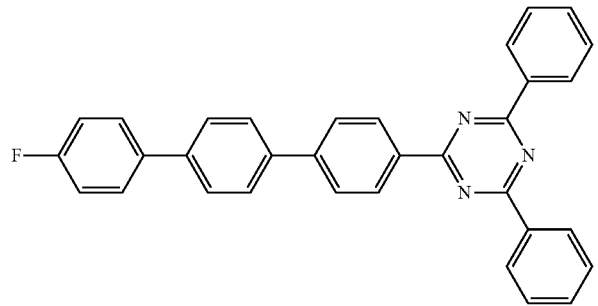
60
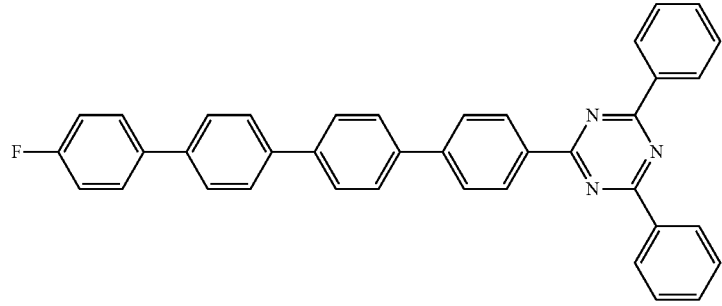
61
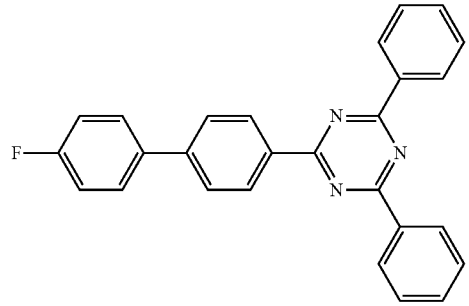

62
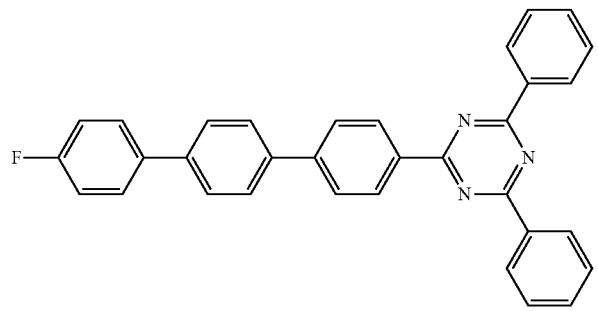
63
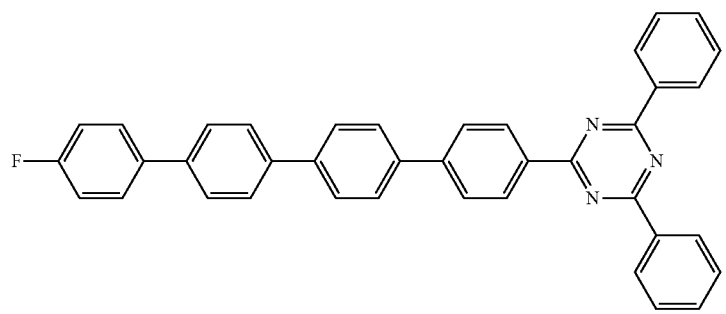
64
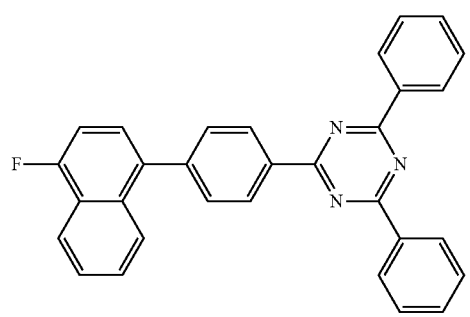
65
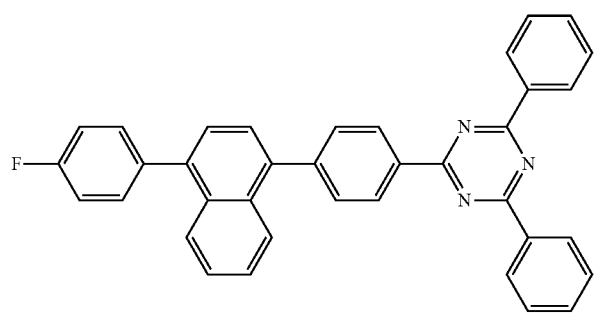
66
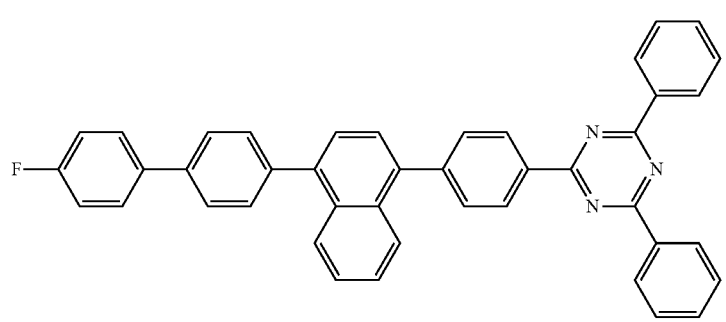

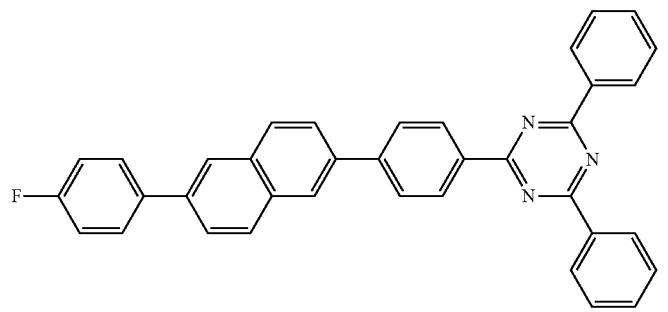
67
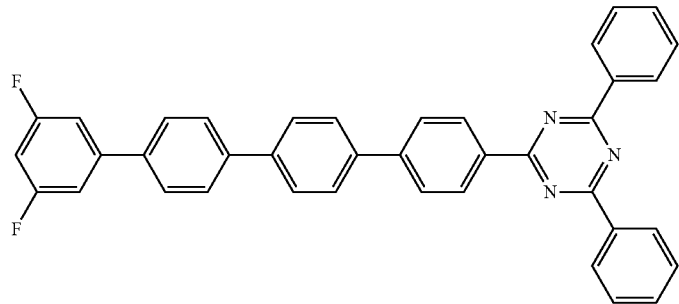
68
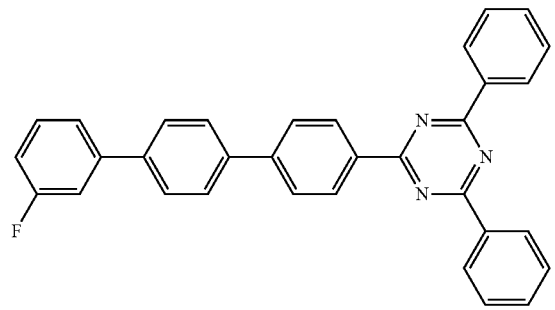
69
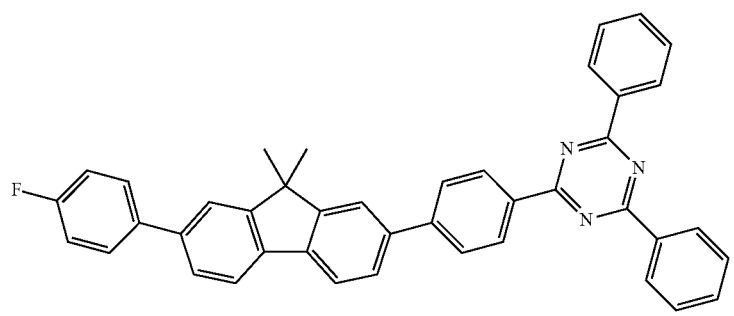
70
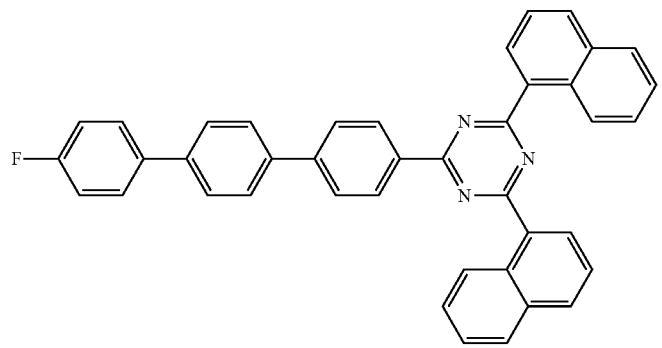
71

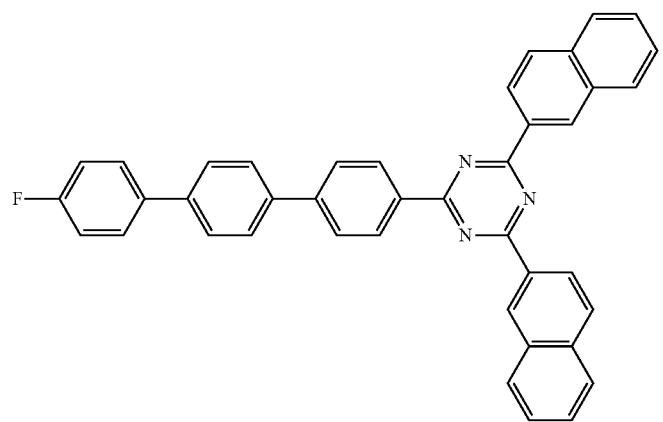
72
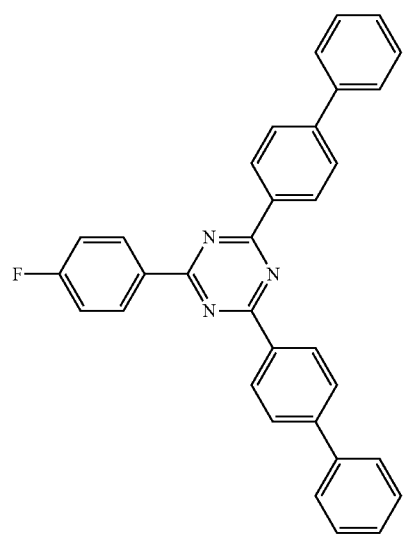
73
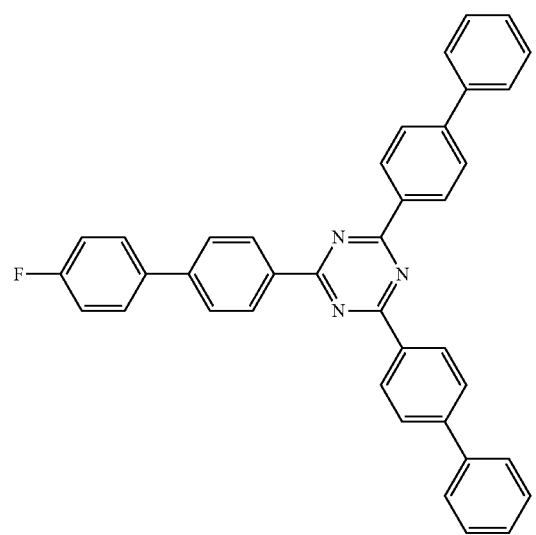
74
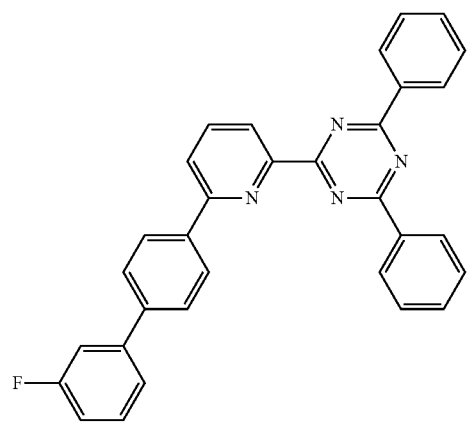
75

76
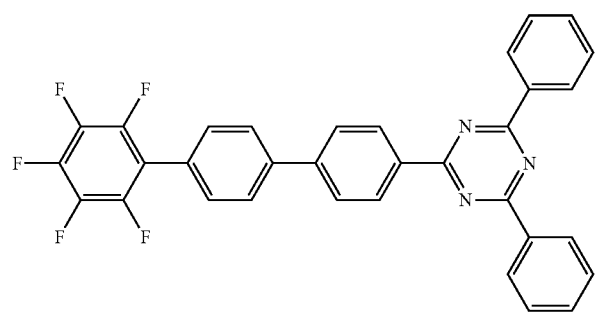
77
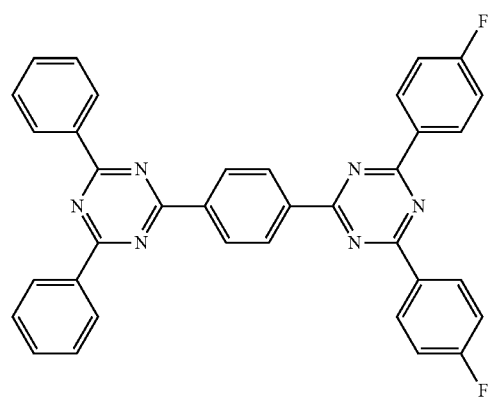
78
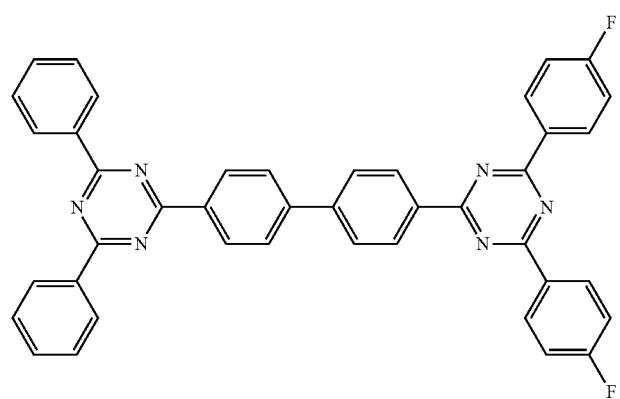

79
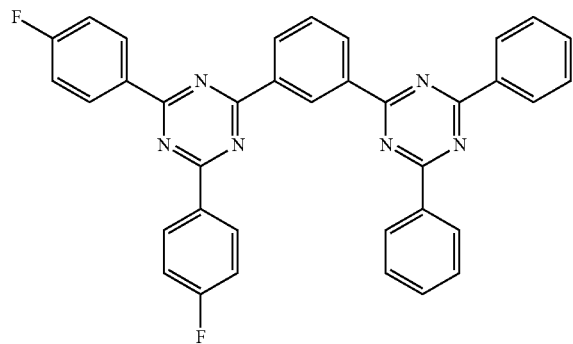
80
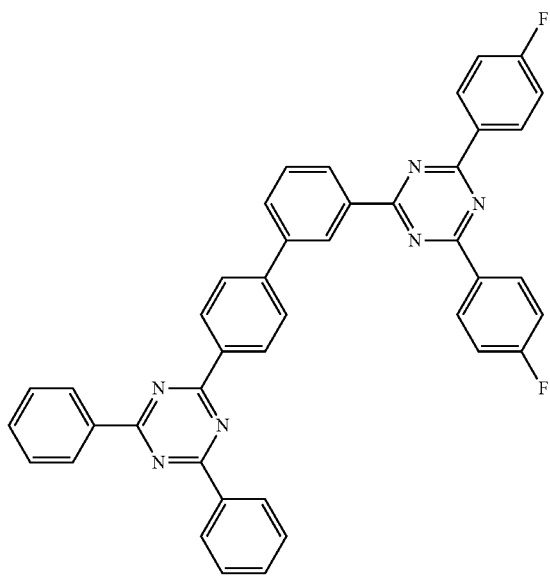
81
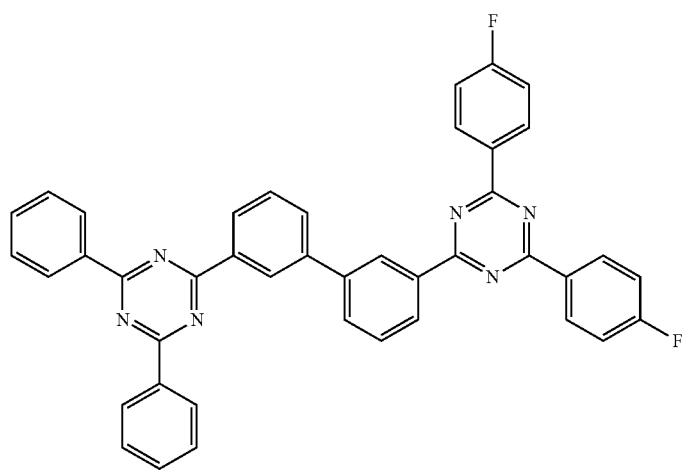
82
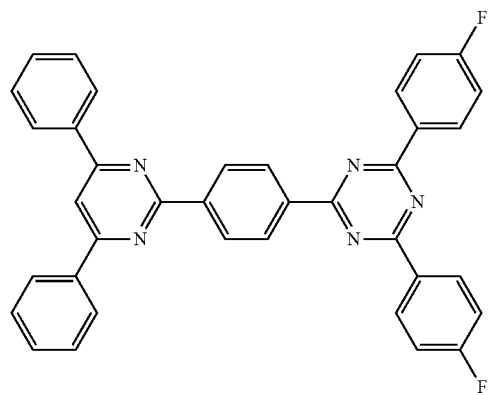

83
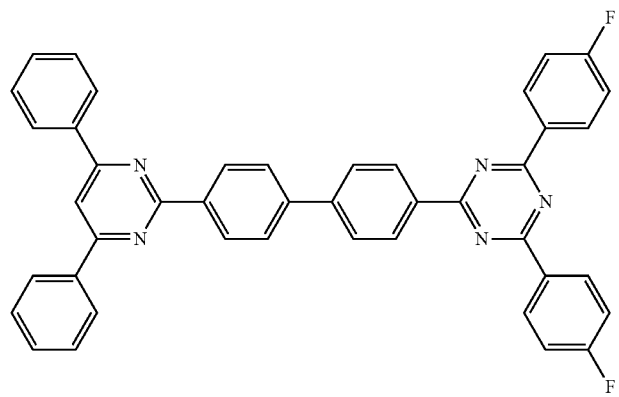
84
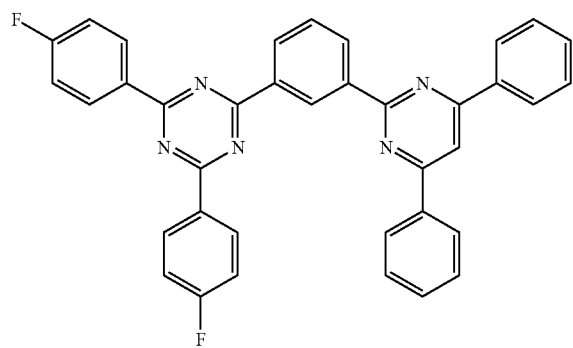
85
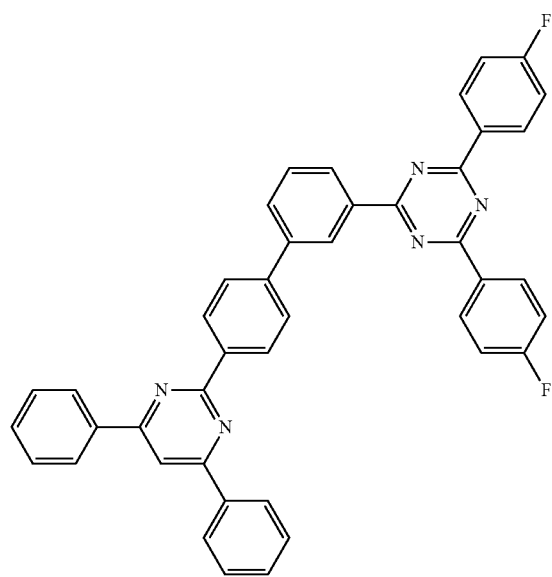

86
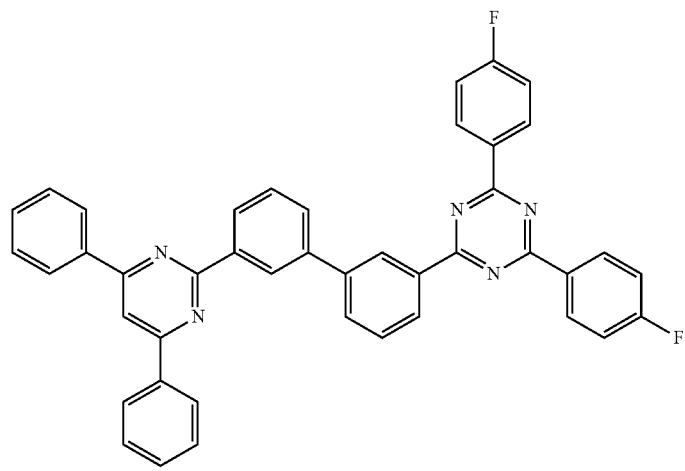
87
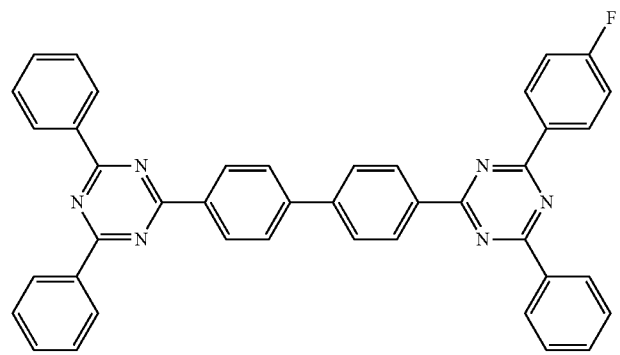
88
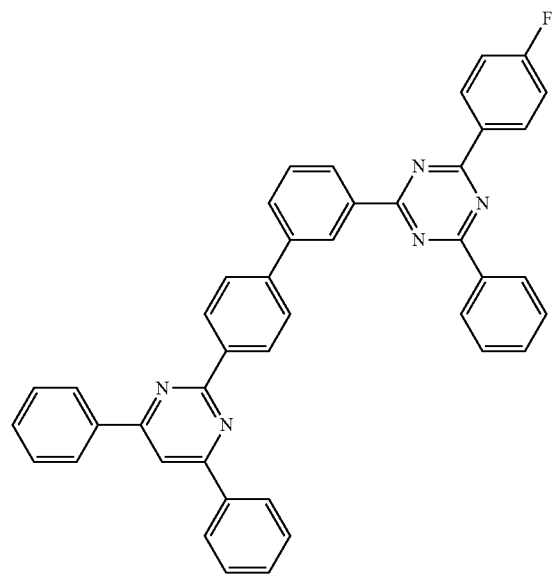

-continued

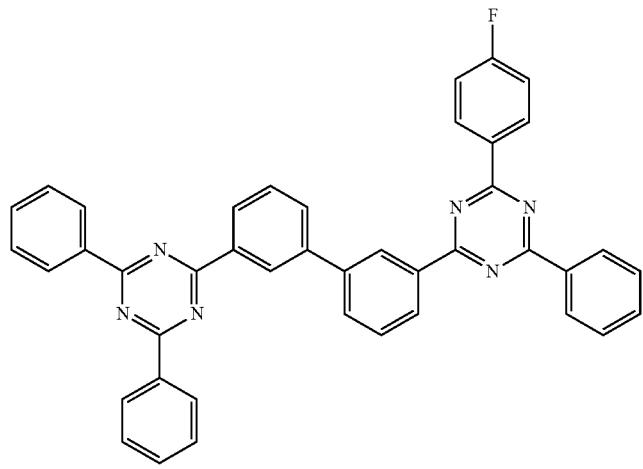
89

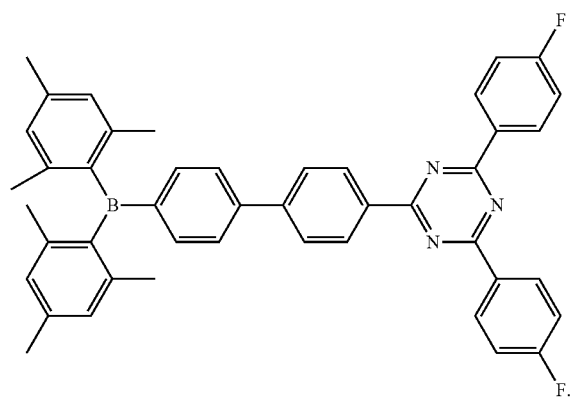
90

13. An organic light-emitting device comprising:
   a first electrode;
   a second electrode facing the first electrode; and
   an organic layer between the first electrode and the second electrode, wherein the organic layer comprises an emission layer and at least one of the heterocyclic compound of claim 1.

14. The organic light-emitting device of claim 13, wherein:
   the first electrode is an anode,
   the second electrode is a cathode,
   the organic layer further comprises a hole transport region between the first electrode and the emission layer and an electron transport region between the emission layer and the second electrode,
   the hole transport region comprises a hole injection layer, a hole transport layer, an emission auxiliary layer, an electron blocking layer, or any combination thereof, and
   the electron transport region comprises a buffer layer, a hole blocking layer, an electron control layer, an electron transport layer, an electron injection layer, or any combination thereof.

15. The organic light-emitting device of claim 14, wherein:
   the electron transport region comprises the heterocyclic compound.

16. The organic light-emitting device of claim 14, wherein:
   the electron transport region comprises an electron transport layer which includes the heterocyclic compound.

17. The organic light-emitting device of claim 16, wherein:
   the electron transport region comprises an emission auxiliary layer, and the emission auxiliary layer comprises the heterocyclic compound.

18. The organic light-emitting device of claim 14, wherein:
   the hole transport region comprises a p-dopant, and
   the p-dopant has a lowest unoccupied molecular orbital (LUMO) energy level of −3.5 eV or less.

19. The organic light-emitting device of claim 18, wherein:
   the p-dopant comprises a cyano group-containing compound.

20. The organic light-emitting device of claim 13, wherein:
   the emission layer is a first emission layer for emitting first color light,
   the organic light-emitting device further comprises, between the first electrode and the second electrode, i) at least one second emission layer for emitting second color light or ii) at least one second emission layer for emitting second color light and at least one third emission layer for emitting third color light,
   a maximum emission wavelength of the first color light, a maximum emission wavelength of the second color light, and a maximum emission wavelength of the third color light are identical to or different from one another, and
the first color light and the second color light are emitted in the form of mixed light, or the first color light, the second color light, and the third color light are emitted in the form of mixed light.

* * * * *